(12) United States Patent
Sheppeck et al.

(10) Patent No.: US 7,482,372 B2
(45) Date of Patent: Jan. 27, 2009

(54) HYDANTOINS AND RELATED HETEROCYCLES AS INHIBITORS OF MATRIX METALLOPROTEINASES AND/OR TNF-α CONVERTING ENZYME (TACE)

(75) Inventors: James E. Sheppeck, Wilmington, DE (US); Jingwu Duan, Newark, DE (US); Chu-Biao Xue, Hockessin, DE (US); Zelda Wasserman, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 590 days.

(21) Appl. No.: 11/093,670

(22) Filed: Mar. 30, 2005

(65) Prior Publication Data

US 2005/0171096 A1      Aug. 4, 2005

Related U.S. Application Data

(62) Division of application No. 10/844,219, filed on May 12, 2004, now Pat. No. 6,906,053, which is a division of application No. 10/155,575, filed on May 23, 2002, now Pat. No. 6,890,915.

(60) Provisional application No. 60/293,571, filed on May 25, 2001.

(51) Int. Cl.
C07D 487/00 (2006.01)
C07D 233/00 (2006.01)
C07D 221/00 (2006.01)
C07D 215/00 (2006.01)

(52) U.S. Cl. .................. 514/393; 548/300.1; 548/300.7; 548/407; 548/408; 548/409; 546/112; 546/134; 546/16

(58) Field of Classification Search ................. 514/183, 514/311, 385, 396, 399, 409, 412, 422, 425, 514/393; 548/300.1, 300.7, 407, 408, 409; 546/112, 134, 16
See application file for complete search history.

(56) References Cited

U.S. PATENT DOCUMENTS

| 4,315,031 | A | 2/1982 | Vincent et al. |
|---|---|---|---|
| 4,816,454 | A | 3/1989 | Zoller et al. |
| 5,567,725 | A | 10/1996 | Hemmerle et al. |
| 5,811,459 | A | 9/1998 | Breault et al. |
| 5,821,241 | A | 10/1998 | Claremon et al. |
| 5,861,380 | A | 1/1999 | Gyorkos et al. |
| 6,048,877 | A | 4/2000 | Ahmad et al. |
| 6,268,379 | B1 | 7/2001 | Xue et al. |

FOREIGN PATENT DOCUMENTS

| CS | 151744 | 11/1973 |
|---|---|---|
| JP | 5213957 | 8/1993 |
| WO | WO 99/24416 | 5/1999 |
| WO | WO 00/35886 | 6/2000 |
| WO | WO 01/12189 | 2/2001 |
| WO | WO 01/23363 | 4/2001 |
| WO | WO 01/44217 | 6/2001 |
| WO | WO 02/074748 | 9/2002 |
| WO | WO 02/074749 | 9/2002 |
| WO | WO 02/074750 | 9/2002 |
| WO | WO 02/074751 | 9/2002 |
| WO | WO 02/074752 | 9/2002 |
| WO | WO 02/074767 | 9/2002 |

OTHER PUBLICATIONS

Aharony et al., "Pharmacacological Characterization of a New Class of Non-Peptide Neurokinln A Antagonists that Demonstrate Species Selectivity", *J. Pharmacol. Exp. Ther.*, 1995, 274(3), pp. 1216-1221.
PubMed Abstract 145790524, also cited as *Curr. Opin. Drug Disc.*, 6/5, 2003, pp. 742-759.
PubMed Abstract 11934805, also cited as *Br. J. Pharmacol.*, 135/7, 2002, pp. 1655-1664.
PubMed Abstract 12082286, also cited as *Biorheology*, 39/1-2, 2002, pp. 237-246.
PubMed Abstract 14524529, also cited as *Clin. Exp. Metastasis*, 20/5, 2003, pp. 407-412.
Knabe et al., "Racemates and enantiomers of basic substituted 5-phenylhydantoins. Synthesis and antiarrhythmic activity,"Pharmazie, vol. 52, No. 12, 1997, pp. 912-919.

*Primary Examiner*—James O. Wilson
*Assistant Examiner*—Paul V. Ward
(74) *Attorney, Agent, or Firm*—Jing G. Sun

(57) ABSTRACT

The present application describes novel hydantoin derivatives of formula (I):

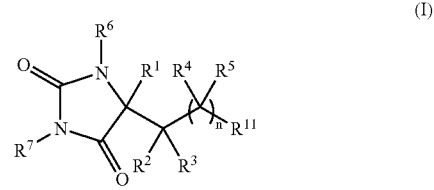

(I)

or pharmaceutically acceptable salt or prodrug forms thereof, wherein A, B, $R^1$, $R^2$, $R^3$, $R^4$, $R^5$, $R^6$, $R^7$, $R^{11}$, and n are defined in the present specification, which are useful as inhibitors of matrix metalloproteinases (MMP), TNF-α converting enzyme (TACE), aggrecanase, or a combination thereof.

6 Claims, No Drawings

HYDANTOINS AND RELATED HETEROCYCLES AS INHIBITORS OF MATRIX METALLOPROTEINASES AND/OR TNF-α CONVERTING ENZYME (TACE)

CROSS-REFERENCE TO RELATED APPLICATIONS

This application is a Divisional of U.S. Ser. No. 10/844,219, filed May 12, 2004, now allowed, which is a divisional of U.S. Ser. No. 10/155,575, filed May 23, 2002, now allowed, which in turn claims the priority benefit of U.S. Provisional Application No. 60/293,571, filed May 25, 2001, all of which are expressly incorporated fully herein by reference.

FIELD OF THE INVENTION

This invention relates generally to novel hydantoin derivatives as inhibitors of matrix metalloproteinases (MMP), TNF-α converting enzyme (TACE), aggrecanse or a combination thereof, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424-434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. *Arthritis Rheum.* 1978, 21, 761-766, Woessner et al. *Arthritis Rheum.* 1983, 26, 63-68 and Woessner et al. *Arthritis Rheum.* 1984, 27, 305-312). In addition, aggrecanase has been identified as providing the specific cleavage product of proteoglycan found in RA and OA patients (Lohmander L. S. et al. *Arthritis Rheum.* 1993, 36, 1214-22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175-184, AP, San Diego).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al. *Lancet* 1994, 344, 1105), non-insulin dependent diabetes melitus (Lohmander, L. S. et al. *Arthritis Rheum.* 1993, 36, 1214-22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

Prostaglandins (PG) play a major role in the inflammation process and the inhibition of PG production has been a common target of anti-inflammatory drug discovery. Many NSAIDS have been found to prevent the production of PG by inhibiting the enzyme cyclooxygenase (COX). Among the two isoforms of COXs, COX-1 is constitutively expressed. COX-2 is an inducible isozyme associated with inflammation. Selective COX-2 inhibitor was believed to maintain the efficacy of traditional NSAIDs, which inhibit both isozymes, and produce fewer and less drastic side effects. As a result, development of selective COX-2 inhibitors has attracted major interest in the pharmaceutical industry. Because of the significant roles of PGs and TNF-α in inflammation, combined use of COX-2 and TACE inhibitors may have superior efficacy to either therapy alone in some inflammatory diseases.

U.S. Pat. No. 6,048,877 discloses antiarrhythmic agents of the following formula:

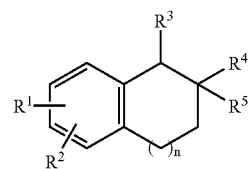

wherein $R^3$ can be a spiro-hydantoin moiety; $R^5$ is (4-phenyl-1-piperidinyl)ethyl; n is 0-2; and $R^1$, $R^2$, and $R^4$ are a variety of groups. Compounds specifically described in U.S. Pat. No. 6,048,877 are not considered to be part of the present invention.

WO01/44217 and WO99/24416 describe cyclin dependent kinases inhibitors of the following formula:

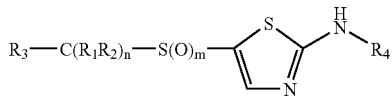

wherein $R_3$ is aryl or heteroaryl; $R_1$ and $R_2$ are independently H, F or alkyl; n is 1-3; m is 0-2; and $R_4$ can be —CO-alkylene-hydantoin or —CONH-alkylene-hydantoin. Compounds specifically described in WO01/44217 and WO99/24416 are not considered to be part of the present invention.

WO01/23363 describes matrix metalloproteinase 13 and aggrecanase inhibitors of the following formula:

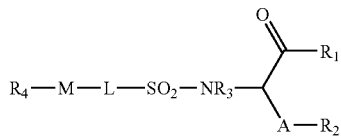

wherein $R_1$ is OH or optionally protected hydroxamino; $R_2$ can be a hydantoin moiety; $R_4$ can be aryl or heteroaryl; L is arylene or heteroarylene; and M is O or S. Compounds specifically described in WO01/23363 are not considered to be part of the present invention.

WO01/12189 discloses antitumor agents of the following formula:

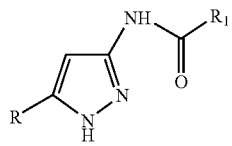

wherein R is a $C_3$-$C_6$ cycloalkyl; and $R_1$ can be —CH$_2$-hydantoin. Compounds specifically described in WO01/12189 are not considered to be part of the present invention.

WO00/35886 illustrates serine protease inhibitors of the following formula:

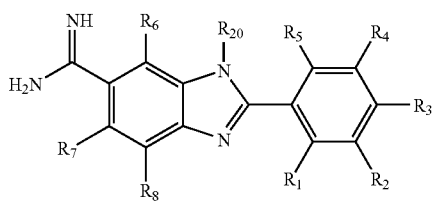

wherein $R_2$ can be —OCH$_2$CH$_2$NHCOCH$_2$-hydantoin; and $R_1$, $R_3$-$R_8$, and $R_{20}$ are a variety of groups. Compounds specifically described in WO00/35886 are not considered to be part of the present invention.

U.S. Pat. No. 5,861,380 depicts serine protease inhibitors of the following formula:

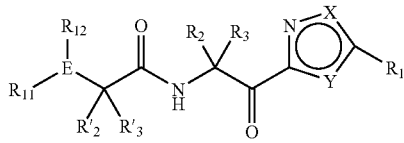

wherein $R_1$ can be aryl, aralkyl, heteroaryl or heteroaralkyl; X and Y are N, O or S; $R_{11}$, $R_{12}$ and E can form a hydantoinyl moiety; $R_2$, $R_3$, $R'_2$, and $R'_3$ are a variety of groups. Compounds specifically described in U.S. Pat. No. 5,861,380 are not considered to be part of the present invention.

U.S. Pat. No. 5,811,459 describes analgesics & prostaglandin antagonists of the following formula:

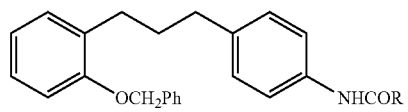

wherein R can be —CH$_2$-hydantoin. Compounds specifically described in U.S. Pat. No. 5,811,459 are not considered to be part of the present invention.

U.S. Pat. No. 5,567,725 discloses glucose-6-phosphatase inhibitors of the following formula:

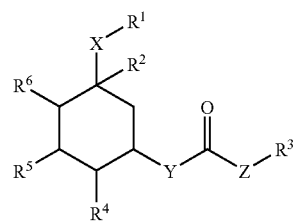

wherein $R^1$ can be a hydantoin moiety; X can be —CH$_2$—O—CH$_2$—, —CH$_2$—S—CH$_2$—, or —CH$_2$—NR$^8$—CH$_2$—; Y is (CH$_2$)$_{0-4}$, O, S or NR$^8$; Z is a linear linker, $C_3$-$C_{10}$-cycloalkylene, or $C_3$-$C_{10}$-cycloalkenylene; $R^3$ can be cycloalkyl, aryl or heteroaryl; and $R^4$, $R^5$, and $R^6$ are a variety of groups. Compounds specifically described in U.S. Pat. No. 5,567,725 are not considered to be part of the present invention.

U.S. Pat. No. 5,821,241 illustrates fibrinogen receptor antagonists of the following formula:

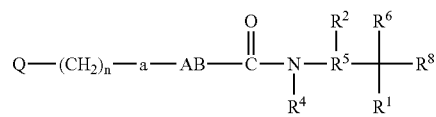

wherein Q can be a 4-9 membered mono or bicyclic heterocyclic ring system; n is 0-7; a is an amide linker or a bond; AB is a fused ring system sharing adjacent C and N atoms in which each ring is a 5-7 membered saturated or unsaturated ring containing 1-3 heteroatoms selected from O, S or N; $R^5$ can a bond, CH, —CH(CH$_2$)$_n$, or —C(O)(CH$_2$)$_n$; R$^1$ and R$^6$ can form a hydantoinyl moiety; and R$^6$ are a variety of groups. Compounds specifically described in U.S. Pat. No. 5,821,241 are not considered to be part of the present invention.

U.S. Pat. No. 4,816,454 discloses compounds of the following formula:

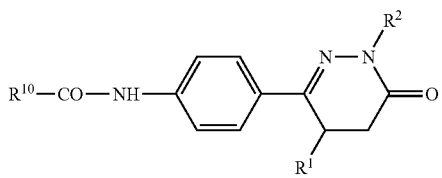

wherein R$^{10}$ can be —CH$_2$-hydantoin; and R$^4$, R$^5$, and R$^6$ are a variety of groups. Compounds specifically described in U.S. Pat. No. 4,816,454 are not considered to be part of the present invention.

The compounds of the present invention act as inhibitors of MPs, in particular TACE, MMPs, and/or aggrecanase. These novel molecules are provided as anti-inflammatory compounds and cartilage protecting therapeutics. The inhibition of aggrecanase, TACE, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, the present invention provides novel hydantoin derivatives useful as MMP and/or TACE inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory disorders, comprising: administering to a host, in need of such treatment, a therapeutically effective amount of at least one of the compounds of the present invention or a pharmaceutically acceptable salt or prodrug form thereof.

The present invention provides a method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt or prodrug form thereof.

The present invention provides a method comprising: administering a compound of the present invention or a pharmaceutically acceptable salt or prodrug form thereof in an amount effective to treat a condition or disease mediated by MMPs, TACE, aggrecanase, or a combination thereof.

The present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

It is another object of the present invention to provide novel compounds of the present invention for use in therapy.

It is another object of the present invention to provide the use of novel compounds of the present invention for the manufacture of a medicament for the treatment of a condition or disease mediated by MMPs, TACE, aggrecanase, or a combination thereof.

These and other objects, which will become apparent during the following detailed description, have been achieved by the inventors' discovery that compounds of formula (I):

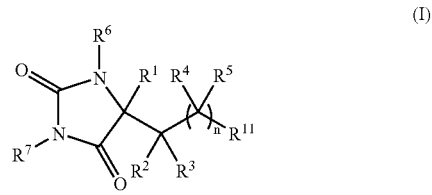

or pharmaceutically acceptable salt or prodrug forms thereof, wherein R$^1$, R$^2$, R$^3$, R$^4$, R$^5$, R$^6$, R$^7$, R$_{11}$, and n are defined below, are effective as MMP and/or TACE inhibitors.

DETAILED DESCRIPTION OF PREFERRED EMBODIMENTS

[1] Thus, in an embodiment, the present invention provides a novel compound of formula (I):

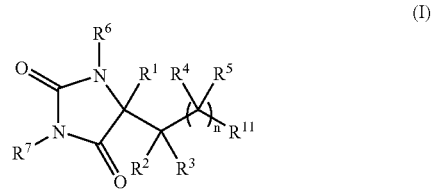

or a stereoisomer or pharmaceutically acceptable salt form thereof, wherein;

R$_{11}$ is -W-U-X-Y-Z-U$^a$-X$^a$-Y$^a$-Z$^a$;

W is selected from (CR$^a$R$^{a1}$)$_m$, C$_{2-3}$ alkenylene, and C$_{2-3}$ alkynylene;

U is absent or is selected from O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, and NR$^{a1}$SO$_2$NR$^{a1}$;

X is absent or is selected from C$_{1-3}$ alkylene, C$_{2-3}$ alkenylene, and C$_{2-3}$ alkynylene;

Y is absent or is selected from O, NR$^{a1}$, S(O)$_p$, and C(O);

Z is selected from:
 a C$_{3-13}$ carbocycle substituted with 0-5 R$^b$; and
 a 5-14 membered heterocycle consisting of carbon atoms and 1-4 heteroatoms selected from the group consisting of N, O, and S(O)$_p$, and substituted with 0-5 R$^b$;

U$^a$ is absent or is selected from O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, and NR$^{a1}$SO$_2$NR$^{a1}$;

X$^a$ is absent or is selected from C$_{1-10}$ alkylene, C$_{2-10}$ alkenylene, and C$_{2-10}$ alkynylene;

Y$^a$ is absent or is selected from O, NR$^{a1}$, S(O)$_p$, and C(O);

$Z^a$ is selected from:
  a $C_{3-13}$ carbocycle substituted with 0-5 $R^c$; and
  a 5-14 membered heterocycle consisting of carbon atoms and 1-4 heteroatoms selected from the group consisting of N, O, and $S(O)_p$, and substituted with 0-5 $R^c$;

provided that U, Y, Z, $U^a$, $Y^a$, and $Z^a$ do not combine to form a N—N, N—O, O—N, O—O, $S(O)_p$—O, O—S$(O)_p$ or $S(O)_p$—$S(O)_p$ group;

$R^1$ and $R^2$, together with the carbon atoms to which they are attached, combine to form a 3-8 membered carbocyclic or heterocyclic ring consisting of carbon atoms,
  0-2 ring heteroatoms selected from O, N, $NR^{10}$, and $S(O)_p$, 0-2 carbonyl groups, and 0-2 double bonds, and substituted with 0-3 $R^9$; and the carbocyclic or heterocyclic ring is optionally fused to a 5-6 membered aromatic or non-aromatic carbocycle substituted with 0-3 $R^9$ or a 5-6 membered aromatic or non-aromatic heterocycle consisting of carbon atoms and 1-3 heteroatoms selected from the group consisting of N, O, and $S(O)_p$, and substituted with 0-3 $R^9$, provided that when the carbocyclic ring is fused to a 6 membered aromatic carbocycle, Z is other than a 1,4-piperidinyl ring;

$R^3$ is selected from Q, $C_{1-6}$ alkylene-Q, $C_{2-6}$ alkenylene-Q, $C_{2-6}$ alkynylene-Q, $(CR^aR^{a1})_rO(CR^aR^{a1})_s$-Q, $(CR^aR^{a1})_rNR^a(CR^aR^{a1})_s$-Q, $(CR^aR^{a1})_rC(O)(CR^aR^{a1})_s$-Q, $(CR^aR^{a1})_rC(O)O(CR^aR^{a1})_s$-Q, $(CR^aR^{a1})_rOC(O)(CR^aR^{a1})_s$-Q, $(CR^aR^{a1})_rC(O)NR^aR^{a1}$, $(CR^aR^{a1})_rC(O)NR^a(CR^aR^{a1})_s$-Q, $(CR^aR^{a1})_rNR^aC(O)(CR^aR^{a1})_s$-Q, $(CR^aR^{a1})_rOC(O)O(CR^aR^{a1})_s$-Q, $(CR^aR^{a1})_rOC(O)NR^a(CR^aR^{a1})_s$-Q, $(CR^aR^{a1})_rNR^aC(O)O(CR^aR^{a1})_s$-Q, $(CR^aR^{a1})_rNR^aC(O)NR^a(CR^aR^{a1})_s$-Q, $(CR^aR^{a1})_rS(O)_p(CR^aR^{a1})_s$-Q, $(CR^aR^{a1})_rSO_2NR^a(CR^aR^{a1})_s$-Q, $(CR^aR^{a1})_rNR^aSO_2(CR^aR^{a1})_s$-Q, and $(CR^aR^{a1})_rNR^aSO_2NR^a(CR^aR^{a1})_s$-Q;

Q, at each occurrence, is selected from H, $CHF_2$, $CH_2F$, $CF_3$, a $C_{3-13}$ carbocycle substituted with 0-5 $R^d$, and a 5-14 membered heterocycle consisting of carbon atoms and 1-4 heteroatoms selected from the group consisting of N, O, and $S(O)_p$, and substituted with 0-5 $R^d$;

$R^4$ is selected from H, $C_{1-6}$ alkyl substituted with 0-1 $R^b$, $C_{2-6}$ alkenyl substituted with 0-1 $R^b$, and $C_{2-6}$ alkynyl substituted with 0-1 $R^b$;

$R^5$ is selected from H, $C_{1-6}$ alkyl substituted with 0-1 $R^b$, $C_{2-6}$ alkenyl substituted with 0-1 $R^b$, and $C_{2-6}$ alkynyl substituted with 0-1 $R^b$;

n is 0 or 1;

alternatively, when n is 1, $R^4$ and $R^5$, together with the carbon atom to which they are attached, combine to form a 3-8 membered carbocyclic or heterocyclic ring consisting of carbon atoms, 0-2 ring heteroatoms selected from O, N, $NR^{10}$, and $S(O)_p$, and 0-2 double bonds, and substituted with 0-3 $R^9$;

$R^a$, at each occurrence, is independently selected from H, $C_{1-6}$ alkyl, phenyl, and benzyl;

$R^{a1}$, at each occurrence, is independently selected from H, $C_{1-6}$ alkyl substituted with 0-1 $R^{c1}$, $C_{2-6}$ alkenyl substituted with 0-1 $R^{c1}$, $C_{2-6}$ alkynyl substituted with 0-1 $R^{c1}$, and —$(CH_2)_r$-3-8 membered carbocyclic or heterocyclic ring consisting of carbon atoms and 0-2 ring heteroatoms selected from N, $NR^{a2}$, O, and $S(O)_p$ and substituted with 0-3 $R^{c1}$;

alternatively, $R^a$ and $R^{a1}$ when attached to a nitrogen, together with the nitrogen to which they are attached, combine to form a 5 or 6 membered heterocycle consisting of carbon atoms and 0-1 additional heteroatoms selected from N, $NR^{a2}$, O, and $S(O)_p$;

$R^{a2}$, at each occurrence, is independently selected from $C_{1-4}$ alkyl, phenyl, and benzyl;

$R^{a3}$, at each occurrence, is independently selected from H, $C_{1-6}$ alkyl substituted with 0-1 $R^{c1}$, $C_{2-6}$ alkenyl substituted with 0-1 $R^{c1}$, $C_{2-6}$ alkynyl substituted with 0-1 $R^{c1}$, and —$(CH_2)_r$-3-8 membered carbocyclic or heterocyclic ring consisting of carbon atoms and 0-2 ring heteroatoms selected from N, $NR^{a2}$, O, and $S(O)_p$, and substituted with 0-3 $R^{c1}$;

$R^b$, at each occurrence, is independently selected from $C_{1-6}$ alkyl substituted with 0-1 $R^{c1}$, $OR^a$, $SR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $NR^aC(O)NR^aR^{a1}$, $OC(O)NR^aR^{a1}$, $NR^aC(O)OR^a$, $S(O)_2NR^aR^{a1}$, $NR^aS(O)_2R^{a3}$, $NR^aS(O)_2NR^aR^{a1}$, $OS(O)_2NR^aR^{a1}$, $S(O)_pR^{a3}$, $CF_3$, $CF_2CF_3$, $CHF_2$, $CH_2F$, and phenyl;

$R^c$, at each occurrence, is independently selected from H, $OR^a$, Cl, F, Br, I, =O, —CN, $NO_2$, $CF_3$, $CF_2CF_3$, $CH_2F$, $CHF_2$, $(CR^aR^{a1})_rNR^aR^{a1}$, $(CR^aR^{a1})_rC(=NCN)NR^aR^{a1}$, $(CR^aR^{a1})_rC(=NR^a)NR^aR^{a1}$, $(CR^aR^{a1})_rC(=NOR^a)NR^aR^{a1}$, $(CR^aR^{a1})_rC(O)NR^aOH$, $(CR^aR^{a1})_rC(O)R^{a1}$, $(CR^aR^{a1})_rC(O)OR^{a1}$, $(CR^aR^{a1})_rC(S)OR^{a1}$, $(CR^aR^{a1})_rC(O)NR^aR^{a1}$, $(CR^aR^{a1})_rNR^aC(O)R^{a1}$, $(CR^aR^{a1})_rC(S)NR^aR^{a1}$, $(CR^aR^{a1})_rOC(O)NR^aR^{a1}$, $(CR^aR^{a1})_rNR^aC(O)OR^{a1}$, $(CR^aR^{a1})_rNR^aC(O)NR^aR^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, $(CR^aR^{a1})_rNR^aSO_2NR^aR^{a1}$;
$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$-$C_{3-10}$ carbocycle substituted with 0-2 $R^{c1}$; and $(CR^aR^{a1})_r$-5-14 membered heterocycle consisting of carbon atoms and 1-4 heteroatoms selected from the group consisting of N, O, and $S(O)_p$ and substituted with 0-2 $R^{c1}$;

alternatively, when two $R^c$ groups are attached to the same carbon atom, they form a 3-8 membered carbocyclic or heterocyclic spiro ring C substituted with
  0-2 $R^{c1}$ and consisting of carbon atoms, 0-4 ring heteroatoms selected from O, N, and $S(O)_p$, and 0-2 double bonds, provided that ring C contains other than a S—S, O—O, or S—O bond;

alternatively, when two $R^c$ groups are attached to adjacent carbon atoms, together with the carbon atoms to which they are attached they form a 5-7 membered carbocyclic or heterocyclic ring D substituted with 0-2 $R^{c1}$ and consisting of carbon atoms, 0-2 heteroatoms selected from the group consisting of N, O, and $S(O)_p$, and 0-3 double bonds;

$R^{c1}$, at each occurrence, is independently selected from H, $C_{1-4}$ alkyl, $OR^a$, Cl, F, Br, I, =O, $CF_3$, —CN, $NO_2$, $C(O)R^a$, $C(O)OR^a$, $C(O)NR^aR^a$, and $S(O)_pR^a$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a3}$, $NR^aS(O)_2NR^aR^{a1}$, $OS(O)_2NR^aR^{a1}$, $S(O)_pR^{a3}$, $CF_3$, $CF_2CF_3$, $C_{3-10}$ carbocycle, and a 5-14 membered heterocycle consisting of carbon atoms and 1-4 heteroatoms selected from the group consisting of N, O, and $S(O)_p$;

$R^e$, at each occurrence, is independently selected from H, $C_{1-6}$ alkyl, $C_{1-6}$ alkoxy, phenoxy, benzoxy, $C_{3-10}$ carbocycle substituted with 0-2 $R^{c1}$, and a 5-10 membered heterocycle consisting of carbon atoms and 1-4 heteroatoms selected from the group consisting of N, O, and S(O)$_p$, and substituted with 0-2 R$^{c1}$;

R$^6$ is selected from H, C$_{1-4}$ alkyl, C$_{2-4}$ alkenyl, and C$_{2-4}$ alkynyl;

R$^7$ is selected from H, C$_{1-4}$ alkyl, C$_{2-4}$ alkenyl, and C$_{2-4}$ alkynyl;

R$^9$, at each occurrence, is independently selected from H, (CR$^a$R$^{a1}$)$_r$NR$^a$R$^{a1}$, (CR$^a$R$^{a1}$)$_r$C(O)NR$^a$OH, (CR$^a$R$^{a1}$)$_r$C(O)(CR$^a$R$^{a1}$)$_s$R$^e$, (CR$^a$R$^{a1}$)$_r$C(O)OR$^{a1}$, (CR$^a$R$^{a1}$)$_r$C(S)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$C(S)NR$^a$R$^{a1}$, (CR$^a$R$^{a1}$)$_r$OC(O)NR$^a$R$^{a1}$, (CR$^a$R$^{a1}$)$_r$NR$^a$C(O)OR$^{a1}$, (CR$^a$R$^{a1}$)$_r$NR$^a$C(O)NR$^a$R$^{a1}$, (CR$^a$R$^{a1}$)$_s$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$, (CR$^a$R$^{a1}$)$_r$NR$^a$SO$_2$NR$^a$R$^{a1}$;

C$_{1-6}$ alkyl substituted with 0-2 R$^{c1}$;
C$_{2-6}$ alkenyl substituted with 0-2 R$^{c1}$;
C$_{2-6}$ alkynyl substituted with 0-2 R$^{c1}$;
(CR$^a$R$^{a1}$)$_r$—C$_{3-10}$ carbocycle substituted with 0-2 R$^{c1}$;
and (CR$^a$R$^{a1}$)$_r$-5-10 membered heterocycle consisting of carbon atoms and 1-4 heteroatoms selected from the group consisting of N, O, and S(O)$_p$, and substituted with 0-2 R$^{c1}$;

R$^{10}$, at each occurrence, is independently selected from H, (CR$^a$R$^{a1}$)$_r$NR$^a$R$^{a1}$, (CR$^a$R$^{a1}$)$_r$C(O)NR$^a$OH, (CR$^a$R$^{a1}$)$_r$C(O)(CR$^a$R$^{a1}$)$_s$R$^e$, (CR$^a$R$^{a1}$)$_r$C(O)OR$^{a1}$, (CR$^a$R$^{a1}$)$_r$C(S)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$C(S)NR$^a$R$^{a1}$, (CR$^a$R$^{a1}$)$_r$OC(O)NR$^a$R$^{a1}$, (CR$^a$R$^{a1}$)$_r$NR$^a$C(O)OR$^{a1}$, (CR$^a$R$^{a1}$)$_t$NR$^a$C(O)NR$^a$R$^{a1}$, (CR$^a$R$^{a1}$)$_s$S(O)$_p$R$^{a3}$, (CR$^a$R$^{a1}$)$_r$SO$_2$NR$^a$R$^{a1}$, (CR$^a$R$^{a1}$)$_t$NR$^a$SO$_2$R$^{a3}$, (CR$^a$R$^{a1}$)$_r$NR$^a$SO$_2$NR$^a$R$^{a1}$;

C$_{1-6}$ alkyl substituted with 0-2 R$^{c1}$;
C$_{2-6}$ alkenyl substituted with 0-2 R$^{c1}$;
C$_{2-6}$ alkynyl substituted with 0-2 R$^{c1}$;
(CR$^a$R$^{a1}$)$_r$—C$_{3-10}$ carbocycle substituted with 0-2 R$^{c1}$;
and (CR$^a$R$^{a1}$)$_r$-5-10 membered heterocycle consisting of carbon atoms and 1-4 heteroatoms selected from the group consisting of N, O, and S(O)$_p$, and substituted with 0-2 R$^{c1}$;

m, at each occurrence, is selected from 0, 1, 2 and 3;
p, at each occurrence, is selected from 0, 1, and 2;
r, at each occurrence, is selected from 0, 1, 2, 3, and 4;
s, at each occurrence, is selected from 0, 1, 2, 3, and 4; and,
t, at each occurrence, is selected from 1, 2, 3, and 4.

[2] In another embodiment, the present invention provides a novel compound of formula (I), wherein;

W is (CR$^a$R$^{a1}$)$_m$;

U is absent or is selected from O, NR$^{a1}$, C(O), CR$^a$(OH), C(O)O, OC(O), C(O)NR$^{a1}$, NR$^{a1}$C(O), S(O)$_p$, S(O)$_p$NR$^{a1}$, and NR$^{a1}$S(O)$_p$;

X is absent or is C$_{1-3}$ alkylene;

Y is absent or is selected from O, NR$^{a1}$, S(O)$_p$, and C(O);

U$^a$ is absent or is selected from O, NR$^{a1}$, C(O), CR$^a$(OH), C(O)O, C(O)NR$^{a1}$, NR$^{a1}$C(O), S(O)$_p$, S(O)$_p$NR$^{a1}$, and NR$^{a1}$S(O)$_p$;

X$^a$ is absent or is selected from C$_{1-4}$ alkylene, C$_{2-4}$ alkenylene, and C$_{2-4}$ alkynylene;

Y$^a$ is absent or is selected from O and NR$^{a1}$;

R$^1$ and R$^2$, together with the carbon atoms to which they are attached, combine to form a 3-8 membered carbocyclic or heterocyclic ring consisting of carbon atoms, 0-2 ring heteroatoms selected from O, N, NR$^{10}$, and S(O)$_p$, 0-2 carbonyl groups, and 0-2 double bonds, and substituted with 0-3 R$^9$;

R$^3$ is selected from Q, C$_{1-6}$ alkylene-Q, C$_{2-6}$ alkenylene-Q, C$_{2-6}$ alkynylene-Q, (CR$^a$R$^{a1}$)$_r$O(CR$^a$R$^{a1}$)$_s$-Q, (CR$^a$R$^{a1}$)$_r$NR$^a$(CR$^a$R$^{a1}$)$_s$-Q, (CR$^a$R$^{a1}$)$_r$C(O)(CR$^a$R$^{a1}$)$_s$-Q, (CR$^a$R$^{a1}$)$_r$C(O)O(CR$^a$R$^{a1}$)$_s$-Q, (CR$^a$R$^{a1}$)$_r$C(O)NR$^a$R$^{a1}$, (CR$^a$R$^{a1}$)$_r$C(O)NR$^a$(CR$^a$R$^{a1}$)$_s$-Q, (CR$^a$R$^{a1}$)$_r$NR$^a$C(O)(CR$^a$R$^{a1}$)$_s$-Q, (CR$^a$R$^{a1}$)$_r$S(O)$_p$(CR$^a$R$^{a1}$)$_s$-Q, (CR$^a$R$^{a1}$)$_r$SO$_2$NR$^a$(CR$^a$R$^{a1}$)$_s$-Q, and (CR$^a$R$^{a1}$)$_r$NR$^a$SO$_2$(CR$^a$R$^{a1}$)$_s$-Q;

Q, at each occurrence, is selected from H, CHF$_2$, CH$_2$F, CF$_3$, a C$_{3-13}$ carbocycle substituted with 0-3 R$^d$, and a 5-14 membered heterocycle consisting of carbon atoms and 1-4 heteroatoms selected from the group consisting of N, O, and S(O)$_p$, and substituted with 0-3 R$^d$;

R$^4$ is selected from H, C$_{1-6}$ alkyl substituted with 0-1 R$^b$, C$_{2-6}$ alkenyl substituted with 0-1 R$^b$, and C$_{2-6}$ alkynyl substituted with 0-1 R$^b$;

R$^5$ is selected from H, C$_{1-6}$ alkyl substituted with 0-1 R$^b$, C$_{2-6}$ alkenyl substituted with 0-1 R$^b$, and C$_{2-6}$ alkynyl substituted with 0-1 R$^b$;

R$^a$, at each occurrence, is independently selected from H, C$_{1-6}$ alkyl, phenyl, and benzyl;

R$^{a1}$, at each occurrence, is independently selected from H, C$_{1-6}$ alkyl, C$_{2-6}$ alkenyl, C$_{2-6}$ alkynyl, and —(CH$_2$)$_r$-3-8 membered carbocyclic or heterocyclic ring consisting of carbon atoms and 0-2 ring heteroatoms selected from N, NR$^{a2}$, O, and S(O)$_p$;

alternatively, R$^a$ and R$^{a1}$ when attached to a nitrogen, together with the nitrogen to which they are attached, combine to form a 5 or 6 membered heterocycle consisting of carbon atoms and from 0-1 additional heteroatoms selected from N, NR$^{a2}$, O, and S(O)$_p$;

R$^c$, at each occurrence, is independently selected from H, OR$^a$, Cl, F, Br, =O, —CN, NO$_2$, CF$_3$, CH$_2$F, CHF$_2$, CF$_2$CF$_3$, (CR$^a$R$^{a1}$)$_r$NR$^a$R$^{a1}$, (CR$^a$R$^{a1}$)$_r$C(O)R$^{a1}$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_s$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$;

C$_{1-6}$ alkyl substituted with 0-1 R$^{c1}$;
C$_{2-6}$ alkenyl substituted with 0-1 R$^{c1}$;
C$_{2-6}$ alkynyl substituted with 0-1 R$^{c1}$;
(CH$_2$)$_r$-C$_{3-6}$ carbocycle substituted with 0-2 R$^{c1}$; and
(CH$_2$)$_r$-5-6 membered heterocycle consisting of carbon atoms and 1-4 heteroatoms selected from the group consisting of N, O, and S(O)$_p$, and substituted with 0-2 R$^{c1}$;

alternatively, when two R$_c$ groups are attached to the same carbon atom, they form a 3-8 membered carbocyclic or heterocyclic spiro ring C substituted with 0-2 R$^{c1}$ and consisting of carbon atoms, 0-4 ring heteroatoms selected from O, N, and S(O)$_p$, and 0-2 double bonds, provided that ring C contains other than a S—S, O—O, or S—O bond;

alternatively, when two R$^c$ groups are attached to adjacent carbon atoms, together with the carbon atoms to which they are attached they form a 5-7 membered carbocyclic or heterocyclic ring D substituted with 0-2 R$^{c1}$ and consisting of carbon atoms, 0-2 heteroatoms selected from the group consisting of N, O, and S(O)$_p$, and 0-3 double bonds;

R$^d$, at each occurrence, is independently selected from C$_{1-6}$ alkyl, OR$^a$, Cl, F, Br, =O, —CN, NO$_2$, NR$^a$R$^{a1}$, C(O)R$^a$, C(O)OR$^a$, C(O)NR$^a$R$^{a1}$, S(O)$_2$NR$^a$R$^{a1}$, NR$^a$S(O)$_2$R$^{a3}$, S(O)$_p$R$^{a3}$, CF$_3$, C$_{3-6}$ carbocycle and a 5-6 membered heterocycle consisting of carbon atoms and 1-4 heteroatoms selected from the group consisting of N, O, and S(O)$_p$;

R$^6$ is selected from H and C$_{1-4}$ alkyl;
R$^7$ is selected from H and C$_{1-4}$ alkyl;
R$^9$, at each occurrence, is independently selected from H, (CR$^a$R$^{a1}$)$_r$NR$^a$R$^{a1}$, (CR$^a$R$^{a1}$)$_r$C(O)NR$^a$OH, (CR$^a$R$^{a1}$)$_r$ C(O)(CR$^a$R$^{a1}$)$_s$R$^e$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$OC(O)NR$^a$R$^{a1}$, (CR$^a$R$^{a1}$)$_t$NR$^a$C(O)OR$^{a1}$, (CR$^a$R$^{a1}$)$_r$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$;

C$_{1-6}$ alkyl substituted with 0-2 R$^{c1}$;
C$_{2-6}$ alkenyl substituted with 0-2 R$^{c1}$;
C$_{2-6}$ alkynyl substituted with 0-2 R$^{c1}$;
(CR$^a$R$^{a1}$)$_r$-C$_{3-10}$ carbocycle substituted with 0-2 R$^{c1}$;
and (CR$^a$R$^{a1}$)$_r$-5-10 membered heterocycle consisting of carbon atoms and 1-4 heteroatoms selected from the group consisting of N, O, and S(O)$_p$, and substituted with 0-2 R$^{c1}$; and, R$^{10}$, at each occurrence, is independently selected from H, (CR$^a$R$^{a1}$)$_t$NR$^a$R$^{a1}$, (CR$^a$R$^{a1}$)$_r$C(O)NR$^a$OH, (CR$^a$R$^{a1}$)$_r$C(O)(CR$^a$R$^{a1}$)$_s$R$^e$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$OC(O)NR$^a$R$^{a1}$, (CR$^a$R$^{a1}$)$_t$NR$^a$C(O)OR$^{a1}$, (CR$^a$R$^{a1}$)$_r$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$;

C$_{1-6}$ alkyl substituted with 0-2 R$^{c1}$;
C$_{2-6}$ alkenyl substituted with 0-2 R$^{c1}$;
C$_{2-6}$ alkynyl substituted with 0-2 R$^{c1}$;
(CR$^a$R$^{a1}$)$_r$-C$_{3-10}$ carbocycle substituted with 0-2 R$^{c1}$;
and (CR$^a$R$^{a1}$)$_r$-5-10 membered heterocycle consisting of carbon atoms and 1-4 heteroatoms selected from the group consisting of N, O, and S(O)$_p$, and substituted with 0-2 R$^{c1}$.

[3] In another embodiment, the present invention provides a novel compound of formula (I), wherein;
U is absent or is selected from O, NR$^{a1}$, C(O), C(O)NR$^{a1}$, NR$^{a1}$C(O), S(O)$_p$, S(O)$_p$NR$^{a1}$, and NR$^{a1}$S(O)$_p$;
X is absent or is methylene or ethylene;
Z is selected from:
 a C$_{3-8}$ cycloalkyl substituted with 0-5 R$^b$;
 a C$_{3-8}$ cycloalkenyl substituted with 0-5 R$^b$;
 phenyl substituted with 0-4 R$^b$;
 naphthyl substituted with 0-5 R$^b$; and
 a 5-14 membered heterocycle consisting of carbon atoms and 1-4 heteroatoms selected from the group consisting of N, O, and S(O)$_p$ and substituted with 0-5 R$^b$;

U$^a$ is absent or is selected from O, NR$^{a1}$, C(O), C(O)NR$^{a1}$, NR$^{a1}$C(O), S(O)$_p$, S(O)$_p$NR$^{a1}$, and NR$^{a1}$S(O)$_p$;
R$^3$ is selected from Q, C$_{1-6}$ alkylene-Q, C$_{2-6}$ alkenylene-Q, C$_{2-6}$ alkynylene-Q, (CH$_2$)$_r$O(CH$_2$)$_s$-Q, (CH$_2$)$_r$NR$^a$(CH$_2$)$_s$-Q, (CH$_2$)$_r$C(O)(CH$_2$)$_s$-Q, (CH$_2$)$_r$C(O)O(CH$_2$)$_s$-Q, (CH$_2$)$_r$C(O)NR$^a$R$^{a1}$, (CH$_2$)$_r$C(O)NR$^a$(CH$_2$)$_s$-Q, (CH$_2$)$_r$NR$^a$C(O)(CH$_2$)$_s$-Q, (CH$_2$)$_r$S(O)$_p$(CH$_2$)$_s$-Q, (CH$_2$)$_r$SO$_2$NR$^a$(CH$_2$)$_s$-Q, and (CH$_2$)$_r$NR$^a$SO$_2$(CH$_2$)$_s$-Q;

Q, at each occurrence, is selected from H, a C$_{3-8}$ carbocycle substituted with 0-3 R$^d$, and a 5-10 membered heterocycle consisting of carbon atoms and 1-4 heteroatoms selected from the group consisting of N, O, and S(O)$_p$, and substituted with 0-3 R$^d$;
R$^4$ is selected from H and C$_{1-6}$ alkyl;
R$^5$ is selected from H and C$_{1-6}$ alkyl;
R$^{a3}$, at each occurrence, is independently selected from H, C$_{1-6}$ alkyl, C$_{2-6}$ alkenyl, and —(CH$_2$)$_r$-3-8 membered carbocyclic or heterocyclic ring consisting of carbon atoms and 0-2 ring heteroatoms selected from N, NR$^{a2}$, O, and S(O)$_p$ and substituted with 0-3 R$^{c1}$;
R$^c$, at each occurrence, is independently selected from H, OR$^a$, Cl, F, Br, =O, CF$_3$, CH$_2$F, CHF$_2$, (CR$^a$R$^{a1}$)$_r$NR$^a$R$^{a1}$, (CR$^a$R$^{a1}$)$_r$C(O)R$^{a1}$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_s$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$, C$_{1-6}$ alkyl, C$_{2-6}$ alkenyl, C$_{2-6}$ alkynyl;

C$_{3-6}$ cycloalkyl substituted with 0-1 R$^{c1}$;
phenyl substituted with 0-2 R$^{c1}$; and
5-6 membered heterocycle consisting of carbon atoms and 1-4 heteroatoms selected from the group consisting of N, O, and S(O)$_p$, and substituted with 0-2 R$^{c1}$;
alternatively, when two R$^c$ groups are attached to adjacent carbon atoms, together with the carbon atoms to which they are attached they form a 5-7 membered carbocyclic or heterocyclic ring D substituted with 0-2 R$^{c1}$ and consisting of carbon atoms, 0-2 heteroatoms selected from the group consisting of N, O, and S(O)$_p$, and 0-3 double bonds;

R$^d$, at each occurrence, is independently selected from C$_{1-6}$ alkyl, OR$^a$, Cl, F, Br, =O, NR$^a$R$^{a1}$, C(O)R$^a$, C(O)OR$^a$, C(O)NR$^a$R$^{a1}$, S(O)$_2$NR$^a$R$^{a1}$, NR$^a$S(O)$_2$R$^{a3}$, S(O)$_p$R$^{a3}$, CF$_3$ and phenyl;

R$^6$ is H;
R$^7$ is H;
R$^9$, at each occurrence, is independently selected from H, (CR$^a$R$^{a1}$)$_r$NR$^a$R$^{a1}$, (CR$^a$R$^{a1}$)$_r$C(O)(CR$^a$R$^{a1}$)$_s$R$^e$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$S(O)$_p$R$^{a3}$, (CR$^a$R$^{a1}$)$_r$ SO$_2$NR$^a$R$^{a1}$, (CR$^a$R$^{a1}$)$_r$NR$^a$SO$_2$R$^{a3}$;

C$_{1-6}$ alkyl substituted with 0-2 R$^{c1}$;
C$_{2-6}$ alkenyl substituted with 0-2 R$^{c1}$;
C$_{2-6}$ alkynyl substituted with 0-2 R$^{c1}$;
(CR$^a$R$^{a1}$)$_r$—C$_{3-10}$ carbocycle substituted with 0-2 R$^{c1}$;
and (CR$^a$R$^{a1}$)$_r$-5-10 membered heterocycle consisting of carbon atoms and 1-4 heteroatoms selected from the group consisting of N, O, and S(O)$_p$, and substituted with 0-2 R$^{c1}$;

R$^{10}$, at each occurrence, is independently selected from H, (CR$^a$R$^{a1}$)$_t$NR$^a$R$^{a1}$, (CR$^a$R$^{a1}$)$_r$C(O)(CR$^a$R$^{a1}$)$_s$R$^e$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$S(O)$_p$R$^{a3}$, (CR$^a$R$^{a1}$)$_r$ SO$_2$NR$^a$R$^{a1}$, (CR$^a$R$^{a1}$)$_r$NR$^a$SO$_2$R$^{a3}$;

C$_{1-6}$ alkyl substituted with 0-2 R$^{c1}$;
C$_{2-6}$ alkenyl substituted with 0-2 R$^{c1}$;
C$_{2-6}$ alkynyl substituted with 0-2 R$^{c1}$;
(CR$^a$R$^{a1}$)$_r$—C$_{3-10}$ carbocycle substituted with 0-2 R$^{c1}$;
and (CR$^a$R$^{a1}$)$_r$-5-10 membered heterocycle consisting of carbon atoms and 1-4 heteroatoms selected from the group consisting of N, O, and S(O)$_p$, and substituted with 0-2 R$^{c1}$;

r, at each occurrence, is selected from 0, 1, 2, and 3;
s, at each occurrence, is selected from 0, 1, 2, and 3; and,
t, at each occurrence, is selected from 1, 2, and 3.

[4] In another embodiment, the present invention provides a novel compound of formula (I), wherein;
Z is selected from:
 a C$_{4-8}$ cycloalkyl substituted with 0-3 R$^b$;
 a C$_{4-8}$ cycloalkenyl substituted with 0-3 R$^b$;
 phenyl substituted with 0-4 R$^b$;
 naphthyl substituted with 0-5 R$^b$; and
 a heterocycle substituted with 0-3 R$^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl;

$Z^a$ is selected from:
  phenyl substituted with 0-3 $R^c$;
  naphthyl substituted with 0-3 $R^c$; and
  a heterocycle substituted with 0-3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

$R^1$ and $R^2$, together with the carbon atoms to which they are attached, combine to form a 4-7 membered carbocyclic or heterocyclic ring consisting of carbon atoms, 0-2 ring heteroatoms selected from O, N, $NR^{10}$, and $S(O)_p$, 0-2 carbonyl groups, and 0-2 double bonds, and substituted with 0-3 $R^9$;

Q, at each occurrence, is selected from H,
  a $C_{3-6}$ cycloalkyl substituted with 0-2 $R^d$;
  phenyl substituted with 0-3 $R^d$; and
  a 5-6 membered heterocycle consisting of carbon atoms and 1-4 heteroatoms selected from the group consisting of N, O, and $S(O)_p$, and substituted with 0-3 $R^d$;

$R^a$, at each occurrence, is independently selected from H, $C_{1-6}$ alkyl, phenyl, and benzyl;

$R^{a1}$, at each occurrence, is independently selected from H, $C_{1-6}$ alkyl, phenyl, and benzyl;

$R^{a3}$, at each occurrence, is independently selected from H, $C_{1-6}$ alkyl, phenyl, and benzyl;

$R^c$, at each occurrence, is independently selected from H, $OR^a$, Cl, F, Br, =O, $CF_3$, $CH_2F$, $CHF_2$, $(CR^aR^{a1})_rNR^aR^{a1}$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, $C_{1-6}$ alkyl, $C_{2-6}$ alkenyl, $C_{2-6}$ alkynyl;
  phenyl substituted with 0-2 $R^{c1}$; and
  5-6 membered heterocycle consisting of carbon atoms and 1-4 heteroatoms selected from the group consisting of N, O, and $S(O)_p$, and substituted with 0-2 $R^{c1}$;

alternatively, when two $R^c$ groups are attached to adjacent carbon atoms, together with the carbon atoms to which they are attached they form a 5-6 membered carbocyclic or heterocyclic ring D substituted with 0-2 $R^{c1}$ and consisting of carbon atoms, 0-2 heteroatoms selected from the group consisting of N, O, and $S(O)_p$, and 0-3 double bonds; and, $R^9$, at each occurrence, is independently selected from H, $(CR^aR^{a1})_rNR^aR^{a1}$, $(CR^aR^{a1})_rC(O)(CR^aR^{a1})_sR^e$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_{NR}{}^aSO_2R^{a3}$, $C_{1-6}$ alkyl $C_{2-6}$ alkenyl, $C_{2-6}$ alkynyl;
$(CR^aR^{a1})_r$—$C_{3-7}$ carbocycle substituted with 0-2 $R^{c1}$; and $(CR^aR^{a1})_r$-5-6 membered heterocycle consisting of carbon atoms and 1-4 heteroatoms selected from the group consisting of N, O, and $S(O)_p$, and substituted with 0-2 $R^{c1}$.

[5] In another embodiment, the present invention provides a novel compound of formula (I), wherein;
X is absent or is methylene;
Y is absent or is O;
Z is selected from:
  phenyl substituted with 0-4 $R^b$;
  thienyl substituted with 0-2 $R^b$;
  thiazolyl substituted with 0-1 $R^b$;
  oxazolyl substituted with 0-1 $R^b$;
  isoxazolyl substituted with 0-1 $R^b$; and
  imidazolyl substituted with 0-1 $R^b$;

$U^a$ is absent or is O;
$X^a$ is absent or is selected from $C_{1-4}$ alkylene, $C_{2-4}$ alkenylene, and $C_{2-4}$ alkynylene;
$Y^a$ is absent or is O;
$Z^a$ is selected from:
  phenyl substituted with 0-3 $R^c$;
  naphthyl substituted with 0-3 $R^c$; and
  a heterocycle substituted with 0-3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, pyranyl, pyrazinyl, pyrazolyl, pyridoimidazolyl, pyrrolidinyl, pyrrolyl, quinolinyl, tetrahydroquinolinyl, isoquinolinyl, tetrahydro-isoquinolinyl, imidazolyl, benzimidazolyl, benzothiazinyl, benzofuranyl, benzothiophenyl, benzoxazolyl, benzthiazolyl, benztriazolyl, benzisoxazolyl, benzisothiazolyl, indolyl, indolinyl, indazolyl, isobenzofuranyl, isoindazolyl, isoindolinyl, isoindolyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

$R^1$ and $R^2$, together with the carbon atoms to which they are attached, combine to form a 5-6 membered carbocyclic or heterocyclic ring consisting of carbon atoms, 0-2 ring heteroatoms selected from O, N, $NR^{10}$, and $S(O)_p$, 0-2 carbonyl groups, and 0-2 double bonds, and substituted with 0-3 $R^9$;

$R^3$ is selected from H, $C_{1-4}$ alkyl, $C_{2-4}$ alkenyl, $C_{2-4}$ alkynyl, phenyl, and benzyl;

$R^a$, at each occurrence, is independently selected from H, and $C_{1-4}$ alkyl;

$R^{a1}$, at each occurrence, is independently selected from H, and $C_{1-4}$ alkyl;

$R^{a3}$, at each occurrence, is independently selected from H, $C_{1-4}$ alkyl, phenyl, and benzyl;

$R^c$, at each occurrence, is independently selected from $C_{1-6}$ alkyl, $C_{2-6}$ alkenyl, $C_{2-6}$ alkynyl, $OR^a$, Cl, F, Br, =O, $CF_3$, $CH_2F$, $CHF_2$, $NR^aR^{a1}$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_r SO_2NR^aR^{a1}$, $(CR^aR^{a1})_rNR^aSO_2R^{a3}$, and phenyl;

alternatively, when two $R^c$ groups are attached to adjacent carbon atoms, together with the carbon atoms to which they are attached they form a 5-6 membered carbocyclic or heterocyclic ring D substituted with 0-2 $R^{c1}$ and consisting of carbon atoms, 0-2 heteroatoms selected from the group consisting of N, O, and $S(O)_p$, and 0-3 double bonds;

$R^e$, at each occurrence, is independently selected from H, $C_{1-6}$ alkyl, $C_{1-6}$ alkoxy, phenoxy, benzoxy, $C_{3-6}$ carbocycle substituted with 0-2 $R^{c1}$, and a 5-6 membered heterocycle consisting of carbon atoms and 1-4 heteroatoms selected from the group consisting of N, O, and $S(O)_p$, and substituted with 0-2 $R^{c1}$;

$R^9$, at each occurrence, is independently selected from H, $(CH_2)_rC(O)(CH_2)_sR^e$, $(CH_2)_rC(O)OR^{a1}$, $(CR^aR^{a1})_rC(O)NR^aR^{a1}$, $(CH_2)_rS(O)_pR^{a3}$, $(CH_2)_rSO_2NR^aR^{a1}$;
$C_{1-4}$ alkyl substituted with 0-1 $R^{c1}$;
$C_{2-4}$ alkenyl substituted with 0-1 $R^{c1}$;
$C_{2-4}$ alkynyl substituted with 0-1 $R^{c1}$;
$(CH_2)_r$—$C_{3-6}$ carbocycle substituted with 0-2 $R^{c1}$; and
$(CH_2)_r$-5-6 membered heterocycle consisting of carbon atoms and 1-4 heteroatoms selected from the group consisting of N, O, and $S(O)_p$ and substituted with 0-2 $R^{c1}$; and, $R^{10}$, at each occurrence, is independently selected from H, $(CH_2)_rNR^aR^{a1}$, $(CH_2)_rC(O)(CH_2)_sR^e$, $(CH_2)_rC(O)OR^{a1}$, $(CH_2)_rC(O)NR^aR^{a1}$, $(CH_2)_rNR^aC(O)R^{a1}$, $(CH_2)_r$ $S(O)_pR^{a3}$, $(CH_2)_rSO_2NR^aR^{a1}$, $(CH_2)_t NR^aSO_2R^{a3}$;
$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CH_2)_r$—$C_{3-10}$ carbocycle substituted with 0-2 $R^{c1}$; and
$(CH_2)_r$-5-10 membered heterocycle consisting of carbon atoms and 1-4 heteroatoms selected from the group consisting of N, O, and $S(O)_p$ and substituted with 0-2 $R^{c1}$.

[6] In another embodiment, the present invention provides a novel compound, wherein the compound is selected from:

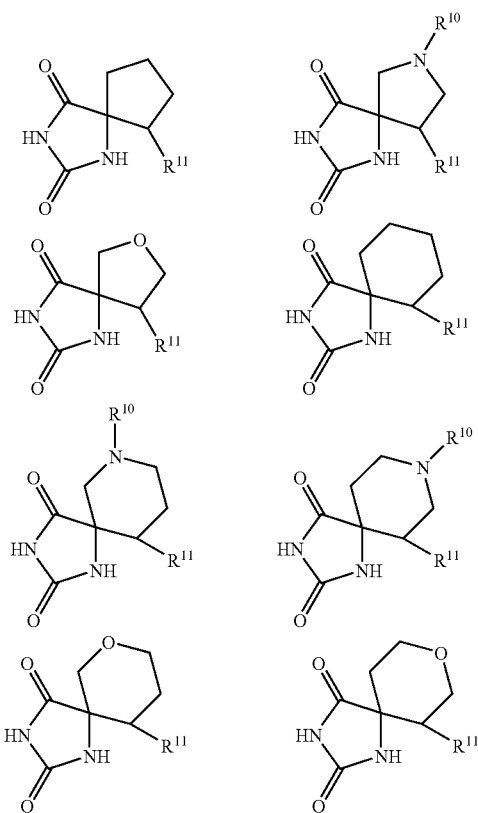

$R^{11}$ is -W-U-X-Y-Z-$U^a$-$X^a$-$Y^a$-$Z^a$;

W is $(CH_2)_m$;
Y is absent;
$R^{10}$, at each occurrence, is independently selected from H, $(CH_2)_rC(O)(CH_2)_sR^e$, $(CH_2)_rC(O)OR^{a1}$, $(CR^aR^{a1})_rC(O)NR^aR^{a1}$, $(CH_2)_rS(O)_pR^{a3}$, $(CH_2)_rSO_2NR^aR^{a1}$;
$C_{1-4}$ alkyl substituted with 0-1 $R^{c1}$;
$C_{2-4}$ alkenyl substituted with 0-1 $R^{c1}$;
$C_{2-4}$ alkynyl substituted with 0-1 $R^{c1}$;
$(CH_2)_r$—$C_{3-6}$ cycloalkyl substituted with 0-2 $R^{c1}$;
$(CH_2)_r$-phenyl substituted with 0-2 $R^{c1}$; and
$(CH_2)_r$-5-6 membered heterocycle consisting of carbon atoms and 1-4 heteroatoms selected from the group consisting of N, O, and $S(O)_p$, and substituted with 0-2 $R^{c1}$;
m, at each occurrence, is selected from 0, 1, and 2;
r, at each occurrence, is selected from 0, 1, and 2; and,
s, at each occurrence, is selected from 0, 1, and 2.

[7] In another embodiment, the present invention provides a novel compound, wherein;
Z is phenyl substituted with 0-1 $R^b$;
$Z^a$ is selected from:
phenyl substituted with 0-3 $R^c$;
naphthyl substituted with 0-3 $R^c$; and
a heterocycle substituted with 0-3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

$R^b$, at each occurrence, is independently selected from $C_{1-6}$ alkyl, $OR^a$, Cl, F, Br, $NR^aR^{a1}$, $C(O)R^a$, $C(O)OR^a$, $C(O)NR^aR^{a1}$, $S(O)_2NR^aR^{a1}$, $NR^aS(O)_2R^{a3}$, $S(O)_pR^{a3}$, and $CF_3$;

$R^c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, and $(CR^aR^{a1})_rNR^aSO_2R^{a3}$;
alternatively, when two $R^c$ groups are attached to adjacent carbon atoms, together with the carbon atoms to which they are attached they form a 5-6 membered carbocyclic or heterocyclic ring consisting of: carbon atoms and 0-1 heteroatoms selected from the group consisting of N, O, and $S(O)_p$; and,
$R^e$, at each occurrence, is independently selected from H, $C_{1-6}$ alkyl, $C_{1-6}$ alkoxy, phenoxy, benzoxy, phenyl substituted with 0-1 $R^{c1}$, and a 5-6 membered heterocycle consisting of carbon atoms and 1-4 heteroatoms selected from the group consisting of N, O, and $S(O)_p$, and substituted with 0-1 $R^{c1}$.

[8] In another embodiment, the present invention provides a novel compound selected from the group:
(cis,trans)-N-{4-[(2-methyl-4-quinolinyl)methoxy]phenyl}-2,4-dioxo-1,3-diazaspiro[4.5]decane-6-carboxamide;
(cis,trans)-N-{4-[(2-methyl-4-quinolinyl)methoxy]phenyl}-2,4-dioxo-1,3-diazaspiro[4.4]nonane-6-carboxamide;
(cis,trans)-2-(2,4-dioxo-1,3-diazaspiro[4.4]non-6-yl)-N-{4-[(2-methyl-4-quinolinyl)methoxy]phenyl}acetamide;
(cis,trans)-N-(2,4-dioxo-1,3-diazaspiro[4.4]non-6-yl)-4-[(2-methyl-4-quinolinyl)methoxy]benzamide;
(cis,trans)-N-(2,4-dioxo-1,3-diazaspiro[4.4]non-6-yl)-2-{4-[(2-methyl-4-quinolinyl)methoxy]phenyl}acetamide;

(cis,trans)-N-(2,4-dioxo-1,3-diazaspiro[4.4]non-6-yl)-4-[(2-methyl-4-quinolinyl)methoxy]benzenesulfonamide;
(trans)-N-[(2,4-dioxo-1,3-diazaspiro[4.5]dec-6-yl)methyl]-4-[(2-methyl-4-quinolinyl)methoxy]-benzamide;
(trans)-N-[(2,4-dioxo-1,3-diazaspiro[4.5]dec-6-yl)methyl]-4-[(2-methyl-4-quinolinyl)methoxy]benzenesulfonamide;
(cis)-N-[(2,4-dioxo-1,3-diazaspiro[4.5]dec-6-yl)methyl]-4-[(2-methyl-4-quinolinyl)methoxy]benzamide;
(cis)-N-[(2,4-dioxo-1,3-diazaspiro[4.5]dec-6-yl)methyl]-4-[(2-methyl-4-quinolinyl)methoxy]benzenesulfonamide;
6({4-[(2-methyl-4-quinolinyl)methoxy]phenyl}sulfonyl)-1,3-diazaspiro[4.4]nonane-2,4-dione;
6({4-[(2-methyl-4-quinolinyl)methoxy]phenyl}sulfonyl)-1,3-diazaspiro[4.5]decanane-2,4-dione;
2-(2,4-dioxo-1,3-diazaspiro[4.5]dec-6yl)-N-{4-[(2-methyl-4-quinolinyl)methoxy]phenyl}acetamide;
6-({4-[(2-methyl-4-quinolinyl)methoxy]phenyl}sulfonyl)methyl]-1,3-diazaspiro[4.4]nonane-2,4-dione;
N-(2,4-dioxo-1,3-diazaspiro[4.5]dec-6yl)-4-[(2-methyl-4-quinolinyl)methoxy]benzamide;
4-[(1,1-dioxido-2,3-dihydro-4H-1,4-benzothiazin-4-yl)methyl]-N-(2,4-dioxo-1,3-diazaspiro[4.5]dec-6yl)benzamide;
(cis,trans)-N-(2,4-dioxo-1,3-diazaspiro[4.5]dec-6-yl)-4-[(2-methyl-4-quinolinyl)methoxy]benzenesulfonamide;
(cis,trans)-N-(2,4-dioxo-7-oxa-1,3-diazaspiro[4.4]non-9-yl)-4-[(2-methyl-4-quinolinyl)methoxy]benzamide;
(cis,trans)-N-(2,4-dioxo-8-oxa-1,3-diazaspiro[4.5]dec-6-yl)-4-[(2-methyl-4-quinolinyl)methoxy]benzamide;
4-[(1,1-dioxido-2,3-dihydro-4H-1,4-benzothiazin-4-yl)methyl]-N-(2,4-dioxo-8-oxa-1,3-diazaspiro[4.5]dec-6-yl)benzamide;
(cis,trans)-N-(2,4-dioxo-8-oxa-1,3-diazaspiro[4.5]dec-6-yl)-4-[(2-methyl-4-quinolinyl)methyl]benzamide;
(trans)-N-(2,4-dioxo-7-oxa-1,3-diazaspiro[4.5]dec-10-yl)-4-[(2-methyl-4-quinolinyl)methoxy]benzamide;
(cis,trans)-N-(2,4-dioxo-7-oxa-1,3-diazaspiro[4.5]dec-10-yl)-4-[(2-methyl-4-quinolinyl)methyl]benzamide;
(trans)-N-(2,4-dioxo-7-oxa-1,3-diazaspiro[4.5]dec-10-yl)-4-[(2-methyl-4-quinolinyl)methyl]benzamide
(cis,trans)-N-(2,4-dioxo-7-oxa-1,3-diazaspiro[4.5]dec-10-yl)-4-{[(2-trifluoromethyl-1H-benzimidazol-1-yl])methyl}benzamide;
(cis,trans)-N-(2,4-dioxo-7-oxa-1,3-diazaspiro[4.5]dec-10-yl)-4-[(2-ethylpyrazolo[1,5-a]pyridin-3-yl)-methyl]benzamide;
(cis,trans)-4-(1,3-dihydrofuro[3,4-b]quinolin-9-ylmethyl)-N-(2,4-dioxo-7-oxa-1,3-diazaspiro[4.5]dec-10-yl)benzamide;
(cis,trans)-N-(2,4-dioxo-7-oxa-1,3-diazaspiro[4.5]dec-10-yl)-4-[(2-ethyl-4-quinolinyl)-methyl]benzamide;
(cis,trans)-4-[(3,5-dimethyl-1H-pyrazol-4-yl)methyl]-N-(2,4-dioxo-7-oxa-1,3-diazaspiro[4.5]dec-10-yl)benzamide;
(cis,trans)-N-(2,4-dioxo-7-oxa-1,3-diazaspiro[4.5]dec-10-yl)-4-{[2-(trifluoromethyl)-4-quinolinyl]methyl}benzamide;
(cis,trans)-N-(2,4-dioxo-7-oxa-1,3-diazaspiro[4.5]dec-10-yl)-4-[(2-methyl-1h-indol-3-yl)methyl]benzamide;
(cis,trans)-N-(2,4-dioxo-7-oxa-1,3-diazaspiro[4.5]dec-10-yl)-4-[(1,3,5-trimethyl-1H-pyrazol-4-yl)methyl]benzamide;

(cis,trans)-N-(2,4-dioxo-7-oxa-1,3-diazaspiro[4.5]dec-10-yl)-4-[(2-isopropyl-1H-benzimidazol-1-yl)methyl]benzamide;
(cis,trans)-N-(2,4-dioxo-7-oxa-1,3-diazaspiro[4.5]dec-10-yl)-4-[(2-methyl-1-oxido-4-quinolinyl)methoxy]benzamide;
(cis,trans)-N-(2,4-dioxo-7-oxa-1,3-diazaspiro[4.5]dec-10-yl)-4-[(2,3,5-trimethyl-4-pyridinyl)methyl]benzamide;
(cis,trans)-N-(2,4-dioxo-7-oxa-1,3-diazaspiro[4.5]dec-10-yl)-4-{[(2-(methylthio)-1H-benzimidazol-1-yl]methyl}benzamide;
(cis,trans)-N-(2,4-dioxo-7-oxa-1,3-diazaspiro[4.5]dec-10-yl)-4-[(2-methyl-1H-indol-1-yl)-methyl]benzamide;
(cis,trans)-4-[(1,1-dioxido-2,3-dihydro-4H-1,4-benzothiazin-4-yl)methyl]-N-(2,4-dioxo-7-oxa-1,3-diazaspiro[4.5]dec-10-yl)benzamide;
(cis,trans)-N-(2,4-dioxo-7-oxa-1,3-diazaspiro[4.5]dec-10-yl)-4-[(2-methyl-4-quinolinyl)methoxy]benzenesulfonamide;
(cis,trans)-tert-butyl 9-[2-({4-[2-methyl-4-quinolinyl)methoxy]phenyl}amino)-2-oxoethyl]-2,4-dioxo-1,3,7-triazaspiro[4.4]nonane-7-carboxylate;
(cis,trans)-2-(2,4-dioxo-1,3,7-triazaspiro[4.4]non-9-yl)-N-{4-[(2-methyl-4-quinolinyl)methoxy]phenyl}acetamide;
(cis,trans)-tert-butyl 9-({4-[(2-methyl-4-quinolinyl)methoxy]benzoyl}amino)-2,4-dioxo-1,3,7-triazaspiro[4.4]nonane-7-carboxylate;
(cis,trans)-N-(2,4-dioxo-1,3,7-triazaspiro[4.4]non-9-yl)-4-[(2-methyl-4-quinolinyl)methoxy]benzamide;
(cis,trans)-N-[7-acetyl-(2,4-dioxo-1,3,7-triazaspiro[4.4]non-9-yl]-4-[(2-methyl-4-quinolinyl)methoxy]benzamide;
(cis,trans)-4-[(2-methyl-4-quinolinyl)methoxy]-N-[7-(methylsulfonyl)-2,4-dioxo-1,3,7-triazaspiro[4.4]non-9-yl]-benzamide;
(cis,trans)-tert-butyl-4-{[9-[(2-methyl-4-quinolinyl)methoxy]benzoyl}amino)-2,4-dioxo-1,3,7-triazaspiro[4.4]non-7-yl]carbonyl)-1-piperidinecarboxylate;
(cis,trans)-N-[2,4-dioxo-7-(4-piperidinylcarbonyl)-1,3,7-triazaspiro[4.4]non-9-yl]-4-[(2-methyl-4-quinolinyl)methoxy]benzamide;
(cis,trans)-N-[7-isonicotinoyl-2,4-dioxo-1,3,7-triazaspiro[4.4]non-9-yl]-4-[(2-methyl-4-quinolinyl)methoxy]benzamide;
(cis,trans)-N-[2,4-dioxo-7-(phenoxyacetyl)-1,3,7-triazaspiro[4.4]non-9-yl]-4-[(2-methyl-4-quinolinyl)methoxy]benzamide;
((cis,trans)-N-[7-(3-methylbutanoyl)-2,4-dioxo-1,3,7-triazaspiro[4.4]non-9-yl]-4-[(2-methyl-4-quinolinyl)methoxy]benzamide;
(cis,trans)-N-[2,4-dioxo-7-(3-pyridinylcarbonyl)-1,3,7-triazaspiro[4.4]non-9-yl]-4-[(2-methyl-4-quinolinyl)methoxy]benzamide
(cis,trans)-N-[7-isobutyryl-2,4-dioxo-1,3,7-triazaspiro[4.4]non-9-yl]-4-[(2-methyl-4-quinolinyl)methoxy]benzamide;
(cis,trans)-4-[(2-methyl-4-quinolinyl)methoxy]-N-[7-(4-morpholinylacetyl)-2,4-dioxo-1,3,7-triazaspiro[4.4]non-9-yl]benzamide;
(cis,trans)-N-[2,4-dioxo-7-(3-pyridinylmethyl)-1,3,7-triazaspiro[4.4]non-9-yl]-4-[(2-methyl-4-quinolinyl)methoxy]benzamide;

(cis,trans)-N-[2,4-dioxo-7-(4-pyridinylmethyl)-1,3,7-triazaspiro[4.4]non-9-yl]-4-[(2-methyl-4-quinolinyl)methoxy]benzamide;

(cis,trans)-N-[(7-isopropyl-2,4-dioxo-1,3,7-triazaspiro[4.4]non-9-yl]-4-[(2-methyl-4-quinolinyl)methoxy]benzamide;

(cis,trans)-N-[(7-isobutyl-2,4-dioxo-1,3,7-triazaspiro[4.4]non-9-yl]-4-[(2-methyl-4-quinolinyl)methoxy]benzamide;

(cis,trans)-tert-butyl 9-({4-[2-methyl-4-quinolinyl)methyl]benzoyl}amino)-2,4-dioxo-1,3,7-triazaspiro[4.4]nonane-7-carboxylate;

(cis,trans)-N-(2,4-dioxo-1,3,7-triazaspiro[4.4]non-9-yl)-4-[(2-methyl-4-quinolinyl)methyl]benzamide;

(cis,trans)-tert-butyl-4-{[9-[(2-methyl-4-quinolinyl)methyl]benzoyl}amino)-2,4-dioxo-1,3,7-triazaspiro[4.4]non-7-yl]carbonyl}-1-piperidinecarboxylate;

(cis,trans)-N-[2,4-dioxo-7-(4-piperidinylcarbonyl)-1,3,7-triazaspiro[4.4]non-9-yl]-4-[(2-methyl-4-quinolinyl)methyl]benzamide;

(cis,trans)-N-[7-isonicotinoyl-2,4-dioxo-1,3,7-triazaspiro[4.4]non-9-yl]-4-[(2-methyl-4-quinolinyl)methyl]benzamide;

(cis,trans)-N-[2,4-dioxo-7-(phenoxyacetyl)-1,3,7-triazaspiro[4.4]non-9-yl]-4-[(2-methyl-4-quinolinyl)methyl]benzamide;

((cis,trans)-N-[7-(3-methylbutanoyl)-2,4-dioxo-1,3,7-triazaspiro[4.4]non-9-yl]-4-[(2-methyl-4-quinolinyl)methyl]benzamide;

(cis,trans)-N-[2,4-dioxo-7-(3-pyridinylcarbonyl)-1,3,7-triazaspiro[4.4]non-9-yl]-4-[(2-methyl-4-quinolinyl)methyl]benzamide;

((cis,trans)-N-[7-isobutyryl-2,4-dioxo-1,3,7-triazaspiro[4.4]non-9-yl]-4-[(2-methyl-4-quinolinyl)methyl]benzamide;

(cis,trans)-4-[(2-methyl-4-quinolinyl)methyl]-N-[7-(4-morpholinylacetyl)-2,4-dioxo-1,3,7-triazaspiro[4.4]non-9-yl]benzamide;

(cis,trans)-N-[2,4-dioxo-7-(3-pyridinylmethyl)-1,3,7-triazaspiro[4.4]non-9-yl]-4-[(2-methyl-4-quinolinyl)methyl]benzamide;

(cis,trans)-N-[2,4-dioxo-7-(4-pyridinylmethyl)-1,3,7-triazaspiro[4.4]non-9-yl]-4-[(2-methyl-4-quinolinyl)methyl]benzamide;

(cis,trans)-N-[(7-isopropyl-2,4-dioxo-1,3,7-triazaspiro[4.4]non-9-yl]-4-[(2-methyl-4-quinolinyl)methyl]benzamide;

(cis,trans)-N-[(7-isobutyl-2,4-dioxo-1,3,7-triazaspiro[4.4]non-9-yl]-4-[(2-methyl-4-quinolinyl)methyl]benzamide;

(cis,trans)-tert-butyl 9-({4-[(1,1-dioxido-2,3-dihydro-4H-1,4-benzothiazin-4-yl)methyl]benzoyl})amino)-2,4-dioxo-1,3,7-triazaspiro[4.4]nonane-7-carboxylate;

(cis,trans)-4-[(1,1-dioxido-2,3-dihydro-4H-1,4-benzothiazin-4-yl)methyl]-N-(2,4-dioxo-1,3,7-triazaspiro[4.4]non-9-yl)benzamide;

(cis,trans)-tert-butyl-4-{[9-({4-[(1,1-dioxido-2,3-dihydro-4H-1,4-benzothiazin-4-yl)methyl]benzoyl}amino)-2,4-dioxo-1,3,7-triazaspiro[4.4]non-7-yl]carbonyl}-1-piperidinecarboxylate;

(cis,trans)-4-[(1,1-dioxido-2,3-dihydro-4H-1,4-benzothiazin-4-yl)methyl]-N-[2,4-dioxo-7-(4-piperidinylcarbonyl)-1,3,7-triazaspiro[4.4]non-9-yl]benzamide;

(cis,trans)-4-[(1,1-dioxido-2,3-dihydro-4H-1,4-benzothiazin-4-yl)methyl]-N-[7-isonicotinoyl-2,4-dioxo-1,3,7-triazaspiro[4.4]non-9-yl]benzamide;

(cis,trans)-4-[(1,1-dioxido-2,3-dihydro-4H-1,4-benzothiazin-4-yl)methyl]-N-[2,4-dioxo-7-(phenoxyacetyl)-1,3,7-triazaspiro[4.4]non-9-yl]benzamide;

(cis,trans)-4-[(1,1-dioxido-2,3-dihydro-4H-1,4-benzothiazin-4-yl)methyl]-N-[7-(3-methylbutanoyl)-2,4-dioxo-1,3,7-triazaspiro[4.4]non-9-yl]benzamide;

(cis,trans)-4-[(1,1-dioxido-2,3-dihydro-4H-1,4-benzothiazin-4-yl)methyl]-N-[2,4-dioxo-7-(3-pyridinylcarbonyl)-1,3,7-triazaspiro[4.4]non-9-yl]benzamide;

(cis,trans)-4-[(1,1-dioxido-2,3-dihydro-4H-1,4-benzothiazin-4-yl)methyl]-N-[7-isobutyryl-2,4-dioxo-1,3,7-triazaspiro[4.4]non-9-yl]benzamide;

((cis,trans)-4-[(1,1-dioxido-2,3-dihydro-4H-1,4-benzothiazin-4-yl)methyl]-N-[7-(4-morpholinylacetyl)-2,4-dioxo-1,3,7-triazaspiro[4.4]non-9-yl]benzamide;

(cis,trans)-4-[(1,1-dioxido-2,3-dihydro-4H-1,4-benzothiazin-4-yl)methyl]-N-[2,4-dioxo-7-(3-pyridinylmethyl)-1,3,7-triazaspiro[4.4]non-9-yl]benzamide;

(cis,trans)-4-[(1,1-dioxido-2,3-dihydro-4H-1,4-benzothiazin-4-yl)methyl]-N-[2,4-dioxo-7-(4-pyridinylmethyl)-1,3,7-triazaspiro[4.4]non-9-yl]benzamide;

(cis,trans)-4-[(1,1-dioxido-2,3-dihydro-4H-1,4-benzothiazin-4-yl)methyl]-N-(7-isopropyl-2,4-dioxo-1,3,7-triazaspiro[4.4]non-9-yl)benzamide;

(cis,trans)-4-[(1,1-dioxido-2,3-dihydro-4H-1,4-benzothiazin-4-yl)methyl]-N-(7-isobutyl-2,4-dioxo-1,3,7-triazaspiro[4.4]non-9-yl)benzamide;

(cis,trans)-tert-butyl-9-({4-[(2isopropyl-1H-benzimidazol-1-yl)methyl]benzoyl}amino)-2,4-dioxo-1,3,7-triazaspiro[4.4]nonane-7-carboxylate;

(cis,trans)-N-[2,4-dioxo-1,3,7-triazaspiro[4.4]non-9-yl]-4-[(2-isopropyl-1H-benzimidazol-1-yl)methyl]benzamide;

(cis,trans)-tert-butyl 9-[({4-[(2-methyl-4-quinolinyl)methoxy]phenyl}sulfonyl)amino]-[2,4-dioxo-1,3,7-triazaspiro[4.4]nonane-7-yl]-carboxylate;

(cis,trans)-N-[2,4-dioxo-1,3,7-triazaspiro[4.4]non-9-yl]-4-[(2-methyl-4-quinolinyl)methoxy]benzenesulfonamide;

(cis,trans)-tert-butyl 9-[({4-[(2-methyl-4-quinolinyl)methoxy]benzoyl}amino)methyl]-2,4-dioxo-1,3,7-triazaspiro[4.4]nonane-7-carboxylate;

(cis,trans)-N-[(2,4-dioxo-1,3,7-triazaspiro[4.4]non-9-yl)methyl]-4-[(2-methyl-4-quinolinyl)methoxy]benzamide;

(cis,trans)-tert-butyl 9-[({4-[(2-methyl-4-quinolinyl)methyl]benzoyl}amino)methyl]-2,4-dioxo-1,3,7-triazaspiro[4.4]nonane-7-carboxylate;

(cis,trans)-tert-butyl 9-[((4-[(2-isopropyl-1H-benzimidazol-1-yl)methyl]benzoyl)amino)methyl]-2,4-dioxo-1,3,7-triazaspiro[4.4]nonane-7-carboxylate;

(cis,trans)-tert-butyl 6-({4-[2-methyl-4-quinolinyl)methoxy]benzoyl}amino)-2,4-dioxo-1,3,8-triazaspiro[4.5]decane-8-carboxylate;

(cis,trans)-N-(2,4-dioxo-1,3,8-triazaspiro[4.5]dec-6-yl)-4-[(2-methyl-4-quinolinyl)methoxy]benzamide;

(cis,trans)-N-[8-acetyl-(2,4-dioxo-1,3,8-triazaspiro[4.5]dec-6-yl]-4-[(2-methyl-4-quinolinyl)methoxy]benzamide; and (cis,trans)-tert-butyl 10-[2-({4-[2-methyl-4-quinolinyl)methoxy]phenyl}amino)-2-oxoethyl]-2,4-dioxo-1,3,7-triazaspiro[4.5]decane-7-carboxylate;

or a pharmaceutically acceptable salt form thereof.

[9] In another embodiment, the present invention provides a novel compound of formula (I):

(I)

[Chemical structure showing a hydantoin-like ring with substituents R⁶, R⁷ on nitrogens, R¹, R² , R³, R⁴, R⁵, and R¹¹ with n repeating unit]

or a stereoisomer or pharmaceutically acceptable salt form thereof, wherein;

$R^{11}$ is -W-U-X-Y-Z-$U^a$-$X^a$-$Y^a$-$Z^a$;

W is selected from $(CR^aR^{a1})_m$, $C_{2-3}$ alkenylene, and $C_{2-3}$ alkynylene;

U is selected from O, $NR^{a1}$, C(O), $CR^a(OH)$, C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

X is absent or is selected from $C_{1-3}$ alkylene, $C_{2-3}$ alkenylene, and $C_{2-3}$ alkynylene;

Y is absent or is selected from O, $NR^{a1}$, $S(O)_p$, and C(O);

Z is selected from:
  a $C_{3-13}$ carbocycle substituted with 0-5 $R^b$; and
  a 5-14 membered heterocycle consisting of carbon atoms and 1-4 heteroatoms selected from the group consisting of N, O, and $S(O)_p$ and substituted with 0-5 $R^b$;

$U^a$ is absent or is selected from O, $NR^{a1}$, C(O), $CR^a(OH)$, C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

$X^a$ is absent or is selected from $C_{1-10}$ alkylene, $C_{2-10}$ alkenylene, and $C_{2-10}$ alkynylene;

$Y^a$ is absent or is selected from O, $NR^{a1}$, $S(O)_p$, and C(O);

$Z^a$ is selected from:
  a $C_{3-13}$ carbocycle substituted with 0-5 $R^c$; and
  a 5-14 membered heterocycle consisting of carbon atoms and 1-4 heteroatoms selected from the group consisting of N, O, and $S(O)_p$ and substituted with 0-5 $R^c$;

provided that U, Y, Z, $U^a$, $Y^a$, and $Z^a$ do not combine to form a N—N, N—O, O—N, O—O, $S(O)_p$—O, O—S$(O)_p$ or $S(O)_p$—$(O)_p$ group;

$R^1$ is selected from Q, $C_{1-6}$ alkylene-Q, $C_{2-6}$ alkenylene-Q, $C_{2-6}$ alkynylene-Q, $(CR^aR^{a1})_rO(CR^aR^{a1})_s$-Q, $(CR^aR^{a1})_rNR^a(CR^aR^{a1})_s$-Q, $(CR^aR^{a1})_rC(O)(CR^aR^{a1})_s$-Q, $(CR^aR^{a1})_rC(O)O(CR^aR^{a1})_s$-Q, $(CR^aR^{a1})_rOC(O)(CR^aR^{a1})_s$-Q, $(CR^aR^{a1})_rC(O)NR^aR^{a1}$, $(CR^aR^{a1})_rC(O)NR^a(CR^aR^{a1})_s$-Q, $(CR^aR^{a1})_rNR^aC(O)(CR^aR^{a1})_s$-Q, $(CR^aR^{a1})_rOC(O)O(CR^aR^{a1})_s$-Q, $(CR^aR^{a1})_rOC(O)NR^a(CR^aR^{a1})_s$-Q, $(CR^aR^{a1})_rNR^aC(O)O(CR^aR^{a1})_s$-Q, $(CR^aR^{a1})_rNR^aC(O)NR^a(CR^aR^{a1})_s$-Q, $(CR^aR^{a1})_rS(O)_p(CR^aR^{a1})_s$-Q, $(CR^aR^{a1})_rSO_2NR^a(CR^aR^{a1})_s$-Q, $(CR^aR^{a1})_rNR^aSO_2(CR^aR^{a1})_s$-Q, and $(CR^aR^{a1})_rNR^aSO_2NR^a(CR^aR^{a1})_s$-Q;

$R^2$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_rO(CR^aR^{a1})_s$-$Q^1$, $(CR^aR^{a1})_rNR^a(CR^aR^{a1})_{s\text{-}Q}^1$, $(CR^aR^{a1})_rC(O)(CR^aR^{a1})_s$-$Q^1$, $(CR^aR^{a1})_rC(O)O(CR^aR^{a1})_s$-$Q^1$, $(CR^aR^{a1})_rOC(O)(CR^aR^{a1})_s$-$Q^1$, $(CR^aR^{a1})_rC(O)NR^aR^{a1}$, $(CR^aR^{a1})_rC(O)NR^a(CR^aR^{a1})_s$-$Q^1$, $(CR^aR^{a1})_rNR^aC(O)(CR^aR^{a1})_s$-$Q^1$, $(CR^aR^{a1})_rOC(O)O(CR^aR^{a1})_s$-$Q^1$, $(CR^aR^{a1})_rOC(O)NR^a(CR^aR^{a1})_s$-$Q^1$, $(CR^aR^{a1})_rNR^aC(O)NR^a(CR^aR^{a1})_s$-$Q^1$, $(CR^aR^{a1}_2)_rS(O)_p(CR^aR^{a1})_s$-$Q^1$, $(CR^aR^{a1})_rSO_2NR^a(CR^aR^{a1})_s$-$Q^1$, $(CR^aR^{a1})_rNR^aSO_2(CR^aR^{a1})_s$-$Q^1$, and $(CR^aR^{a1})_rNR^aSO_2NR^a(CR^aR^{a1})_s$-$Q^1$;

$R^3$ is selected from Q, $C_{1-6}$ alkylene-Q, $C_{2-6}$ alkenylene-Q, $C_{2-6}$ alkynylene-Q, $(CR^aR^{a1})_rO(CR^aR^{a1})_s$-Q, $(CR^aR^{a1})_rNR^a(CR^aR^{a1})_s$-Q, $(CR^aR^{a1})_rC(O)(CR^aR^{a1})_s$-Q, $(CR^aR^{a1})_rC(O)O(CR^aR^{a1})_s$-Q, $(CR^aR^{a1})_rC(O)NR^aR^{a1}$, $(CR^aR^{a1})_rC(O)NR^a(CR^aR^{a1})_s$-Q, $(CR^aR^{a1})_rNR^aC(O)(CR^aR^{a1})_s$-Q, $(CR^aR^{a1})_rS(O)_p(CR^aR^{a1})_s$-Q, $(CR^aR^{a1})_rSO_2NR^a(CR^aR^{a1})_s$-Q, and $(CR^aR^{a1})_rNR^aSO_2(CR^aR^{a1})_s$-Q;

Q, at each occurrence, is selected from H, $CHF_2$, $CH_2F$, $CF_3$, a $C_{3-13}$ carbocycle substituted with 0-5 $R^d$ and a 5-14 membered heterocycle consisting of carbon atoms and 1-4 heteroatoms selected from the group consisting of N, O, and $S(O)_p$, and substituted with 0-5 $R^d$;

$Q^1$, at each occurrence, is selected from H, a $C_{3-13}$ carbocycle substituted with 0-5 $R^d$ and a 5-14 membered heterocycle consisting of carbon atoms and 1-4 heteroatoms selected from the group consisting of N, $NR^{10}$, O, and $S(O)_p$, and substituted with 0-5 $R^d$;

$R^4$ is selected from H, $C_{1-6}$ alkyl substituted with 0-1 $R^b$, $C_{2-6}$ alkenyl substituted with 0-1 $R^b$, and $C_{2-6}$ alkynyl substituted with 0-1 $R^b$;

$R^5$ is selected from H, $C_{1-6}$ alkyl substituted with 0-1 $R^b$, $C_{2-6}$ alkenyl substituted with 0-1 $R^b$, and $C_{2-6}$ alkynyl substituted with 0-1 $R^b$;

n is 0 or 1;

alternatively, $R^2$ and $R^3$, together with the carbon atom to which they are attached, combine to form a 3-8 membered carbocyclic or heterocyclic ring consisting of carbon atoms and 0-2 ring heteroatoms selected from O, N, $NR^{10}$, and $S(O)_p$, and 0-2 double bonds, and substituted with 0-3 $R^9$; and the carbocyclic or heterocyclic ring is optionally fused to a 5-6 membered carbocycle or heterocycle consisting of carbon atoms and 0-2 ring heteroatoms selected from O, N, $NR^{10}$, and $S(O)_p$, and 0-2 double bonds, and substituted with 0-3 $R^9$;

alternatively, when n is 1, $R^3$ and $R^4$, together with the carbon atom to which they are attached, combine to form a 3-8 membered carbocyclic or heterocyclic ring consisting of carbon atoms and 0-2 ring heteroatoms selected from O, N, $NR^{10}$, and $S(O)_p$, and 0-2 double bonds, and substituted with 0-3 $R^9$; and the carbocyclic or heterocyclic ring is optionally fused to a 5-6 membered carbocycle or heterocycle consisting of carbon atoms and 0-2 ring heteroatoms selected from O, N, $NR^{10}$, and $S(O)_p$, and 0-2 double bonds, and substituted with 0-3 $R^9$;

alternatively, when n is 1, $R^4$ and $R^5$, together with the carbon atom to which they are attached, combine to form a 3-8 membered carbocyclic or heterocyclic ring consisting of carbon atoms and 0-2 ring heteroatoms selected from O, N, $NR^{10}$, and $S(O)_p$, and 0-2 double bonds, and substituted with 0-3 $R^9$; and the carbocyclic or heterocyclic ring is optionally fused to a 5-6 membered carbocycle or heterocycle consisting of carbon atoms and 0-2 ring heteroatoms selected from O, N, $NR^{10}$, and $S(O)_p$, and 0-2 double bonds, and substituted with 0-3 $R^9$;

$R^a$, at each occurrence, is independently selected from H, $C_{1-6}$ alkyl, phenyl, and benzyl;

$R^{a1}$, at each occurrence, is independently selected from H, $C_{1-6}$ alkyl substituted with 0-1 $R^{c1}$, $C_{2-6}$ alkenyl substituted with 0-1 $R^{c1}$, $C_{2-6}$ alkynyl substituted with 0-1 $R^{c1}$, and —$(CH_2)_r$-3-8 membered carbocyclic or heterocyclic ring consisting of carbon atoms and 0-2 ring heteroatoms selected from N, $NR^{a2}$, O, and $S(O)_p$, and substituted with 0-3 $R^{c1}$;

alternatively, $R^a$ and $R^{a1}$ when attached to a nitrogen, together with the nitrogen to which they are attached, combine to form a 5 or 6 membered heterocycle consisting of carbon atoms and from 0-1 additional heteroatoms selected from N, $NR^{a2}$, O, and $S(O)_p$; $R^{a2}$, at each occurrence, is independently selected from $C_{1-4}$ alkyl, phenyl, and benzyl; $R^{a3}$, at each occurrence, is independently selected from H, $C_{1-6}$ alkyl substituted with 0-1 $R^{c1}$, $C_{2-6}$ alkenyl substituted with 0-1 $R^{c1}$, $C_{2-6}$ alkynyl substituted with 0-1 $R^{c1}$, and $-(CH_2)_r$-3-8 membered carbocyclic or heterocyclic ring consisting of carbon atoms and 0-2 ring heteroatoms selected from N, $NR^{a2}$, O, and $S(O)_p$, and substituted with 0-3 $R^{c1}$;

$R^b$, at each occurrence, is independently selected from $C_{1-6}$ alkyl substituted with 0-1 $R^{c1}$, $OR^a$, $SR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $NR^aC(O)NR^aR^{a1}$, $OC(O)NR^aR^{a1}$, $NR^aC(O)OR^{a1}$, $S(O)_2NR^aR^{a1}$, $NR^aS(O)_2R^{a3}$, $NR^aS(O)_2NR^aR^{a1}$, $OS(O)_2NR^aR^{a1}$, $S(O)_pR^{a3}$, $CF_3$, $CF_2CF_3$, $CHF_2$, $CH_2F$, and phenyl; $R^c$, at each occurrence, is independently selected from H, $OR^a$, Cl, F, Br, I, =O, —CN, $NO_2$, $CF_3$, $CF_2CF_3$, $CH_2F$, $CHF_2$, $(CR^aR^{a1})_rNR^aR^{a1}$, $(CR^aR^{a1})_rC(=NCN)NR^aR^{a1}$, $(CR^aR^{a1})_rC(=NR^a)NR^aR^{a1}$, $(CR^aR^{a1})_rC(=NOR^a)NR^aR^{a1}$, $(CR^aR^{a1})_rC(O)NR^aOH$, $(CR^aR^{a1})_rC(O)R^{a1}$, $(CR^aR^{a1})_rC(O)OR^{a1}$, $(CR^aR^{a1})_rC(S)OR^{a1}$, $(CR^aR^{a1})_rC(O)NR^aR^{a1}$, $(CR^aR^{a1})_rNR^aC(O)R^{a1}$, $(CR^aR^{a1})_rC(S)NR^aR^{a1}$, $(CR^aR^{a1})_rOC(O)NR^aR^{a1}$, $(CR^aR^{a1})_rNR^aC(O)OR^{a1}$, $(CR^aR^{a1})_rNR^aC(O)NR^aR^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, and $(CR^aR^{a1})_rNR^aSO_2NR^aR^{a1}$;

$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$; and $(CR^aR^{a1})_r$-5-14 membered heterocycle consisting of carbon atoms and 1-4 heteroatoms selected from the group consisting of N, O, and $S(O)_p$, and substituted with 0-2 $R^{c1}$;

alternatively, when two $R^c$ groups are attached to the same carbon atom, they form a 3-8 membered carbocyclic or heterocyclic spiro ring C substituted with 0-2 $R^{c1}$ and consisting of carbon atoms, 0-4 ring heteroatoms selected from O, N, and $S(O)_p$, and 0-2 double bonds, provided that ring C contains other than a S—S, O—O, or S—O bond;

alternatively, when two $R^c$ groups are attached to adjacent carbon atoms, together with the carbon atoms to which they are attached they form a 5-7 membered carbocyclic or heterocyclic ring D substituted with 0-2 $R^{c1}$ and consisting of carbon atoms, 0-2 heteroatoms selected from the group consisting of N, O, and $S(O)_p$, and 0-3 double bonds;

$R^{c1}$, at each occurrence, is independently selected from H, $C_{1-4}$ alkyl, $OR^a$, Cl, F, Br, I, =O, $CF_3$, —CN, $NO_2$, $C(O)R^a$, $C(O)OR^a$, $C(O)NR^aR^a$, and $S(O)_pR^a$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a3}$, $NR^aS(O)_2NR^aR^{a1}$, $OS(O)_2NR^aR^{a1}$, $S(O)_pR^{a3}$, $CF_3$, $CF_2CF_3$, $C_{3-10}$ carbocycle and a 5-14 membered heterocycle consisting of carbon atoms and 1-4 heteroatoms selected from the group consisting of N, O, and $S(O)_p$;

$R^e$, at each occurrence, is independently selected from H, $C_{1-6}$ alkyl, $C_{1-6}$ alkoxy, phenoxy, benzoxy, $C_{3-10}$ carbocycle substituted with 0-2 $R^{c1}$, and a 5-10 membered heterocycle consisting of carbon atoms and 1-4 heteroatoms selected from the group consisting of N, O, and $S(O)_p$, and substituted with 0-2 $R^{c1}$;

$R^6$ is selected from H, $C_{1-4}$ alkyl, $C_{2-4}$ alkenyl, and $C_{2-4}$ alkynyl;

$R^7$ is selected from H, $C_{1-4}$ alkyl, $C_{2-4}$ alkenyl, and $C_{2-4}$ alkynyl;

$R^9$, at each occurrence, is independently selected from H, $(CR^aR^{a1})_rNR^aR^{a1}$, $(CR^aR^{a1})_rC(O)NR^aOH$, $(CR^aR^{a1})_rC(O)(CR^aR^{a1})_sR^e$, $(CR^aR^{a1})_rC(O)OR^{a1}$, $(CR^aR^{a1})_rC(S)OR^{a1}$, $(CR^aR^{a1})_rC(O)NR^aR^{a1}$, $(CR^aR^{a1})_rNR^aC(O)R^{a1}$, $(CR^aR^{a1})_rC(S)NR^aR^{a1}$, $(CR^aR^{a1})_rOC(O)NR^aR^{a1}$, $(CR^aR^{a1})_rNR^aC(O)OR^{a1}$, $(CR^aR^{a1})_rNR^aC(O)NR^aR^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, $(CR^aR^{a1})_rNR^aSO_2NR^aR^{a1}$;

$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$; and $(CR^aR^{a1})_r$-5-10 membered heterocycle consisting of carbon atoms and 1-4 heteroatoms selected from the group consisting of N, O, and $S(O)_p$, and substituted with 0-2 $R^{c1}$;

$R^{10}$, at each occurrence, is independently selected from H, $(CR^aR^{a1})_tNR^aR^{a1}$, $(CR^aR^{a1})_rC(O)NR^aOH$, $(CR^aR^{a1})_rC(O)(CR^aR^{a1})_sR^e$, $(CR^aR^{a1})_rC(O)OR^{a1}$, $(CR^aR^{a1})_rC(S)OR^{a1}$, $(CR^aR^{a1})_rC(O)NR^aR^{a1}$, $(CR^aR^{a1})_rNR^aC(O)R^{a1}$, $(CR^aR^{a1})_rC(S)NR^aR^{a1}$, $(CR^aR^{a1})_tOC(O)NR^aR^{a1}$, $(CR^aR^{a1})_rNR^aC(O)OR^{a1}$, $(CR^aR^{a1})_rNR^aC(O)NR^aR^{a1}$, $(CR^aR^{a1})_rS(O)_pR^{a3}$, $(CR^aR^{a1})_rSO_2NR^aR^{a1}$, $(CR^aR^{a1})_tNR^aSO_2R^{a3}$, $(CR^aR^{a1})_rNR^aSO_2NR^aR^{a1}$;

$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$;
and $(CR^aR^{a1})_r$-5-10 membered heterocycle consisting of carbon atoms and 1-4 heteroatoms selected from the group consisting of N, O, and $S(O)_p$, and substituted with 0-2 $R^{c1}$;

m, at each occurrence, is selected from 0, 1, 2 and 3;
p, at each occurrence, is selected from 0, 1, and 2;
r, at each occurrence, is selected from 0, 1, 2, 3, and 4;
s, at each occurrence, is selected from 0, 1, 2, 3, and 4;
t, at each occurrence, is selected from 1, 2, 3, and 4; and,
provided that:

(i) when Z is 2,4-thiazolyl or 1,3-cyclohexyl, then U is other than O, $NR^{a1}$ or $S(O)_p$;

(ii) when Z is 3,5-pyrazolyl, then $Z^a$ is other than $C_3$-$C_6$ cycloalkyl;

(iii) when Z is 1,4-piperazinyl, then $Z^a$ is other than 7-oxo-5H-pyrrolo[3,4-d]-pyrimidinyl;

(iv) when Z is phenylene, then $Z^a$ is other than 4,5-dihydro-pyridazinonyl, phenyl substituted with benzoxy, or benzimidazolyl substituted with $C(=NR^a)NR^{a1}$;

(v) when Z is a 8-14 membered bicyclic heterocycle, then $Z^a$ is other than a 5-9 membered mono or bicyclic heterocycle;

(vi) when $R^2$ is —C(O)OH, then U is other than $NR^{a1}S(O)_2$;

(vii) when —U—X—Y— forms —OCH$_2$—, —U$^a$—X$^a$—Y$^a$— forms —OCH$_2$—, and Z is phenylene, then Z$^a$ is other than phenyl;

(viii) when —U—X—Y— forms —CONHCH$_2$CO—, then Z is other than a 5 membered heterocycle.

[10] In another embodiment, the present invention provides a novel compound of formula (I), wherein;

W is (CR$^a$R$^{a1}$)$_m$;

U is selected from O, NR$^{a1}$, C(O), CR$^a$(OH), C(O)O, OC(O), C(O)NR$^{a1}$, NR$^{a1}$C(O), S(O)$_p$, S(O)$_p$NR$^{a1}$, and NR$^{a1}$S(O)$_p$;

X is absent or C$_{1-3}$ alkylene;

Z is selected from:
  phenyl substituted with 0-4 R$^b$;
  naphthyl substituted with 0-5 R$^b$;
  pyridyl substituted with 0-3 R$^b$;
  thienyl substituted with 0-2 R$^b$;
  thiazolyl substituted with 0-2 R$^b$;
  oxazolyl substituted with 0-2 R$^b$;
  isoxazolyl substituted with 0-2 R$^b$; and
  imidazolyl substituted with 0-2 R$^b$;

U$^a$ is absent or is selected from O, NR$^{a1}$, C(O), CR$^a$(OH), C(O)O, C(O)NR$^{a1}$, NR$^{a1}$C(O), S(O)$_p$, S(O)$_p$NR$^{a1}$, and NR$^{a1}$S(O)$_p$;

X$^a$ is absent or selected from C$_{1-4}$ alkylene, C$_{2-4}$ alkenylene, and C$_{2-4}$ alkynylene;

Y$^a$ is absent or selected from O and NR$^{a1}$;

Z$^a$ is selected from:
  a C$_{6-13}$ carbocycle substituted with 0-5 R$^c$; and
  a 5-14 membered heterocycle consisting of carbon atoms and 1-4 heteroatoms selected from the group consisting of N, O, and S(O)$_p$, and substituted with 0-5 R$^c$;

R$^1$ is selected from Q, C$_{1-6}$ alkylene-Q, C$_{2-6}$ alkenylene-Q, C$_{2-6}$ alkynylene-Q, (CR$^a$R$^{a1}$)$_r$O(CR$^a$R$^{a1}$)$_s$-Q, (CR$^a$R$^{a1}$)$_r$NR$^a$(CR$^a$R$^{a1}$)$_s$-Q, (CR$^a$R$^{a1}$)$_r$C(O)(CR$^a$R$^{a1}$)$_s$-Q, (CR$^a$R$^{a1}$)$_r$C(O)O(CR$^a$R$^{a1}$)$_s$-Q, (CR$^a$R$^{a1}$)$_r$C(O)NR$^a$R$^{a1}$, (CR$^a$R$^{a1}$)$_r$C(O)NR$^a$(CR$^a$R$^{a1}$)$_s$-Q, (CR$^a$R$^{a1}$)$_r$S(O)$_p$(CR$^a$R$^{a1}$)$_s$-Q, (CR$^a$R$^{a1}$)$_r$SO$_2$NR$^a$(CR$^a$R$^{a1}$)$_s$-Q, and (CR$^a$R$^{a1}$)$_r$NR$^a$SO$_2$(CR$^a$R$^{a1}$)$_s$-Q;

R$^2$ is selected from Q$^1$, C$_{1-6}$ alkylene-Q$^1$, C$_{2-6}$ alkenylene-Q$^1$, C$_{2-6}$ alkynylene-Q$^1$, (CR$^a$R$^{a1}$)$_r$O(CR$^a$R$^{a1}$)$_s$-Q$^1$, (CR$^a$R$^{a1}$)$_r$NR$^a$(CR$^a$R$^{a1}$)$_s$-Q$^1$, (CR$^a$R$^{a1}$)$_r$C(O)(CR$^a$R$^{a1}$)$_s$-Q$^1$, (CR$^a$R$^{a1}$)$_s$-Q$^1$, (CR$^a$R$^{a1}$)$_r$C(O)O(CR$^a$R$^{a1}$)$_s$-Q$^1$, (CR$^a$R$^{a1}$)$_r$OC(O)(CR$^a$R$^{a1}$)$_s$-Q$^1$, (CR$^a$R$^{a1}$)$_r$C(O)NR$^a$R$^{a1}$, (CR$^a$R$^{a1}$)$_r$C(O)NR$^a$(CR$^a$R$^{a1}$)$_s$-Q$^1$, (CR$^a$R$^{a1}$)$_r$NR$^a$C(O)(CR$^a$R$^{a1}$)$_s$-Q$^1$, (CR$^a$R$^{a1}$)$_r$S(O)$_p$(CR$^a$R$^{a1}$)$_s$-Q$^1$, (CR$^a$R$^{a1}$)$_r$SO$_2$NR$^a$(CR$^a$R$^{a1}$)$_s$-Q$^1$, and (CR$^a$R$^{a1}$)$_r$NR$^a$SO$_2$(CR$^a$R$^{a1}$)$_s$-Q$^1$;

R$^3$ is selected from Q, C$_{1-6}$ alkylene-Q, C$_{2-6}$ alkenylene-Q, C$_{2-6}$ alkynylene-Q, (CH$_2$)$_r$O(CH$_2$)$_s$-Q, (CH$_2$)$_r$NR$^a$(CH$_2$)$_s$-Q, (CH$_2$)$_r$C(O)(CH$_2$)$_s$-Q, (CH$_2$)$_r$C(O)O(CH$_2$)$_s$-Q, (CH$_2$)$_r$C(O)NR$^a$R$^{a1}$, (CH$_2$)$_r$C(O)NR$^a$(CH$_2$)$_s$-Q, (CH$_2$)$_r$NR$^a$C(O)(CH$_2$)$_s$-Q, (CH$_2$)$_r$S(O)$_p$(CH$_2$)$_s$-Q, (CH$_2$)$_r$SO$_2$NR$^a$(CH$_2$)$_s$-Q, and (CH$_2$)$_r$NR$^a$SO$_2$(CH$_2$)$_s$-Q;

R$^4$ is selected from H, C$_{1-6}$ alkyl substituted with 0-1 R$^b$, C$_{2-6}$ alkenyl substituted with 0-1 R$^b$, and C$_{2-6}$ alkynyl substituted with 0-1 R$^b$;

R$^5$ is selected from H, C$_{1-6}$ alkyl substituted with 0-1 R$^b$, C$_{2-6}$ alkenyl substituted with 0-1 R$^b$, and C$_{2-6}$ alkynyl substituted with 0-1 R$^b$;

alternatively, R$^2$ and R$^3$, together with the carbon atom to which they are attached, combine to form a 3-8 membered carbocyclic or heterocyclic ring consisting of carbon atoms and 0-2 ring heteroatoms selected from O, N, NR$^{10}$, and S(O)$_p$, and 0-2 double bonds, and substituted with 0-2 R$^9$;

alternatively, when n is 1, R$^3$ and R$^4$, together with the carbon atoms to which they are attached, combine to form a 3-8 membered carbocyclic or heterocyclic ring consisting of carbon atoms and 0-2 ring heteroatoms selected from O, N, NR$^{10}$, and S(O)$_p$, and 0-2 double bonds, and substituted with 0-2 R$^9$;

alternatively, when n is 1, R$^4$ and R$^5$ together with the carbon atom to which they are attached combine to form a 3-8 membered carbocyclic or heterocyclic ring consisting of carbon atoms and 0-2 ring heteroatoms selected from O, N, NR$^{10}$, and S(O)$_p$, and 0-2 double bonds, and substituted with 0-2 R$^9$;

R$^a$, at each occurrence, is independently selected from H, C$_{1-6}$ alkyl, phenyl, and benzyl;

R$^{a1}$, at each occurrence, is independently selected from H, C$_{1-6}$ alkyl, C$_{2-6}$ alkenyl, C$_{2-6}$ alkynyl, and —(CH$_2$)$_r$-3-8 membered carbocyclic or heterocyclic ring consisting of carbon atoms and 0-2 ring heteroatoms selected from N, NR$^{a2}$, O, and S(O)$_p$;

alternatively, R$^a$ and R$^{a1}$ when attached to a nitrogen, together with the nitrogen to which they are attached, combine to form a 5 or 6 membered heterocycle consisting of carbon atoms and from 0-1 additional heteroatoms selected from N, NR$^{a2}$, O, and S(O)$_p$;

R$^c$, at each occurrence, is independently selected from H, OR$^a$, Cl, F, Br, =O, —CN, NO$_2$, CF$_3$, CH$_2$F, CHF$_2$, CF$_2$CF$_3$, (CR$^a$R$^{a1}$)$_r$NR$^a$R$^{a1}$, (CR$^a$R$^{a1}$)$_r$C(O)R$^{a1}$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$;

C$_{1-6}$ alkyl substituted with 0-1 R$^{c1}$;

C$_{2-6}$ alkenyl substituted with 0-1 R$^{c1}$;

C$_{2-6}$ alkynyl substituted with 0-1 R$^{c1}$;

(CH$_2$)$_r$—C$_{3-6}$ carbocycle substituted with 0-2 R$^{c1}$; and (CH$_2$)$_r$-5-6 membered heterocycle consisting of carbon atoms and 1-4 heteroatoms selected from the group consisting of N, O, and S(O)$_p$, and substituted with 0-2 R$^{c1}$;

alternatively, when two R$^c$ groups are attached to the same carbon atom, they form a 3-8 membered carbocyclic or heterocyclic spiro ring C substituted with 0-2 R$^{c1}$ and consisting of carbon atoms, 0-4 ring heteroatoms selected from O, N, and S(O)$_p$, and 0-2 double bonds, provided that ring C contains other than a S—S, O—O, or S—O bond;

alternatively, when two R$^c$ groups are attached to adjacent carbon atoms, together with the carbon atoms to which they are attached they form a 5-7 membered carbocyclic or heterocyclic ring D substituted with 0-2 R$^{c1}$ and consisting of carbon atoms, 0-2 heteroatoms selected from the group consisting of N, O, and S(O)$_p$, and 0-3 double bonds;

R$^d$, at each occurrence, is independently selected from C$_{1-6}$ alkyl, OR$^a$, Cl, F, Br, =O, —CN, NO$_2$, NR$^a$R$^{a1}$, C(O)R$^a$, C(O)OR$^a$, C(O)NR$^a$R$^{a1}$, S(O)$_2$NR$^a$R$^{a1}$, NR$^a$S(O)$_2$R$^{a3}$, S(O)$_p$R$^{a3}$, CF$_3$, C$_{3-6}$ carbocycle and a 5-6 membered heterocycle consisting of carbon atoms and 1-4 heteroatoms selected from the group consisting of N, O, and S(O)$_p$;

R$^6$ is selected from H and C$_{1-4}$ alkyl;

R$^7$ is selected from H and C$_{1-4}$ alkyl;

R$^9$, at each occurrence, is independently selected from H, (CR$^a$R$^{a1}$)$_r$NR$^a$R$^{a1}$, (CR$^a$R$^{a1}$)$_r$C(O)NR$^a$OH, (CR$^a$R$^{a1}$)$_r$C(O)(CR$^a$R$^{a1}$)$_s$R$^e$, (CR$^a$R$^{a1}$)$_r$C(O)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$OC(O)NR$^a$R$^{a1}$, (CR$^a$R$^{a1}$)$_r$NR$^a$C(O)OR$^{a1}$, (CR$^a$R$^{a1}$)$_r$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$;

$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$;
and $(CR^aR^{a1})_r$-5-10 membered heterocycle consisting of carbon atoms and 1-4 heteroatoms selected from the group consisting of N, O, and $S(O)_p$ and substituted with 0-2 $R^{c1}$;

$R^{10}$, at each occurrence, is independently selected from H, $(CR^aR^{a1})_rNR^aR^{a1}$, $(CR^aR^{a1})_rC(O)NR^aOH$, $(CR^aR^{a1})_rC(O)(CR^aR^{a1})_sR^e$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rOC(O)NR^aR^{a1}$, $(CR^aR^{a1})_rNR^aC(O)OR^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$;

$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$;
and $(CR^aR^{a1})_r$-5-10 membered heterocycle consisting of carbon atoms and 1-4 heteroatoms selected from the group consisting of N, O, and $S(O)_p$ and substituted with 0-2 $R^{c1}$; and, provided that:
(i) when Z is 2,4-thiazolyl, then U is other than O, $NR^{a1}$ or $S(O)_p$;
(ii) when Z is phenylene, then $Z^a$ is other than 4,5-dihydro-pyridazinonyl, phenyl substituted with benzoxy, or benzimidazolyl substituted with $C(=NR^a)NR^aR^{a1}$;
(iii) when $R^2$ is —C(O)OH, then U is other than $NR^{a1}S(O)_2$;
(iv) when —U—X—Y— forms —OCH$_2$—, —U$^a$—X$^a$—Y$^a$— forms —OCH$_2$—, and Z is phenylene, then $Z^a$ is other than phenyl;
(v) when —U—X—Y— forms —CONHCH$_2$CO—, then Z is phenyl or naphthylene.

[11] In another embodiment, the present invention provides a novel compound of formula (I), wherein;
U is selected from O, $NR^{a1}$, C(O), $C(O)NR^{a1}$, $NR^{a1}C(O)$, $S(O)_p$, $S(O)_pNR^{a1}$, and $NR^{a1}S(O)_p$;
X is absent, or is methylene or ethylene;
Z is phenyl substituted with 0-4 $R^b$;
$U^a$ is absent or is selected from O, $NR^{a1}$, C(O), $C(O)NR^{a1}$, $NR^{a1}C(O)$, $S(O)_p$, $S(O)_pNR^1$, and $NR^{a1}S(O)_p$;
$R^1$ is selected from Q, $C_{1-6}$ alkylene-Q, $C_{2-6}$ alkenylene-Q, $C_{2-6}$ alkynylene-Q, $(CH_2)_rO(CH_2)_s$-Q, $(CH_2)_rNR^a(CH_2)_s$-Q, $(CH_2)_rC(O)(CH_2)_s$-Q, $(CH_2)_rC(O)O(CH_2)_s$-Q, $(CH_2)_rC(O)NR^aR^{a1}$, $(CH_2)_rC(O)NR^a(CH_2)_s$-Q, $(CH_2)_rNR^aC(O)(CH_2)_s$-Q, $(CH_2)_rS(O)_p(CH_2)_s$-Q, $(CH_2)_rSO_2NR^a(CH_2)_s$-Q, and $(CH_2)_rNR^aSO_2(CH_2)_s$-Q;
$R^2$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_rO(CR^aR^{a1})_s$-$Q^1$, $(CR^aR^{a1})_rNR^a(CR^aR^{a1})_s$-$Q^1$, $(CR^aR^{a1})_rC(O)(CR^aR^{a1})_s$-$Q^1$, $(CR^aR^{a1})_rC(O)O(CR^aR^{a1})_s$-$Q^1$, $(CR^aR^{a1})_rC(O)NR^a(CR^aR^{a1})_s$-$Q^1$, $(CR^aR^{a1})_rNR^aC(O)(CR^aR^{a1})_s$-$Q^1$, $(CR^aR^{a1}_2)_sS(O)_p(CR^aR^{a1})_s$-$Q^1$, $(CR^aR^{a1})_rSO_2NR^a(CR^aR^{a1})_s$-$Q^1$, and $(CR^aR^{a1})_rNR^aSO_2(CR^aR^{a1})_s$-$Q^1$;
$R^3$ is selected from Q, $C_{1-6}$ alkylene-Q, $C_{2-6}$ alkenylene-Q, $C_{2-6}$ alkynylene-Q, $(CH_2)_rO(CH_2)_s$-Q, $(CH_2)_rNR^a(CH_2)_s$-Q, $(CH_2)_rC(O)(CH_2)_s$-Q, $(CH_2)_rC(O)O(CH_2)_s$-Q, $(CH_2)_rC(O)NR^aR^{a1}$, $(CH_2)_rC(O)NR^a(CH_2)_s$-Q, $(CH_2)_rNR^aC(O)(CH_2)_s$-Q, $(CH_2)_rS(O)_p(CH_2)_s$-Q, $(CH_2)_rSO_2NR^a(CH_2)_s$-Q, and $(CH_2)_rNR^aSO_2(CH_2)_s$-Q;

Q, at each occurrence, is selected from H, a $C_{3-10}$ carbocycle substituted with 0-3 $R^d$, and a 5-10 membered heterocycle consisting of carbon atoms and 1-4 heteroatoms selected from the group consisting of N, O, and $S(O)_p$, and substituted with 0-3 $R^d$;
$R^4$ is selected from H and $C_{1-6}$ alkyl;
$R^5$ is selected from H and $C_{1-6}$ alkyl;
alternatively, $R^2$ and $R^3$, together with the carbon atom to which they are attached, combine to form a 3-8 membered carbocyclic or heterocyclic ring consisting of carbon atoms, 0-2 ring heteroatoms selected from O, N, $NR^{10}$, and $S(O)_p$, and 0-2 double bonds, and substituted with 0-2 $R^9$;
alternatively, when n is 1, $R^3$ and $R^4$, together with the carbon atoms to which they are attached, combine to form a 3-8 membered carbocyclic or heterocyclic ring consisting of carbon atoms, 0-2 ring heteroatoms selected from O, N, $NR^{10}$, and $S(O)_p$, and 0-2 double bonds, and substituted with 0-2 $R^9$;
alternatively, when n is 1, $R^4$ and $R^5$, together with the carbon atom to which they are attached, combine to form a 3-8 membered carbocyclic or heterocyclic ring consisting of carbon atoms, 0-2 ring heteroatoms selected from O, N, $NR^{10}$, and $S(O)_p$, and 0-2 double bonds, and substituted with 0-2 $R^9$;

$R^{a3}$, at each occurrence, is independently selected from H, $C_{1-6}$ alkyl, $C_{2-6}$ alkenyl, and —$(CH_2)_r$-3-8 membered carbocyclic or heterocyclic ring consisting of carbon atoms and 0-2 ring heteroatoms selected from N, $NR^{a2}$, O, and $S(O)_p$, and substituted with 0-3 $R^{c1}$;

$R^c$, at each occurrence, is independently selected from H, $OR^a$, Cl, F, Br, =O, $CF_3$, $CH_2F$, $CHF_2$, $(CR^aR^{a1})_rNR^aR^{a1}$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, $C_{1-6}$ alkyl, $C_{2-6}$ alkenyl, $C_{2-6}$ alkynyl;
$C_{3-6}$ cycloalkyl substituted with 0-2 $R^{c1}$;
phenyl substituted with 0-2 $R^{c1}$; and
5-6 membered heterocycle consisting of carbon atoms and 1-4 heteroatoms selected from the group consisting of N, O, and $S(O)_p$, and substituted with 0-2 $R^{c1}$;
alternatively, when two $R^c$ groups are attached to adjacent carbon atoms, together with the carbon atoms to which they are attached they form a 5-7 membered carbocyclic or heterocyclic ring D substituted with 0-2 $R^{c1}$ and consisting of carbon atoms, 0-2 heteroatoms selected from the group consisting of N, O, and $S(O)_p$, and 0-3 double bonds;

$R^d$, at each occurrence, is independently selected from $C_{1-6}$ alkyl, $OR^a$, Cl, F, Br, =O, $NR^aR^{a1}$, $C(O)R^a$, $C(O)OR^a$, $C(O)NR^aR^{a1}$, $S(O)_2NR^aR^{a1}$, $NR^aS(O)_2R^{a3}$, $S(O)_pR^{a3}$, $CF_3$ and phenyl;

$R^6$ is H;
$R^7$ is H;
$R^9$, at each occurrence, is independently selected from H, $(CR^aR^{a1})_rNR^aR^{a1}$, $(CR^aR^{a1})_rC(O)(CR^aR^{a1})_sR^e$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_r SO_2NR^aR^{a1}$, $(CR^aR^{a1})_rNR^aSO_2R^{a3}$;
$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$;
and $(CR^aR^{a1})_r$-5-10 membered heterocycle consisting of carbon atoms and 1-4 heteroatoms selected from the group consisting of N, O, and $S(O)_p$, and substituted with 0-2 $R^{c1}$;

$R^{10}$, at each occurrence, is independently selected from H, $(CR^aR^{a1})_rNR^aR^{a1}$, $(CR^aR^{a1})_rC(O)(CR^aR^{a1})_sR^e$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$;
$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$; and $(CR^aR^{a1})_r$-5-10 membered heterocycle consisting of carbon atoms and 1-4 heteroatoms selected from the group consisting of N, O, and $S(O)_p$, and substituted with 0-2 $R^{c1}$;

r, at each occurrence, is selected from 0, 1, 2, and 3;
s, at each occurrence, is selected from 0, 1, 2, and 3;
t, at each occurrence, is selected from 1, 2, and 3; and,
provided that:
  (i) $Z^a$ is other than 4,5-dihydro-pyridazinonyl, phenyl substituted with benzoxy, or benzimidazolyl substituted with $C(=NR^a)NR^aR^{a1}$;
  (ii) when $R^2$ is —C(O)OH, then U is other than $NR^{a1}S(O)_2$;
  (iii) when —U—X—Y— forms —OCH$_2$—, and —U$^a$—X$^a$—Y$^a$— forms —OCH$_2$—, then $Z^a$ is other than phenyl.

[12] In another embodiment, the present invention provides a novel compound of formula (I), wherein;
$Z^a$ is selected from:
  phenyl substituted with 0-3 $R^c$;
  naphthyl substituted with 0-3 $R^c$; and a heterocycle substituted with 0-3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

Q, at each occurrence, is selected from H, a $C_{3-8}$ carbocycle substituted with 0-3 $R^d$ and a 5-10 membered heterocycle consisting of carbon atoms and 1-4 heteroatoms selected from the group consisting of N, O, and $S(O)_p$, and substituted with 0-3 $R^d$;

$Q^1$, at each occurrence, is selected from H, a C3-10 carbocycle substituted with 0-5 $R^d$ and a 5-10 membered heterocycle consisting of carbon atoms and 1-4 heteroatoms selected from the group consisting of N, $NR^{10}$, O, and $S(O)_p$, and substituted with 0-3 $R^d$;

$R^a$, at each occurrence, is independently selected from H, $C_{1-6}$ alkyl, phenyl, and benzyl;

$R^{a1}$, at each occurrence, is independently selected from H, $C_{1-6}$ alkyl, phenyl, and benzyl;

$R^{a3}$, at each occurrence, is independently selected from H, $C_{1-6}$ alkyl, phenyl, and benzyl;

$R^c$, at each occurrence, is independently selected from H, $OR^a$, Cl, F, Br, =O, $CF_3$, $CH_2F$, $CHF_2$, $(CR^aR^{a1})_rNR^aR^{a1}$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, $C_{1-6}$ alkyl, $C_{2-6}$ alkenyl, $C_{2-6}$ alkynyl;
phenyl substituted with 0-2 $R^{c1}$; and 5-6 membered heterocycle consisting of carbon atoms and 1-4 heteroatoms selected from the group consisting of N, O, and $S(O)_p$ and substituted with 0-2 $R^{c1}$;
alternatively, when two $R^c$ groups are attached to adjacent carbon atoms, together with the carbon atoms to which they are attached they form a 5-6 membered carbocyclic or heterocyclic ring D substituted with 0-2 $R^{c1}$ and consisting of carbon atoms, 0-2 heteroatoms selected from the group consisting of N, O, and $S(O)_p$, and 0-3 double bonds;

$R^9$, at each occurrence, is independently selected from H, $(CR^aR^{a1})_rNR^aR^{a1}$, $(CR^aR^{a1})_rC(O)(CR^aR^{a1})_sR^e$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_r$ $SO_2NR^aR^{a1}$, $(CR^aR^{a1})_rNR^aSO_2R^{a3}$, $C_{1-6}$ alkyl $C_{2-6}$ alkenyl, $C_{2-6}$ alkynyl;
$(CR^aR^{a1})_r$—$C_{3-7}$ carbocycle substituted with 0-2 $R^{c1}$; and
$(CR^aR^{a1})_r$-5-6 membered heterocycle consisting of carbon atoms and 1-4 heteroatoms selected from the group consisting of N, O, and $S(O)_p$, and substituted with 0-2 $R^{c1}$; and, $R^{10}$, at each occurrence, is independently selected from H, $(CR^aR^{a1})_rNR^aR^{a1}$, $(CR^aR^{a1})_rC(O)(CR^aR^{a1})_sR^e$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$;
$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CR^aR^{a1})_r$—$C_{3-10}$ carbocycle substituted with 0-2 $R^{c1}$;
and $(CR^aR^{a1})_r$-5-10 membered heterocycle consisting of carbon atoms and 1-4 heteroatoms selected from the group consisting of N, O, and $S(O)_p$, and substituted with 0-2 $R^{c1}$.

[13] In another embodiment, the present invention provides a novel compound of formula (I), wherein;
U is selected from $NR^{a1}$, C(O), $C(O)NR^{a1}$, $NR^{a1}C(O)$, $S(O)_p$, $S(O)_pNR^{a1}$, and $NR^{a1}S(O)_p$;
X is absent or is methylene;
Y is absent or is O;
Z is phenyl substituted with 0-3 $R^b$;
$U^a$ is absent or is O;
$Y^a$ is absent or is O;
$R^2$ is selected from $Q^1$, $C_{1-6}$ alkylene-$Q^1$, $C_{2-6}$ alkenylene-$Q^1$, $C_{2-6}$ alkynylene-$Q^1$, $(CH_2)_rO(CH_2)_s$-$Q^1$, $(CH_2)_rNR^a(CH_2)_s$-$Q^1$, $(CH_2)_rC(O)(CH_2)_s$-$Q^1$, $(CH_2)_rC(O)O(CH_2)_s$-$Q^1$, $(CH_2)_rC(O)NR^a(CH_2)_s$-$Q^1$, $(CH_2)_rNR^aC(O)(CH_2)_s$-$Q^1$, $(CH_2)_rS(O)_p(CH_2)_s$-$Q^1$, $(CH_2)_rSO_2NR^a(CH_2)_s$-$Q^1$, and $(CH_2)_rNR^aSO_2(CH_2)_s$-$Q^1$;
$R^3$ is selected from Q, $C_{1-6}$ alkylene-Q, $C_{2-6}$ alkenylene-Q, $C_{2-6}$ alkynylene-Q, $(CH_2)_rO(CH_2)_s$-Q, $(CH_2)_rNR^a(CH_2)_s$-Q, $(CH_2)_rC(O)(CH_2)_s$-Q, $(CH_2)_rC(O)O(CH_2)_s$-Q, $(CH_2)_rC(O)NR^aR^{a1}$, $(CH_2)_rC(O)NR^a(CH_2)_s$-Q, $(CH_2)_rNR^aC(O)(CH_2)_s$-Q, $(CH_2)_rS(O)_p(CH_2)_s$-Q, $(CH_2)_rSO_2NR^a(CH_2)_s$-Q, and $(CH_2)_rNR^aSO_2(CH_2)_s$-Q;
$R^4$ is selected from H and $C_{1-6}$ alkyl;
$R^5$ is selected from H and $C_{1-6}$ alkyl;
Q, at each occurrence, is selected from H, a $C_{3-6}$ carbocycle and a 5-6 membered heterocycle consisting of carbon atoms and 1-4 heteroatoms selected from the group consisting of N, O, and $S(O)_p$; alternatively, $R^2$ and $R^3$, together with the carbon atom to which they are attached, combine to form a 5-6 membered carbocyclic or heterocyclic ring consisting of carbon atoms, 0-2 ring heteroatoms selected from O, N, $NR^{10}$, and $S(O)_p$, and 0-2 double bonds, and substituted with 0-2 $R^9$;

alternatively, when n is 1, $R^3$ and $R^4$, together with the carbon atoms to which they are attached, combine to form a 5-6 membered carbocyclic or heterocyclic ring consisting of carbon atoms, 0-2 ring heteroatoms selected from O, N, $NR^{10}$, and $S(O)_p$, and 0-2 double bonds, and substituted with 0-2 $R^9$;

$R^a$, at each occurrence, is independently selected from H, and $C_{1-4}$ alkyl;

$R^{a1}$, at each occurrence, is independently selected from H, and $C_{1-4}$ alkyl;

$R^{a3}$, at each occurrence, is independently selected from H, $C_{1-4}$ alkyl, phenyl, and benzyl;

$R^c$, at each occurrence, is independently selected from $C_{1-6}$ alkyl, $C_{2-6}$ alkenyl, $C_{2-6}$ alkynyl, $OR^a$, Cl, F, Br, =O, $CF_3$, $CH_2F$, $CHF_2$, $NR^aR^{a1}$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_r$ $SO_2NR^aR^{a1}$, $(CR^aR^{a1})_rNR^aSO_2R^{a3}$, and phenyl;

alternatively, when two $R^c$ groups are attached to adjacent carbon atoms, together with the carbon atoms to which they are attached they form a 5-6 membered carbocyclic or heterocyclic ring D substituted with 0-1 $R^{c1}$ and consisting of carbon atoms, 0-2 heteroatoms selected from the group consisting of N, O, and $S(O)_p$, and 0-3 double bonds;

$R^e$, at each occurrence, is independently selected from H, $C_{1-6}$ alkyl, $C_{1-6}$ alkoxy, phenoxy, benzoxy, $C_{3-6}$ carbocycle substituted with 0-2 $R^{c1}$, and a 5-6 membered heterocycle consisting of carbon atoms and 1-4 heteroatoms selected from the group consisting of N, O, and $S(O)_p$, and substituted with 0-2 $R^{c1}$;

$R^9$, at each occurrence, is independently selected from H, $(CH_2)_rC(O)(CH_2)_sR^e$, $(CH_2)_rC(O)OR^{a1}$, $(CH_2)_rC(O)NR^aR^{a1}$, $(CH_2)_rS(O)_pR^{a3}$, $(CH_2)_rSO_2NR^aR^{a1}$;
$C_{1-4}$ alkyl substituted with 0-1 $R^{c1}$;
$C_{2-4}$ alkenyl substituted with 0-1 $R^{c1}$;
$C_{2-4}$ alkynyl substituted with 0-1 $R^{c1}$;
$(CH_2)_r$—$C_{3-6}$ carbocycle substituted with 0-2 $R^{c1}$; and
$(CH_2)_r$-5-6 membered heterocycle consisting of carbon atoms and 1-4 heteroatoms selected from the group consisting of N, O, and $S(O)_p$, and substituted with 0-2 $R^{c1}$;

$R^{10}$, at each occurrence, is independently selected from H, $(CH_2)_rNR^aR^{a1}$, $(CH_2)_rC(O)(CH_2)_sR^e$, $(CH_2)_rC(O)OR^{a1}$, $(CH_2)_rC(O)NR^aR^{a1}$, $(CH_2)_tNR^aC(O)R^{a1}$, $(CH_2)_r$ $S(O)_pR^{a3}$, $(CH_2)_rSO_2NR^aR^{a1}$, $(CH_2)_t$ $NR^aSO_2R^{a3}$;
$C_{1-6}$ alkyl substituted with 0-2 $R^{c1}$;
$C_{2-6}$ alkenyl substituted with 0-2 $R^{c1}$;
$C_{2-6}$ alkynyl substituted with 0-2 $R^{c1}$;
$(CH_2)_r$—$C_{3-10}$ carbocycle substituted with 0-2 $R^{c1}$; and
$(CH_2)_r$-5-10 membered heterocycle consisting of carbon atoms and 1-4 heteroatoms selected from the group consisting of N, O, and $S(O)_p$, and substituted with 0-2 $R^{c1}$; and, provided that:
(i) $Z^a$ is other than phenyl substituted with benzoxy, or benzimidazolyl substituted with $C(=NR^a)NR^aR^{a1}$;
(ii) when $R^2$ is —C(O)OH, then U is other than $NR^{a1}S(O)_2$;
(iii) when -U-X-Y- forms —$OCH_2$—, and -$U^a$-$X^a$-$Y^a$- forms —$OCH_2$—, then $Z^a$ is other than phenyl.

[14] In another embodiment, the present invention provides a novel compound of formula (I), wherein:

W is $(CH_2)_m$;
Y is absent;
Z is phenyl substituted with 0-1 $R^b$;
$Z^a$ is selected from:
 phenyl substituted with 0-3 $R^c$;
 naphthyl substituted with 0-3 $R^c$; and
 a heterocycle substituted with 0-3 $R^c$ and selected from the group: pyridyl, quinolinyl, tetrahydroquinolinyl, isoquinolinyl, tetrahydroisoquinolinyl, imidazolyl, pyridoimidazolyl, benzimidazolyl, indolyl, indolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, andpyrazolo[1,5-a]pyridinyl;

$R^1$ is selected from H and $C_{1-6}$ alkylene;
$R^2$ is selected from $Q^1$, $C_{1-6}$ alkylene-$Q^1$, $C_{2-6}$ alkenylene-$Q^1$, $C_{2-6}$ alkynylene-$Q^1$, $(CH_2)_rO(CH_2)_s$-$Q^1$, $(CH_2)_r$ $NR^a(CH_2)_s$-$Q^1$, $(CH_2)_rC(O)(CH_2)_s$-$Q^1$, $(CH_2)_rC(O)O$ $(CH_2)_s$-$Q^1$, $(CH_2)_rC(O)NR^a(CH_2)_s$-$Q^1$, $(CH_2)_rNR^aC(O)(CH_2)_s$-$Q^1$, $(CH_2)_rS(O)_p(CH_2)_s$-$Q^1$, $(CH_2)_rSO_2NR^a(CH_2)_s$-$Q^1$, and $(CH_2)_rNR^aSO_2(CH_2)_s$-$Q^1$;

$R^3$ is selected from H and $C_{1-6}$ alkylene;
$Q^1$, at each occurrence, is selected from H, $C_{3-6}$ cycloalkyl substituted with 0-1 $R^d$, phenyl substituted with 0-2 $R^d$, and a 5-6 membered heterocycle consisting of carbon atoms and 1-4 heteroatoms selected from the group consisting of N, $NR^{10}$, O, and $S(O)_p$, and substituted with 0-2 $R^d$;

alternatively, $R^2$ and $R^3$, together with the carbon atom to which they are attached, combine to form a 5-6 membered carbocyclic or heterocyclic ring consisting of carbon atoms, 0-2 ring heteroatoms selected from O, N, $NR^{10}$, and $S(O)_p$, and 0-2 double bonds;

alternatively, when n is 1, $R^3$ and $R^4$, together with the carbon atoms to which they are attached, combine to form a 5-6 membered carbocyclic or heterocyclic ring consisting of carbon atoms, 0-2 ring heteroatoms selected from O, N, $NR^{10}$, and $S(O)_p$, and 0-2 double bonds;

$R^b$, at each occurrence, is independently selected from $C_{1-6}$ alkyl, $OR^a$, Cl, F, Br, $NR^aR^{a1}$, $C(O)R^a$, $C(O)OR^a$, $C(O)NR^aR^{a1}$, $S(O)_2NR^aR^{a1}$, $NR^aS(O)_2R^{a3}$, $S(O)_pR^{a3}$, and $CF_3$;

$R^c$, at each occurrence, is independently selected from $C_{1-6}$ alkyl, $C_{2-6}$ alkenyl, $C_{2-6}$ alkynyl, $OR^a$, Cl, F, Br, =O, $CF_3$, $NR^aR^{a1}$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, and $(CR^aR^{a1})_rNR^aSO_2R^{a3}$;

alternatively, when two $R^c$ groups are attached to adjacent carbon atoms, together with the carbon atoms to which they are attached they form a 5-6 membered carbocyclic or heterocyclic ring consisting of carbon atoms and 0-2 heteroatoms selected from the group consisting of N, O, and $S(O)_p$;

$R^e$, at each occurrence, is independently selected from H, $C_{1-6}$ alkyl, $C_{1-6}$ alkoxy, phenoxy, benzoxy, phenyl substituted with 0-1 $R^{c1}$, and a 5-6 membered heterocycle consisting of carbon atoms and 1-4 heteroatoms selected from the group consisting of N, O, and $S(O)_p$, and substituted with 0-1 $R^{c1}$;

$R^{10}$, at each occurrence, is independently selected from H, $(CH_2)_rC(O)(CH_2)_sR^e$, $(CH_2)_rC(O)OR^{a1}$, $(CH_2)_rC(O)NR^aR^{a1}$, $(CH_2)_rS(O)_pR^{a3}$, $(CH_2)_rSO_2NR^aR^{a1}$;
$C_{1-4}$ alkyl substituted with 0-1 $R^{c1}$;
$C_{2-4}$ alkenyl substituted with 0-1 $R^{c1}$;
$C_{2-4}$ alkynyl substituted with 0-1 $R^{c1}$;

(CH$_2$)$_r$—C$_{3-6}$ cycloalkyl substituted with 0-2 R$^{c1}$;
(CH$_2$)$_r$-phenyl substituted with 0-2 R$^{c1}$; and
(CH$_2$)$_r$-5-6 membered heterocycle consisting of carbon atoms and 1-4 heteroatoms selected from the group consisting of N, O, and S(O)$_p$, and substituted with 0-2 R$^{c1}$;

m, at each occurrence, is selected from 0, 1, and 2;
r, at each occurrence, is selected from 0, 1, and 2;
s, at each occurrence, is selected from 0, 1, and 2; and
provided that:
(i) Z$^a$ is other than phenyl substituted with benzoxy, or benzimidazolyl substituted with C(=NR$^a$)NR$^a$R$^{a1}$;
(ii) when R$^2$ is —C(O)OH, then U is other than NR$^{a1}$S(O)$_2$;
(iii) when -U-X-Y- forms —OCH$_2$—, and -U$^a$-X$^a$-Y$^a$- forms —OCH$_2$—, then Z$^a$ is other than phenyl.

[15] In another embodiment, the present invention provides a novel compound selected from the group:
2-(2,5-dioxo-4-imidazolidinyl)-N-{4-[(2-methyl-4-quinolinyl)methoxy]phenyl}acetamide;
2-(2,5-dioxo-4-imidazolidinyl)-N-{4-[(2-isopropyl-1H-benzimidazol-1-yl)methyl]phenyl}acetamide;
2-(4-methyl-2,5-dioxo-4-imidazolidinyl)-N-{4-[(2-methyl-4-quinolinyl)methoxy]phenyl}acetamide;
2-(4-methyl-2,5-dioxo-4-imidazolidinyl)-N-(4-phenoxybenzyl)acetamide;
2-(2,5-dioxo-4-imidazolidinyl)-N-{4-[(2-methyl-4-quinolinyl)methoxy]phenyl}propanamide;
3-(2,5-dioxo-4-imidazolidinyl)-N-{4-[(2-methyl-4-quinolinyl)methoxy]phenyl}propanamide;
5-methyl-5-[({4-[(2-methyl-4-quinolinyl)methoxy]phenyl}sulfonyl)methyl]-2,4-imidazolidinedione;
N-[(4-methyl-2,5-dioxo-4-imidazolidinyl)methyl]-4-phenoxybenzamide;
N-[(4-methyl-2,5-dioxo-4-imidazolidinyl)methyl]-4-[(2-methyl-4-quinolinyl)methoxy]benzamide;
N-[(4-methyl-2,5-dioxo-4-imidazolidinyl)methyl]-2-{4-[(2-methyl-4-quinolinyl)methoxy]phenyl}acetamide
N-[(4-methyl-2,5-dioxo-4-imidazolidinyl)methyl]-4-{[2-(methylthio)-1H-benzimidazol-1-yl]methyl}benzamide;
N-[(4-methyl-2,5-dioxo-4-imidazolidinyl)methyl]-4-[(2-methyl-4-quinolinyl)methoxy]benzenesulfonamide;
N-[1-(2,5-dioxo-4-imidazolidinyl)cyclopentyl]-4-[(2-methyl-4-quinolinyl)methoxy]benzamide;
(cis,trans)-N-[1-(2,5-dioxo-4-imidazolidinyl)ethyl]-4-[(2-methyl-4-quinolinyl)methoxy]benzamide;
(cis,trans)-N-[1-(2,5-dioxo-4-imidazolidinyl)-2-(4-morpholinyl)ethyl]-4-[(2-methyl-4-quinolinyl)methoxy]benzamide;
(cis,trans)-N-[1-(2,5-dioxo-4-imidazolidinyl)-2-methylpropyl]-4-[(2-methyl-4-quinolinyl)methoxy]benzamide;
(cis,trans)-N-[1-(2,5-dioxo-4-imidazolidinyl)-3-methylbutyl]-4-[(2-methyl-4-quinolinyl)methoxy]benzamide;
(cis,trans)-N-[cyclopentyl(2,5-dioxo-4-imidazolidinyl)methyl]-4-[(2-methyl-4-quinolinyl)methoxy]benzamide;
(cis,trans)-N-[1-(2,5-dioxo-4-imidazolidinyl)-2-phenylethyl]-4-[(2-methyl-4-quinolinyl)methoxy]benzamide;
(cis,trans)-N-[(2,5-dioxo-4-imidazolidinyl)-(tetrahydro-2H-pyran-4-yl)methyl]-4-[(2-methyl-4-quinolinyl)methoxy]benzamide;
(cis,trans)-tert-butyl-4-[(2,5-dioxo-4-imidazolidinyl)-({4-[(2-methyl-4-quinolinyl)methoxy]benzoyl}amino)methyl]-1-piperidinecarboxylate;
(cis,trans)-N-[(2,5-dioxo-4-imidazolidinyl)-(4-piperidinyl)methyl]-4-[(2-methyl-4-quinolinyl)methoxy]benzamide;
(cis,trans)-N-{(2,5-dioxo-4-imidazolidinyl)-[1-(3-pyridinylmethyl)-4-piperidinyl]methyl}-4-[(2-methyl-4-quinolinyl)methoxy]benzamide;
(cis,trans)-N-{(2,5-dioxo-4-imidazolidinyl)-[1-(4-pyridinylmethyl)-4-piperidinyl]methyl}-4-[(2-methyl-4-quinolinyl)methoxy]benzamide;
(cis,trans)-N-[(1-acetyl-4-piperidinyl)-(2,5-dioxo-4-imidazolidinyl)methyl]-4-[(2-methyl-4-quinolinyl)methoxy]benzamide;
(cis,trans)-N-{(2,5-dioxo-4-imidazolidinyl)-[1-(2-propynyl)-4-piperidinyl]methyl}-4-[(2-methyl-4-quinolinyl)methoxy]benzamide;
(cis,trans)-N-[[1-(2,2-dimethylpropanoyl)-4-piperidinyl](2,5-dioxo-4-imidazolidinyl)methyl]-4-[(2-methyl-4-quinolinyl)methoxy]benzamide;
(cis,trans)-N-{(2,5-dioxo-4-imidazolidinyl)-[1-(methylsulfonyl)-4-piperidinyl]methyl}-4-[(2-methyl-4-quinolinyl)methoxy]benzamide;
(cis,trans)-N-[(1-acetyl-4-piperidinyl)-(2,5-dioxo-4-imidazolidinyl)methyl]-4-[(2-methyl-4-quinolinyl)methyl]benzamide;
(cis,trans)-N-[(1-acetyl-4-piperidinyl)-(2,5-dioxo-4-imidazolidinyl)methyl]-4-[(1,1-dioxido-2,3-dihydro-4H-1,4-benzothiazin-4-yl)methyl]benzamide;
(cis,trans)-N-[(1-acetyl-4-piperidinyl)-(2,5-dioxo-4-imidazolidinyl)methyl]-4-(1,1-dioxido-3,4-dihydro-2H-1-benzothiopyran-4-yl)benzamide;
(cis,trans)-N-[(1-acetyl-4-piperidinyl)-(2,5-dioxo-4-imidazolidinyl)methyl]-4-(2-methyl-4-quinolinyl)benzamide;
(cis,trans)-N-[(1-acetyl-4-piperidinyl)-(2,5-dioxo-4-imidazolidinyl)methyl]-4-(1-naphthylmethoxy)benzamide;
(cis,trans)-N-[(1-acetyl-4-piperidinyl)-(2,5-dioxo-4-imidazolidinyl)methyl]-4-[(5-quinolinyloxy)methyl]benzamide;
(cis,trans)-N-[(1-acetyl-4-piperidinyl)-(2,5-dioxo-4-imidazolidinyl)methyl]-4-[(5-isoquinolinyloxy)methyl]benzamide;
(cis,trans)-N-[(1-acetyl-4-piperidinyl)-(2,5-dioxo-4-imidazolidinyl)methyl]-4-{[(2-methyl-8-quinolinyl)oxy]methyl}benzamide;
(cis,trans)-N-[(1-acetyl-4-piperidinyl)-(2,5-dioxo-4-imidazolidinyl)methyl]-4-[(2-methyl-4-quinolinyl)methoxy]benzenesulfonamide;
(cis,trans)-N-[1-(2,5-dioxo-4-imidazolidinyl)-2-(4-morpholinyl)-2-oxoethyl]-4-[(2-methyl-4-quinolinyl)methoxy]benzamide;
(cis,trans)-tert-butyl 3-(2,5-dioxo-4-imidazolidinyl)-3-({4-[(2-methyl-4-quinolinyl)methoxy]benzoyl}amino)propanoate;
(cis,trans)-3-(2,5-dioxo-4-imidazolidinyl)-3-({4-[(2-methyl-4-quinolinyl)methoxy]benzoyl}amino)propanoic acid;
(cis,trans)-N-[1-(2,5-dioxo-4-imidazolidinyl)-3-(4-morpholinyl)-3-oxopropyl]-4-[(2-methyl-4-quinolinyl)methoxy]benzamide;
(cis,trans)-N-[1-(2,5-dioxo-4-imidazolidinyl)-3-(methylamino)-3-oxopropyl]-4-[(2-methyl-4-quinolinyl)methoxy]benzamide;
(cis,trans)-N-[3-(tert-butylamino)-1-(2,5-dioxo-4-imidazolidinyl)-3-oxopropyl]-4-[(2-methyl-4-quinolinyl)methoxy]benzamide;
(cis,trans)-N-[1-(2,5-dioxo-4-imidazolidinyl)-3-oxo-3-(1-piperazinyl)propyl]-4-[(2-methyl-4-quinolinyl)methoxy]benzamide;
(cis,trans)-N-[1-(2,5-dioxo-4-imidazolidinyl)-3-(4-methyl-1-piperazinyl)-3-oxopropyl]-4-[(2-methyl-4-quinolinyl)methoxy]benzamide;

(cis,trans)-N-[1-(2,5-dioxo-4-imidazolidinyl)-3-(4-morpholinyl)-3-oxopropyl]-4-[(2-methyl-4-quinolinyl)methyl]benzamide;

(cis,trans)-4-[(1,1-dioxido-2,3-dihydro-4H-1,4-benzothiazin-4-yl)methyl]-N-[1-(2,5-dioxo-4-imidazolidinyl)-3-(4-morpholinyl)-3-oxopropyl]benzamide;

N-[3-(2,5-dioxo-4-imidazolidinyl)tetrahydro-2H-pyran-4-yl]-4-[(2-methyl-4-quinolinyl)methoxy]benzamide;

N-[2-(2,5-dioxo-4-imidazolidinyl)cyclopentyl]-4-[(2-methyl-4-quinolinyl)methoxy]benzamide; and N-[2-(2,5-dioxo-4-imidazolidinyl)cyclopentyl]-4-{[2-(trifluoromethyl)-1H-benzimidazol-1-yl]methyl}benzamide;

or a pharmaceutically acceptable salt form thereof.

In another embodiment, the present invention provides a novel pharmaceutical composition, comprising:

a pharmaceutically acceptable carrier and a therapeutically effective amount of a compound of the present invention or a pharmaceutically acceptable salt form thereof.

In another embodiment, the present invention provides a novel method for treating or preventing an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TACE, aggrecanase, or a combination thereof in a mammal, comprising:

administering to the mammal in need of such treatment a therapeutically effective amount of a compound of the present invention or a pharmaceutically acceptable salt form thereof.

In another embodiment, the present invention provides a novel method comprising: administering a compound of the present invention or a pharmaceutically acceptable salt form thereof in an amount effective to treat a condition or disease mediated by MMPs, TACE, aggrecanase, or a combination thereof.

In another embodiment, the present invention provides a novel method of treating a disease or condition, wherein the disease or condition is selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, aggrecanase, or a combination thereof.

In another embodiment, the present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "independently selected from", "independently, at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

It is understood by one skilled in the art that in Formula I, once $R^2$ and $R^3$ together with the carbon atom to which they are attached combine to form a ring, $R^3$ is not available to form a ring with $R^4$. Similarly, once $R^3$ and $R^4$ together with the carbon atom to which they are attached combine to form a ring, $R^4$ is not available to form a ring with $R^5$.

In cases wherein there are amines on the compounds of this invention, these can be converted to amine N-oxides by treatment with MCPBA and or hydrogen peroxides to afford other compounds of this invention. Thus, all shown amines are considered to cover both the shown amine and its N-oxide (N→O) derivative.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalky" is intended to include both branched and straight-chain saturated aliphatic hydrocarbon groups having the specified number of carbon atoms, substituted with 1 or more halogen (for example —$C_vF_w$ wherein v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4H-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, imidazo[1,2-a]pyridinyl, imidazo[1,5-a]pyridinyl, and pyrazolo[1,5-a]pyridinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is, bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e, =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anti-inflammatory effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Hydantoin heterocycles of Formula I in the present invention can be synthesized using a variety of literature methods both in solution and on solid support (see for instance, Matthews, J. and Rivero, R. A. *J. Org. Chem.* 1997, 62, 6090-6092). Several syntheses of these heterocycles are listed in Scheme 1.

Scheme 1.
Heterocycle Synthetic Routes (1) hydantoins from α-amino acids and esters

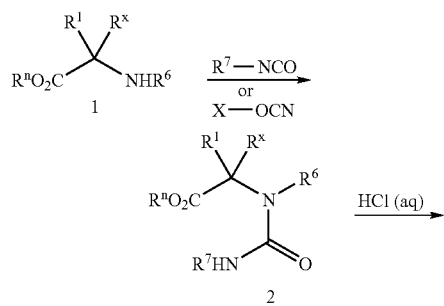

(2) hydantoins from ketones and aldehydes (the Bucherer-Bergs reaction)

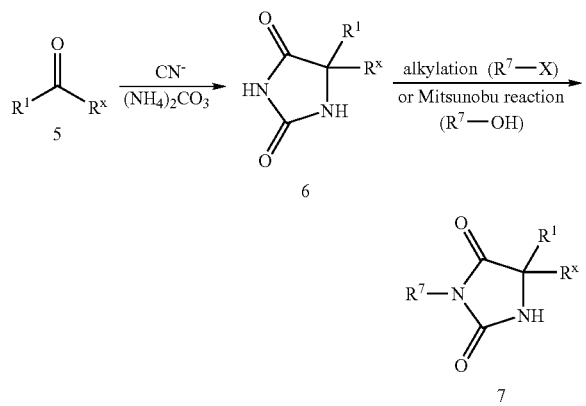

(3) hydantoins from amino nitriles (the Strecker Reaction)

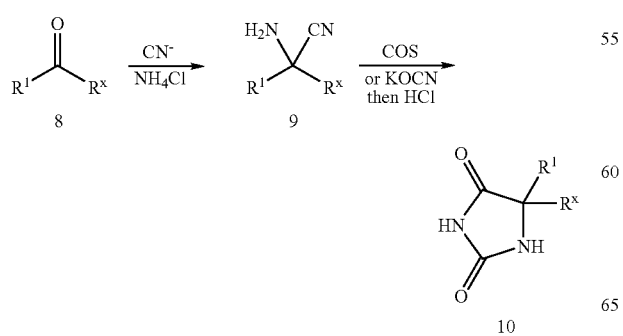

(4) hydantoins from carboxylic acids

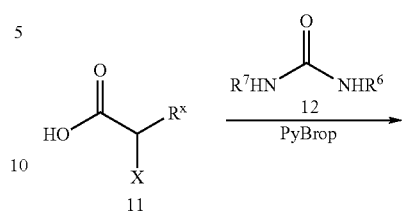

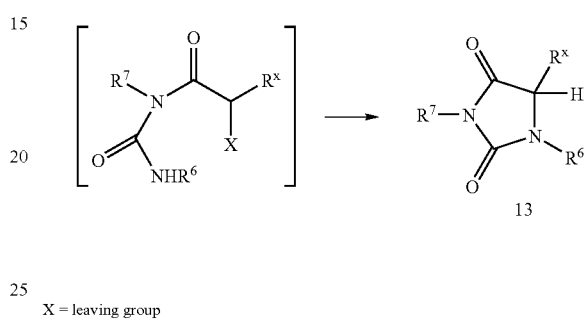

X = leaving group (5) hydantoins and thiohydantoins from α-amino amides

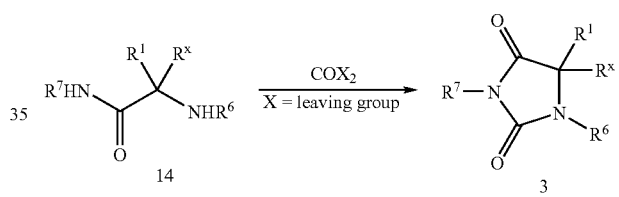

(6) hydantoins and thiohydantoins from α-amino esters

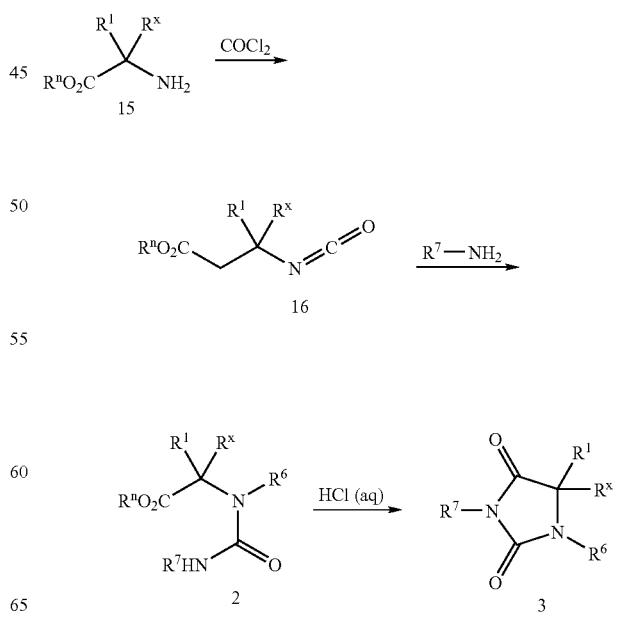

Route (1) in Scheme 1 involves reacting an α-amino acid (or its ester) 1 possessing variable substitution with either an isocyanate to form an intermediate substituted urea or with a cyanic acid salt (X—OCN; wherein X is a cationic group eg. $Na^+$, $Me_4N^+$, etc.) to form an intermediate unsubstituted urea 2. Treatment with acid results in cyclization to form the fully functionalized hydantoin core structure 3 that can be optionally deprotected if $R^6$ and $R^7$ are protecting groups (e.g. benzyl, trimethylsilyl, etc.; see Greene and Wuts, "Protecting Groups in Organic Synthesis" $3^{rd}$ Ed. 1999) to give compound 4.

Route (2) in Scheme 1 is the classical Bucherer-Bergs reaction used to form hydantoins from ketones or aldehydes 5 in the presence of cyanide ion and ammonium carbonate (see Bucherer and Steiner *J. Prakt. Chem.* 1934, 140, 291). The resulting hydantoin 6 can be optionally functionalized at the 3-position using standard alkylation or a Mitsunobu reaction known to one skilled in the art to give 7.

Route (3) in Scheme 1 is another route to hydantoins that takes advantage of the Strecker reaction (see Sacripante, G. and Edward, J. T. *Can J. Chem.* 1982, 60, 1982-1988). Treatment of ketone 8 with cyanide ion and ammonium chloride gives an intermediate amino nitrile 9 that can further react with carbonyl sulfide to give the product of substructure 10. Alternatively, intermediate 9 can be hydrolyzed in aqueous acid to form α-amino acids that can serve as starting materials for Route (1). In this respect, a variety of hydantoins can be synthesized following literature procedures used to make α-amino acids.

Route (4) in Scheme 1 shows a method for making hydantoins by coupling substituted ureas to a carboxylic acid that contains a leaving group at the α position 11 (e.g. α-chloro carboxylate). Coupling the acid 11 and a urea 12 can be accomplished using a peptide coupling reagent (e.g. PyBrop) or by converting the carboxyic acid to an acid chloride and reacting it with the urea. The urea intermediate then undergoes an intramolecular SN2 reaction to yield the final product 13.

Route (5) in Scheme 1 illustrates hydantoin synthesis from α-amino amides 14, which are made using well-established amide bond forming reactions known to one skilled in the art. Treatment of 14 with phosgene (and equivalents such as carbonyl diimidazole) directly yields the final substituted hydantoin 3.

Route (6) in Scheme 1 depicts a method used by Nowick et al. (*J. Org. Chem.* 1996, 61, 3929-3934) to synthesize hydantoins from amino acid esters. Treatment of an amino acid ester 15 with phosgene provides an intermediate isocyanate of structure 16. This intermediate is then reacted with variously susbstituted amines to give a urea of structure 2 which is cyclized under acidic conditions as described earlier to give the product heterocycle 3.

Compounds possessing the spirocyclic ring systems in formula I can be synthesized following the representative routes described below.

Scheme 2 shows that an ester substituted carbocyclic or heterocyclic ketone can undergo the Bucherer-Bergs reaction (Scheme 1, route 2) followed by saponification to compound 18. This intermediate can be coupled using a peptide coupling reagent to furnish spirocyclic hydantoin 19.

Scheme 2.
Amide substituted spirocyclic hydantoin synthesis

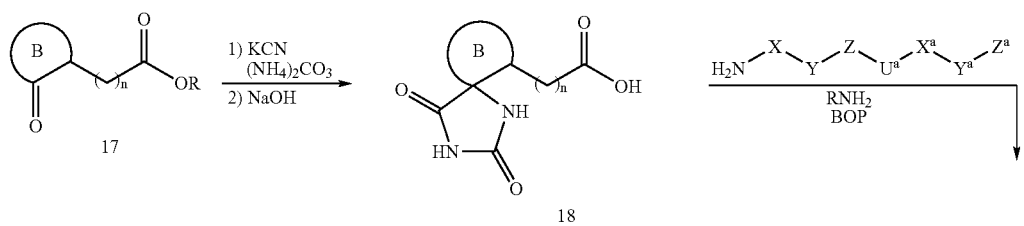

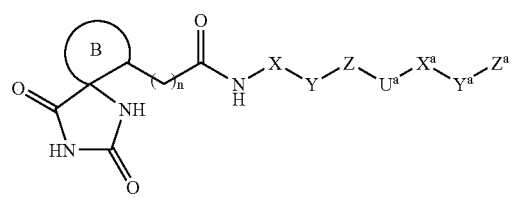

A series of compounds of formula (I) wherein ring B is a pyrrolidine are prepared following the route shown in Scheme 3. Epoxide 20 derived from commercially available Boc-3-pyrroline can be opened with vinylmagnesium bromide to furnish alcohol 21. The alkene is transposed to a carboxylic acid using ozonolysis followed by oxidation to the acid and then coupled to a diverse set of amines using a reagent such as PYBOP to give compound 23. Dess-Martin periodinane oxidation of the alcohol followed by the Bucherer-Bergs reaction (Scheme 1, route 2) gives the hydantoin product 24. The Boc-protected pyrrolidine can be unmasked with TFA and futher diversified using either reductive amination conditions or acylation to give the final analogs 25.

Scheme 4.
Spirocyclic hydantoin synthesis-reversed amide

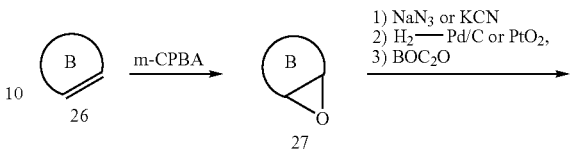

Scheme 3.
Spirocyclic pyrrolidine synthesis

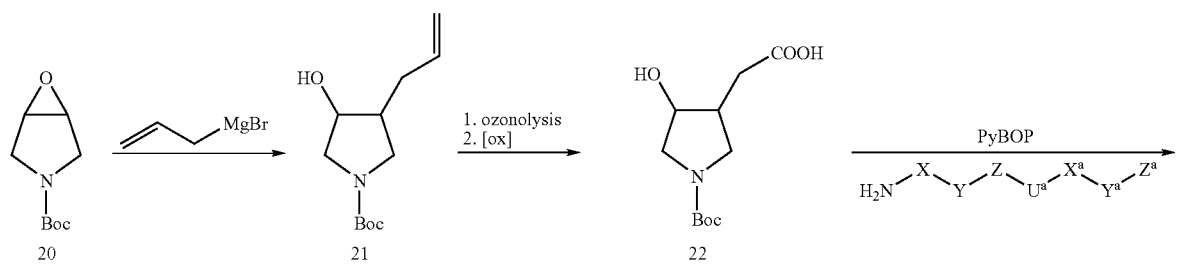

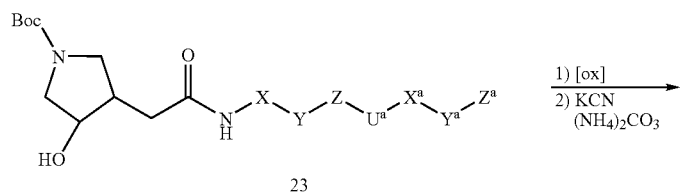

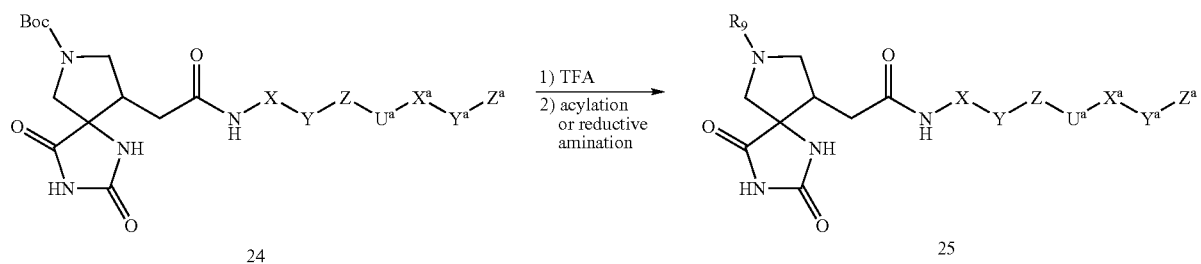

Synthesis of spirocyclic hydantoins wherein the side chain functionality contains a reversed amide to those found in Schemes 2 and 3 is illustrated in Scheme 4. These compounds can be synthesized starting from a cyclic alkene that is epoxidized using mCPBA. Epoxide 27 can be nucleophilically opened using either azide or cyanide followed by reduction to give the amino or aminomethyl substituted ring system. Boc protection of the primary amine followed by alcohol oxidation, Bucherer-Bergs reaction, and Boc deprotection gives intermediate 30 that is coupled using peptide coupling reagents to give products 31.

-continued

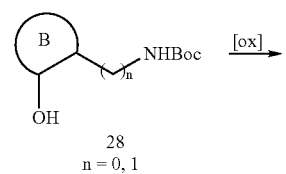

-continued
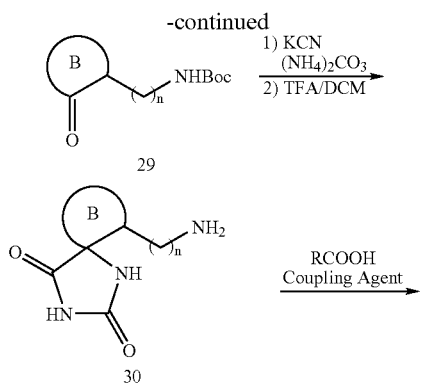
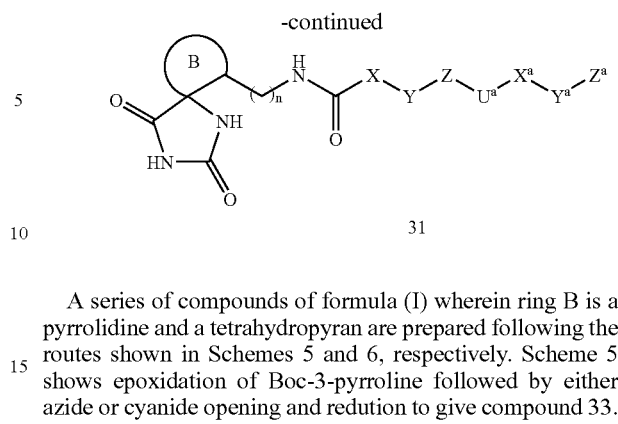
A series of compounds of formula (I) wherein ring B is a pyrrolidine and a tetrahydropyran are prepared following the routes shown in Schemes 5 and 6, respectively. Scheme 5 shows epoxidation of Boc-3-pyrroline followed by either azide or cyanide opening and reduction to give compound 33.
Scheme 5.
Spirocyclic pyrrolidine hydantoin synthesis
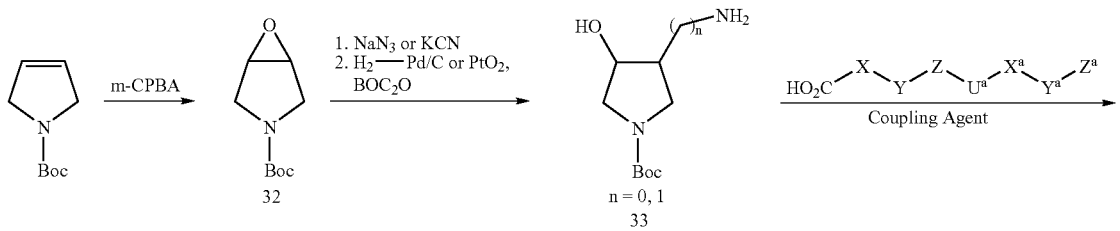
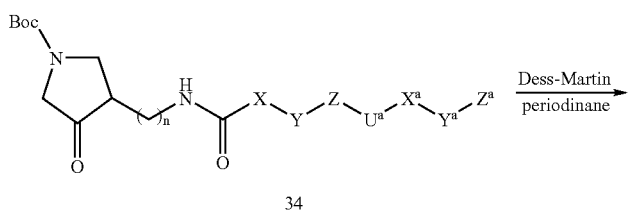
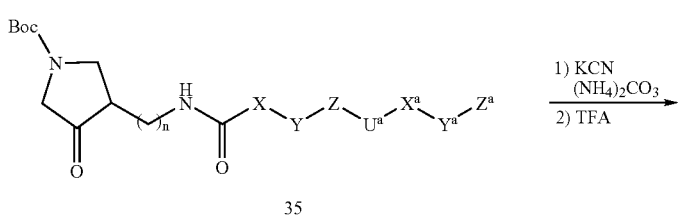
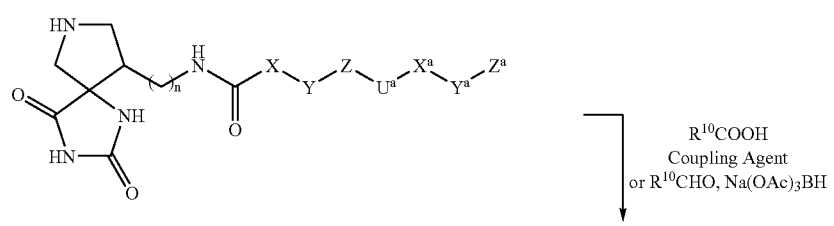

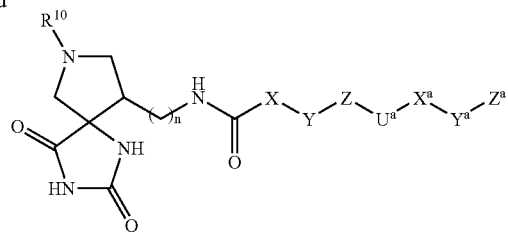

37

Coupling of diverse acids to intermediate 33 followed by Dess-Martin periodinane oxidation, the Bucherer-Bergs reaction, and TFA-mediated Boc deprotection gives compound 36. The pyrrolidine nitrogen can be either reductively aminated or acylated to give final compounds of structure 37.

Compound 38 in Scheme 6 is synthesized according to the literature (Tetrahedron, 1995, 11075-11086) and the azide was reduced with Pd on carbon and hydrogen followed by Boc protection of the amine. Bucherer-Bergs reaction gives compound 40 which is deprotected with TFA and the resulting amine coupled to various acids to give the product 41.

ketone 42 or an enone 43 (prepared from paraformaldehyde and the ketone) with thiols such as 4-hydroxythiophenol forms sulfides of general structure 44. The free phenol is then alkylated under standard conditions to provide compound 45 which undergoes the Bucherer-Bergs reaction to give compound 46. This intermediate may be optionally oxidized to a sulfoxide or sulfone using Oxone® or other oxidants giving product 47.

Scheme 6.
Spirocyclic tetrahydropyran hydantoin synthesis

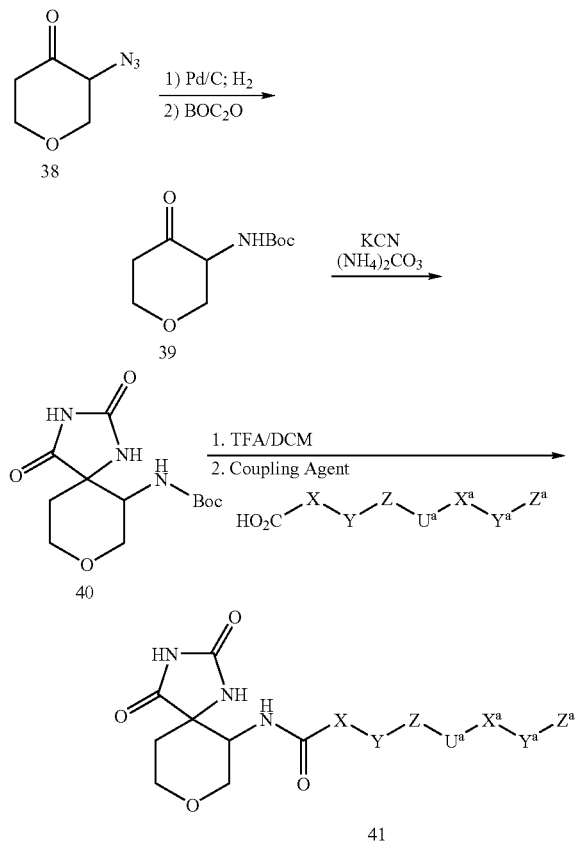

Scheme 7.
Spirocyclic hydantoin synthesis with sulfur-containing side chain

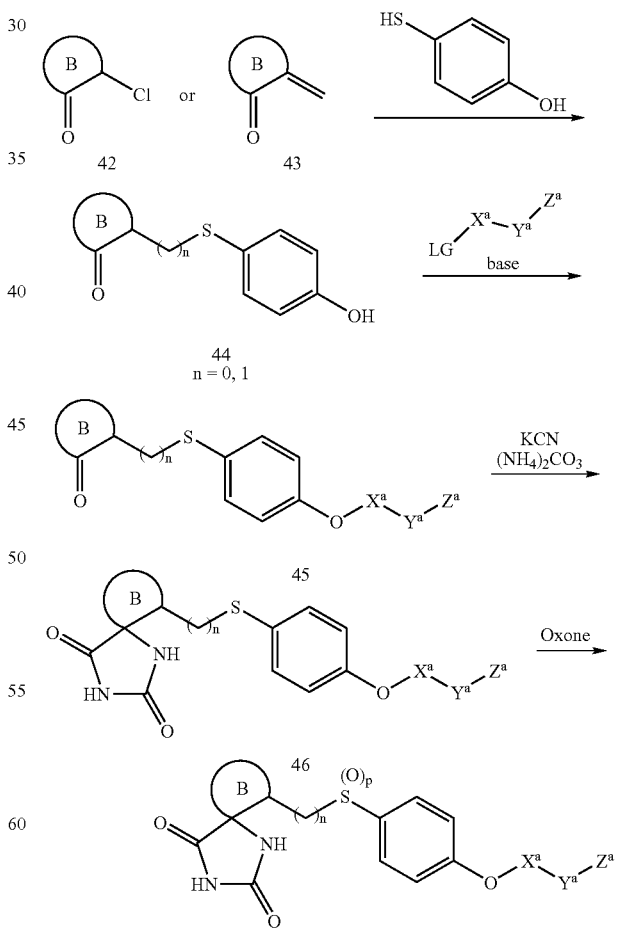

The synthesis of sulfur-containing side chains of the spirocyclic hydantoins is achieved using the synthetic methods outlined in Scheme 7. Reaction of either an α-chloro cyclic Another class of compounds of Formula I are the non-spirocyclic hydantoins. Various substitution patterns can be synthesized using the route depicted in Scheme 8. Starting from an optionally substituted aspartic or glutamic acid, treatment with potassium cyanate followed by acid-promoted cyclization gives the hydantoin 49 which can be coupled under standard conditions to give the product compound 50.

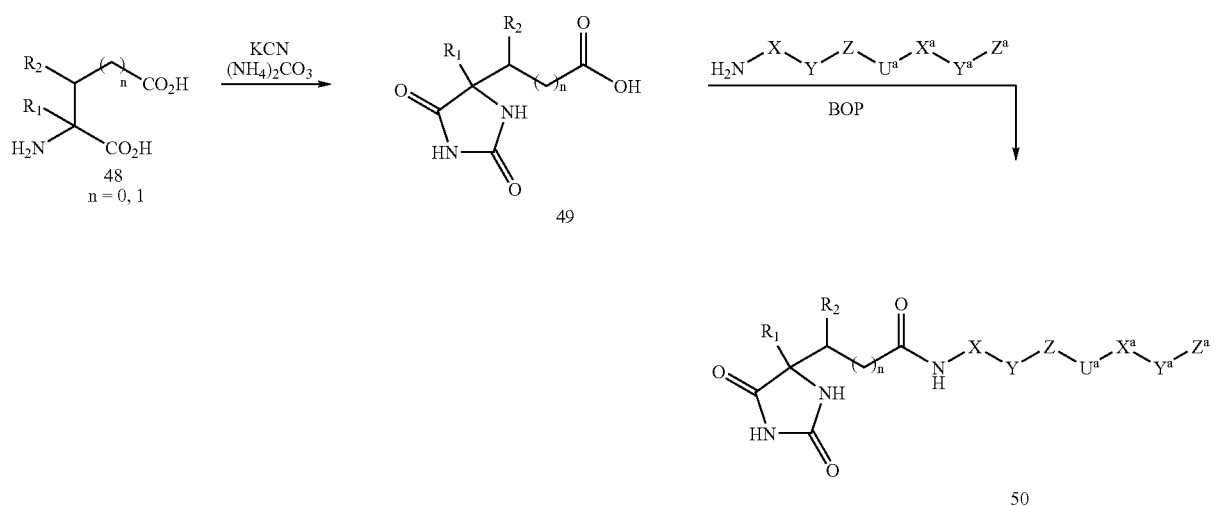

Another synthetic approach is shown in Scheme 9. CBZ-protected amino acid 51 can be reduced with borane-THF complex to give a primary alcohol that can be oxidized back to the aldehyde using Dess-Martin periodinane or $SO_3$-pyridine complex. Bucherer-Bergs reaction installs the hydantoin and the α amine is deprotected using hydrogenolysis and functionalized by coupling to a diverse set of acylators such as a carboxylic acid under peptide coupling conditions. When the amino acid 51 is aspartic acid ester ($R=CH_2CO_2tBu$), the ester may be deprotected with acid and coupled to amines to form amides of the structure 54.

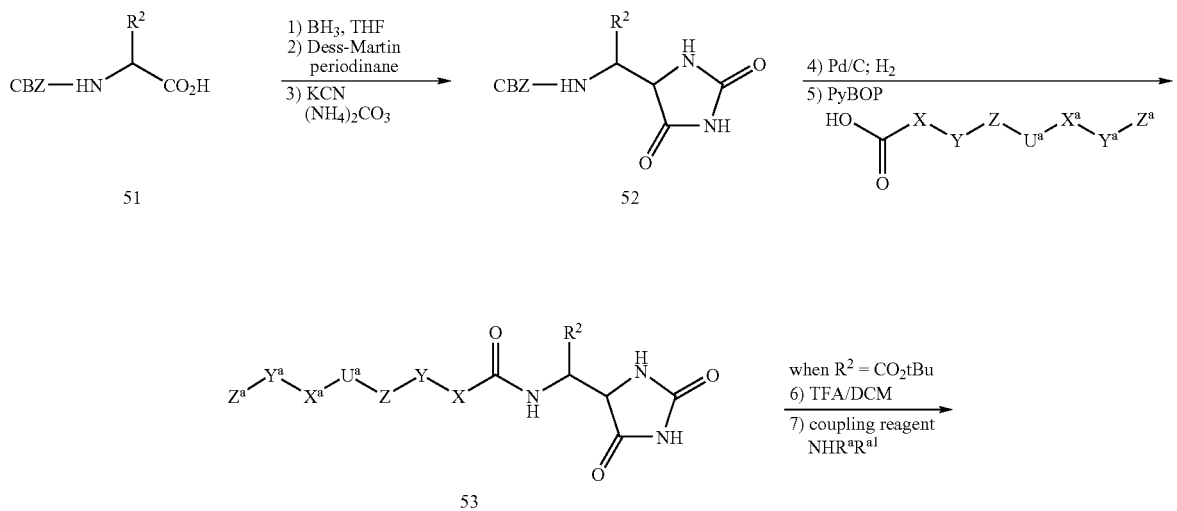

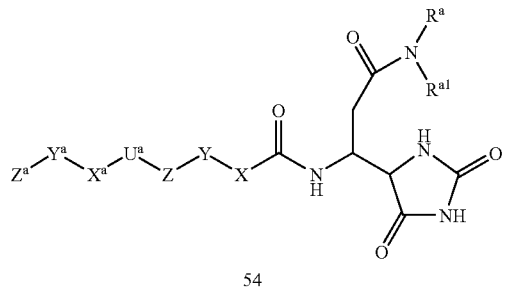

54

The one carbon shorter homolog of compound 54 can be prepared from Boc-serine as illustrated in Scheme 10. CBZ-serine is coupled with an amine, oxidized to an aldehyde which is in turn converted to the hydantoin using the Bucherer-Bergs reaction to yield compound 56. Deprotection of the CBZ group followed by coupling to the amine gives compound 57.

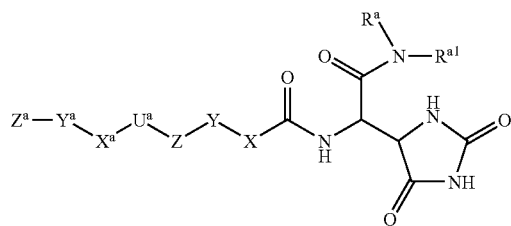

57

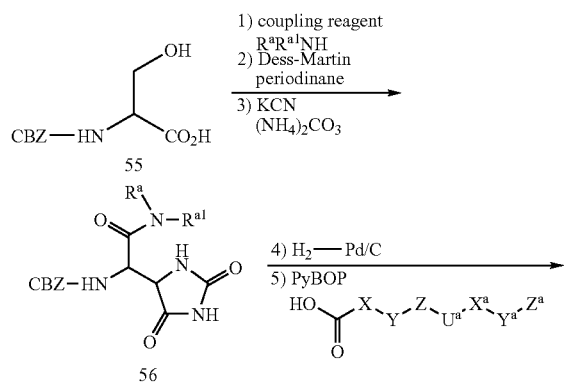

As previously shown in Schemes 9 and 10, amino alcohols serve as convenient starting materials for the synthesis of a variety of amide-substituted hydantoins. Schemes 11 and 12 show more general syntheses of non-spirocyclic hydantoins starting from either 1,2-aminoalcohols or, as shown by compound 62, 1,3-aminoalcohols. Products 60 and 63 can have a wide variety of substitution patterns and ring systems.

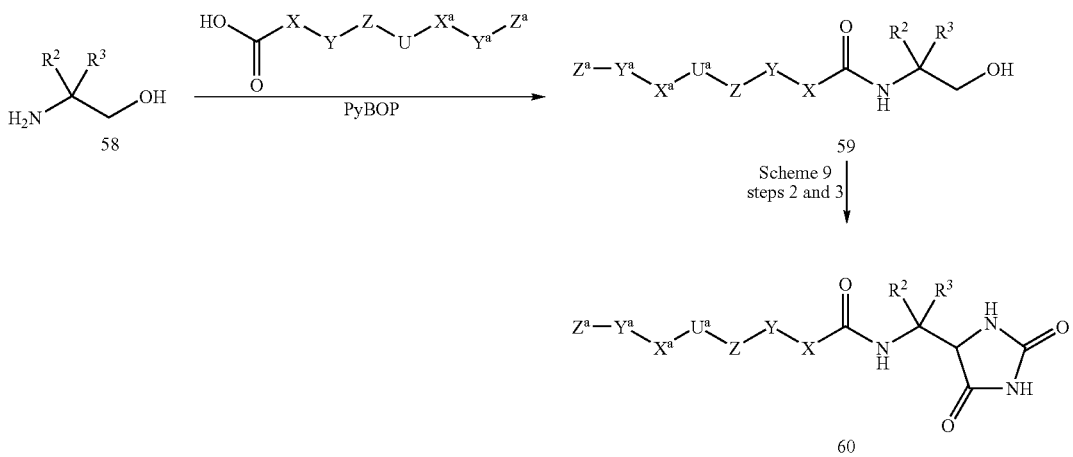

Scheme 12.
Synthesis of non-spirocyclic hydantoins

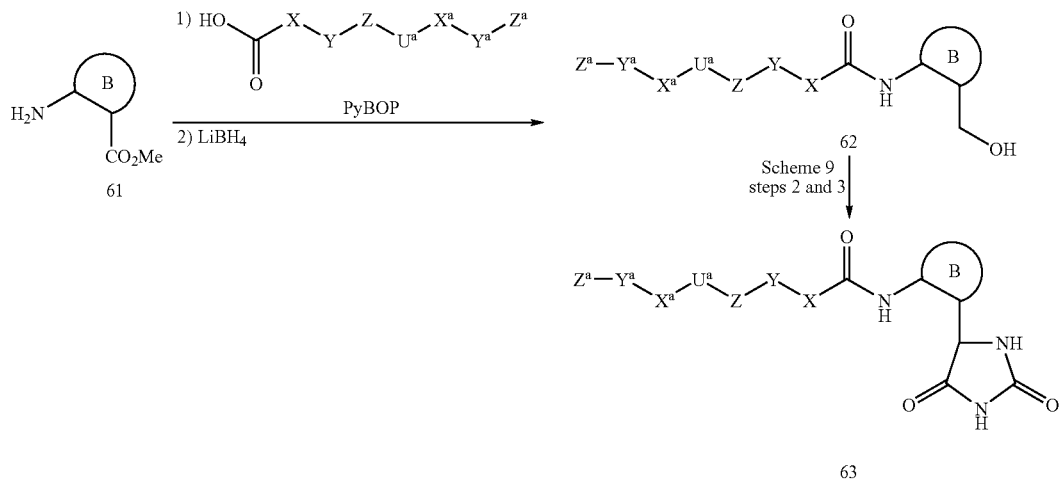

A convenient means of synthesizing α-amino acids with heterocyclic substitution at the α-position is using the synthetic route in Scheme 13. Commercially available phosphonate 64 can be condensed with either carbocyclic, heterocyclic, or acyclic ketones and aldehydes followed by reduction with Pd on carbon which concomittantly removes the CBZ protecting group and saturates the olefin installed by the Horner-Emmons-Wadsworth reaction. Coupling with a variety of side chains gives compound 66 which is transposed to the hydantoin using synthetic sequences already described.

Scheme 13.
Synthesis of non-spirocyclic hydantoins

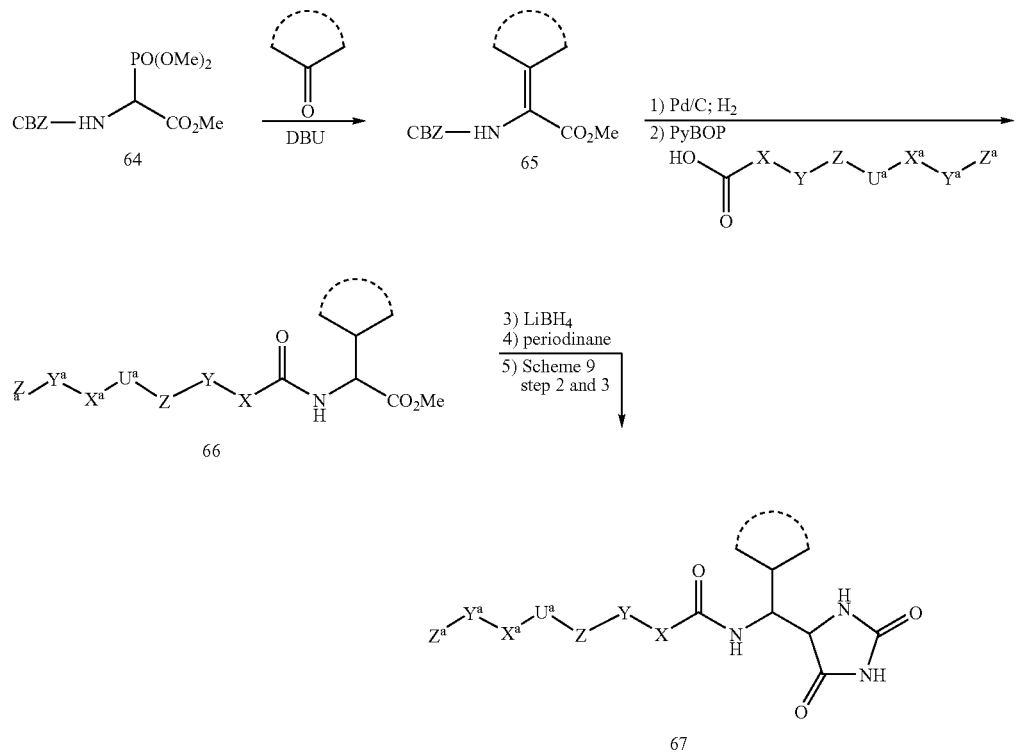

Scheme 14 shows the generality of scaffold acylation using diverse coupling partners to make compounds of Formula I. Diverse carboxylic acids may be coupled to the various scaffold amines 68 and 71 using peptide coupling reagents described in the literature (see Humphrey, J. M. and Chamberlin, A. R. *Chem. Rev.* 1997, 97, 2243-2266) to form amides such as 69 and 72 and related structures described in Formula I. Alternatively, the carboxylic acids may be converted into their respective acid chlorides, acid fluorides, mixed anhydrides, etc using methods known to one skilled in the art and likewise reacted with the amines such as 68 and 71. Use of sulfonyl chlorides yields compounds such as 70 and 73. Acylations of scaffolds 73 and 75 and the like with diverse amines yield "reversed amides" products of structures 74 and 76. These reactions, like the other amide bond forming reactions, can be accomplished as described above using suitable peptide coupling reagents.

Scheme 14.
Representative Acylation Reactions of Scaffolds

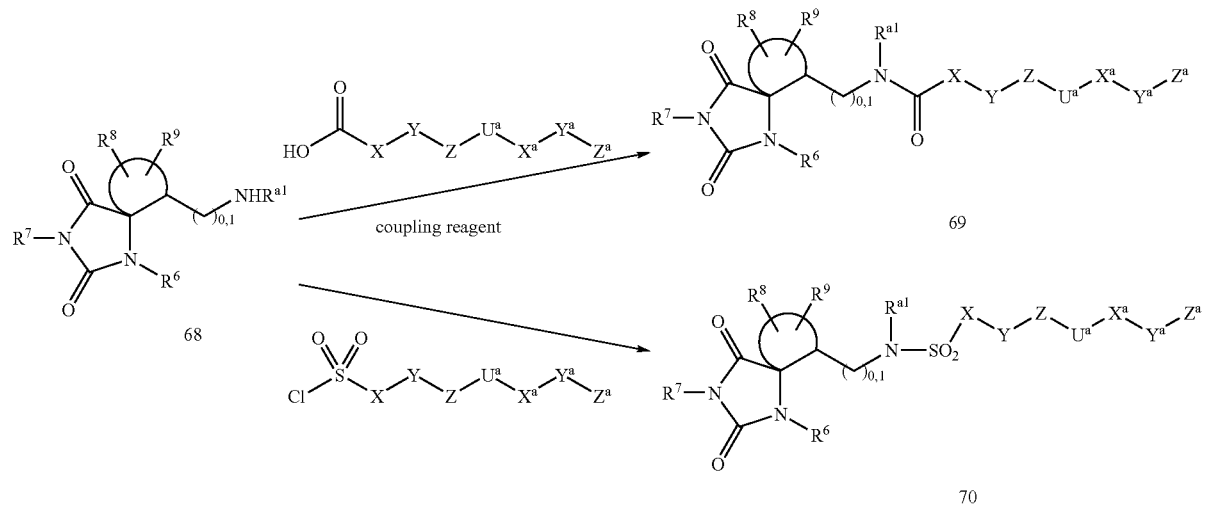

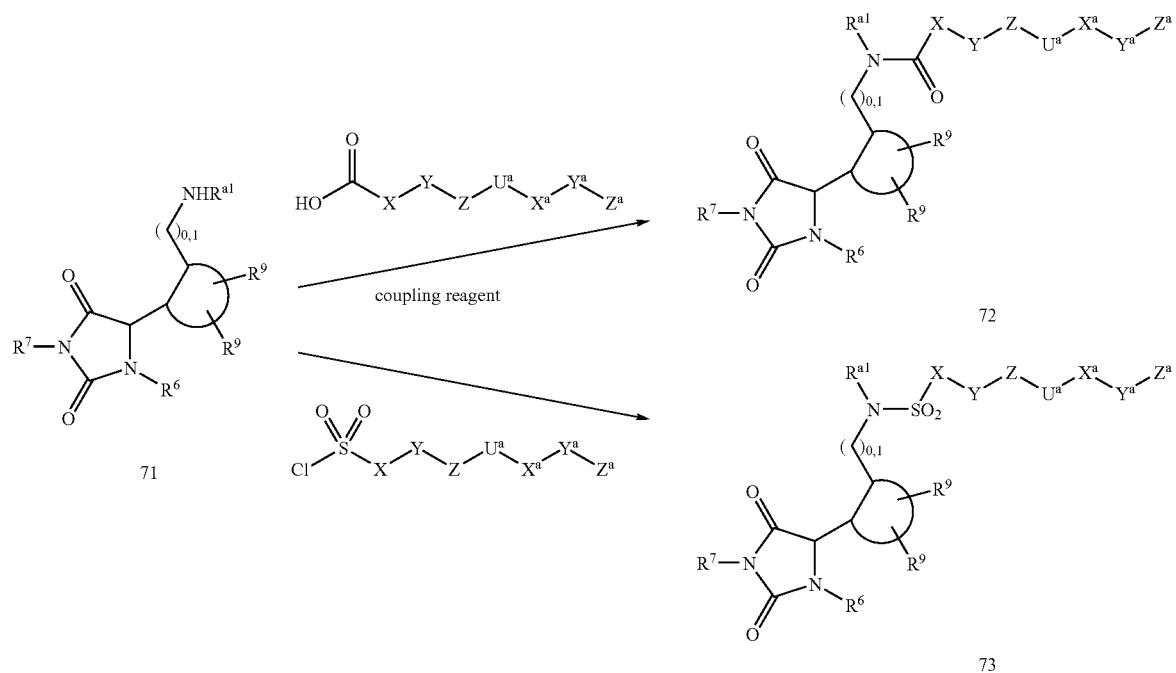

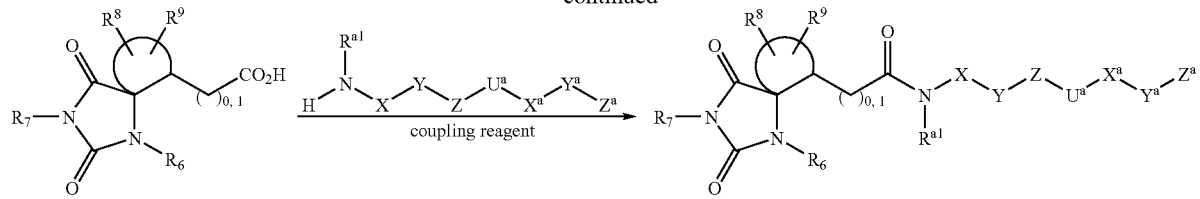

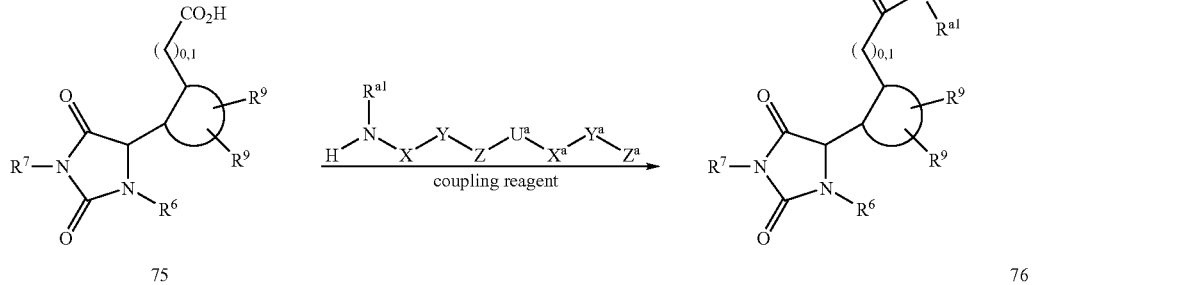

One diastereomer of a compound of Formula I may display superior activity compared with the others. Thus, the following stereochemistries are considered to be a part of the present invention.

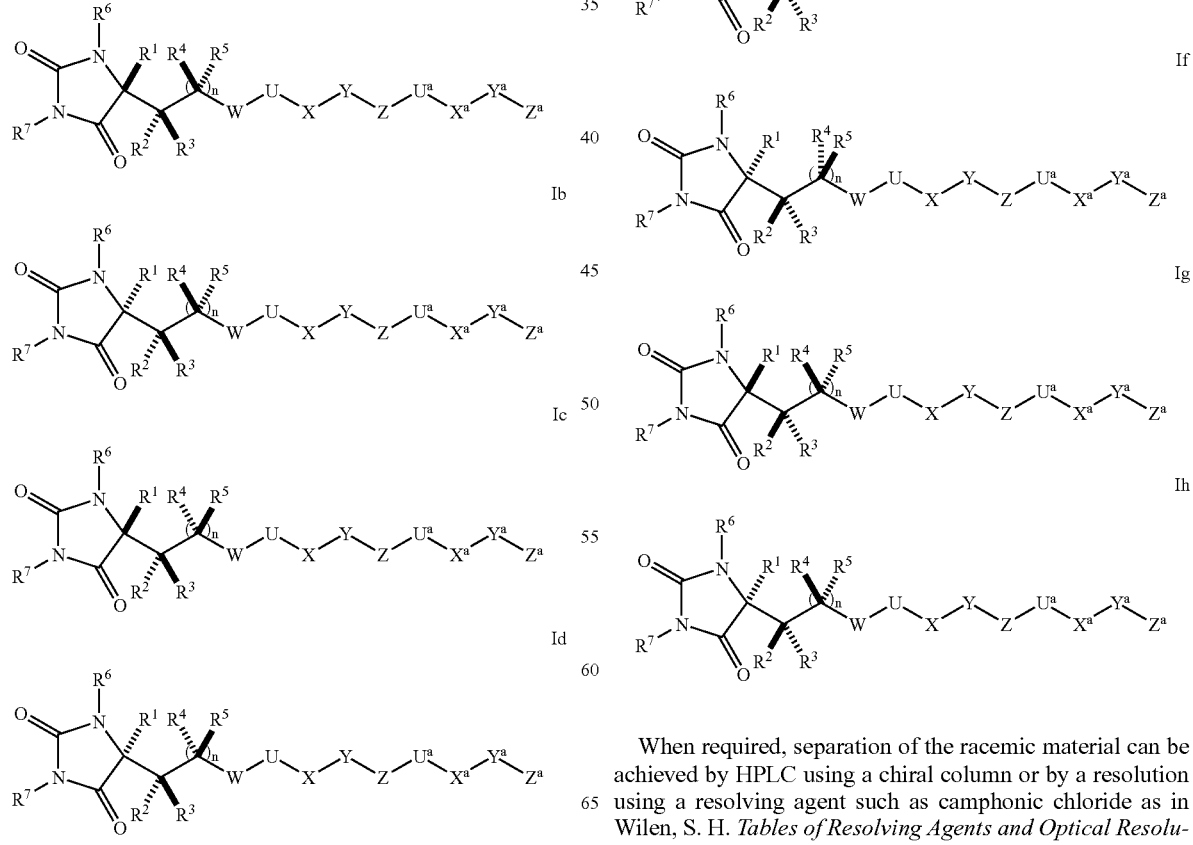

When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

General Coupling Method A: The starting carboxylic acid or amine was dissolved in either DMF or DMSO (0.2 to 1.5 M) followed by the carboxylic acid or amine coupling partner (1-1.2 molar equivalents) and organic base (iPr$_2$NEt, 4-methylmorpholine, or Et$_3$N; 2-5 molar equivalents). An equimolar amount of PYBOP was added and the reaction stirred at rt for 1-18 h using TLC monitoring. The reaction was worked up by extraction from sat KH$_2$PO$_4$ or NaHCO$_3$ buffer into EtOAc×3, the organic layers were combined, dried over MgSO$_4$, filtered, and concentrated. Crude reactions were purified by HPLC on a C$_{18}$ reversed-phase column using CH$_3$CN/H$_2$O (containing 0.1% TFA) gradients followed by lyophilization unless otherwise indicated.

General Coupling Method B: The starting carboxylic acid or amine was dissolved in either DMF or DMSO (0.2 to 1.5 M) followed by the carboxylic acid or amine coupling partner (1-1.2 molar equivalents) and organic base (iPr$_2$NEt, 4-methylmorpholine, or Et$_3$N; 2-5 molar equivalents). An equimolar amount of BOP reagent was added and the reaction stirred at rt for 1-18 h using TLC monitoring. The reaction was worked up by extraction from sat KH$_2$PO$_4$ or NaHCO$_3$ buffer with EtOAc×3, the organic layers were combined, dried over MgSO$_4$, filtered, and concentrated. Crude reactions were purified by HPLC on a C$_{18}$ reversed-phase column using CH$_3$CN/H$_2$O (containing 0.1% TFA) gradients followed by lyophilization unless otherwise indicated.

General Method C (Bucherer-Bergs Reaction): The starting aldehyde or ketone is dissolved in a mixture of ethanol/water (between 80% to 50% EtOH) in a thick-walled sealed glass tube or stainless steel vessel and treated with KCN (4 eq) and ammonium carbonate (6-10 eq). The reaction was heated to between 70 and 120° C. for 4-24 h after which it was extracted from sat NaHCO$_3$ buffer into EtOAc×3, the organic layers were combined, dried over MgSO$_4$, filtered, and concentrated. Crude reactions were purified by HPLC on a C$_{18}$ reversed-phase column using CH$_3$CN/H$_2$O (containing 0.1% TFA) gradients followed by lyophilization unless otherwise indicated.

Example 1

(cis,trans)-N-{4-[(2-methyl-4-quinolinyl)methoxy]phenyl}-2,4-dioxo-1,3-diazaspiro[4.5]decane-6-carboxamide (1a) Following the general procedure of Sacripante and Edward (*Can. J. Chem.* 1982, 60, 1982-1987) a solution of 2-(ethylcarboxy)cyclohexanone (1.41 g, 7.89 mmol) in 20 mL 1:1 EtOH/water was added ammonium carbonate (2.51 g, 26.0 mmol) and potassium cyanide (617 mg, 9.48 mmol). The reaction was heated in a 50° C. oil bath for 24 hr. The reaction was concentrated on a rotary evaporator and the aqueous solution acidified with conc HCl. The reaction was filtered through a sintered glass funnel and the filtrate washed with water, EtOAc, and dried in vacuum dessicator to give 1.08 g (57% yield) of the target. MS found: (M+H)$^+$=241.

(1b) The hydantoin ester 1a (1.08 g, 4.50 mmol) was refluxed for 18 hr in 4 M HCl, concentrated on a rotary evaporator and cooled in a refridgerator overnight. The solid was filtered, washed with water and EtOAc and dried in a vacuum dessicator to give 539 mg (56% yield) of the carboxylic acid 1b. MS found: (M+H)$^+$=213.

(1c) A solution of 1b (94 mg, 0.44 mmol) in 1 mL DMSO was treated with diisopropylethylamine (207 uL, 1.18 mmol) and PyBOP (231 mg, 0.44 mmol) for 30 min followed by the addition of 4-[(2-methyl-4-quinolinyl)methoxy]-aniline bis HCl salt (100 mg, 0.296 mmol). The reaction was stirred at rt overnight and then extracted from 1:1 brine/sat NaHCO$_3$ with EtOAc×3. The combined organic extracts were dried over MgSO$_4$, filtered, concentrated on a rotary evaporator and purified by reverse-phase HPLC to give 45 mg of the product hydantoin as a TFA salt (26% yield). MS found: (M+H)$^+$=459.

Example 2

(cis,trans)-N-{4-[(2-methyl-4-quinolinyl)methoxy]phenyl}-2,4-dioxo-1,3-diazaspiro[4.4]nonane-6-carboxamide (2a) Following the procedure of Curry et al. (*Can. J. Chem.* 1993, 71, 76-83) a solution 2-(ethylcarboxy)cyclopentanone (1.33 g, 8.09 mmol) in 20 mL 1:1 EtOH/water was added ammonium carbonate (2.57 g, 26.7 mmol) and potassium cyanide (617 mg, 9.49 mmol). The reaction was heated in a 50° C. oil bath for 21 hr. The reaction was partitioned between EtOAc and water and the aqueous phase was concentrated on rotary evaporator, acidified with 4 M HCl (9 mL), and refluxed overnight. The aqueous layer was concentrated giving a white solid that was filtered and dried in vacuum dessicator to give 590 mg (37% yield for two steps) of 2a. MS found: (M+H)$^{30}$=199.

(2b) Carboxylic acid 2a (65 mg, 0.328 mmol) was dissolved in 1 mL DMSO and treated with diisopropylethylamine (171 uL, 0.982 mmol) and HATU (131 mg, 0.345 mmol) for 30 min followed by the addition of 4-[(2-methyl-4-quinolinyl)methoxy]aniline bis-HCl salt (166 mg, 0.492 mmol). The reaction was stirred at rt overnight and then extracted from 1:1 brine/sat NaHCO$_3$ with EtOAc×3. The combined organic extracts were dried over MgSO$_4$, filtered, concentrated on a rotary evaporator and purified by reverse-phase HPLC. 5 mg of one diastereomer 2b-1 and 10 mg of the other diastereomeric product 2b-2 as TFA salts (8% yield) were obtained. MS found: (M+H)$^+$=445.

Example 3

(cis,trans)-2-(2,4-dioxo-1,3-diazaspiro[4.4]non-6-yl)-N-{4-[(2-methyl-4-quinolinyl)methoxy]phenyl}acetamide (3a) Starting from commercially available methyl 2-oxocyclopentyl acetate (2.8 g, 18 mmol) the 3 step procedure used to make compound 1 was followed. The product amide 3a was synthesized and purified by reverse phase HPLC to give two diastereomeric compounds 3a-1 and 3a-2 as TFA salts (30 mg and 18 mg, respectively, 12% total). MS found: (M+H)$^+$=459.

Example 4

(cis,trans)-N-(2,4-dioxo-1,3-diazaspiro[4.4]non-6-yl)-4-[(2-methyl-4-quinolinyl)methoxy]benzamide (4a) Following the general procedure of Sacripante and Edward (*Can. J. Chem.* 1982, 60, 1982-1987), a solution of N-t-butoxycarbonyl-2-aminocyclopentanone (350 mg, 1.76 mmol); prepared using the procedure of Aube et al.; (*Synthetic Commun.* 1992, 22, 3003-3012) in 9 mL 2:1 EtOH/water was treated with ammonium carbonate (676 mg, 7.04 mmol) and potassium cyanide (231 mg, 3.52 mmol). The reaction was heated in a 50° C. oil bath for 24 hr. The reaction was concentrated on a rotary evaporator and the aqueous solution acidified with conc HCl. The reaction was filtered through a sintered glass funnel and the filtrate washed with water, EtOAc, concentrated on a rotary evaporator and purified by silica gel chromatography to give 0.118 g (25% yield) of the hydantoin.

(4b) Compound 4a (120 mg, 4.50 mmol) was stirred for 1 hr in TFA/CH$_2$Cl$_2$ (2:1, 5 mL) and concentrated on a rotary evaporator to give 125 mg (100% yield) of the amine 4b which was taken to the next step without purification.

(4c) A solution of 4b (42 mg, 0.148 mmol) in 10 mL 10% aq. NaHCO$_3$/CH$_2$Cl$_2$ (1:1) was treated with 4-[(2-methyl-4-quinolinyl)methoxy]benzoyl chloride (0.060 g, 0.16 mmol). The reaction was stirred at rt for 2 hr and then extracted from 1:1 brine/sat NaHCO$_3$ with EtOAc×3. The combined organic extracts were dried over MgSO$_4$, filtered, concentrated on a rotary evaporator and purified by reverse-phase HPLC to yield 15 mg of one diastereomeric hydantoin as a TFA salt (18% yield). MS found: (M+H)$^+$=445.

Example 5

(cis,trans)-N-(2,4-dioxo-1,3-diazaspiro[4.4]non-6-yl)-2-{4-[(2-methyl-4-quinolinyl)methoxy]phenyl}acetamide A solution of 4b (42 mg, 0.148 mmol) was dissolved in 3 mL DMSO and treated with cesium carbonate (652 mg, 2.0 mmol), PyBOP (104 mg, 0.20 mmol), 4-[(2-methyl-4-quinolinyl)methoxy]phenyl acetyl chloride HCl salt (61 mg, 0.20 mmol). The reaction was stirred at 50° C. overnight and then extracted from KH$_2$PO$_4$ with EtOAc×3. The combined organic extracts were dried over MgSO$_4$, filtered, concentrated on a rotary evaporator and purified by reverse-phase HPLC to give 10 mg one diastereomeric product as a TFA salt (12% yield). MS found: (M+H)$^+$=459.

Example 6

(cis,trans)-N-(2,4-dioxo-1,3-diazaspiro[4.4]non-6-yl)-4-[(2-methyl-4-quinolinyl)methoxy]benzenesulfonamide A solution of 4b (42 mg, 0.148 mmol) was dissolved in 3 mL CH$_2$Cl$_2$ and treated with triethylamine (0.14 mL, 1.0 mmol), DMAP (24 mg, 0.20 mmol) and [(2-methyl-4-quinolinyl)methoxy]benzenesulfonyl chloride HCl salt (77 mg, 0.22 mmol). The reaction was stirred at rt overnight and then extracted from KH$_2$PO$_4$ with EtOAc×3. The combined organic extracts were dried over MgSO$_4$, filtered, concentrated on a rotary evaporator and purified by reverse-phase HPLC to give 5 mg one diastereomer product 6a and 5 mg of the other diastereomeric product 6b as TFA salts (6% yield each). MS found: (M+H)$^+$=481.

Example 7

(trans)-N-[(2,4-dioxo-1,3-diazaspiro[4.5]dec-6-yl)methyl]-4-[(2-methyl-4-quinolinyl)methoxy]benzamide (7a) To a solution of (2-hydroxycyclohexyl)methylamine (5.0 g, 38.7 mmol) in 60 mL dioxane/water (2:1 v/v) was added sodium carbonate (8.2 g, 77.4 mmol), 20 mg of DMAP, and di-t-butyldicarbonate (12.7 g, 58 mmol). After stirring overnight, the reaction was filtered, partitioned between EtOAc and sat NaHSO$_4$, and separated. The organic phase was washed with brine, dried over MgSO$_4$, filtered, concentrated on a rotary evaporator, and taken up in ether. 5.4 g (61% yield) of a white solid crystallized out. MS found: (M+H)$^+$=230.

(7b) Alcohol 7a (5.4 g, 23.5 mmol) was dissolved in 50 mL CH$_2$Cl$_2$ followed by N-methylmorpholine-N-oxide (5.5 g, 46.9 mmol) and tetrapropylammonium perruthenate (TPAP, 413 mg, 5 mol%) and stirred overnight. The reaction mixture was filtered, partitioned between DCM and sat NaHCO$_3$, separated, and the organic layer was washed with brine, dried over MgSO$_4$, filtered, and concentrated by rotary evaporator. The residue was chromatographed on silica gel to give 4.68 g of a clear oil (88% yield). MS found: (M+H)$^+$=228.

(7c) Ketone 7b (3.1 g, 12.2 mmol) was dissolved in 40 mL 1:1 v/v water/MeOH followed by 10 mL NH$_4$OH. Ammonium chloride (718 mg, 13.4 mmol) and potassium cyanide (837 mg, 12.85 mmol) were added and the reaction was heated in a 55° C. oil bath overnight. The MeOH was removed by rotary evaporator, the residue was extracted with EtOAc and 1 N HCl. The aqueous layer was adjusted to pH 12 with 1 N NaOH and extracted 2×EtOAc. The combined organic extracts were dried over MgSO$_4$, filtered, and concentrated to give 1.82 of the aminonitrile 7c. MS found: (M+H)$^+$=254.

(7d) Crude 7c (1.82 g, 7.2 mmol) was taken up in 10 mL glacial HOAc and 1 mL water, treated with potassium cyanate (701 mg, 8.64 mmol), and heated to 100° C. for 5.5 hr. The reaction was treated with 6 mL conc HCl, stirred for 15 min, and cooled whereupon a white solid separated out. The solid was treated with 1:1 v/v DCM/trifluoroacetic acid for 2 hr and concentrated to give the amine 7d as a TFA salt. MS found: (M+H)$^+$=198.

(7e) To crude 7d (72 mg, 0.23 mmol) in a mixture of 2 mL 10% NaHCO$_3$ and 2 mL DCM was added 4-[(2-methyl-4-quinolinyl)methoxy]benzoyl chloride HCl salt (97 mg, 0.28 mmol). After stirring 2 hr, the reaction was extracted with NaHCO$_3$ and 3×DCM. The combined organic extracts were concentrated and purified by HPLC to give 15 mg (11% yield) of the amide product. MS found: (M+H)$^+$=473.

Example 8

(trans)-N-[(2,4-dioxo-1,3-diazaspiro[4.5]dec-6-yl) methyl]-4-[(2-methyl-4-quinolinyl)methoxy]benzenesulfonamide A solution of 7d (180 mg, 0.578 mmol) was dissolved in 1 mL CH$_2$Cl$_2$ and 1 mL of DMSO and treated with triethylamine (0.24 mL, 1.7 mmol), DMAP (24 mg, 0.20 mmol) and [(2-methyl-4-quinolinyl)methoxy]benzenesulfonyl chloride HCl salt (201 mg, 0.578 mmol). The reaction was stirred at rt overnight and then extracted from sat. NaHCO$_3$ with EtOAc× 3. The combined organic extracts were dried over MgSO$_4$, filtered, concentrated on a rotary evaporator and purified by reverse-phase HPLC to give 20 mg of sulfonamide product as a TFA salt. MS found: (M+H)$^+$=509.

Example 9

(cis)-N-[(2,4-dioxo-1,3-diazaspiro[4.5]dec-6-yl)methyl]-4-[(2-methyl-4-quinolinyl)methoxy]benzamide (9a) Ketone 7b (3.1 g, 12.2 mmol) was dissolved in 50 mL 4:1 EtOH/water and treated with ammonium carbonate (2.07 g, 21.6 mmol) and potassium cyanide (700 mg, 10.7 mmol). The reaction was heated in a 65° C. oil bath for 24 hr. The EtOH was removed by rotary evaporator, the residue was extracted from brine with 3×EtOAc. The combined organic extracts were dried over MgSO$_4$, filtered, and concentrated to give 1.08 g of the hydantoin which was treated with 1:1 v/v DCM/trifluoroacetic acid for 2 hr and concentrated to give the amine 9a as a TFA salt.

To crude 9a (109 mg, 0.36 mmol) in 1 mL DMSO was treated with diisopropylethylamine (207 uL, 1.18 mmol) and BOP (116 mg, 0.28 mmol) for 30 min followed by the addition of 4-[(2-methyl-4-quinolinyl)methoxy]-benzoic acid (70 mg, 0.24 mmol). The reaction was stirred at rt overnight and then extracted from 1:1 brine/sat NaHCO$_3$ with EtOAc×3. The combined organic extracts were dried over MgSO$_4$, filtered, concentrated on a rotary evaporator and purified by reverse-phase HPLC to give 55 mg of the product hydantoin as a TFA salt (26% yield). MS found: (M+H)$^+$=473.

Example 10

(cis)-N-[(2,4-dioxo-1,3-diazaspiro[4.5]dec-6-yl)methyl]-4-[(2-methyl-4-quinolinyl)methoxy]benzenesulfonamide A solution of 9a (104 mg, 0.35 mmol) was dissolved in 1 mL CH$_2$Cl$_2$ and 1 mL of DMSO and treated with triethylamine (96 ul, 0.69 mmol), DMAP (24 mg, 0.20 mmol) and [(2-methyl-4-quinolinyl)methoxy]benzenesulfonyl chloride HCl salt (80 mg, 0.23 mmol). The reaction was stirred at rt overnight and then extracted from sat. NaHCO$_3$ with EtOAc× 3. The combined organic extracts were dried over MgSO$_4$, filtered, concentrated on a rotary evaporator and purified by reverse-phase HPLC to give 20 mg of sulfonamide product as TFA salt (9% yield). MS found: (M+H)$^+$=509.

Example 11

6({4-[(2-methyl-4-quinolinyl)methoxy] phenyl}sulfonyl)-1,3-diazaspiro[4.4]nonane-2,4-dione (11a) To a solution of 4-mercaptophenol (1.0 g, 11.0 mmol) in 20 mL THF was added sodium hydride (500 mg, 12.6 mmol). After stirring 30 min, added 2-chlorocyclopentanone. The reaction was stirred overnight and then partitioned between EtOAc and brine and separated. The organic phase was dried over MgSO$_4$, filtered, and concentrated on a rotary evaporator. The residue was chromatographed on silica gel to give 2.2 g (96%) of 11a.

(11b) A solution of 11a (1.0 g, 4.8 mmol), 4-(chloromethyl)-2-methyl-quinoline (900 mg, 4.7 mmol), and potassium carbonate (2.0 g, 14.4 mmol) in 50 mL CH$_3$CN was refluxed overnight. The reaction was cooled, partitioned between EtOAc and brine and the organic phase was dried over MgSO$_4$, filtered, and concentrated on a rotary evaporator. The residue was chromatographed on silica gel to give 1.1 g (64%) of ketone 11b.

(11c) Ketone 11b (435 mg, 1.2 mmol) was dissolved in 30 mL 2:1 EtOH water and treated with ammonium carbonate (1.15 g, 12.0 mmol) and potassium cyanide (158 mg, 2.4 mmol). The reaction was heated in a 65° C. oil bath for 24 hr. The EtOH was removed by rotary evaporator, the residue was extracted from sat KH$_2$PO$_4$ with 3×EtOAc. The combined organic extracts were dried over MgSO$_4$, filtered, and concentrated to give 270 mg of the hydantoin. MS found: (M+H)$^+$=434.

(11d) Hydantoin 11c (435 mg, 1.2 mmol) was dissolved in 2.0 mL MeOH, 2.0 mL CH$_2$Cl$_2$ and 1.0 mL water and treated with Oxone® (1.1 g, 1.8 mmol). The reaction was stirred 2 h and the residue was extracted from sat NaHSO$_3$ with 3×EtOAc. The combined organic extracts were dried over MgSO$_4$, filtered, concentrated, and purified by reverse-phase HPLC to give 40 mg of the hydantoin (5.7% yield). MS found: (M+H)$^+$=466.

Example 12

6({4-[(2-methyl-4-quinolinyl)methoxy] phenyl}sulfonyl)-1,3-diazaspiro[4.5]decanane-2,4-dione (12a) Starting from commercially available 2-chlorocyclohexanone (2.8 g, mmol) the 4 step procedure used to make compound 11 was followed. The product hydantoin 3a was synthesized and purified by reverse phase HPLC to give 105 mg of 12 as a TFA salt (29% yield). MS found: (M+H)$^+$=480.

Example 13

2-(2,4-dioxo-1,3-diazaspiro[4.5]dec-6yl)-N-{4-[(2-methyl-4-quinolinyl)methoxy]phenyl}acetamide (13a) Starting from commercially available methyl 2-oxocyclohexyl acetate (2.55 g, 13.8 mmol) the 3 step procedure used to make compound 1 was followed. The product amide 13a was synthesized and purified by reverse phase HPLC to give 60 mg of 13a as a TFA salt (23% yield). MS found: $(M+H)^+=473$.

Example 14

6-({4-[(2-methyl-4-quinolinyl)methoxy]phenyl}sulfonyl)methyl]-1,3-diazaspiro[4.4]nonane-2,4-dione (14a) A solution of cyclopentanone (2.0 g, 23.8 mmol), paraformaldehyde (2.0 g), and N-methylaniline trifluoroacetic acid salt (12.7 g, 57.4 mmol) in 25 mL of THF was refluxed for 15 min and then partitioned between ether and 2×1N HCl and separated. The organic phase was dried over $MgSO_4$, filtered, and concentrated on a rotary evaporator to give 2-methylene-cyclopentanone.

(14b) NaH (1.0 g, 24 mmol) was added portionwise to a solution of 4-mercaptophenol (3.0 g, 23.8 mmol) in 25 mL of THF. After 30 min, a solution of 2-methylene-cyclopentanone in 10 mL of THF was added dropwise. The reaction was stirred overnight and then quenched with water. The residue was extracted from brine with 3×EtOAc. The organic phase was dried over $MgSO_4$, filtered, concentrated on a rotary evaporator, and purified by silica gel chromatography to give 489 mg (10% yield) of mercapto-ketone 14b.

(14c) Diethyl azodicarboxylate (453 mg, 2.6 mmol) was added to a solution of 14b (489 mg, 2.2 mmol), 4-(hydroxymethyl)-2-methylquinoline (383 mg, 2.2 mmol), and triphenylphosphine (682 mg, 2.6 mmol) in 10 mL of THF. The reaction was stirred overnight and then the residue was extracted from sat $KH_2PO_4$ with 3×EtOAc. The organic phase was dried over $MgSO_4$, filtered, concentrated on a rotary evaporator, and purified by silica gel chromatography to give 300 mg (36% yield) of 14c. MS found: $(M+H)^+=378$.

(14d) Ketone 14c (300 mg, 0.8 mmol) was dissolved in 15 mL 2:1 EtOH/water and treated with ammonium carbonate (770 mg, 8.0 mmol) and potassium cyanide (105 mg, 1.6 mmol). The reaction was heated in a 65° C. oil bath for 24 hr. The EtOH was removed by rotary evaporator, the residue was extracted from sat $KH_2PO_4$ with 3×EtOAc. The combined organic extracts were dried over $MgSO_4$, filtered, and concentrated to give the crude hydantoin. MS found: $(M+H)^+=448$.

(14e) Hydantoin 14d was dissolved in 4.0 mL MeOH, 4.0 mL $CH_2Cl_2$ and 2.0 mL water and treated with Oxone® (1.5 g, 2.4 mmol). The reaction was stirred 2h and the residue was extracted from sat $NaHSO_3$ with 3×EtOAc. The combined organic extracts were dried over $MgSO_4$, filtered, concentrated, and purified by reverse-phase HPLC to give 10 mg of the hydantoin sulfone 14e. MS found: $(M+H)^+=480$.

Example 15

N-(2,4-dioxo-1,3-diazaspiro[4.5]dec-6yl)-4-[(2-methyl-4-quinolinyl)methoxy]benzamide (15a) A mixture of cyclohexene oxide (8.2 g, 83.4 mmol), sodium azide (27.1 g, 417 mmol), and ammonium chloride (8.9 g, 167 mmol) in 20 mL of water and 200 mL of MeOH was refluxed overnight. The reaction mixture was cooled, filtered through a sintered glass funnel, concentrated on a rotary evaporator, and purified by silica gel chromatography to give 9.85 g (84% yield) of the azido alcohol 15a.

(15b) A solution of 15a (9.85 g, 69.8 mmol) and t-butyldicarbonate (18.3 g, 83.8 mmol) in 50 mL of MeOH was placed in a Parr bottle with 20% $Pd(OH)_2$ (2.0 g) and hydrogenated under 50 psi of $H_2$ overnight. The reaction mixture was filtered through a sintered glass funnel and concentrated on a rotary evaporator. The residue was triturated with ether and the solid was collected and dried to give 3.64 g (24% yield) of Boc-amino alcohol 15b.

(15c) Boc-amino alcohol 15b (3.63 g, 16.9 mmol) was dissolved in 80 mL DCM followed by N-methylmorpholine-N-oxide (3.95 g, 34 mmol) and tetrapropylammonium perruthenate (TPAP, 300 mg, 5 mol %) and stirred overnight. The reaction mixture was filtered, partitioned between DCM and sat $NaHCO_3$, separated, and the organic layer was washed with brine, dried over $MgSO_4$, filtered, and concentrated by rotary evaporator. The residue was chromatographed on silica gel to give 3.16 g of a clear oil (88% yield). MS found: $(M+H)^+=228$.

(15d) Ketone 15c (1.16 g, 5.44 mmol) was dissolved in 50 mL 2:1 EtOH/water and treated with ammonium carbonate (2.09 g, 21.8 mmol) and potassium cyanide (708 mg, 10.8 mmol). The reaction was heated in a 65° C. oil bath for 24 hr. The EtOH was removed by rotary evaporator, the residue was extracted from dil. HCl with 3×EtOAc. The combined organic extracts were dried over $MgSO_4$, filtered, and concentrated to give the crude hydantoin. MS found: $(M+H)^+=284$.

(15e) Compound 15d (1.25 g, 4.41 mmol) was stirred for 1 hr in $TFA/CH_2Cl_2$ (2:1, 5 mL) and concentrated on a rotary evaporator to give 1.63 g (100% yield) of the amine 4b which was taken to the next step without purification.

(15f) A solution of 15e (107 mg, 0.36 mmol) was dissolved in 1 mL DMSO and 1 mL EtOAc and treated with diisopropylethylamine (208 uL, 1.2 mmol), BOP (116 mg, 0.26 mmol), 4-[(2-methyl-4-quinolinyl)methoxy]benzoic acid (70 mg, 0.24 mmol). The reaction was stirred overnight and then extracted from sat $NaHCO_3$ with EtOAc×3. The combined organic extracts were dried over $MgSO_4$, filtered, concentrated on a rotary evaporator and purified by reverse-phase HPLC to give 18 mg of one diastereomeric product as a TFA salt (13% yield). MS found: $(M+H)^+=459$.

Example 16

4-[(1,1-dioxido-2,3-dihydro-4H-1,4-benzothiazin-4-yl)methyl]-N-(2,4-dioxo-1,3-diazaspiro[4.5]dec-6yl)benzamide A solution of 15e (105 mg, 0.36 mmol) was dissolved in 1 mL DMSO and 1 mL EtOAc and treated with diisopropylethylamine (208 uL, 1.2 mmol), BOP (116 mg, 0.26 mmol), 4-[(1,1-dioxido-2,3-dihydro-4H-1,4-benzothiazin-4-yl)methyl]benzoic acid (76 mg, 0.24 mmol). The reaction was stirred overnight and then extracted from sat $NaHCO_3$ with EtOAc×3. The combined organic extracts were dried over $MgSO_4$, filtered, concentrated on a rotary evaporator and purified by reverse-phase HPLC to give 40 mg of one diastereomeric product as a TFA salt (28% yield). MS found: $(M+H)^+=483$.

Example 17

(cis,trans)-N-(2,4-dioxo-1,3-diazaspiro[4.5]dec-6-yl)-4-[(2-methyl-4-quinolinyl)methoxy]benzenesulfonamide A solution of 15e (105 mg, 0.345 mmol) was dissolved in 1 mL $CH_2Cl_2$ and 1 mL DMSO and treated with triethylamine (96 ul, 0.69 mmol), DMAP (10 mg) and [(2-methyl-4-quinolinyl)methoxy]benzenesulfonyl chloride HCl salt (80 mg, 0.23 mmol). The reaction was stirred overnight and then extracted from sat. $NaHCO_3$ with EtOAc×3. The combined organic extracts were dried over $MgSO_4$, filtered, concentrated on a rotary evaporator and purified by reverse-phase HPLC to give 45 mg of one diastereomeric product (31% yield). MS found: $(M+H)^+=509$.

Example 18

(cis,trans)-N-(2,4-dioxo-7-oxa-1,3-diazaspiro[4.4]non-9-yl)-4-[(2-methyl-4-quinolinyl)methoxy]benzamide (18a) A solution of 2,5-dihydrofuran (3.0 g, 42.8 mmol) was dissolved in 200 mL $CH_2Cl_2$ and treated with m-chloroperbenzoic acid (26.0 g, 145 mmol). The reaction was stirred at rt overnight and then extracted from 1 n NaOH with $CH_2Cl_2$×3. The combined organic extracts were dried over $MgSO_4$, filtered, and concentrated on a rotary evaporator to give 3.0 g (81% yield) of the furan epoxide 18a which was used without further purification.

(18b) A mixture of compound 18a (3.0 g, 34.8 mmol), sodium azide (3.25 g, 50 mmol), and ammonium chloride (2.7 g, 50 mmol) in 15 mL of water and 15 mL of MeOH was refluxed overnight. The reaction mixture was cooled, filtered through a sintered glass funnel and concentrated on a rotary evaporator. The crude residue was carried to the next step without purification.

(18c) A solution of 18b and t-butyldicarbonate (7.6 g, 35 mmol) in 50 mL of EtOAc was placed in a Parr bottle with 10% Pd/C (300 mg) and hydrogenated under 50 psi of $H_2$ overnight. The reaction mixture was filtered through Celite in a sintered glass funnel and concentrated on a rotary evaporator. The residue was purified by silica gel chromatography to give 1.5 g (21% yield) of Boc-amino alcohol 18c.

(18d) Boc-amino alcohol 18c (1.0 g, 5.0 mmol) was dissolved in 50 mL $CH_2Cl_2$, treated with Dess-Martin periodinane (5.0 g, 11.8 mmol) and stirred for 3 hr. The reaction mixture was partitioned between DCM and 1N NaOH, separated, and the organic layer was dried over $MgSO_4$, filtered, and concentrated by rotary evaporator. The residue was taken to the next step without purification.

(18e) Ketone 18d was dissolved in 50 mL 2:1 EtOH/water and treated with ammonium carbonate (4.8 g, 50 mmol) and potassium cyanide (657 mg, 10 mmol). The reaction was heated in a 65° C. oil bath for 24 hr. The EtOH was removed by rotary evaporator, the residue was extracted from dil. HCl with 3×EtOAc. The combined organic extracts were dried over $MgSO_4$, filtered, and concentrated to give the crude hydantoin. MS found: $(M+H)^+=284$.

(18f) Compound 18e (202 mg, 0.74 mmol) was stirred for 1 hr in $TFA/CH_2Cl_2$ (1:1, 5 mL) and concentrated on a rotary evaporator to give 128 mg (100% yield) of the amine 18f which was taken to the next step without purification.

(18g) A solution of 18f (128 mg, 0.74 mmol) was dissolved in 10 mL DMSO and treated with triethylamine (0.6 mL, 4.3 mmol), BOP (500 mg, 1.1 mmol), 4-[(2-methyl-4-quinolinyl)methoxy]benzoic acid (322 mg, 1.1 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 85 mg of the product as a TFA salt (20% yield). MS found: $(M+H)^+=447$.

Example 19

(cis,trans)-N-(2,4-dioxo-8-oxa-1,3-diazaspiro[4.5]dec-6-yl)-4-[(2-methyl-4-quinolinyl)methoxy]benzamide (19a) To a solution of tetrahydro-4H-pyran-4-one (3.0 g, 42.8 mmol) and triethylamine (9.1 mL, 65.6 mmol) in 60 mL DCM at 0° C. was added triisopropylsilyl trifluoromethanesulfonate (9.3 mL, 34.4 mmol) dropwise. The reaction was stirred at rt for 2 hr and then extracted from water with $CH_2Cl_2$×3. The combined organic extracts were dried over $MgSO_4$, filtered, concentrated on a rotary evaporator, and purified by silica gel chromatography to give 7.93 g (94% yield) of 19a.

(19b) To a solution of compound 19a (7.9 g, 30.8 mmol) and sodium azide (9.0 g, 138.6 mmol) in 77 mL MeCN at −20° C. was added a solution of ceric ammonium nitrate (50.7 g, 92.4 mmol) in 231 mL MeCN dropwise. The reaction mixture was stirred for 2 hr, extracted from water with 3× ether, and concentrated on a rotary evaporator. The crude residue was purified by silica gel chromatography to give 2.6 g of azido ketone 19b.

(19c) A solution of 19b (550 mg, 3.1 mmol) and t-butyldicarbonate (1.36 g, 6.2 mmol) in 50 mL of MeOH was placed in a Parr bottle with 20% $Pd(OH)_2$ (200 mg) and hydrogenated under 50 psi of $H_2$ for 6 hr. The reaction mixture was filtered through Celite in a sintered glass funnel and concentrated on a rotary evaporator. The residue was purified by silica gel chromatography to give 370 mg (55% yield) of Boc-amino ketone 19c.

(19d) Ketone 19c (366 mg, 1.70 mmol) was dissolved in 15 mL 2:1 EtOH/water and treated with ammonium carbonate (1.63 g, 17 mmol) and potassium cyanide (222 mg, 3.4 mmol). The reaction was heated in a 65° C. oil bath for 24 hr. The EtOH was removed by rotary evaporator, the residue was extracted from dil. HCl with 3×EtOAc. The combined organic extracts were dried over $MgSO_4$, filtered, and concentrated to give 421 mg of the crude hydantoin 19d. MS found: $(M+H)^+=284$.

(19e) Compound 19d (202 mg, 0.74 mmol) was stirred for 1 hr in $TFA/CH_2Cl_2$ (1:1, 5 mL) and concentrated on a rotary evaporator to give 530 mg (100% yield) of the amine 19e which was taken to the next step without purification.

(19f) A solution of 19e (70 mg, 0.23 mmol) in 1 mL DMSO and 1 mL EtOAc was treated with diisopropylethylamine (0.2 mL, 1.15 mmol), BOP (104 mg, 0.23 mmol), 4-[(2-methyl-4-quinolinyl)methoxy]benzoic acid (69 mg, 0.23 mmol). The reaction was stirred overnight and then extracted from sat $KH_2PO_4$ with EtOAc×3. The combined organic extracts were dried over $MgSO_4$, filtered, concentrated on a rotary evapo-

Example 20

4-[(1,1-dioxido-2,3-dihydro-4H-1,4-benzothiazin-4-yl)methyl]-N-(2,4-dioxo-8-oxa-1,3-diazaspiro[4.5]dec-6-yl)benzamide A solution of 19e (64 mg, 0.2146 mmol) in 1 mL DMSO and 1 mL EtOAc was treated with diisopropylethylamine (186 uL, 1.07 mmol), BOP (95 mg, 0.214 mmol), 4-[(1,1-dioxido-2,3-dihydro-4H-1,4-benzothiazin-4-yl)methyl]benzoic acid (68 mg, 0.214 mmol). The reaction was stirred overnight and then extracted from sat $KH_2PO_4$ with EtOAc× 3. The combined organic extracts were dried over $MgSO_4$, filtered, concentrated on a rotary evaporator and purified by reverse-phase HPLC to give 32 mg of one diastereomeric product as a TFA salt (25% yield). MS found: $(M+TFA)^-=597$.

Example 21

(cis,trans)-N-(2,4-dioxo-8-oxa-1,3-diazaspiro[4.5]dec-6-yl)-4-[(2-methyl-4-quinolinyl)methyl]benzamide A solution of 19e (62 mg, 0.207 mmol) in 1 mL DMSO and 1 mL EtOAc was treated with diisopropylethylamine (186 uL, 1.04 mmol), BOP (92 mg, 0.207 mmol), 4-[(2-methyl-4-quinolinyl)methyl]benzoic acid (57 mg, 0.207 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 25 mg of the product as a TFA salt (22% yield). MS found: $(M+H)^+=445$.

Example 22

(trans)-N-(2,4-dioxo-7-oxa-1,3-diazaspiro[4.5]dec-10-yl)-4-[(2-methyl-4-quinolinyl)methoxy]benzamide (22a) A solution of trans 3-hydroxy-4-azidotetrahydropyran prepared by the procedure of Crotti et al. (*Tetrahedron* 1994, 50, 1261-1274). (7.0 g, 48.9 mmol) and t-butyldicarbonate (11.2 g, 51.3 mmol) in 90 mL of MeOH was placed in a Parr bottle with 20% $Pd(OH)_2$ (1.4 g) and hydrogenated under 50 psi of overnight. The reaction mixture was filtered through Celite in a sintered glass funnel and concentrated on a rotary evaporator. The residue was triturated in ether and solid was collected and dried to give 6.67 g (63% yield) of Boc-amino alcohol 22a.

(22b) DMSO (6.3 mL, 88 mmol) was added dropwise to a 2M solution of oxalyl chloride in $CH_2Cl_2$ (24.3 mL, 48.6 mmol) at −78° C. After 15 min, amino alcohol 22a (9.6 g, 44 mmol) in 80 mL $CH_2Cl_2$/THF (1:1) was added dropwise followed by dropwise addition of triethylamine (30.8 mL, 220 mmol) The reaction mixture was warmed to rt and stirred for 2. The reaction mixture was partitioned between EtOAc and sat $KH_2PO_4$, separated, and the organic layer was washed with brine, dried over $MgSO_4$, filtered, and concentrated by rotary evaporator. The residue was purified by silica gel chromatography to give 8.0 g (85% yield) of Boc-amino ketone 22b.

(22c) Ketone 22b (6.64 g, 30.8 mmol) was dissolved in 66 mL 1:1 EtOH/water and treated with ammonium carbonate (23.7 g, 247 mmol) and potassium cyanide (2.41 g, 36.7 mmol). The reaction was heated in a 65° C. oil bath for 24 hr. The EtOH was removed by rotary evaporator, the residue was extracted from dil. HCl with 3×EtOAc. The combined organic extracts were dried over $MgSO_4$, filtered, and concentrated by rotary evaporator. The residue was triturated in EtOAc at 60° C. and the solid was collected by filtration to give 6.63 g of hydantoin 22c-1 as a single diastereomer (75% yield). The filtrate was concentrated by rotary evaporator to give 3.11 g of hydantion 22c-2 as a 3:2 mixture of diastereomers. MS found: $(M+H)^-=284$.

(22d) Compound 22c-2 (3.11 g, 10.9 mmol) was stirred for 1 hr in TFA/$CH_2Cl_2$ (1:1, 30 mL) and concentrated on a rotary evaporator to give 4.46 g (100% yield) of the amine 22d (3:2 mixture of diastereomers) which was used for preparation of other analogues.

(22e) Compound 22c-1 (1.48 g, 10.9 mmol) was stirred for 1 hr in TFA/$CH_2Cl_2$ (1:1, 12 mL) and concentrated on a rotary evaporator to give 1.55 g (100% yield) of the amine 22e (single diastereomer) which was taken to the next step without purification.

(22f) A solution of 22e (70 mg, 0.23 mmol) was dissolved in 1 mL DMSO and 1 mL EtOAc and treated with diisopropylethylamine (0.2 mL, 1.15 mmol), BOP (104 mg, 0.23 mmol), 4-[(2-methyl-4-quinolinyl)methoxy]benzoic acid (69 mg, 0.23 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 28 mg of the product as a TFA salt (21% yield). MS found: $(M+H)^+=461$.

Example 23

(cis,trans)-N-(2,4-dioxo-7-oxa-1,3-diazaspiro[4.5]dec-10-yl)-4-[(2-methyl-4-quinolinyl)methyl]benzamide 22d (111 mg, 0.372 mmol) was dissolved in 1 mL DMSO and treated with diisopropylethylamine (324 uL, 1.86 mmol), BOP (165 mg, 0.372 mmol), 4-[(2-methyl-4-quinolinyl)methyl]benzoic acid (103 mg, 0.372 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 22 mg of 3:2 diastereomeric mixture of 23 as a TFA salt (11% yield). MS found: $(M+H)^+=445$.

Example 24

(trans)-N-(2,4-dioxo-7-oxa-1,3-diazaspiro[4.5]dec-10-yl)-4-[(2-methyl-4-quinolinyl)methyl]benzamide 22e (715 mg, 2.39 mmol) was dissolved in 1 mL DMSO and treated with diisopropylethylamine (8 mL, 19.2 mmol), BOP (1.06 g, 2.39 mmol), 4-[(2-methyl-4-quinolinyl)methyl]benzoic acid (662 mg, 2.39 mmol). The reaction was stirred overnight and then extracted from sat $KH_2PO_4$ with EtOAc× 3. The combined organic extracts were dried over $MgSO_4$, filtered, concentrated on a rotary evaporator and purified by

Example 25

(cis,trans)-N-(2,4-dioxo-7-oxa-1,3-diazaspiro[4.5]
dec-10-yl)-4-{[(2-trifluoromethyl-1H-benzimidazol-
1-yl])methyl}benzamide 22d (95 mg, 0.315 mmol) was dissolved in 1 mL DMSO and treated with diisopropylethylamine (275 uL, 1.58 mmol), BOP (140 mg, 0.315 mmol), 4-{[(2-trifluoromethyl)-1H-benzimidazol-1-yl]methyl}benzoic acid (101 mg, 0.315 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 73 mg of a 3:2 diastereomeric mixture of 25 as a TFA salt (39% yield). MS found: $(M+H)^+$=488.

Example 26

(cis,trans)-N-(2,4-dioxo-7-oxa-1,3-diazaspiro[4.5]
dec-10-yl)-4-[(2-ethylpyrazolo[1,5-a]pyridin-3-yl)-
methyl]benzamide 22d (16 mg, 0.0535 mmol) was dissolved in 1 mL DMSO and treated with diisopropylethylamine (47 uL, 0.27), BOP (24 mg, 0.0535 mmol), 4-[(2-ethylpyrazolo[1,5-a]pyridin-3-yl)methyl]benzoic acid (15 mg, 0.0535 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 4 mg of 3:2 diastereomeric mixture and 7.7 mg of a single diastereomer (50% yield). MS found: $(M+H)^+$=448.

Example 29

(cis,trans)-4-(1,3-dihydrofuro[3,4-b]quinolin-9-ylm-
ethyl)-N-(2,4-dioxo-7-oxa-1,3-diazaspiro[4.5]dec-
10-yl)benzamide 22d (108 mg, 0.36 mmol) was dissolved in 1 mL DMSO and treated with diisopropylethylamine (313 uL, 1.8), BOP (159 mg, 0.36 mmol), 4-(1,3-dihydrofuro[3,4-b]quinolin-9-ylmethyl)benzoic acid (110 mg, 0.36 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 40 mg of 3:2 diastereomeric mixture (19% yield). MS found: $(M+H)^+$=473.

Example 30

(cis,trans)-N-(2,4-dioxo-7-oxa-1,3-diazaspiro[4.5]
dec-10-yl)-4-[(2-ethyl-4-quinolinyl)-methyl]benza-
mide 22d (111 mg, 0.37 mmol) was dissolved in 1 mL DMSO and treated with diisopropylethylamine (323 uL, 1.85 mmol), BOP (164 mg, 0.37 mmol), and 4-[(2-ethyl-4-quinolinyl)methyl]benzoic acid (108 mg, 0.37 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 106 mg of 3:2 diastereomeric mixture as a TFA salt (50% yield). MS found: $(M+H)^+$=459.

Example 31

(cis,trans)-4-[(3,5-dimethyl-1H-pyrazol-4-yl)me-
thyl]-N-(2,4-dioxo-7-oxa-1,3-diazaspiro[4.5]dec-10-
yl)benzamide 22d (106 mg, 0.353 mmol) was dissolved in 1 mL DMSO and treated with diisopropylethylamine (307 uL, 1.77 mmol), BOP (156 mg, 0.353 mmol), and 4-[(3,5-dimethyl-1H-pyrazol-4-yl)methyl]benzoic acid (84 mg, 0.353 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 43 mg of 3:2 diastereomeric mixture (50% yield). MS found: $(M+H)^+$=398.

Example 32

(cis,trans)-N-(2,4-dioxo-7-oxa-1,3-diazaspiro[4.5]
dec-10-yl)-4-{[2-(trifluoromethyl)-4-quinolinyl]
methyl}benzamide 22d (104 mg, 0.347 mmol) was dissolved in 1 mL DMSO and treated with diisopropylethylamine (302 uL, 1.74 mmol), BOP (154 mg, 0.3.47 mmol), and 4-[(2-trifluoromethyl-4-quinolinyl)methyl]benzoic acid (106 mg, 0.347 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 70 mg of 2:1 diastereomeric mixture as a TFA salt (33% yield). MS found: $(M+H)^+$=499.

Example 33

(cis,trans)-N-(2,4-dioxo-7-oxa-1,3-diazaspiro[4.5]
dec-10-yl)-4-[(2-methyl-1H-indol-3-yl)methyl]ben-
zamide 22d (24 mg, 0.041 mmol) was dissolved in 1 mL DMSO and treated with diisopropylethylamine (36 uL, 0.27), BOP (19 mg, 0.041 mmol), 4-[(2-methyl-1H-indol-3-yl)methyl]benzoic acid (11 mg, 0.041 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 12 mg of 2:1 diastereomeric mixture (68% yield). MS found: $(M+H)^+$=433.

Example 34

(cis,trans)-N-(2,4-dioxo-7-oxa-1,3-diazaspiro[4.5]
dec-10-yl)-4-[(1,3,5-trimethyl-1H-pyrazol-4-yl)me-
thyl]benzamide 22d (16 mg, 0.0535 mmol) was dissolved in 1 mL DMSO and treated with diisopropylethylamine (47 uL, 0.27), BOP (24 mg, 0.0535 mmol), 4-[(1,3,5-trimethyl-1H-pyrazol-4-yl)methyl]benzoic acid (15 mg, 0.0535 mmol). The reaction was stirred overnight and then extracted from sat $KH_2PO_4$ with EtOAc×3. The combined organic extracts were dried over $MgSO_4$, filtered, concentrated on a rotary evaporator and

Example 35

(cis,trans)-N-(2,4-dioxo-7-oxa-1,3-diazaspiro[4.5]
dec-10-yl)-4-[(2-isopropyl-1H-benzimidazol-1-yl)
methyl]benzamide 22d (18 mg, 0.060 mmol) was dissolved in 1 mL DMSO and treated with diisopropylethylamine (26 uL, 0.015), BOP (14 mg, 0.0305 mmol), and 4-{[(2-isopropyl-1H-benzimidazol-1-yl]methyl}benzoic acid (9 mg, 0.0305 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 6.5 mg of 2:1 diastereomeric mixture as a TFA salt (37% yield). MS found: $(M+H)^+=462$.

Example 36

(cis,trans)-N-(2,4-dioxo-7-oxa-1,3-diazaspiro[4.5]
dec-10-yl)-4-[(2-methyl-1-oxido-4-quinolinyl)methoxy]benzamide 22e (20 mg, 0.45 mmol) and $NaHCO_3$ (155 mg, 1.84 mmol) in 2 mL MeOH and 0.5 mL water was treated with Oxone® (90 mg, 0.146 mmol) and the reaction mixture was stirred at 50° C. overnight. The reaction was filtered and the filtrate was purified by reverse-phase HPLC to give 9.6 mg of 36 (46% yield). MS found: $(M+H)^+=461$.

Example 37

(cis,trans)-N-(2,4-dioxo-7-oxa-1,3-diazaspiro[4.5]
dec-10-yl)-4-[(2,3,5-trimethyl-4-pyridinyl)methyl]
benzamide 22e (32 mg, 0.071 mmol) was dissolved in 1 mL DMSO and treated with diisopropylethylamine (62 uL, 0.355), BOP (32 mg, 0.071 mmol), and 4-[(2,3,5-trimethyl-4-pyridinyl)methyl]benzoic acid (18 mg, 0.071 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 7 mg of a single diastereomer as a TFA salt (18% yield). MS found: $(M+H)^+=423$.

Example 38

(cis,trans)-N-(2,4-dioxo-7-oxa-1,3-diazaspiro[4.5]
dec-10-yl)-4-{[(2-(methylthio)-1H-benzimidazol-1-yl]methyl}benzamide 22d (101 mg, 0.338 mmol) was dissolved in 1 mL DMSO and treated with diisopropylethylamine (294 uL, 1.69 mmol), BOP (150 mg, 0.338 mmol), and 4-{[(2-(methylthio)-1H-benzimidazol-1-yl]methyl)benzoic acid (101 mg, 0.338 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 98 mg of 3:2 diastereomeric mixture (62% yield). MS found: $(M+H)^+=466$.

Example 39

(cis,trans)-N-(2,4-dioxo-7-oxa-1,3-diazaspiro[4.5]
dec-10-yl)-4-[(2-methyl-1H-indol-1-yl)-methyl]benzamide 22d (8 mg, 0.026 mmol) was dissolved in 1 mL DMSO and treated with diisopropylethylamine (23 uL, 0.13), BOP (12 mg, 0.026 mmol), and 4-[(2-methyl-1H-indol-1-yl)methyl]benzoic acid (7 mg, 0.026 mmol). The reaction was stirred overnight and then extracted from sat $KH_2PO_4$ with EtOAc× 3. The combined organic extracts were dried over $MgSO_4$, filtered, concentrated on a rotary evaporator and purified by reverse-phase HPLC to give 3 mg of 3:2 diastereomeric mixture as a TFA salt (27% yield). MS found: $(M+H)^+=461$.

Example 40

(cis,trans)-4-[(1,1-dioxido-2,3-dihydro-4H-1,4-benzothiazin-4-yl)methyl]-N-(2,4-dioxo-7-oxa-1,3-diazaspiro[4.5]dec-10-yl)benzamide 22d (97 mg, 0.325 mmol) was dissolved in 1 mL DMSO and treated with diisopropylethylamine (283 uL, 1.63 mmol), BOP (144 mg, 0.325 mmol), and 4-[(1,1-dioxido-2,3-dihydro-4H-1,4-benzothiazin-4-yl)methyl]benzoic acid (103 mg, 0.325 mmol). The reaction was stirred overnight and then extracted from sat $KH_2PO_4$ with EtOAc×3. The combined organic extracts were dried over $MgSO_4$, filtered, concentrated on a rotary evaporator and purified by reverse-phase HPLC to give 37 mg of 3:2 diastereomeric mixture as a TFA salt (19% yield). MS found: $(M+H)^+=485$.

Example 41

(cis,trans)-N-(2,4-dioxo-7-oxa-1,3-diazaspiro[4.5]
dec-10-yl)-4-[(2-methyl-4-quinolinyl)methoxy]benzenesulfonamide 22d (56 mg, 0.19 mmol) was dissolved in 1 mL of DMF and treated with diisopropylethylamine (325 uL, 1.9 mmol), and [(2-methyl-4-quinolinyl)methoxy]benzenesulfonyl chloride HCl salt (130 mg, 0.19 mmol). The reaction was stirred at rt overnight and then extracted from sat. $KH_2PO_4$ with EtOAc× 3. The combined organic extracts were dried over $MgSO_4$, filtered, concentrated on a rotary evaporator and purified by reverse-phase HPLC to give 6 mg of sulfonamide product as a single diastereomer B and 10 mg of 2:1 mixture of diastereomers A and B both as a TFA salts. MS found: $(M+H)^+=497$.

Example 43

(cis,trans)-tert-butyl 9-[2-({4-[2-methyl-4-quinolinyl)methoxy]phenyl}amino)-2-oxoethyl]-2,4-dioxo-1,3,7-triazaspiro[4.4]nonane-7-carboxylate (43a) A solution of t-butyl 2,5-dihydro-1H-pyrrole-1-carboxylate (3.0 g, 17.7 mmol) was dissolved in 200 mL $CHCl_3$ and treated with m-chloroperbenzoic acid (9.2 g, 53.1 mmol). The reaction was stirred at rt overnight and then extracted from 1N NaOH with $CHCl_3$×3. The combined organic extracts were dried over $MgSO_4$, filtered, concentrated on a rotary evaporator, and purified by silica gel chromatography to give 2.0 g (61% yield) of the epoxide 43a. MS found: $(M+H)^+=186$.

(43b) To a solution of compound 43a (1.0 g, 5.4 mmol) in 15 mL of ether at 0° C. was added a solution of allyl magnesium bromide in 10 mL of ether dropwise. The reaction mixture was stirred for 1 hr at rt and then quenched with water. Extracted residue from water with ether×3, separated, and the organic layer was dried over MgSO$_4$, filtered, and concentrated by rotary evaporator. The compound 43b was taken to the next step without purification.

(43c) A solution of 43b and Dess-Martin periodinane (1.8 g, 4.24 mmol) in 50 mL of CH$_2$Cl$_2$ was stirred overnight. The reaction was extracted from sat NaHCO$_3$ with 3×EtOAc. The combined organic extracts were dried over MgSO$_4$, filtered, concentrated by rotary evaporator, and purified by silica gel chromatography to give 767 mg (63% yield) of the ketone 43c.

(43d) Compound 43c (350 mg, 1.55 mmol) was dissolved in 50 mL CH$_2$Cl$_2$ and cooled to −78° C. A stream of ozone was passed through for 15 min followed by a stream of N2 for 30 min. Triphenylphosphine (447 mg, 1.7 mmol) was added and stirred for 1 hr. The reaction mixture was concentrated by rotary evaporator and purified by silica gel chromatography to give 260 mg (74% yield) of the aldehyde 43d.

(43e) Compound 43d (260 mg, 1.14 mmol) was dissolved in 10 mL t-BuOH, 10 mL of water, and 10 mL of 2-methyl-2-butene and cooled to 0° C. Sodium chlorite (721 mg, 5.7 mmol) and sodium dihydrogenphosphate monohydrate (925 mg, 6.7 mmol) were added and stirred for 2 hr. The reaction was extracted from sat KH$_2$PO$_4$ with 3×EtOAc. The combined organic extracts were dried over MgSO$_4$, filtered, and concentrated by rotary evaporator to give a quantitative yield of the acid which was used without further purification.

(43f) A solution of 43e (277 mg, 1.14 mmol) was dissolved in 10 mL DMSO and treated with triethylamine (1.0 mL, 7.2 mmol), PyBOP (884 mg, 1.7 mmol), 4-[(2-methyl-4-quinolinyl)methoxy]aniline bis-HCl salt (573 mg, 1.7 mmol). The reaction was stirred overnight and then extracted from sat KH$_2$PO$_4$ with EtOAc×3. The combined organic extracts were dried over MgSO$_4$, filtered, concentrated on a rotary evaporator and purified by silica gel chromatography to give 360 mg of the product 43f (65% yield). MS found: (M+H)$^+$=490.

(43f) Ketone 43f (360 mg, 0.74 mmol) was dissolved in 15 mL 2:1 EtOH/water and treated with ammonium carbonate (711 mg, 7.4 mmol) and potassium cyanide (100 mg, 1.52 mmol). The reaction was heated in a 65° C. oil bath for 24 hr. The EtOH was removed by rotary evaporator, the residue was extracted from dil. HCl with 3×EtOAc. The combined organic extracts were dried over MgSO$_4$, filtered, concentrated, and purified by reverse-phase chromatography to give 43f as a TFA salt. MS found: (M+H)$^+$=560.

Example 44

(cis,trans)-2-(2,4-dioxo-1,3,7-triazaspiro[4.4]non-9-yl)-N-{4-[(2-methyl-4-quinolinyl)methoxy]phenyl}acetamide

(44) Compound 43f (90 mg {crude}, 0.16 mmol) was stirred for 1 hr in TFA/CH$_2$Cl$_2$ (1:1, 5 mL) and concentrated on a rotary evaporator and purified by reverse-phase chromatography to give compound 44 as a bis TFA salt. MS found: (M+H)$^+$=460.

Example 45

(cis,trans)-tert-butyl 9-({4-[2-methyl-4-quinolinyl)methoxy]benzoyl}amino)-2,4-dioxo-1,3,7-triazaspiro[4.4]nonane-7-carboxylate (45a) A mixture of compound 43a (26.0 g, 141 mmol), sodium azide (43.9 g, 676 mmol), and ammonium chloride (37.6 g, 704 mmol) in 200 mL of water and 200 mL of MeOH was refluxed overnight. The reaction mixture was cooled, filtered through a sintered glass funnel, and concentrated on a rotary evaporator to give 23.25 g (84% yield) of the azido alcohol 45a.

(45b) A solution of 45a (23.25 g, 69.8 mmol) in 200 mL MeOH was placed in a Parr bottle with 20% Pd(OH)2 (2.0 g) and hydrogenated under 50 psi of H$_2$ overnight. The reaction mixture was filtered through a sintered glass funnel and concentrated on a rotary evaporator to give 19.9 g (70% yield) of the amino alcohol 45b.

(45c) A solution of 45b (3.0 g, 14.8 mmol) and diisopropylamine (7.75 mL, 44.5 mmol) in 8 mL DMF was treated with 4-[(2-methyl-4-quinolinyl)methoxy]benzoyl chloride (5.68 g, 16.3 mmol). The reaction was stirred at rt for overnight and then extracted from brine EtOAc×3. Organic layer was washed with sat KH$_2$PO$_4$×2 and water×2. The combined organic extracts were dried over MgSO$_4$, filtered, and concentrated on a rotary evaporator to give 7.0 g of 45c (93% yield). MS found: (M+H)$^+$=464.

(45d) DMSO (2.0 mL, 28 mmol) was added dropwise to a 2M solution of oxalyl chloride in CH$_2$Cl$_2$ (7.0 mL, 14 mmol) at −78° C. After 15 min, amino alcohol 45c (6.0 g, 16.9 mmol) in 80 mL CH$_2$Cl$_2$/THF (1:1) was added dropwise followed by dropwise addition of triethylamine (8.8 mL, 63.1 mmol). The reaction mixture was warmed to rt and stirred for 2. The reaction mixture was partitioned between EtOAc and sat KH$_2$PO$_4$, separated, and the organic layer was washed with brine, dried over MgSO$_4$, filtered, and concentrated by rotary evaporator. The residue was chromatographed on silica gel to give 3.6 g of 45d (60% yield). MS found: (M+H)$^+$=476.

(45e) Ketone 45d (3.6 g, 7.6 mmol) was dissolved in 60 mL 2:1 EtOH/water and treated with ammonium carbonate (7.3 g, 76 mmol) and potassium cyanide (1.0 mg, 15.2 mmol). The reaction was heated in a 65° C. oil bath for 24 hr. The EtOH was removed by rotary evaporator, the residue was extracted from dil. HCl with 3×EtOAc. The combined organic extracts were dried over MgSO$_4$, filtered, and concentrated to give 2.47 g of the hydantoin. A portion of compound 45e (80 mg, 0.12 mmol) was purified by reverse-phase chromatography to give 20 mg of the hydantoin 45e (25% yield). MS found: (M+H)$^+$=546.

Example 46

(cis,trans)-N-(2,4-dioxo-1,3,7-triazaspiro[4.4]non-9-yl)-4-[(2-methyl-4-quinolinyl)methoxy]benzamide

(46) Compound 45e (2.0 mg, 3.66 mmol) was stirred for 1 hr in TFA/CH$_2$Cl$_2$ (1:1, 50 mL) and concentrated on a rotary evaporator to give 2.5 g of hydantoin 46 (100% yield). MS found: (M+H)$^+$=446.

Example 47

(cis,trans)-N-[7-acetyl-(2,4-dioxo-1,3,7-triazaspiro[4.4]non-9-yl]-4-[(2-methyl-4-quinolinyl)methoxy]benzamide

(47) To solution of compound 45e (88 mg, 0.13 mmol) and triethylamine (0.1 mL, 0.72 mmol) in DCM was added acetic anhydride (0.03 mL, 0.32 mmol) and the mixture was stirred overnight. 10 mL of 10% NaHCO$_3$ solution was added and stirred at 60° C. for 1 hr. The residue was extracted from sat. KH$_2$PO$_4$ with 3×EtOAc. The combined organic extracts were dried over MgSO$_4$, filtered, concentrated on a rotary evaporator and purified by reverse-phase chromatography to give 5 mg of hydantoin 47 (6.4% yield). MS found: (M+H)$^+$=488.

Example 48

(cis,trans)-4-[(2-methyl-4-quinolinyl)methoxy]-N-[7-(methylsulfonyl)-2,4-dioxo-1,3,7-triazaspiro[4.4]non-9-yl]-benzamide

(48) To solution of compound 45e (88 mg, 0.13 mmol) and triethylamine (0.1 mL, 0.72 mmol) in DCM was added methanesulfonic anhydride (45 mg, 0.26 mmol) and the mixture was stirred overnight. To the solution, 10 mL of 10% NaHCO$_3$ solution was added and stirred at 60° C. for 1 hr. The residue was extracted from sat. KH$_2$PO$_4$ with 3×EtOAc. The combined organic extracts were dried over MgSO$_4$, filtered, concentrated on a rotary evaporator and purified by reverse-phase chromatography to give 6 mg of hydantoin 47 (7.2% yield). MS found: (M+H)$^+$=524.

Example 49

(cis,trans)-tert-butyl 4-{[9-[(2-methyl-4-quinolinyl)methoxy]benzoyl)amino)-2,4-dioxo-1,3,7-triazaspiro[4.4]non-7-yl]carbonyl}-1-piperidinecarboxylate

(49) A mixture of compound 45e (67 mg, 0.10 mmol), BOP (66 mg, 0.15 mmol), t-butoxycarbonylisonipecotic acid (34 mg, 0.15 mmol) and cesium carbonate (325 mg, 1.0 mmol) in 2 mL of DMF was stirred for 2 hr. The reaction mixture was filtered and the filtrate was purified by reverse-phase chromatography to give hydantoin 49 (38% yield). MS found: (M+H)$^+$=658.

Example 50

(cis,trans)-N-[2,4-dioxo-7-(4-piperidinylcarbonyl)-1,3,7-triazaspiro[4.4]non-9-yl]-4-[(2-methyl-4-quinolinyl)methoxy]benzamide

(50) Compound 49 (15 mg, 0.023 mmol) was stirred for 1 hr in TFA/CH$_2$Cl$_2$ (1:1, 2 mL) and concentrated on a rotary evaporator to give hydantoin 50 (100% yield). MS found: (M+H)$^+$=557.

Example 51

(cis,trans)-N-[7-isonicotinoyl-2,4-dioxo-1,3,7-triazaspiro[4.4]non-9-yl]-4-[(2-methyl-4-quinolinyl)methoxy]benzamide

(51) A mixture of compound 45e (67 mg, 0.10 mmol), BOP (66 mg, 0.15 mmol), isonicotinic acid (18 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 51 (54% yield). MS found: (M+H)$^+$=551.

Example 52

(cis,trans)-N-[2,4-dioxo-7-(phenoxyacetyl)-1,3,7-triazaspiro[4.4]non-9-yl]-4-[(2-methyl-4-quinolinyl)methoxy]benzamide

(52) A mixture of compound 45e (67 mg, 0.10 mmol), BOP (66 mg, 0.15 mmol), phenoxyacetic acid (23 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 49 (23% yield). MS found: (M+H)$^+$=580.

Example 53

((cis,trans)-N-[7-(3-methylbutanoyl)-2,4-dioxo-1,3,7-triazaspiro[4.4]non-9-yl]-4-[(2-methyl-4-quinolinyl)methoxy]benzamide

(53) A mixture of compound 45e (67 mg, 0.10 mmol), BOP (66 mg, 0.15 mmol), isovaleric acid (14 uL, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 53 (28% yield). MS found: (M+H)$^+$=530.

Example 54

(cis,trans)-N-[2,4-dioxo-7-(3-pyridinylcarbonyl)-1,3,7-triazaspiro[4.4]non-9-yl]-4-[(2-methyl-4-quinolinyl)methoxy]benzamide

(54) A mixture of compound 45e (67 mg, 0.10 mmol), BOP (66 mg, 0.15 mmol), nicotinic acid (18 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 54 (46% yield). MS found: (M+H)$^+$=551.

Example 55

(cis,trans)-N-[7-isobutyryl-2,4-dioxo-1,3,7-triazaspiro[4.4]non-9-yl]-4-[(2-methyl-4-quinolinyl)methoxy]benzamide

(55) A mixture of compound 45e (67 mg, 0.10 mmol), BOP (66 mg, 0.15 mmol), isobutyric acid (14 uL, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 55 (37% yield). MS found: $(M+H)^+=516$.

Example 56

(cis,trans)-4-[(2-methyl-4-quinolinyl)methoxy]-N-[7-(4-morpholinylacetyl)-2,4-dioxo-1,3,7-triazaspiro[4.4]non-9-yl]benzamide (56a) NaH (500 mg, 12.5 mmol) was added portionwise to a solution of morpholine (1.0 mL, 11.5 mmol) in 10 mL THF. After bubling ceased, t-butylbromoacetate was added and the mixture was stirred overnight. The reaction was quenched with water and then partitioned between EtOAc and brine. The organic extracts were dried over $MgSO_4$, filtered, and concentrated on a rotary evaporator. Crude residue was treated with $TFA/CH_2Cl_2$ (1:1, 10 mL) for 1 hour and then concentrated on a rotary evaporator to give morpholineacetic acid 56a which was used without purification.

(56b) A mixture of compound 45e (67 mg, 0.10 mmol), BOP (66 mg, 0.15 mmol), morpholineacetic acid (56a) (22 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 56 (40% yield). MS found: $(M+H)^+=573$.

Example 57

(cis,trans)-N-[2,4-dioxo-7-(3-pyridinylmethyl)-1,3,7-triazaspiro[4.4]non-9-yl]-4-[(2-methyl-4-quinolinyl)methoxy]benzamide

(57) A mixture of compound 45e (67 mg, 0.10 mmol), triethylamine (0.7 mL, 0.5 mmol), and 3-pyridinecarboxaldehyde (18 mg, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat $NaHCO_3$ and the organic layer was washed with sat $KH_2PO_4$. The organic layer was dried over $MgSO_4$, filtered, and purified by reverse-phase chromatography to give hydantoin 57 (28% yield). MS found: $(M+H)^+=537$.

Example 58

(cis,trans)-N-[2,4-dioxo-7-(4-pyridinylmethyl)-1,3,7-triazaspiro[4.4]non-9-yl]-4-[(2-methyl-4-quinolinyl)methoxy]benzamide

(58) A mixture of compound 45e (67 mg, 0.10 mmol), triethylamine (0.7 mL, 0.5 mmol), and 4-pyridinecarboxaldehyde (18 mg, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat $NaHCO_3$ and the organic layer was washed with sat $KH_2PO_4$. The organic layer was dried over $MgSO_4$, filtered, and purified by reverse-phase chromatography to give hydantoin 58 (11% yield). MS found: $(M+H)^+=537$.

Example 59

(cis,trans)-N-[(7-isopropyl-2,4-dioxo-1,3,7-triazaspiro[4.4]non-9-yl]-4-[(2-methyl-4-quinolinyl)methoxy]benzamide

(59) A mixture of compound 45e (67 mg, 0.10 mmol), triethylamine (0.7 mL, 0.5 mmol), and acetone (22 uL, 0.30 mmol) in 5 mL of DCM was stirred for 2 hr. Sodium triacetoxyborohydride (42 mg, 0.2 mmol) was added and the reaction was stirred overnight. The residue was partitioned between EtOAc and sat $NaHCO_3$ and the organic layer was washed with sat $KH_2PO_4$. The organic layer was dried over $MgSO_4$, filtered, and purified by reverse-phase chromatography to give hydantoin 59 (11% yield). MS found: $(M+H)^+=488$.

Example 60

(cis,trans)-N-[(7-isobutyl-2,4-dioxo-1,3,7-triazaspiro[4.4]non-9-yl]-4-[(2-methyl-4-quinolinyl)methoxy]benzamide

(60) A mixture of compound 45e (67 mg, 0.10 mmol), triethylamine (0.7 mL, 0.5 mmol), and isobutylaldehyde (16 uL, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat $NaHCO_3$ and the organic layer was washed with sat $KH_2PO_4$. The organic layer was dried over $MgSO_4$, filtered, and purified by reverse-phase chromatography to give hydantoin 60 (14% yield). MS found: $(M+H)^+=502$.

Example 61

(cis,trans)-tert-butyl 9-({4-[2-methyl-4-quinolinyl)methyl]benzoyl}amino)-2,4-dioxo-1,3,7-triazaspiro[4.4]nonane-7-carboxylate (61a) A solution of 45b (4.0 g, 20 mmol), HATU (11.4 g, 30 mmol) and triethylamine (4.2 mL, 30 mmol) in 50 mL DMF was treated with 4-[(2-methyl-4-quinolinyl)methyl]benzoic acid (6.0 g, 21.7 mmol). The reaction was stirred overnight and then extracted from brine EtOAc×3. Organic layer was washed with sat $KH_2PO_4$×2 and water×2. The combined organic extracts were dried over $MgSO_4$, filtered, and concentrated on a rotary evaporator to give 7.0 g of 61a (76% yield). MS found: $(M+H)^+=462$.

(61b) DMSO (2.3 mL, 32.4 mmol) was added dropwise to a 2M solution of oxalyl chloride in $CH_2Cl_2$ (8.0 mL, 16 mmol) at −78° C. After 15 min, amino alcohol 61a (6.78 g, 14.7 mmol) in 80 mL $CH_2Cl_2$/THF (1:1) was added dropwise followed by dropwise addition of triethylamine (10.2 mL, 73 mmol) The reaction mixture was warmed to rt and stirred for 2. The reaction mixture was partitioned between EtOAc and sat $KH_2PO_4$, separated, and the organic layer was washed with brine, dried over $MgSO_4$, filtered, and concentrated by rotary evaporator. The residue was chromatographed on silica gel to give 3.4 g of 61b (50% yield). MS found: $(M+H)^+=460$.

(61c) Ketone 61b (3.4 g, 7.4 mmol) was dissolved in 60 mL 2:1 EtOH/water and treated with ammonium carbonate (7.3 g, 76 mmol) and potassium cyanide (1.0 mg, 15.2 mmol). The reaction was heated in a 65° C. oil bath for 24 hr. The EtOH was removed by rotary evaporator, the residue was extracted from sat $KH_2PO_4$ with 3×EtOAc. The combined organic extracts were dried over $MgSO_4$, filtered, and concentrated to give 2.7 g of the hydantoin (69% yield). MS found: $(M+H)^+=530$.

(61d) A portion of compound 61c (74 mg, 0.14 mmol) was purified by reverse-phase chromatography to give 15 mg of the hydantoin 61d as a TFA salt(25% yield). MS found: $(M+H)^+=530$.

Example 62

(cis,trans)-N-(2,4-dioxo-1,3,7-triazaspiro[4.4]non-9-yl)-4-[(2-methyl-4-quinolinyl)methyl]benzamide

(62) Compound 61c (2.3 g, 4.34 mmol) was stirred for 1 hr in $TFA/CH_2Cl_2$ (1:1, 50 mL) and concentrated on a rotary evaporator to give 2.6 g of hydantoin 62 (91% yield). MS found: $(M+H)^+=430$.

Example 63

(cis,trans)-tert-butyl 4-{[9-[(2-methyl-4-quinolinyl)methyl]benzoyl}amino)-2,4-dioxo-1,3,7-triazaspiro[4.4]non-7-yl]carbonyl}-1-piperidinecarboxylate

(63) A mixture of compound 62 (66 mg, 0.10 mmol), BOP (66 mg, 0.15 mmol), t-butoxycarbonylisonipecotic acid (34 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 63 (32% yield). MS found: $(M+H)^+=641$.

Example 64

(cis,trans)-N-[2,4-dioxo-7-(4-piperidinylcarbonyl)-1,3,7-triazaspiro[4.4]non-9-yl]-4-[(2-methyl-4-quinolinyl)methyl]benzamide

(64) Compound 63 (15 mg, 0.023 mmol) was stirred for 1 hr in $TFA/CH_2Cl_2$ (1:1, 2 mL) and concentrated on a rotary evaporator to give hydantoin 64 (100% yield). MS found: $(M+H)^+=541$.

Example 65

(cis,trans)-N-[7-isonicotinoyl-2,4-dioxo-1,3,7-triazaspiro[4.4]non-9-yl]-4-[(2-methyl-4-quinolinyl)methyl]benzamide

(65) A mixture of compound 62 (66 mg, 0.10 mmol), BOP (66 mg, 0.15 mmol), isonicotinic acid (18 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 65 (33% yield). MS found: $(M+H)^+=535$.

Example 66

(cis,trans)-N-[2,4-dioxo-7-(phenoxyacetyl)-1,3,7-triazaspiro[4.4]non-9-yl]-4-[(2-methyl-4-quinolinyl)methyl]benzamide

(66) A mixture of compound 62 (66 mg, 0.10 mmol), BOP (66 mg, 0.15 mmol), phenoxyacetic acid (23 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 66 (53% yield). MS found: $(M+H)^+=564$.

Example 67

((cis,trans)-N-[7-(3-methylbutanoyl)-2,4-dioxo-1,3,7-triazaspiro[4.4]non-9-yl]-4-[(2-methyl-4-quinolinyl)methyl]benzamide

(67) A mixture of compound 62 (67 mg, 0.10 mmol), BOP (66 mg, 0.15 mmol), isovaleric acid (14 uL, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 67 (32% yield). MS found: $(M+H)^+=514$.

Example 68

(cis,trans)-N-[2,4-dioxo-7-(3-pyridinylcarbonyl)-1,3,7-triazaspiro[4.4]non-9-yl]-4-[(2-methyl-4-quinolinyl)methyl]benzamide

(68) A mixture of compound 62 (66 mg, 0.10 mmol), BOP (66 mg, 0.15 mmol), nicotinic acid (18 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 68 (16% yield). MS found: $(M+H)^+=535$.

Example 69

((cis,trans)-N-[7-isobutyryl-2,4-dioxo-1,3,7-triazaspiro[4.4]non-9-yl]-4-[(2-methyl-4-quinolinyl)methyl]benzamide

(69) A mixture of compound 62 (66 mg, 0.10 mmol), BOP (66 mg, 0.15 mmol), isobutyric acid (14 uL, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 69 (49% yield). MS found: $(M+H)^+=500$.

Example 70

(cis,trans)-4-[(2-methyl-4-quinolinyl)methyl]-N-[7-(4-morpholinylacetyl)-2,4-dioxo-1,3,7-triazaspiro[4.4]non-9-yl]benzamide

(70) A mixture of compound 62 (67 mg, 0.10 mmol), BOP (66 mg, 0.15 mmol), morpholineacetic acid (56a) (22 mg, 0.15 mmol) and cesium carbonate (325 mg, 1.0 mmol) in 2 mL of DMF was for 2 hr. The reaction mixture was filtered and the

Example 71

(cis,trans)-N-[2,4-dioxo-7-(3-pyridinylmethyl)-1,3,7-triazaspiro[4.4]non-9-yl]-4-[(2-methyl-4-quinolinyl)methyl]benzamide

(71) A mixture of compound 62 (66 mg, 0.10 mmol), triethylamine (0.7 mL, 0.5 mmol), and 3-pyridinecarboxaldehyde (18 mg, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat NaHCO$_3$ and the organic layer was washed with sat KH$_2$PO$_4$. The organic layer was dried over MgSO$_4$, filtered, and purified by reverse-phase chromatography to give hydantoin 71 (11% yield). MS found: (M+H)$^+$=521.

Example 72

(cis,trans)-N-[2,4-dioxo-7-(4-pyridinylmethyl)-1,3,7-triazaspiro[4.4]non-9-yl]-4-[(2-methyl-4-quinolinyl)methyl]benzamide

(72) A mixture of compound 62 (66 mg, 0.10 mmol), triethylamine (0.7 mL, 0.5 mmol), and 4-pyridinecarboxaldehyde (18 mg, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat NaHCO$_3$ and the organic layer was washed with sat KH$_2$PO$_4$. The organic layer was dried over MgSO$_4$, filtered, and purified by reverse-phase chromatography to give hydantoin 72 (13% yield). MS found: (M+H)$^+$=521.

Example 73

(cis,trans)-N-[(7-isopropyl-2,4-dioxo-1,3,7-triazaspiro[4.4]non-9-yl]-4-[(2-methyl-4-quinolinyl)methyl]benzamide

(73) A mixture of compound 62 (66 mg, 0.10 mmol), triethylamine (0.7 mL, 0.5 mmol), and acetone (22 uL, 0.30 mmol) in 5 mL of DCM was stirred for 2 hr. Sodium triacetoxyborohydride (42 mg, 0.2 mmol) was added and the reaction was stirred overnight. The residue was partitioned between EtOAc and sat NaHCO$_3$ and the organic layer was washed with sat KH$_2$PO$_4$. The organic layer was dried over MgSO$_4$, filtered, and purified by reverse-phase chromatography to give hydantoin 73 (11% yield). MS found: (M+H)$^+$=472.

Example 74

(cis,trans)-N-[(7-isobutyl-2,4-dioxo-1,3,7-triazaspiro[4.4]non-9-yl]-4-[(2-methyl-4-quinolinyl)methyl]benzamide

(74) A mixture of compound 45e (66 mg, 0.10 mmol), triethylamine (0.7 mL, 0.5 mmol), and isobutylaldehyde (16 uL, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat NaHCO$_3$ and the organic layer was washed with sat KH$_2$PO$_4$. The organic layer was dried over MgSO$_4$, filtered, and purified by reverse-phase chromatography to give hydantoin 74 (21% yield). MS found: (M+H)$^+$=486.

Example 75

(cis,trans)-tert-butyl 9-({4-[(1,1-dioxido-2,3-dihydro-4H-1,4-benzothiazin-4-yl)methyl]benzoyl}amino)-2,4-dioxo-1,3,7-triazaspiro[4.4]nonane-7-carboxylate (75a) A solution of 45b (3.5 g, 17 mmol), PyBOP (13.0 g, 25 mmol) and triethylamine (3.5 mL, 25 mmol) in 50 mL DMF was treated with 4-[(1,1-dioxido-2,3-dihydro-4H-1,4-benzothiazin-4-yl)methyl]benzoic acid (5.45 g, 17 mmol). The reaction was stirred overnight and then extracted from brine EtOAc×3. Organic layer was washed with sat KH$_2$PO$_4$×2 and water×2. The combined organic extracts were dried over MgSO$_4$, filtered, and concentrated on a rotary evaporator to give 6.7 g of 75a (77% yield). MS found: (M+H)$^+$=502.

(75b) DMSO (2.3 mL, 32.4 mmol) was added dropwise to a 2M solution of oxalyl chloride in CH$_2$Cl$_2$ (8.0 mL, 16 mmol) at −78° C. After 15 min, amino alcohol 75b (6.74 g, 13.4 mmol) in 80 mL CH$_2$Cl$_2$/THF (1:1) was added dropwise followed by dropwise addition of triethylamine (10.2 mL, 73 mmol) The reaction mixture was warmed to rt and stirred for 2. The reaction mixture was partitioned between EtOAc and sat KH$_2$PO$_4$, separated, and the organic layer was washed with brine, dried over MgSO$_4$, filtered, and concentrated by rotary evaporator. Residue was carried on to the next step without purification. MS found: (M+H)$^+$=500.

(75c) Ketone 75b was dissolved in 60 mL 2:1 EtOH/water and treated with ammonium carbonate (7.3 g, 76 mmol) and potassium cyanide (1.0 mg, 15.2 mmol). The reaction was heated in a 65° C. oil bath for 24 hr. The EtOH was removed by rotary evaporator, the residue was extracted from sat KH$_2$PO$_4$ with 3×EtOAc. The combined organic extracts were dried over MgSO$_4$, filtered, and concentrated to give 4.2 g of the hydantoin (55% yield). MS found: (M+H)$^+$=570.

(75d) A portion of compound 75c (250 mg, 0.5 mmol) was purified by reverse-phase chromatography to give 108 mg of the hydantoin 75d as a TFA salt (38% yield). MS found: (M+H)$^+$=570.

Example 76

(cis,trans)-4-[(1,1-dioxido-2,3-dihydro-4H-1,4-benzothiazin-4-yl)methyl]-N-(2,4-dioxo-1,3,7-triazaspiro[4.4]non-9-yl]benzamide

(76) Compound 75c (2.0 g, 3.5 mmol) was stirred for 1 hr in TFA/CH$_2$Cl$_2$ (1:1, 50 mL) and concentrated on a rotary evaporator to give 2.2 g of hydantoin 76 (90% yield). MS found: (M+H)$^+$=470.

Example 77

(cis,trans)-tert-butyl 4-{[9-({4-[(1,1-dioxido-2,3-dihydro-4H-1,4-benzothiazin-4-yl)methyl]benzoyl}amino)-2,4-dioxo-1,3,7-triazaspiro[4.4]non-7-yl]carbonyl}-1-piperidinecarboxylate

(77) A mixture of compound 76 (70 mg, 0.10 mmol), BOP (66 mg, 0.15 mmol), t-butoxycarbonylisonipecotic acid (34 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 77 (24% yield). MS found: $(M+H)^+=681$.

Example 78

(cis,trans)-4-[(1,1-dioxido-2,3-dihydro-4H-1,4-benzothiazin-4-yl)methyl]-N-[2,4-dioxo-7-(4-piperidinylcarbonyl)-1,3,7-triazaspiro[4.4]non-9-yl]benzamide

(78) Compound 77 (15 mg, 0.023 mmol) was stirred for 1 hr in TFA/$CH_2Cl_2$ (1:1, 2 mL) and concentrated on a rotary evaporator to give hydantoin 78 (100% yield). MS found: $(M+H)^+=581$.

Example 79

(cis,trans)-4-[(1,1-dioxido-2,3-dihydro-4H-1,4-benzothiazin-4-yl)methyl]-N-[7-isonicotinoyl-2,4-dioxo-1,3,7-triazaspiro[4.4]non-9-yl]benzamide

(79) A mixture of compound 76 (70 mg, 0.10 mmol), BOP (66 mg, 0.15 mmol), isonicotinic acid (18 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 79 (43% yield). MS found: $(M+H)^+=575$.

Example 80

(cis,trans)-4-[(1,1-dioxido-2,3-dihydro-4H-1,4-benzothiazin-4-yl)methyl]-N-[2,4-dioxo-7-(phenoxyacetyl)-1,3,7-triazaspiro[4.4]non-9-yl]benzamide

(80) A mixture of compound 76 (66 mg, 0.10 mmol), BOP (66 mg, 0.15 mmol), phenoxyacetic acid (23 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 80 (49% yield). MS found: $(M+H)^+=604$.

Example 81

(cis,trans)-4-[(1,1-dioxido-2,3-dihydro-4H-1,4-benzothiazin-4-yl)methyl]-N-[7-(3-methylbutanoyl)-2,4-dioxo-1,3,7-triazaspiro[4.4]non-9-yl]benzamide

(81) A mixture of compound 76 (70 mg, 0.10 mmol), BOP (66 mg, 0.15 mmol), isovaleric acid (14 uL, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 81 (52% yield). MS found: $(M+H)^+=554$.

Example 82

(cis,trans)-4-[(1,1-dioxido-2,3-dihydro-4H-1,4-benzothiazin-4-yl)methyl]-N-[2,4-dioxo-7-(3-pyridinylcarbonyl)-1,3,7-triazaspiro[4.4]non-9-yl]benzamide

(82) A mixture of compound 76 (66 mg, 0.10 mmol), BOP (66 mg, 0.15 mmol), nicotinic acid (18 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 82 (56% yield). MS found: $(M+H)^+=575$.

Example 83

(cis,trans)-4-[(1,1-dioxido-2,3-dihydro-4H-1,4-benzothiazin-4-yl)methyl]-N-[7-isobutyryl-2,4-dioxo-1,3,7-triazaspiro[4.4]non-9-yl]benzamide

(83) A mixture of compound 76 (70 mg, 0.10 mmol), BOP (66 mg, 0.15 mmol), isobutyric acid (14 uL, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 83 (54% yield). MS found: $(M+H)^+=540$.

Example 84

((cis,trans)-4-[(1,1-dioxido-2,3-dihydro-4H-1,4-benzothiazin-4-yl)methyl]-N-[7-(4-morpholinylacetyl)-2,4-dioxo-1,3,7-triazaspiro[4.4]non-9-yl]benzamide

(84) A mixture of compound 76 (70 mg, 0.10 mmol), BOP (66 mg, 0.15 mmol), morpholineacetic acid (56a) (22 mg, 0.15 mmol) and cesium carbonate (325 mg, 1.0 mmol) in 2 mL of DMF was for 2 hr. The reaction mixture was filtered and the filtrate was purified by reverse-phase chromatography to give hydantoin 84 (51% yield). MS found: $(M+H)^+=597$.

Example 85

(cis,trans)-4-[(1,1-dioxido-2,3-dihydro-4H-1,4-benzothiazin-4-yl)methyl]-N-[2,4-dioxo-7-(3-pyridinylmethyl)-1,3,7-triazaspiro[4.4]non-9-yl]benzamide

(85) A mixture of compound 76 (70 mg, 0.10 mmol), triethylamine (0.7 mL, 0.5 mmol), and 3-pyridinecarboxaldehyde (18 mg, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat $NaHCO_3$ and the organic layer was washed with sat $KH_2PO_4$. The organic layer was dried over $MgSO_4$, filtered, and purified by reverse-phase chromatography to give hydantoin 85 (35% yield). MS found: $(M+H)^+=561$.

Example 86

(cis,trans)-4-[(1,1-dioxido-2,3-dihydro-4H-1,4-benzothiazin-4-yl)methyl]-N-[2,4-dioxo-7-(4-pyridinylmethyl)-1,3,7-triazaspiro[4.4]non-9-yl]benzamide

(86) A mixture of compound 76 (70 mg, 0.10 mmol), triethylamine (0.7 mL, 0.5 mmol), and 4-pyridinecarboxaldehyde (18 mg, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat NaHCO$_3$ and the organic layer was washed with sat KH$_2$PO$_4$. The organic layer was dried over MgSO$_4$, filtered, and purified by reverse-phase chromatography to give hydantoin 86 (34% yield). MS found: (M+H)$^+$=561.

Example 87

(cis,trans)-4-[(1,1-dioxido-2,3-dihydro-4H-1,4-benzothiazin-4-yl)methyl]-N-(7-isopropyl-2,4-dioxo-1,3,7-triazaspiro[4.4]non-9-yl)benzamide

(87) A mixture of compound 76 (70 mg, 0.10 mmol), triethylamine (0.7 mL, 0.5 mmol), and acetone (22 uL, 0.30 mmol) in 5 mL of DCM was stirred for 2 hr. Sodium triacetoxyborohydride (42 mg, 0.2 mmol) was added and the reaction was stirred overnight. The residue was partitioned between EtOAc and sat NaHCO$_3$ and the organic layer was washed with sat KH$_2$PO$_4$. The organic layer was dried over MgSO$_4$, filtered, and purified by reverse-phase chromatography to give hydantoin 87 (22% yield). MS found: (M+H)$^+$=512.

Example 88

(cis,trans)-4-[(1,1-dioxido-2,3-dihydro-4H-1,4-benzothiazin-4-yl)methyl]-N-(7-isobutyl-2,4-dioxo-1,3,7-triazaspiro[4.4]non-9-yl)benzamide

(88) A mixture of compound 76 (70 mg, 0.10 mmol), triethylamine (0.7 mL, 0.5 mmol), and isobutylaldehyde (16 uL, 0.15 mmol) in 5 mL of DCM was stirred for 2 hr. Sodium triacetoxyborohydride (42 mg, 0.2 mmol) was added and the reaction was stirred overnight. The residue was partitioned between EtOAc and sat NaHCO$_3$ and the organic layer was washed with sat KH$_2$PO$_4$. The organic layer was dried over MgSO$_4$, filtered, and purified by reverse-phase chromatography to give hydantoin 88 (43% yield). MS found: (M+H)$^+$=526.

Example 89

(cis,trans)-tert-butyl-9-({4-[(2-isopropyl-1H-benzimidazol-1-yl)methyl]benzoyl}amino)-2,4-dioxo-1,3,7-triazaspiro[4.4]nonane-7-carboxylate (89a) A solution of 45b (202 mg, 1.0 mmol), PyBOP (780 mg, 1.5 mmol) and triethylamine (0.2 mL, 1.4 mmol) in 5 mL DMF was treated with 4-[(2-isopropyl-1H-benzimidazol-1-yl)methyl]benzoic acid (5.68 g, 16.3 mmol). The reaction was stirred at rt for overnight and then extracted from brine EtOAc×3. Organic layer was washed with sat KH$_2$PO$_4$×2 and water×2. The combined organic extracts were dried over MgSO$_4$, filtered, and concentrated on a rotary evaporator. Crude residue was taken to next step. MS found: (M+H)$^+$=477.

(89b) Dess-Martin periodinane (1.0 g, 2.36 mmol) was added to a solution of 89a in 10 mL DCM. The reaction mixture was stirred overnight and then extracted from sat NaHCO$_3$ with 3×EtOAc. The combined organic extracts were dried over MgSO$_4$, filtered, concentrated on a rotary evaporator, and chromatographed on silica gel to give 120 mg of 89b (25% yield). MS found: (M+H)$^+$=500.

(89c) Ketone 89b (120 mg, 0.25 mmol) was dissolved in 3 mL 2:1 EtOH/water and treated with ammonium carbonate (135 mg, 1.4 mmol) and potassium cyanide (18 mg, 0.28 mmol). The reaction was heated in a 65° C. oil bath for 24 hr. The EtOH was removed by rotary evaporator, the residue was extracted from dil. HCl with 3×EtOAc. The combined organic extracts were dried over MgSO$_4$, filtered, concentrated, and purified by reverse-phase chromatography to give 10 mg of the hydantoin 89c as a TFA salt (5.7% yield). MS found: (M+H)$^+$=547.

Example 90

(cis,trans)-N-[2,4-dioxo-1,3,7-triazaspiro[4.4]non-9-yl]-4-[(2-isopropyl-1H-benzimidazol-1-yl])methyl] benzamide

(90) Compound 89c (15 mg, 0.027 mmol) was stirred for 1 hr in TFA/CH$_2$Cl$_2$ (1:1, 1 mL) and concentrated on a rotary evaporator to give 15 mg of hydantoin 90 (71% yield). MS found: (M+H)$^+$=447.

Example 91

(cis,trans)-tert-butyl 9-[({4-[(2-methyl-4-quinolinyl) methoxy]phenyl}sulfonyl)amino]-[2,4-dioxo-1,3,7-triazaspiro[4.4]nonane-7-yl]-carboxylate (91a) A solution of 45b (172 mg, 0.85 mmol) was dissolved in 10 mL CH$_2$Cl$_2$ and 1 mL of DMSO and treated with triethylamine (0.25 mL, 1.8 mmol), DMAP (104 mg, 0.85 mmol) and [(2-methyl-4-quinolinyl)methoxy]benzenesulfonyl chloride HCl salt (345 mg, 0.90 mmol). The reaction was stirred at rt overnight and then extracted from sat. NaHCO$_3$ with EtOAc×3. The combined organic extracts were dried over MgSO$_4$, filtered, and concentrated on a rotary evaporator to give the sulfonamide product 91a which was used without purification. MS found: (M+H)$^+$=514.

(91b) Dess-Martin periodinane (1.0 g, 2.36 mmol) was added to a solution of 89a in 10 mL DCM. The reaction mixture was stirred overnight and then extracted from sat NaHCO$_3$ with 3×EtOAc. The combined organic extracts were dried over MgSO$_4$, filtered, concentrated on a rotary evaporator, and chromatographed on silica gel to give 25 mg of 91b (5.7% yield). MS found: (M+H)$^+$=512.

(91c) Ketone 91b (25 mg, 0.05 mmol) was dissolved in 3 mL 2:1 EtOH/water and treated with ammonium carbonate (48 mg, 0.5 mmol) and potassium cyanide (7.0 mg, 0.1 mmol). The reaction was heated in a 65° C. oil bath for 24 hr. The residue was acidified with TFA and purified by reverse-phase chromatography to give 10 mg of the hydantoin 91c as a TFA salt (29% yield). MS found: $(M+H)^+=582$.

Example 92

(cis,trans)-N-[2,4-dioxo-1,3,7-triazaspiro[4.4]non-9-yl]-4-[(2-methyl-4-quinolinyl)methoxy]benzenesulfonamide

(92) Compound 91c (4.0 mg, 0.0057 mmol) was stirred for 1 hr in TFA/CH$_2$Cl$_2$ (1:1, 1 mL) and concentrated on a rotary evaporator to give 4 mg of hydantoin 92 (100% yield). MS found: $(M+H)^+=482$.

Example 93

(cis,trans)-tert-butyl 9-[({4-[(2-methyl-4-quinolinyl)methoxy]benzoyl}amino)methyl]-2,4-dioxo-1,3,7-triazaspiro[4.4]nonane-7-carboxylate (93a) A mixture of compound 43a (1.66 g, 8.97 mmol), potassium cyanide (3.0 g, 45.7 mmol), and ammonium chloride (2.4 g, 44.9 mmol) in 25 mL of water and 25 mL of MeOH was refluxed overnight. The reaction mixture was cooled and extracted from brine with EtOAc×3. The combined organic extracts were dried over MgSO$_4$, filtered, and concentrated on a rotary evaporator to give 93a which was used without purification.

(93b) A solution of 93a in 50 mL MeOH was placed in a Parr bottle with PtO$_2$ (200 mg) and hydrogenated under 50 psi of H$_2$ overnight. The reaction mixture was filtered through a sintered glass funnel and concentrated on a rotary evaporator to give the amino alcohol 93b.

(93c) To crude 93b in a mixture of 20 mL 10% NaHCO$_3$ and 20 mL DCM was added 4-[(2-methyl-4-quinolinyl)methoxy]benzoyl chloride HCl salt (700 mg, 2.0 mmol). After stirring 2 hr, the reaction was extracted with NaHCO$_3$ and 3×DCM. The combined organic extracts were concentrated and purified by silica gel chromatography to give 125 mg (4% yield) of the amide product. MS found: $(M+H)^+=492$.

(93d) Dess-Martin periodinane (424 mg, 1.0 mmol) was added to a solution of 93c in 10 mL DCM. The reaction mixture was stirred overnight and then extracted from sat NaHCO$_3$ with 3×EtOAc. The combined organic extracts were dried over MgSO$_4$, filtered, and concentrated on a rotary evaporator to give ketone 93d. MS found: $(M+H)^+=490$.

(93e) Ketone 93d was dissolved in 15 mL 2:1 EtOH/water and treated with ammonium carbonate (240 mg, 2.5 mmol) and potassium cyanide (33 mg, 0.5 mmol). The reaction was heated in a 65° C. oil bath for 24 hr. The EtOH was removed by rotary evaporator and the residue was extracted from sat KH$_2$PO$_4$ with 3×EtOAc. The combined organic extracts were dried over MgSO$_4$, filtered, concentrated on a rotary evaporator, and purified by reverse-phase chromatography to 108 mg of the hydantoin 93e as a TFA salt (77% yield). MS found: $(M+H)^+=560$.

Example 94

(cis,trans)-N-[(2,4-dioxo-1,3,7-triazaspiro[4.4]non-9-yl)methyl]-4-[(2-methyl-4-quinolinyl)methoxy]benzamide

(94) Compound 93e (7 mg, 0.013 mmol) was stirred for 1 hr in TFA/CH$_2$Cl$_2$ (1:1, 1 mL) and concentrated on a rotary evaporator to give 7 mg of hydantoin 94 (40% yield). MS found: $(M+H)^+=460$.

Example 95

(cis,trans)-tert-butyl 9-[({4-[(2-methyl-4-quinolinyl)methyl]benzoyl}amino)methyl]-2,4-dioxo-1,3,7-triazaspiro[4.4]nonane-7-carboxylate (95a) A solution of 93b (264 mg, 1.2 mmol) was dissolved in 10 mL DMF and treated with triethylamine (0.35 mL, 2.5 mmol), BOP (664 mg, 1.5 mmol), 4-[(2-methyl-4-quinolinyl)methyl]benzoic acid (416 mg, 1.5 mmol). The reaction was stirred overnight and then extracted from sat KH$_2$PO$_4$ with EtOAc×3. The combined organic extracts were dried over MgSO$_4$, filtered, and concentrated on a rotary evaporator to give the product 95a which was taken to the next step without purification. MS found: $(M+H)^+=476$.

(95b) Dess-Martin periodinane (1.5 g, 3.5 mmol) was added to a solution of 95a in 50 mL DCM. The reaction mixture was stirred overnight and then extracted from sat NaHCO$_3$ with 3×EtOAc. The combined organic extracts were dried over MgSO$_4$, filtered, concentrated on a rotary evaporator, and purified by silica gel chromatography to give 72 mg of ketone 95b (12.6% yield). MS found: $(M+H)^+=474$.

(95c) Ketone 95b (72 mg, 0.152 mmol) was dissolved in 15 mL 2:1 EtOH/water and treated with ammonium carbonate (144 mg, 1.5 mmol) and potassium cyanide (20 mg, 0.3 mmol). The reaction was heated in a 65° C. oil bath for 24 hr. The EtOH was removed by rotary evaporator and the residue was extracted from sat KH$_2$PO$_4$ with 3×EtOAc. The combined organic extracts were dried over MgSO$_4$, filtered, concentrated on a rotary evaporator, and purified by reverse-phase chromatography to 7 mg of the hydantoin 95c as a TFA salt (7% yield). MS found: $(M+H)^+=544$.

Example 96

(cis,trans)-tert-butyl 9-[({4-[(2-isopropyl-1H-benzimidazol-1-yl)methyl]benzoyl}amino)methyl]-2,4-dioxo-1,3,7-triazaspiro[4.4]nonane-7-carboxylate (96a) A solution of 93b (216 mg, 1.0 mmol) was dissolved in 10 mL DMF and treated with triethylamine (0.4 mL, 2.9 mmol), BOP (800 mg, 1.8 mmol), 4-[(2-isopropyl-1H-benzimidazol-1-yl)methyl]benzoic acid (310 mg, 1.05 mmol). The reaction was stirred overnight and then extracted from sat KH$_2$PO$_4$ with EtOAc×3. The combined organic extracts were dried over MgSO$_4$, filtered, and concentrated on a rotary evaporator to give the product 96a which was taken to the next step without purification. MS found: $(M+H)^+=494$.

(96b) Dess-Martin periodinane (1.2 g, 2.8 mmol) was added to a solution of 96a in 50 mL DCM. The reaction mixture was stirred overnight and then extracted from sat NaHCO$_3$ with 3×EtOAc. The combined organic extracts were dried over MgSO$_4$, filtered, concentrated on a rotary evaporator, and purified by silica gel chromatography to give 85 mg of ketone 96b (17% yield). MS found: (M+H)$^+$=492.

(96c) Ketone 96b (85 mg, 0.173 mmol) was dissolved in 15 mL 2:1 EtOH/water and treated with ammonium carbonate (163 mg, 1.7 mmol) and potassium cyanide (23 mg, 0.35 mmol). The reaction was heated in a 65° C. oil bath for 24 hr. The EtOH was removed by rotary evaporator and the residue was extracted from sat KH$_2$PO$_4$ with 3×EtOAc. The combined organic extracts were dried over MgSO$_4$, filtered, concentrated on a rotary evaporator, and purified by reverse-phase chromatography to 5 mg of the hydantoin 95c as a TFA salt (4.3% yield). MS found: (M+H)$^+$=561.

Example 97

(cis,trans)-tert-butyl 6-({4-[2-methyl-4-quinolinyl) methoxy]benzoyl}amino)-2,4-dioxo-1,3,8-triaza-spiro[4.5]decane-8-carboxylate (97a) A solution of 1,2,3,6-tetrahydropyridine (2.65 g, 31.9 mmol), triethylamine (8.9 mL, 64 mmol) was dissolved in 150 mL MeCN and treated with t-butyldicarbonate (8.35 g, 38.4 mmol) and DMAP (195 mg, 1.6 mmol). The reaction was stirred overnight at RT. MeCN was remove on a rotary evaporator and the residue was extracted from 10% NaHSO4 with EtOAc×3. The combined organic extracts were dried over MgSO$_4$ and filtered. The filtrate was treated with Amberlite CG-50 (R—COOH) for 10 min, filtered and then treated with Amberlite-IR-45 (R—NH$_2$), filtered and concentrated on a rotary evaporator to give 5.7 g (96% yield) of 97a. MS found: (M+H)$^+$=184.

(97b) A solution of 97a (5.67 g, 30.9 mmol) was dissolved in 200 mL CHCl$_3$ and treated with m-chloroperbenzoic acid (26.7 g, 155 mmol). The reaction was stirred at overnight and then extracted from 1N NaOH with CHCl$_3$×3. The combined organic extracts were dried over MgSO$_4$, filtered, and concentrated on a rotary evaporator to give 4.45 g (72% yield) of the epoxide 97b. MS found: (M+H)$^+$=200

(97c) A mixture of compound 97b (4.45 g, 22.3 mmol), sodium azide (7.26 g, 111.5 mmol), and ammonium chloride (5.97 g, 111.5 mmol) in 500 mL of water and 100 mL of MeOH was refluxed overnight. The reaction mixture was extracted brine with 3×EtOAc. The combined organic extracts were dried over MgSO$_4$, filtered, concentrated by rotary evaporator, and purified by silica gel chromatography to give a 4:1 mixture of regioisomers. 860 mg of 97c-1 tert-butyl 4-azido-3-hydroxy-1-piperidine carboxylate and 220 mg of 97c-2 tert-butyl 3-azido-4-hydroxy-1-piperidine carboxylate (20% yield).

(97d) A solution of 97c-2 (220 mg, 0.908 mmol) in 20 mL MeOH was placed in a Parr bottle with 20% Pd(OH)2 (44 mg) and hydrogenated under 50 psi of H$_2$ overnight. The reaction mixture was filtered through a sintered glass funnel and concentrated on a rotary evaporator to give 187 mg (97% yield) of the amino alcohol 97d.

(97e) A solution of 97d (187 mg, 0.865 mmol) in 4 mL DCM and 4 mL 10% NaHCO$_3$ was treated with 4-[(2-methyl-4-quinolinyl)methoxy]benzoyl chloride (452 mg, 1.3 mmol).

The reaction was stirred overnight and then extracted from brine EtOAc×3. The combined organic extracts were dried over MgSO$_4$, filtered, concentrated on a rotary evaporator, and purified by silica gel chromatography to give 310 mg of 97e (73% yield). MS found: (M+H)$^+$=464.

(97f) Dess-Martin periodinane (669 mg, 1.58 mmol) was added to a solution of 97e in 6 mL DCM. The reaction mixture was stirred overnight and then extracted from sat NaHCO$_3$ with 3×EtOAc. The combined organic extracts were dried over MgSO$_4$, filtered, and concentrated on a rotary evaporator to give ketone 96b (17% yield). MS found: (M+H)$^+$=562.

(97 g) Ketone 97f was dissolved in 8 mL 4:1 EtOH/water and treated with ammonium carbonate (242 mg, 2.52 mmol) and potassium cyanide (83 mg, 1.26 mmol). The reaction was heated in a 65° C. oil bath for 24 hr. The EtOH was removed by rotary evaporator and the residue was extracted from sat KH$_2$PO$_4$ with 3×EtOAc. The combined organic extracts were dried over MgSO$_4$, filtered, concentrated on a rotary evaporator, and purified by reverse-phase chromatography to 140 mg of the hydantoin 97 g as a TFA salt (33% yield). MS found: (M+H)$^+$=560.

Example 98

(cis,trans)-N-(2,4-dioxo-1,3,8-triazaspiro[4.5]dec-6-yl)-4-[(2-methyl-4-quinolinyl)methoxy]benzamide

(98) Compound 97 g (11 mg, 0.016 mmol) was stirred for 1 hr in TFA/CH$_2$Cl$_2$ (1:1, 5 mL) and concentrated on a rotary evaporator to give 10 mg of hydantoin 98 (91% yield). Ms found: (M+H)$^+$=460.

Example 99

(cis,trans)-N-[8-acetyl-(2,4-dioxo-1,3,8-triazaspiro [4.5]dec-6-yl]-4-[(2-methyl-4-quinolinyl)methoxy] benzamide

(99) A mixture of compound 98 (28 mg, 0.0416 mmol), BOP (28 mg, 0.0624 mmol), acetic acid (4 mg, 0.062 mmol) and cesium carbonate (135 mg, 0.416 mmol) in 1 mL of DMF was for 2 hr. The reaction mixture was filtered and the filtrate was purified by reverse-phase chromatography to give 6 mg of hydantoin 99 (23% yield). MS found: (M+H)$^+$=502.

Example 100

(cis,trans)-tert-butyl 10-[2-({4-[2-methyl-4-quinolinyl)methoxy]phenyl}amino)-2-oxoethyl]-2,4-dioxo-1,3,7-triazaspiro[4.5]decane-7-carboxylate (100a) A solution of 97c-1 (860 mg, 3.55 mmol) in 20 mL MeOH was placed in a Parr bottle with 20% Pd(OH)$_2$ (172 mg) and hydrogenated under 50 psi of H$_2$ overnight. The reaction mixture was filtered through a sintered glass funnel and concentrated on a rotary evaporator to give 767 mg (100% yield) of the amino alcohol 100a.

(100b) A solution of 100a (767 mg, 3.55 mmol) in 15 mL DCM and 15 mL 10% NaHCO$_3$ was treated with 4-[(2-methyl-4-quinolinyl)methoxy]benzoyl chloride (1.85 g, 5.33 mmol). The reaction was stirred overnight and then extracted from brine EtOAc×3. The combined organic extracts were dried over MgSO$_4$, filtered, concentrated on a rotary evaporator, and purified by silica gel chromatography to give 610 mg of 100b (35% yield). MS found: (M+H)$^+$=492.

(100c) Dess-Martin periodinane (1.32 g, 3.1 mmol) was added to a solution of 100b (610 mg, 1.24 mmol) in 10 mL DCM. The reaction mixture was stirred overnight and then extracted from sat NaHCO$_3$ with 3×EtOAc. The combined organic extracts were dried over MgSO₄, filtered, and concentrated on a rotary evaporator to give of ketone 100c which was used without purification. MS found: (M+H)⁺=562.

(100d) Ketone 100c was dissolved in 15 mL 4:1 EtOH/water and treated with ammonium carbonate (476 mg, 4.96 mmol) and potassium cyanide (162 mg, 2.48 mmol). The reaction was heated in a 65° C. oil bath for 24 hr. The EtOH was removed by rotary evaporator and the residue was extracted from sat KH₂PO₄ with 3×EtOAc. The combined organic extracts were dried over MgSO₄, filtered, concentrated on a rotary evaporator, and purified by silica gel chromatography to 6 mg of the hydantoin 100d (0.8% yield). MS found: (M+H)⁺=560.

Example 101

2-(2,5-dioxo-4-imidazolidinyl)-N-{4-[(2-methyl-4-quinolinyl)methoxy]phenyl}acetamide Commercially available (+/−)hydantoin-5-acetic acid (100 mg, 0.63 mmol) and 4-[(2-methyl-4-quinolinyl)methoxy]-aniline bis-HCl salt (213 mg, 0.63 mmol) were warmed in 1 mL dry DMSO and coupled using GENERAL COUPLING METHOD A. Purified on silica gel using 5% MeOH in EtOAc to give 116 mg (46%) of a white waxy solid. MS found:(M+H)⁺=406.

Example 102

2-(2,5-dioxo-4-imidazolidinyl)-N-{4-[(2-isopropyl-1H-benzimidazol-1-yl)methyl]phenyl}acetamide Commercially available (+/−)hydantoin-5-acetic acid (11 mg, 0.07 mmol) and 4-[(2-isopropyl-1H-benzimidazol-1-yl)methyl]aniline (30 mg, 0.06 mmol) were warmed in 1 mL dry DMSO until dissolved and coupled using GENERAL COUPLING METHOD A. Purified on silica gel using 5% MeOH in EtOAc to give 22 mg (89%) of a white solid. MS found: (M+H)⁺=406.

Example 103

2-(4-methyl-2,5-dioxo-4-imidazolidinyl)-N-{4-[(2-methyl-4-quinolinyl)methoxy]phenyl}acetamide (103a) Commercially available (+/−)-2-amino-2-methyl-pentanedioic acid (1.00 g, 6.8 mmol) was dissolved in 10 mL boiling water and treated portionwise with potassium cyanate (1.20 g, 14.8 mmol). After 15 min, 10% aq HCl (15 mL) was added and the reaction refluxed for 30 min after which the solvent was evaporated off and the white solid filtered, washed with cold water, and dried to give 870 mg (75%) of hydantoin derivative. MS found:(M+H)⁺=173.

(103b) 5-methylhydantoin-5-acetic acid (50 mg, 0.30 mmol) and 4-[(2-methyl-4-quinolinyl)methoxy]-aniline bis-HCl salt (101 mg, 0.30 mmol) were coupled using general coupling method A to give 20 mg (13%) of the product hydantoin. MS found:(M+H)⁺=419.

Example 104

2-(4-methyl-2,5-dioxo-4-imidazolidinyl)-N-(4-phenoxybenzyl)acetamide

Hydantoin 103a (50 mg, 0.30 mmol) was coupled to 4-phenoxybenzylamine using general coupling method A to give 45 mg of the product hydantoin. MS found:(M+H)⁺=354.

Example 105

2-(2,5-dioxo-4-imidazolidinyl)-N-{4-[(2-methyl-4-quinolinyl)methoxy]phenyl}propanamide (105a) Commercially available (+/−)-threo-2-amino-3-methyl-butanedioic acid (1.00 g, 6.8 mmol) was converted to the hydantoin using the identical procedure for example 103 to give 36% of 2-(4-hydantoinyl)propionic acid. MS found: (M+H)⁺=173.

(105b) 2-(4-hydantoinyl)propionic acid (50 mg, 0.30 mmol) and 4-[(2-methyl-4-quinolinyl)methoxy]-aniline bis-HCl salt (101 mg, 0.30 mmol) were coupled using general coupling method A to give 20 mg (13%) of the product hydantoin. MS found: (M+H)⁺=419.

Example 106

3-(2,5-dioxo-4-imidazolidinyl)-N-{4-[(2-methyl-4-quinolinyl)methoxy]phenyl}propanamide (106) (+/−)-5-hydantoinpropionic acid (Dakin; Am. Chem. J. 1910, 44, 49) (50 mg, 0.29 mmol) was coupled with 4-[(2-methyl-4-quinolinyl)methoxy]-aniline bis-HCl salt (213 mg, 0.63 mmol) using general coupling method A to give 58 mg (44%) of the product hydantoin. MS found: (M+H)⁺=419.

Example 107

5-methyl-5-[({4-[(2-methyl-4-quinolinyl)methoxy]phenyl}sulfonyl)methyl]-2,4-imidazolidinedione (107a) To a solution of 4-[(2-methyl-4-quinolinyl)-methoxy]benzenethiol (320 mg, 1.14 mmol) in a 5:7 mixture of pyridine/ether (1.2 mL) was added chloroacetone (190 uL, 2.4 mmol) and the reaction was stirred for 18 hr. The reaction was extracted from sat KH₂PO₄ using EtOAc×3, and the combined organic layers were dried over MgSO₄, filtered, concentrated in vacuo and purified on silica gel using 1:1 EtOAc/hexane. 196 mg (51%) of the thioether 107a was obtained. MS found: (M+H)⁺=338.

(107b) Thioether 107a (315 mg, 0.93 mmol) was converted to the hydantoin using general method D to give 92 mg (24%) of product 107b. MS found: (M+H)⁺=408.

(107c) Thioether 107b (42 mg, 0.10 mmol) was dissolved in DCM/MeOH/H₂O (2:2:0.6 mL) and treated with Oxone® (282 mg, 0.46 mmol). After 3 hr, the reaction was extracted from sat NaHCO₃ using EtOAc×4, and the combined organic layers were dried over MgSO₄, filtered, concentrated in vacuo and purified on silica gel using 2% MeOH in EtOAc. 36 mg (79%) of the product sulfone 107 was obtained. MS found: (M+H)⁺=440.

Example 108

N-[(4-methyl-2,5-dioxo-4-imidazolidinyl)methyl]-4-phenoxybenzamide (108a) To a solution of commercially available 4-phenoxybenzoic acid (1.0 g, 4.67 mmol) in 20 mL dry THF was added 1-(3-dimethylaminopropyl)-3-ethylcarbodiimide HCl salt (984 mg, 5.1 mmol). After 30 m, allyl amine (800 mg, 14.0 mmol) was added followed by 20 mg of DMAP. After 18 hr, the reaction was concentrated in vacuo and chromatographed on silica gel using 33% EtOAc in hexane to give 595 mg (50%) of the allyl amide. MS found: $(M+H)^+=254$.

(108b) To N-allyl-4-phenoxybenzamide 108a (298 mg, 1.18 mmol) in 5:1 THF/water (3.6 mL) was added PdCl2 (21 mg, 0.11 mmol) and CuCl2 dihydrate (40 mg, 0.24 mmol). A stream of O2 was passed through the solution which was heated to 50° C. for 48 hr. The reaction was cooled, extracted from brine 3×EtOAc, the organic layers dried over $MgSO_4$, filtered, and concentrated in vacuo to give a residue that was purified by HPLC to give 93 mg (29%) of the ketone. MS found: $(M+H)^+=270$.

(108c) Ketone 108b (93 mg, 0.35 mmol) was subjected to the Bucherer-Bergs conditions of general method D. 117 mg (100%) of compound 108 was obtained. MS found: $(M+H)^+=340$.

Example 109

N-[(4-methyl-2,5-dioxo-4-imidazolidinyl)methyl]-4-[(2-methyl-4-quinolinyl)methoxy]benzamide (109a) 5-(aminomethyl)-5-methylhydantoin was prepared using the procedure of Stratford and Curley (*J. Med. Chem.* 1983, 26, 1463-1469).

(109b) 5-(aminomethyl)-5-methylhydantoin (64 mg, 0.36 mmol) was coupled with 4-[(2-methyl-4-quinolinyl)methoxy]benzoyl chloride HCl salt (186 mg, 0.53 mmol) in a mixture of DCM (4 mL) 10% $NaHCO_3$ (2 mL) for 3 hr. The reaction was extracted from sat $NaHCO_3$/brine 3×EtOAc, dried $MgSO_4$, filtered, and concentrated in vacuo. Purification by HPLC gave 10 mg (7%) of product 109. MS found: $(M+H)^+=419$.

Example 110

N-[(4-methyl-2,5-dioxo-4-imidazolidinyl)methyl]-2-{4-[(2-methyl-4-quinolinyl)methoxy]phenyl}acetamide 5-(aminomethyl)-5-methylhydantoin (109a) (30 mg, 0.17 mmol) was coupled with {4-[(2-methyl-4-quinolinyl)-methoxy]phenyl}acetic acid (46 mg, 0.15 mmol) using general coupling method B to give 20 mg (24%) of the product hydantoin as a TFA salt. MS found: $(M+H)^+=433$.

Example 111

N-[(4-methyl-2,5-dioxo-4-imidazolidinyl)methyl]-4-{[2-(methylthio)-1H-benzimidazol-1-yl]methyl}benzamide 5-(aminomethyl)-5-methylhydantoin (109a)(55 mg, 0.31 mmol) was coupled with 4-{[2-(methylthio)-1H-benzimidazol-1-yl]methyl}benzoic acid (108 mg, 0.37 mmol) using general coupling method B to give 50 mg (39%) of the product hydantoin as a TFA salt. MS found: $(M+H)^+=425$.

Example 112

N-[(4-methyl-2,5-dioxo-4-imidazolidinyl)methyl]-4-[(2-methyl-4-quinolinyl)methoxy]benzenesulfonamide 5-(aminomethyl)-5-methylhydantoin (109a) (60 mg, 0.33 mmol) was coupled with 4-[(2-methyl-4-quinolinyl)-methoxy]benzenesulfonyl chloride HCl salt (174 mg, 0.45 mmol) in a 1:1 mixture of pyridine/DMSO (2 mL) for 18 hr. Extracted from sat $NaHCO_3$ with EtOAc×3 and the combined organic layers were dried over $MgSO_4$, filtered, concentrated in vacuo and purified by HPLC to give 5 mg (3%) of compound 112 as a TFA salt. MS found: $(M+H)^+=456$.

Example 113

N-[1-(2,5-dioxo-4-imidazolidinyl)cyclopentyl]-4-[(2-methyl-4-quinolinyl)methoxy]benzamide (113a) Commercially available 1-amino-1-hydroxymethylcyclopentane (1.0 g, 8.7 mmol) was coupled to 4-[(2-methyl-4-quinolinyl)methoxy]benzoic acid (2.3 g, 8.0 mmol) in 10 mL DMF using general coupling method B to give 320 mg (28%) of the amide 113a as a TFA salt. MS found: $(M+H)^+=391$.

(113b) To amide 113a TFA salt (1.0 g, 1.98 mmol) in DCM (10 mL) was added Dess-Martin periodinane (1.26 g, 2.97 mmol) and the reaction was stirred for 3 hr. Extractive workup from EtOAc and sat $NaHCO_3$. The crude product was purified on a silica gel column using 1:1 DCM/EtOAc to give 660 mg (69%) of the product aldehyde. MS found: $(M+H)^+=389$.

(113c) Aldehyde 113b (660 mg, 1.70 mmol) was subjected to the Bucherer-Bergs conditions of general method D. 480 mg (62%) of compound 113 was obtained. MS found: $(M+H)^+=459$.

Example 114

(cis,trans)-N-[1-(2,5-dioxo-4-imidazolidinyl)ethyl]-4-[(2-methyl-4-quinolinyl)methoxy]benzamide (114a) 2-aminopropanol (1.00 g, 13.3 mmol) was coupled to 4-[(2-methyl-4-quinolinyl)methoxy]benzoic acid using general coupling method B and silica gel column chromatographic purification with 5% MeOH/DCM to give 1.0 g (22%) of the amide 114a as a TFA salt. MS found: $(M+H)^+=351$.

(114b) To 114a (1.0 g, 2.85 mmol) in DCM (18 mL) was added Dess-Martin periodinane (1.45 g, 2.85 mmol) and the reaction was stirred for 2.5 hr. Extractive workup from EtOAc and sat $NaHCO_3$. The crude product was purified on a silica gel column using 5% MeOH/DCM to give 374 mg (38%) of the product aldehyde. MS found: $(M+H)^+=348$.

(114c) The aldehyde 114b (1.00 g, 2.87 mmol) was subjected to the Bucherer-Bergs conditions of general method D. 800 mg (67%) of compound 114 was obtained. MS found: $(M+H)^+=419$.

Example 115

(cis,trans)-N-[1-(2,5-dioxo-4-imidazolidinyl)-2-(4-morpholinyl)ethyl]-4-[(2-methyl-4-quinolinyl)methoxy]benzamide (115a) Boc-Ser-CHO (351 mg, 1.86 mmol, prepared using the procedure of Hermkens et al., J.Org.Chem. 1990, 55, 3998-4006) was converted to the hydantoin using general method D to give 250 mg (52%) of 115a. MS found: $(M+H)^+= 260$.

(115b) Alcohol 115a (250 mg, 0.97 mmol) was converted to the aldehyde using the same procedure as used for 113b to give 115b (69%). MS found: $(M+H)^+=258$.

(115c) Aldehyde 115b (170 mg, 0.66 mmol) was dissolved in 2 mL THF and treated with morpholine (170 mg, 2.0 mmol) followed by NaCNBH$_3$ (42 mg, 0.66 mmol) and stirred for two hours. The reaction was extracted from brine with EtOAc×3, the organic layers dried over MgSO$_4$, filtered, concentrated, and purified by silica gel chromatography using 5% MeOH in DCM to give 87 mg (40%) of product. MS found: $(M+H)^+=329$.

(115d) To compound 115c (87 mg, 0.27 mmol) in 2 mL MeOH was added 4 M HCl in dioxane (1 mL). After 1 hr, the solvents were removed in vacuo and the product amine HCl salt (35 mg, 0.13 mmol) was coupled with 4-[(2-methyl-4-quinolinyl)methoxy]benzoic acid (38 mg, 0.13 mmol) using general coupling method A to give 30 mg (75%) of the product 115. MS found: $(M+H)^+=503$.

Example 116

(cis,trans)-N-[1-(2,5-dioxo-4-imidazolidinyl)-2-methylpropyl]-4-[(2-methyl-4-quinolinyl)methoxy]benzamide Boc-Val-CHO (prepared using the method of Moriwake et al. *J. Org. Chem.* 1989, 54, 4114-4120) was converted to the final product using the analogous procedure to 115 to give 23 mg of the product 116 as a TFA salt. MS found: $(M+H)^+=447$.

Example 117

(cis,trans)-N-[1-(2,5-dioxo-4-imidazolidinyl)-3-methylbutyl]-4-[(2-methyl-4-quinolinyl)methoxy]benzamide (117a) CBZ-Leu-CHO (1.68 g, 6.73 mmol; Misiti, D. *Tetrahedron Lett.* 1990, 50, 7359-7362) was converted to the hydantoin using general method D to give 1.6 g (76%) of product 117a. MS found: $(M+H)^+=320$.

(117b) To compound 117a (100 mg, 0.31 mmol) dissolved in MeOH (5 mL) was added Pd on carbon (15 mg, 10 wt %) and the reaction was exposed to a hydrogen filled balloon for 1 hr. The catalyst was filtered off and the solution concentrated to give 54 mg (94%) of the amine 117b. MS found: $(M+H)^+=186$.

(117c) Amine 117b (27 mg, 0.15 mmol) was coupled with 4-[(2-methyl-4-quinolinyl)methoxy]benzoic acid (40 mg, 0.15 mmol) using general coupling method A to give 28 mg (33%) of the product 117 as a TFA salt. MS found: $(M+H)^+=461$.

Example 118

(cis,trans)-N-[cyclopentyl(2,5-dioxo-4-imidazolidinyl)methyl]-4-[(2-methyl-4-quinolinyl)methoxy]benzamide (118a) N-benzyloxycarbonyl-α-phosphonoglycine trimethyl ester (5.00 g, 15.1 mmol) and cyclopentanone (1.27 g, 15.1 mmol) were dissolved in DCM (10 mL) followed DBU (2.3 g, 15.1 mmol). After 3 hr, the reaction was worked up by extraction from brine with EtOAc×3. The organic layers were dried (MgSO$_4$), filtered, concentrated in vacuo and chromatographed on silica gel using 30% EtOAc in hexane to give 890 mg (20%) of the olefin product 118a. MS found: $(M+H)^+=290$.

(118b) Olefin 118a (890 mg, 3.1 mmol) was dissolved in 5 mL MeOH followed by Pd on carbon (100 mg, 10 wt %) and Pd(OH)$_2$ (100 mg) and hydrogenated at 55 psi for 18 hours. The reaction was degassed with N$_2$, filtered through Celite, and concentrated to give 484 mg (100%) of the saturated amine 118b. The free base was converted to the HCl salt with HCl/dioxane. MS found: $(M+H)^+=158$.

(118c) 2-cyclopentylglycine methyl ester HCl salt 118a (340 mg, 1.76 mmol) was coupled with 4-[(2-methyl-4-quinolinyl)methoxy]benzoic acid (517 mg, 1.76 mmol) using general coupling method A. Purified using silica gel column chromatography to give 718 mg (33%) of the product 118c. MS found: $(M+H)^+=432$.

(118d) Methyl ester 118c (718 mg, 1.66 mmol) was dissolved in dry THF (5 mL), treated with LiBH4 (36 mg, 1.66 mmol) and stirred for 2 hr. The reaction was worked up by extraction from water with EtOAc×3 and the organic layers were dried (MgSO$_4$), filtered, concentrated in vacuo and chromatographed on silica gel using 10% MeOH in DCM to give 660 mg (98%) of the alcohol 118d. MS found: $(M+H)^+=405$.

(118e) Alcohol 118d (660 mg, 1.63 mmol) was dissolved in DCM (5 mL) and treated with Dess-Martin periodinane (660 mg, 1.56 mmol) for 2 hr. The reaction was chromatographed on silica gel using 5% MeOH in DCM to give 470 mg (72%) of the product aldehyde. MS found: $(M+H)^+=403$.

(118f) Aldehyde 118e (45 mg, 0.11 mmol) was converted to the hydantoin using general method D to give 15 mg (63%) of product 118 as a TFA salt. MS found: $(M+H)^+=473$.

Example 119

(cis,trans)-N-[1-(2,5-dioxo-4-imidazolidinyl)-2-phenylethyl]-4-[(2-methyl-4-quinolinyl)methoxy]benzamide (119a) Commercially available CBZ-phenylalaninol (1.20 g, 4.23 mmol) was oxidized to CBZ-Phe-CHO using the Dess-Martin periodinane procedure used for 114b. The product aldehyde was converted to the hydantoin using general method D to give of product 119a as a TFA salt. MS found: $(M+H)^+=354$.

(119b) CBZ-protected hydantoin 119a was deprotected using the same procedure as for 117b to give 100% conversion to the amine 119b. MS found: $(M+H)^+=220$.

(119c) Amine 119b (18 mg, 0.08 mmol) was coupled to 4-[(2-methyl-4-quinolinyl)methoxy]benzoic acid (24 mg, 0.08 mmol) using general coupling method A to give 21 mg (42%) of the product hydantoin as a TFA salt. MS found: $(M+H)^+=495$.

Example 120

(cis,trans)-N-[(2,5-dioxo-4-imidazolidinyl)-(tetrahydro-2H-pyran-4-yl)methyl]-4-[(2-methyl-4-quinolinyl)methoxy]benzamide (120a) Tetrahydro-4H-pyran-4-one (1.51 g, 15.1 mmol) was condensed with N-benzyloxycarbonyl-α-phosphono glycine trimethyl ester (5.00 g, 15.1 mmol) using the same procedure as used for 118a. 4.3 g (94%) of the product olefin was obtained. MS found: $(M+H)^+=307$.

(120b, 120c) Tetrahydropyran 120a (4.3 g, 14.1 mmol) was hydrogenated using the same procedure as used for 118b to give 2.45 g (100%) of the product amine. This material was coupled with 4-[(2-methyl-4-quinolinyl)methoxy]benzoic acid (4.14 g, 14.1 mmol) in 10 mL DMF using general coupling method B and silica gel purification using 5% MeOH in DCM to give 5.8 g (91%) of the amide 120c. MS found: $(M+H)^+=449$.

(120d) Methyl ester 120c (2.24 g, 5.0 mmol) was dissolved in MeOH (20 mL), cooled to 0° C., and treated with sodium borohydride (189 mg, 5 mmol) for 3 hr. Extractive workup from water with EtOAc×3 and the combined organic layers were washed with brine×2, dried over $MgSO_4$, filtered, concentrated in vacuo, and chromatographed using 10% MeOH in DCM to give 1.62 g (77%) of the product alcohol. MS found: $(M+H)^+=421$.

(120e) Alcohol 120d (1.62 g, 4.0 mmol) was oxidized to the aldehyde using the Dess-Martin periodinane procedure used for 114b to give 480 mg (45%) of the aldehyde 120e. MS found: $(M+H)^+=419$.

(120f) The product aldehyde (480 mg, 1.15 mmol) was converted to the hydantoin using general method D to give product 120 as a TFA salt. Yield not determined. MS found: $(M+H)^+=489$.

Example 121

(cis,trans)-tert-butyl 4-[(2,5-dioxo-4-imidazolidinyl)({4-[(2-methyl-4-quinolinyl)methoxy]benzoyl}amino)methyl]-1-piperidinecarboxylate (121a) t-Butyl 4-oxo-piperidinecarboxylate (6.0 g, 30 mmol) was condensed with N-benzyloxycarbonyl-α-phosphono glycine trimethyl ester (10.9 g, 33 mmol) using the same procedure as used for 118a. 11.4 g (94%) of the product olefin was obtained. MS found: $(M+H)^+=405$.

(121b, 121c) Piperidine 121a (11.4 g, 28.2 mmol) was hydrogenated using the same procedure as used for 118b to give 6.4 g (83%) of the product amine 120b. MS found: $(M+H)^+=273$. This material was coupled with 4-[(2-methyl-4-quinolinyl)methoxy]benzoic acid (6.9 g, 23.5 mmol) in 20 mL DMF using general coupling method B and silica gel purification using 5% MeOH in DCM to give 11.4 g (89%) of the amide 121c. MS found: $(M+H)^+=548$.

(121d) Methyl ester 121c (14.0 g, 25.6 mmol) was dissolved in MeOH (50 mL) and treated with sodium borohydride (1.98 g, 52 mmol) for 18 hr. Same workup as for 120c to give 9.8 g (74%) of the product alcohol. MS found: $(M+H)^+=520$.

(121e) Alcohol 121d (1.1 g, 2.1 mmol) was was oxidized to the aldehyde using the using the Dess-Martin periodinane procedure used for 114b to give 864 mg (79%) of the aldehyde 121e. MS found: $(M+H)^+=419$.

(121f) Aldehyde 121e (864 mg, 1.67 mmol) was converted to the hydantoin using general method D to give 563 mg (48%) of two diastereomeric compounds 121 (isomer A and B) as TFA salts. MS found: $(M+H)^+=588$.

Example 122

(cis,trans)-N-[(2,5-dioxo-4-imidazolidinyl)-(4-piperidinyl)methyl]-4-[(2-methyl-4-quinolinyl)methoxy]benzamide Compound 121 (52 mg, 0.88 mmol) was stirred in 1 mL DCM and 1 mL trifluoroacetic acid for 1 hr, concentrated in vacuo, and purified by HPLC to give 26 mg (49%) of compound 122 as a TFA salt. MS found: $(M+H)^+=489$.

Example 123

(cis,trans)-N-{(2,5-dioxo-4-imidazolidinyl)[1-(3-pyridinylmethyl)-4-piperidinyl]methyl}-4-[(2-methyl-4-quinolinyl)methoxy]benzamide Compound 122 (57 mg, 0.95 mmol), 3-pyridinecarboxaldehyde (11 mg, 0.10 mmol), and 4-methylmorpholine (0.06 mL, 0.5 mmol) were dissolved in 1 mL DMF. After 2 hr, the reaction was extracted from water with EtOAc×3 and the combined organic layers were washed with brine×2, dried over $MgSO_4$, filtered, concentrated in vacuo, and purified by HPLC to give 22 mg (34%) of the product as a TFA salt. MS found: $(M+H)^+=579$.

Example 124

(cis,trans)-N-{(2,5-dioxo-4-imidazolidinyl)[1-(4-pyridinylmethyl)-4-piperidinyl]methyl}-4-[(2-methyl-4-quinolinyl)methoxy]benzamide Compound 122 HCl salt (50 mg, 0.09 mmol) and 4-pyridine-carboxaldehyde (11 mg, 0.10 mmol) were dissolved in 1 mL DMF following the same procedure used for Example 123. 18 mg (22%) of the product TFA salt was btained. MS found: $(M+H)^+=579$.

Example 125

(cis,trans)-N-[(1-acetyl-4-piperidinyl)-(2,5-dioxo-4-imidazolidinyl)methyl]-4-[(2-methyl-4-quinolinyl)methoxy]benzamide Compound 122 HCl salt (26 mg, 0.04 mmol), acetic acid N-hydroxysuccinimide ester (8 mg, 0.05 mmol), and 4-methylmorpholine (20 uL, 0.15 mmol) were dissolved in 1 mL DMF. After 1 hr, the reaction was purified by HPLC to give 22 mg (79%) of the product TFA salt. MS found: $(M+H)^+=530$.

Example 126

(cis,trans)-N-{(2,5-dioxo-4-imidazolidinyl)[1-(2-propynyl)-4-piperidinyl]methyl}-4-[(2-methyl-4-quinolinyl)methoxy]benzamide Compound 122 HCl salt (50 mg, 0.09 mmol) and 1-bromo-2-propyne (11 mg, 0.09 mmol) were dissolved in 1 mL DMF at 0° C. After 3 hr, the reaction was purified by HPLC to give 19 mg (28%) of the product TFA salt. MS found: $(M+H)^+=526$.

Example 127

(cis,trans)-N-[[1-(2,2-dimethylpropanoyl)-4-piperidinyl](2,5-dioxo-4-imidazolidinyl)methyl]-4-[(2-methyl-4-quinolinyl)methoxy]benzamide Compound 122 HCl salt (30 mg, 0.05 mmol), trimethylacetyl chloride (7 mg, 0.05 mmol), and diisopropylethylamine (25 mg, 0.20 mmol) were dissolved in 1 mL DMF at 0° C. After 16 hr, the reaction was purified by HPLC to give 15 mg (41%) of the product TFA salt. MS found: $(M+H)^+=572$.

Example 128

(cis,trans)-N-{(2,5-dioxo-4-imidazolidinyl)[1-(methylsulfonyl)-4-piperidinyl]methyl}-4-[(2-methyl-4-quinolinyl)methoxy]benzamide Compound 122 HCl salt (50 mg, 0.08 mmol), methanesulfonyl chloride (10 mg, 0.08 mmol), and 4-methylmorpholine (0.036 mL, 0.33 mmol) were dissolved in 1 mL DMF. After 1 hr, the reaction was purified by HPLC to give 25 mg (44%) of the product as a TFA salt. MS found: $(M+H)^+=566$.

Example 129

(cis,trans)-N-[(1-acetyl-4-piperidinyl)-(2,5-dioxo-4-imidazolidinyl)methyl]-4-[(2-methyl-4-quinolinyl)methyl]benzamide (129a) Compound 121b was reprotected with CBZ-Cl and synthetic steps 121d-f were performed to give the doubly protected hydantoin product 129a. MS found: $(M+H)^+=447$.

(129b) Compound 129a (320 mg, 0.72 mmol) was treated with 1:1 TFA/DCM (2 mL) for 1 hr and concentrated to give 360 mg (100%) of the product amine as a TFA salt. MS found: $(M+H)^+=347$.

(129c) Compound 129b (360 mg, 0.79 mmol) was reacted with acetic acid N-hydroxysuccinimide ester (161 mg, 1.02 mmol), and diisopropylethylamine (350 uL, 2.0 mmol) in 2 mL chloroform. After 1 hr, the reaction was concentrated in vacuo and purified by HPLC to give 233 mg (76%) of the product amide 129c. MS found: $(M+H)^+=389$.

(129d) Compound 129c (233 mg, 0.60 mmol) was dissolved 3 mL MeOH followed by 4 M HCl in dioxane (300 uL). Pd on carbon (30 mg, 10 wt %) was added and the reaction was subjected to a balloon of hydrogen for 1 hr. The catalyst was filtered off through Celite and the solution was concentrated to give 174 mg (100%) of the product 129d as an HCl salt. MS found: $(M+H)^+=255$.

(129e) Compound 129d (21 mg, 0.07 mmol) was coupled with 4-[(2-methyl-4-quinolinyl)methyl]benzoic acid (27 mg, 0.10 mmol) using general coupling method A to give 29 mg (65%) of the product as a TFA salt. MS found: $(M+H)^+=514$.

Example 130

(cis,trans)-N-[(1-acetyl-4-piperidinyl)-(2,5-dioxo-4-imidazolidinyl)methyl]-4-[(1,1-dioxido-2,3-dihydro-4H-1,4-benzothiazin-4-yl)methyl]benzamide Compound 129d (23 mg, 0.07 mmol) was coupled with 4-[(1,2-dioxido-2,3-dihydro-4H-1,4-benzothiazinyl)methyl]benzoic acid (21 mg, 0.07 mmol) using general coupling method A to give 27 mg (57%) of the product as a TFA salt. MS found: $(M+H)^+=554$.

Example 131

(cis,trans)-N-[(1-acetyl-4-piperidinyl)-(2,5-dioxo-4-imidazolidinyl)methyl]-4-(1,1-dioxido-3,4-dihydro-2H-1-benzothiopyran-4-yl)benzamide Compound 129d (21 mg, 0.07 mmol) was coupled with 4-(1,1-dioxido-3,4-dihydro-2H-1-benzothiopyran-4-yl)benzoic acid (21 mg, 0.07 mmol) using general coupling method A to give 29 mg (79%) of the product. MS found: $(M+H)^+=539$.

Example 132

(cis,trans)-N-[(1-acetyl-4-piperidinyl)-(2,5-dioxo-4-imidazolidinyl)methyl]-4-(2-methyl-4-quinolinyl)benzamide Compound 129d (21 mg, 0.07 mmol) was coupled with 4-(2-methyl-4-quinolinyl)benzoic acid (19 mg, 0.07 mmol) using general coupling method A to give 22 mg (50%) of the product as a TFA salt. MS found: $(M+H)^+=500$.

Example 133

(cis,trans)-N-[(1-acetyl-4-piperidinyl)-(2,5-dioxo-4-imidazolidinyl)methyl]-4-(1-naphthylmethoxy)benzamide Compound 129d (21 mg, 0.07 mmol) was coupled with 4-(1-naphthylmethoxy)benzoic acid (20 mg, 0.07 mmol) using general coupling method A to give 27 mg (62%) of the product as a TFA salt. MS found: $(M+H)^+=515$.

Example 134

(cis,trans)-N-[(1-acetyl-4-piperidinyl)-(2,5-dioxo-4-imidazolidinyl)methyl]-4-[(5-quinolinyloxy)methyl]benzamide Compound 129d (20 mg, 0.07 mmol) was coupled with 4-[(5-quinolinyloxy)methyl]benzoic acid (20 mg, 0.07 mmol) using general coupling method A to give 12 mg (27%) of the product as a TFA salt. MS found: $(M+H)^+=516$.

Example 135

(cis,trans)-N-[(1-acetyl-4-piperidinyl)-(2,5-dioxo-4-imidazolidinyl)methyl]-4-[(5-isoquinolinyloxy)methyl]benzamide Compound 129d (39 mg, 0.16 mmol) was coupled with 4-[(5-isoquinolinyloxy)methyl]benzoic acid (43 mg, 0.16 mmol) using general coupling method A to give 26 mg (27%) of two diastereomeric products (isomer A and B; 1.9:1 ratio) as TFA salts. MS found: $(M+H)^+=516$ for both.

Example 136

(cis,trans)-N-[(1-acetyl-4-piperidinyl)-(2,5-dioxo-4-imidazolidinyl)methyl]-4-{[(2-methyl-8-quinolinyl)oxy]methyl}benzamide Compound 129d (39 mg, 0.16 mmol) was coupled with 4-{[(2-methyl-8-quinolinyl)oxy]methyl}benzoic acid (46 mg, 0.16 mmol) using general coupling method A to give 25 mg (25%) of two diastereomeric products (isomer A and B; 1:1.5 ratio) as TFA salts. MS found: $(M+H)^+=530$ for both.

Example 137

(cis,trans)-N-[(1-acetyl-4-piperidinyl)-(2,5-dioxo-4-imidazolidinyl)methyl]-4-[(2-methyl-4-quinolinyl)methoxy]benzenesulfonamide To compound 129d (20 mg, 0.07 mmol) and 4-methylmorpholine (30 uL, 0.29 mmol) in 1 mL DMSO was added with 4-[(2-methyl-4-quinolinyl)methoxy]benzenesulfonyl chloride HCl salt (24 mg, 0.06 mmol). After 1 hr, the reaction was purified by HPLC to give 6 mg (15%) of the product as a TFA salt. MS found: $(M+H)^+=566$.

Example 138

(cis,trans)-N-[1-(2,5-dioxo-4-imidazolidinyl)-2-(4-morpholinyl)-2-oxoethyl]-4-[(2-methyl-4-quinolinyl)methoxy]benzamide (138a) N-Boc-serine-OH (1.03 g, 5.0 mmol) was coupled with morpholine (870 mg, 10 mmol) using general coupling method B. Purification on silica gel using 70% EtOAc in hexanes gave 840 mg (61%) of the amide product. MS found: $(M+H)^+=275$.

(138b) Compound 138a (840 mg, 2.1 mmol) was dissolved in 3 mL chloroform and treated with Dess-Martin periodinane (1.3 g, 3.1 mmol) for 4 hr. The reaction was extracted from aq NaHCO$_3$ with EtOAc×3 and the combined organic layers were dried over MgSO$_4$, filtered, concentrated in vacuo, and purified on silica gel using 1:1 EtOAc/hexanes to give 510 mg (61%) of the product aldehyde as determined by NMR.

(138c) Aldehyde 138b (510 mg, 1.86 mmol) was was subjected to the Bucherer-Bergs conditions of general nethod D. 230 mg (36%) of the product hydantoin was obtained. MS found: $(M+H)^+=341$.

(138d) Hydantoin 138c (230 mg, 0.67 mmol) was treated with 1:1 TFA/DCM (2 mL) for 2 hr and then concentrated in vacuo to give 230 mg of the product amine as a TFA salt which was used without purification.

(138e) Amine 138d TFA salt (200 mg, 0.56 mmol) coupled with 4-[(2-methyl-4-quinolinyl)methoxy]benzoic acid (240 mg, 0.82 mmol) in 2 mL DMF using general coupling method B to give 26 mg (5%) of two diastereomeric products (isomer A and B; 2.7:1 ratio) as TFA salts. MS found: $(M+H)^+=518$ for both.

Example 139

(cis,trans)-tert-butyl 3-(2,5-dioxo-4-imidazolidinyl)-3-({4-[(2-methyl-4-quinolinyl)methoxy]benzoyl}amino)propanoate (139a) Commercially available CBZ-Asp(OtBu)-OH hydrate (6.83 g, 20 mmol) was dissolved in 20 mL dry THF and treated with borane (1 M in THF, 100 mL) for 1 hr. The reaction was concentrated in vacuo, quenched with sat NaHCO$_3$, extracted with EtOAc×3, the combined organic layers were washed 2×brine, dried MgSO$_4$, filtered, concentrated, and chromatographed on silica gel using 40% EtOAc in hexanes to 5% MeOH/40% EtOAc/55% hexane gradient to give 2.0 g (35%) of the product alcohol. MS found: $(M+H)^+=310$.

(139b) Alcohol 139a (2.0 g, 6.5 mmol) was dissolved in 20 mL DCM and oxidized with Dess-Martin periodinane (2.75 g, 6.5 mmol) for 1.5 hr, filtered, extracted from NaHCO$_3$ with EtOAc×3, concentrated, and purified on silica gel using 40% EtOAc in hexane. 1.6 g (80%) of the aldehyde product was obtained. MS found: $(M+H)^+=308$.

(139c) Compound 139b (1.51 g, 4.91 mmol) was converted to the hydantoin using the Bucherer-Bergs conditions of general method D. 1.20 g (65%) of the product hydantoin was obtained. MS found: $(M+H)^+=378$.

(139d) Compound 139c (1.20 g, 3.18 mmol) was taken up in 15 mL MeOH, Pd on carbon (240 mg, 20 wt %) was added, and the reaction was exposed to a hydrogen balloon for 1 hr. The reaction was filtered through Celite, washed with MeOH, and concentrated to give 620 mg (67%) of the product amine. MS found: $(M+H)^+=244$.

(139e) Compound 139d (600 mg, 2.47 mmol) was dissolved in 6 mL DMF, 4-methylmorpholine (814 uL, 7.41 mmol) was added, followed by 4-[(2-methyl-4-quinolinyl)methoxy]benzoyl chloride HCl salt (769 mg, 2.2 mmol). The reaction was stirred for 16 hr, taken up in EtOAc, washed 6×brine, dried with MgSO$_4$, filtered, concentrated in vacuo, and chromatographed using 10% MeOH in DCM on silica gel. 900 mg (79%) of the product 139 as a mixture of diastereomers was obtained. MS found: $(M+H)^+=519$.

Example 140

(cis,trans)-3-(2,5-dioxo-4-imidazolidinyl)-3-({4-[(2-methyl-4-quinolinyl)methoxy]benzoyl}amino)propanoic acid Compound 139 (500 mg, 0.96 mmol) was treated with 1:1 TFA/DCM (10 mL) for 2 hr after which the solvent was removed to give 500 mg (90%) of product as a TFA salt. MS found: $(M+H)^+=463$.

Example 141

(cis,trans)-N-[1-(2,5-dioxo-4-imidazolidinyl)-3-(4-morpholinyl)-3-oxopropyl]-4-[(2-methyl-4-quinolinyl)methoxy]benzamide Compound 140 (100 mg, 0.17 mmol) was coupled with morpholine (50 mg, 0.50 mmol) using general coupling method A to give a mixture of diastereomers (16 mg isomer A and 32 mg isomer B; 43%) as TFA salts. MS found: $(M+H)^+=532$ for both.

Example 142

(cis,trans)-N-[1-(2,5-dioxo-4-imidazolidinyl)-3-(methylamino)-3-oxopropyl]-4-[(2-methyl-4-quinolinyl)methoxy]benzamide Compound 140 (100 mg, 0.17 mmol) was coupled with methylamine HCl salt (25 mg, 0.37 mmol) using general coupling method A to give a mixture of diastereomers (15 mg isomer A and 19 mg isomer B; 34%) as TFA salts. MS found: $(M+H)^+=476$ for both.

Example 143

(cis,trans)-N-[3-(tert-butylamino)-1(2,5-dioxo-4-imidazolidinyl)-3-oxopropyl]-4-[(2-methyl-4-quinolinyl)methoxy]benzamide Compound 140 (100 mg, 0.17 mmol) was coupled with t-butylamine (73 mg, 1.0 mmol) using general coupling method A to give a mixture of diastereomers (9 mg isomer A and 7 mg isomer B; 15%) as TFA salts. MS found: $(M+H)^+=518$ for both.

Example 144

(cis,trans)-N-[1-(2,5-dioxo-4-imidazolidinyl)-3-oxo-3-(1-piperazinyl)propyl]-4-[(2-methyl-4-quinolinyl)methoxy]benzamide Compound 140 (100 mg, 0.17 mmol) was coupled with piperazine (60 mg, 0.7 mmol) using general coupling method A to give a mixture of diastereomers (21 mg isomer A and 17 mg isomer B; 35%) as TFA salts. MS found: $(M+H)^+=531$ for both.

Example 145

(cis,trans)-N-[1-(2,5-dioxo-4-imidazolidinyl)-3-(4-methyl-1-piperazinyl)-3-oxopropyl]-4-[(2-methyl-4-quinolinyl)methoxy]benzamide Compound 140 (100 mg, 0.17 mmol) was coupled with N-methylpiperazine (30 mg, 0.30 mmol) using general coupling method A to give a mixture of diastereomers (6 mg isomer A and 25 mg isomer B; 27%) as TFA salts. MS found: $(M+H)^+=545$ for both.

Example 146

(cis,trans)-N-[1-(2,5-dioxo-4-imidazolidinyl)-3-(4-morpholinyl)-3-oxopropyl]-4-[(2-methyl-4-quinolinyl)methyl]benzamide (146a) Compound 139d (76 mg, 0.32 mmol) was coupled to 4-[(2-methyl-4-quinolinyl)methyl]benzoic acid (100 mg, 0.32 mmol) using the same procedure as used for 139 to give 98 mg (47%) of the amide product as a TFA salt. MS found: $(M+H)^+=543$ for both.

(146b) Compound 146a (132 mg, 0.21 mmol) was converted to the morpholinyl amide using the same sequence described for compounds 140 and 141 to give a mixture of diastereomers (8 mg isomer A and 21 mg isomer B; 35%) as TFA salts. MS found: $(M+H)^+=516$ for both.

Example 147

(cis,trans)-4-[(1,1-dioxido-2,3-dihydro-4H-1,4-benzothiazin-4-yl)methyl]-N-[1-(2,5-dioxo-4-imidazolidinyl)-3-(4-morpholinyl)-3-oxopropyl]benzamide (147a) Compound 139d (76 mg, 0.31 mmol) was coupled to 4-[(1,2-dioxido-2,3-dihydro-4H-1,4-benzothiazinyl)-methyl]-benzoic acid (100 mg, 0.32 mmol) using the same procedure as used for 139 to give 98 mg (47%) as a TFA salt. MS found: $(M+H)^+=543$ for both.

(147b) Compound 147a (132 mg, 0.21 mmol) was converted to the morpholinyl amide using the same sequence described for compounds 140 and 141 to give a mixture of diastereomers (29 mg isomer A and 26 mg isomer B; 55%) as TFA salts. MS found: $(M+H)^+=556$ for both.

Example 148

N-[3-(2,5-dioxo-4-imidazolidinyl)tetrahydro-2H-pyran-4-yl]-4-[(2-methyl-4-quinolinyl)methoxy]benzamide (148a) LiHMDS (1.0 M in THF, 52.5 mL, 1.05 eq) was added dropwise to a −78° C. solution of tetrahydro-4H-pyran-4-one (5.0 g, 50 mmol) in THF (200 mL). The resulting solution was stirred at −20° C. for 1 hr, then cooled back to −78° C. To this mixture was added methyl cyanoformate (4.75 mL, 1.2 eq) dropwise. Ten min after completion of the addition, the reaction was quenched with aqueous $NH_4Cl$ and extracted with ether (200 mL). The organic layer was washed with brine (100 mL), dried ($MgSO_4$), and concentrated. Silica gel column chromatography (ether-hexane, 1:4, 2:3, then 3:2) yielded an oil containing both ketone and enol forms of the product (5.4 g, ca. 30% purity). MS found: $(M+H)^+=159.1$.

(148b) Ester 148a was dissolved in benzene (200 mL) and treated with (R)-α-methylbenzylamine (3 mL) and ytterbium (III) trifluoromethanesulfonate (200 mg). The mixture was heated to reflux under Dean-Stark conditions for 2 hr, concentrated, and purified by silica gel column chromatography (ethyl acetate-hexane, 1:4) to yield the desired enamine as a white solid (3.6 g, 27.5% for 2 steps).

(148c) Enamine 148b (3.5 g, 13.4 mmol) in acetonitrile-acetic acid (1:1, 80 mL) was treated with $NaBH(OAc)_3$ and stirred for 2 hr at 0° C. Following concentration in vacuo, the residue was dissolved in ether (200 mL), washed with saturated $NaHCO_3$ until the aqueous phase was basic, dried ($MgSO_4$), and concentrated to yield an oil (3.39 g, 96%). MS Found: $(M+H)^+=264.3$.

(148d) Intermediate 148c (1.86 g, 7.06 mmol) in methanol (100 mL) was treated with 10% palladium hydroxide on carbon (0.6 g, 3.5% mol) and aqueous 1N hydrochloric acid (10 mL, 1.4 eq) and stirred under a $H_2$-balloon for 72 hr. The catalyst was removed by filtration. Removal of solvent provided the desired amine as hydrochloric acid salt (1.42 g, 100%). MS Found: (M+H)$^+$=160.3.

(148e) A mixture of amine 148d (1.0 g, 5.11 mmol) and 4-[(2-methyl-4-quinolinyl)methoxy]benzoic acid (1.50 g, 1.0 eq) in DMF (20 mL) were coupled using general coupling method B followed by silica gel column chromatography (ethyl acetate-hexane, 3:2 then 4:1) yielded the desired amide (1.6 g, 72%). MS Found: (M+H)$^+$=435.1.

(148f) Ester 148e (155 mg, 0.36 mmol) was dissolved in 2 mL THF, cooled to 0° C., and treated with LiAlH4 (790 uL, 1.0 M in THF). The reaction was allowed to warm to rt for 16 hr and then extracted from NaHCO$_3$ with EtOAc×3, the combined organic layers were dried over MgSO$_4$, filtered, concentrated, and purified on silica gel using 5% MeOH in DCM. 96 mg (66%) of the alcohol product was obtained. MS found: (M+H)$^+$=407.2.

(148 g) Alcohol 148f (95 mg, 0.23 mmol) was converted to the aldehyde using the same procedure as used for 114b. 76 mg (80%) of the aldehyde product was obtained. MS found: (M+H)$^+$=405.2.

(148h) Aldehyde 148 g (76 mg, 0.19 mmol) was subjected to the Bucherer-Bergs conditions of general method D. A mixture of diastereomers (9 mg isomer A, 4 mg isomer B; 12%) were obtained as TFA salts. MS found: (M+H)$^+$=475.2.

Example 149

N-[2-(2,5-dioxo-4-imidazolidinyl)cyclopentyl]-4-[(2-methyl-4-quinolinyl)methoxy]benzamide Commercially available ethyl cis-2-amino-1-cyclopentane-carboxyic acid HCl salt was taken through synthetic sequences 148e-h to give final hydantoin product as a mixture of diastereomers (9 mg isomer A, 4 mg isomer B; 12%) as TFA salts. MS found: (M+H)$^+$=459.2.

Example 150

N-[2-(2,5-dioxo-4-imidazolidinyl)cyclopentyl]-4-{[2-(trifluoromethyl)-1H-benzimidazol-1-yl]methyl}benzamide Commercially available ethyl cis-2-amino-1-cyclopentane-carboxyic acid HCl salt (78 mg, 0.40 mmol) was coupled with 4-{[2-(trifluoromethyl)-1H-benzimidazol-1-yl]methyl}benzoic acid (129 mg, 0.40 mmol) in 2 mL DMSO using using general coupling method B. Synthetic steps 148f-h were reiterated for this substrate as well to give 2.2 mg of the final product hydantoin as a mixture of diastereomeric TFA salts. MS found: (M+H)$^+$=486.2.

Preparation of Side Chain Examples

Example 200

4-[(2-methyl-4-quinolinyl)methoxy]aniline bis-HCl salt

To a solution of 4-nitrophenol (7.2 g, 52.0 mmol) in 400 mL THF was added 4-(chloromethyl)-2-methylquinoline (10.0 g, 52.0 mmol), cesium carbonate (25.4 g, 78 mmol), and sodium iodide (451 mg, 3 mmol). The reaction was heated to reflux for 24 hr, after which the reaction was extracted from sat KH$_2$PO$_4$ with EtOAc×3. The combined organic layers were dried with MgSO$_4$, filtered, and concentrated. This residue was taken up in 200 mL MeOH and refluxed with SnCl$_2$ (156 mmol) for 18 hr after which, the solution was cooled and the reaction was extracted from disodium tartrate with EtOAc×4, the combined organic layers were dried with MgSO$_4$, filtered, and concentrated. The residue was treated with 2 M HCl in dioxane, rotovapped, and recrystallized from EtOH/water to give 12.4 g (71%). MS found: (M+H)=265.

Example 201

4-[(2-isopropyl-1H-benzimidazol-1-yl)methyl]aniline

A solution of 2-isopropylbenzimidazole (4.0 g, 25 mmol) in THF was treated with sodium hydride (1.00 g, 25 mmol, 60% dispersed in oil) under N$_2$ atmosphere and stirred for 2 hr. 4-Chloromethyl-1-nitrobenzene (4.3 g, 25 mmol) was added and the reaction stirred for 16 hr. The reaction was worked by extraction from NaHCO$_3$ with EtOAc×3, the combined organic layers were dried with MgSO$_4$, filtered, and concentrated. This material was converted to the aniline as shown in Example 200. MS found: (M+H)=267.

Example 202

4-{[2-(methylthio)-1H-benzimidazol-1-yl]methyl}benzoic acid (202a) A solution of methyl (4-bromomethyl)benzoate (1.0 g, 4.4 mmol) in dimethylsulfoxide (DMSO) (43 mL) was treated with 2-(methylthio)benzimidazole (0.7 g, 1 eq) and Cs$_2$CO$_3$ (2.1 g, 1.5 eq) and stirred for 2 hr at rt. The mixture was then partitioned between water and ethyl acetate (40 mL each) and the aqueous layer was further extracted with ethyl acetate (40 mL) and the combined organic layers washed with brine (40 mL), dried (Na$_2$SO$_4$), filtered and concentrated. Flash chromatography (SiO$_2$, MeOH/dichloromethane, 1:40 v/v) provided the desired ester (0.8 g, 62%) as a white sold. MS found: (M+H)$^+$=313.

(202b) Ester 202a (0.8 g, 2.7 mmol) was dissolved in MeOH (6 mL) was treated with 1N NaOH (3 mL) and stirred at reflux for 3 hr. The reaction was cooled to 0° C. and acidified with HCl (conc). The white solid was filtered and washed with water and ether and dried on vacuum (0.7 g, 72%). MS found: (M+H)$^+$=299.

Example 203

4-[(2-isopropyl-1H-benzimidazol-1-yl)methyl]benzoic acid

Using procedures analogous to Example 202, 2-isopropyl-benzimidazole (1 g, 4.36 mmol) was converted to the desired acid (446 mg, 32% yield, 2 steps). MS found: (M+H)$^+$=295.

Example 204

4-{[2-(trifluoromethyl)-1H-benzimidazol-1-yl]methyl}benzoic acid (204a) Using procedures analogous to 202, 2-trifluoromethylbenzimidazole (4.12 g, 18 mmol) was converted to the desired acid (5.24 g, 91% yield, 2 steps). MS found: $(M+H)^+$= 321.

Example 205

4-[(2-methyl-1H-indol-3-yl)methyl]benzoic acid (205a) To a solution of trifluoroacetic acid (TFA) (1.16 mL, 15 mmol) in $CH_2Cl_2$ and triethylsilane (4.79 mL, 30 mmol) was added a solution of methyl 4-formylbenzoate (1.81 g, 11 mmol) and 2-methylindole (1.31 g, 10 mmol). The reaction was stirred 10 min at 0° C. and then quenched by adding the reaction solution to NaOH. Additional NaOH was added to get the pH to 8. The aqueous layer was extracted with EtOAc (1×100 mL) to obtain the crude compound. The crude was flashed (hexanes to 25% EtOAc/hexanes) to yield the desired ester (2.18 g, 78%). MS found: $(M+Na)^+$=302.

(205b) To a suspension of (205a) (1.79 mmol, 500 mg) in MeOH (5 mL) was added LiOH (0.9 mL, 1.79 mmol, 2M solution. The reaction was stirred for 16 hr and then quenched to pH 7 with HCl (1N). The reaction mixture was filtered to afford the desired acid (475 mg, 100%). MS found: $(M+H)^+$=266.

Example 206

4-[(2-methyl-1H-indol-1-yl)methyl]benzoic acid (206a) To a solution of 2-methylindole (7.60 mmol, 1.00 g) was added 18-crown-6 (60 mg, 0.06 mmol) and subsequently powdered KOH (416 mg, 7.60 mmol) and methyl 4-(bromomethyl)benzoate (1 eq). The reaction was heated to 100° C. for 2 hr, and was added additional KOH (416 mg, 7.60 mmol). The reaction was stirred for another 1 hr. The reaction was cooled and then quenched with HCl and extracted with EtOAc (2×100 mL). The organic layers were collected, dried and concentrated in vacuo. The crude was flashed to yield the desired acid (798 mg, 40%). MS found: $(M+H)^+$=274.

Example 207

4-[(2-ethylpyrazolo[1,5-a]pyridin-3-yl)methyl]benzoic acid (207a) 2-picoline (3.73 g, 2 eq) was added to phenyllithium (22.2 mL, 1.8 M in ether, 2 eq) in ether (25 mL) at rt, stirred 5 min then heated to reflux for 30 min. Methyl propionate (1.76 g, 20 mmol) was added to the reaction and the mixture was heated at reflux for 30 min. The mixture was cooled to rt and quenched with water (5 mL), then poured onto 6N HCl (20 mL) and water (20 mL). The ether layer was extracted with 6 N Hcl (2×10 mL) and the combine aqueous phases were treated with 20% NaOH until pH 7.8. The aqueous phases were extracted with ether (3×100 mL) and the organic layers washed with brine, dried with $MgSO_4$, filtered and concentrated. Silica gel chromatography (EtOAc/hexane, 70:30) provided the desired ester (2.4 g, 80%). MS Found $(2M+H)^+$=299.

(207b) Ester 207a (2.4 g, 16 mmol) in THF (50 mL) was treated with NaH (768 mg, 1.2 eq) and stirred for 30 min. Methyl 4-(bromomethyl)benzoate (1.1 eq) was added and the reaction stirred at room temp for 2 hr. The mixture was quenched with saturated aqueous $NaHCO_3$ solution (30 mL) and extracted with EtOAc, washed with water and brine, dried with $MgSO_4$, filtered and concentrated. Silica gel chromatography (EtOAc/hexane, 20:80) gave the desired ester [MS Found $(M+H)^+$=298] and the di-alkylated product (3.2 g combined yield) which were inseparable by chromatography.

(207c) Compound 207b (200 mg) was treated with O-mesitylenesulfonylhydroxylamine (304 mg, 1.5 eq) (for preparation see: Tamura, Y; et al. *Synthesis*, 1977, 1) at 0° C. and warmed to rt and stirred overnight. The mixture was concentrated and purified by silica gel chromatography (EtOAc/hexane, 10:90) to give the desired ester (50 mg, 25%). MS Found $(M+H)^+$=295.

(207d) Using procedures analogous to Example 202 the ester 207c (50 mg, 0.17 mmol) was converted to the desired acid (45 mg, 95%). MS Found $(M+H)^+$=279.

Example 208

4-[(1,2-dioxido-2,3-dihydro-4H-1,4-benzothiazinyl)methyl]benzoic acid (208a) $K_2CO_3$ (4.4 g, 31.9 mmol) and 1,2-dibromoethane (0.69 mL, 8.0 mmol) were added to a solution of 2-aminothiophenol (1.0 g, 8.0 mmol) in 20 mL of acetone at room temperature. The reaction mixture was stirred overnight. The insoluble material was filtered off and the solvent was removed under reduced pressure. The residue was purified on silica gel column to provide 3,4-dihydro-2H-1,4-benzothiazine (0.8 g, 66%). MS $(ES^+)$: 152 (M+1).

(208b) $K_2CO_3$ (5.2 g, 37.7 mmol) and methyl 4-(bromomethyl)benzoate (2.8 g, 12.6 mmol) were added to a solution of 208a (1.9 g, 12.6 mmol) in 20 mL of anhydrous DMF. The reaction mixture was heated to 80° C. overnight. After cooling down, the solid was filtered off and rinsed with DMF. The solvent was removed under reduced pressure and the residue was purified on silica gel column to provide methyl 4-(2,3-dihydro-4H-1,4-benzothiazin-4-ylmethyl)benzoate (3.02 g, 80%). MS $(ES^+)$: 300 (M+1).

(208c) A solution of Oxone® (2.2 g, 3.54 mmol) in 20 mL of $H_2O$ was added slowly to a solution of 208b (2.12 g, 7.1 mmol) in 20 mL of MeOH. Upon completion of the reaction, the solution was diluted with ethyl acetate, washed with saturated $NaHCO_3$ and dried over $MgSO_4$. After filtration and concentration, the residue was purified on silica gel column to provide methyl 4-[(1-oxido-2,3-dihydro-4H-1,4-benzothiazin-4-yl)methyl]benzoate (1.39 g, 65%). MS $(AP^+)$: 316 (M+1).

(208d) A solution of KOH (1N, 7.5 mL) was added to a solution of 208c (1.25 g, 3.8 mmol) in 40 mL of MeOH and 40 mL of $H_2O$. The reaction mixture was heated to 60° C. overnight. Upon completion, the aliquot was neutralized with HCl (1N, 1.2 mL). The solvent was removed and the residue was dissolved in MeOH. After filtration and concentration, 4-(2, 3-dihydro-4H-1,4-benzothiazin-4-ylmethyl)benzoic acid was obtained in quantitative yield. MS (AP$^+$): 318 (M+1).

Example 209

4-[(2-methyl-4-quinolinyl)methyl]benzoic acid (209a) 4-hydroxy-2-methylquinoline (17.4 g, 109 mmol) and phosphorus oxytribromide (47.1 g, 164 mmol) were added to a round-bottom flask. The mixture was heated to 130° C. for several hours. After cooling down to room temperature, the residue was partitioned between saturated Na$_2$CO$_3$ and ethyl acetate. The organic layer was separated and the aqueous layer was extracted with ethyl acetate (5×300 mL). The combined organic layer was washed with H$_2$O (2×400 mL) and brine (1×400 mL) and dried over MgSO$_4$. After filtration and concentration, the residue was purified on silica gel to provide 4-bromo-2-methylquinoline, 209a (8.8 g, 36%). MS (AP$^+$): 224 (M+1).

(209b) 4-Bromo-2-methylquinoline, 209a (1.0 g, 4.5 mmol) was dissolved in 10 mL of anhydrous THF and the resulting solution was cooled down to −78° C. A solution of n-BuLi (3.0 mL, 1.6M, 4.8 mmol) was added slowly and the resulting solution was maintained at −78° C. for 5 min.

Meanwhile, in another flask methyl 4-formylbenzoate (0.9 g, 5.4 mmol) was dissolved in 20 mL of anhydrous THF and the resulting solution was cooled to −78° C. before the lithium reagent made above was cannulated. The whole mixture was stirred for 30 min before quenched with MeOH. The solution was then diluted with ethyl acetate and washed with H$_2$O and brine. After dried over MgSO$_4$, the organic solution was filtered and concentrated. The residue was purified on silica gel to provide methyl 4-[hydroxy(2-methyl-4-quinolinyl)methyl]benzoate (0.9 g, 65%). MS (AP$^+$): 308 (M+1).

(209c) Compound 209b (105 mg, 0.34 mmol) was dissolved in 1 mL of dichloromethane. The solution was cooled to 0° C. and triethylamine (0.1 mL, 0.68 mmol) and MsCl (0.03 mL, 0.41 mmol) were added. The ice bath was removed and the reaction was monitored by TLC until the disappearance of starting material. The solution was diluted with ethyl acetate and washed with H$_2$O and brine. The organic layer was dried over MgSO$_4$, filtered, and concentrated. The residue was purified to provide methyl 4-{(2-methyl-4-quinolinyl)[(methylsulfonyl)oxy]methyl}benzoate in quantitative yield. MS (AP$^+$): 386 (M+1).

(209d) A solution of 209c (120 mg, 0.31 mmol) in 3 mL of MeOH was added to a suspension of the Pd/C catalyst (60 mg, 10%) in 2 mL of MeOH. The reaction took place after the flask was purged with H$_2$. The reaction was monitored using TLC until disappearance of the starting material. After filtered, the solution was concentrated and the residue was purified on silica gel to provide methyl 4-[(2-methyl-4-quinolinyl)methyl]benzoate in quantitative yield. MS (AP$^+$): 292 (M+1).

(209e) A solution of aqueous NaOH (1N, 35 mL) was added to a solution of 209d (5.0 g, 17.2 mmol) in 100 mL of MeOH. The reaction mixture was heated up to 60° C. until completion of the reaction, monitored by TLC. Upon the completion, one equivalent of aqueous HCl (1N, 35 mL) was added to neutralize the base. The solution was concentrated to dryness and the residue was redissolved in MeOH. After filtration, the methanolic solution was concentrated again to provide 4-[(2-methyl-4-quinolinyl)methyl]benzoic acid in quantitative yield. MS (ES$^+$): 278 (M+1).

Example 210

4-{[2-(trifluoromethyl)-4-quinolinyl]methyl}benzoic acid
(210a) Following a procedure similar to 209a, 4-hydroxy-2-trifluoromethylquinoline (9.89 g, 46 mmol) was converted to the corresponding bromide (12.5 g, 97%). MS (ES$^+$): 276 (M+1).

(210b) Following a procedure similar to 209b, the product from (210a)(1.0 g, 3.6 mmol) was converted to the corresponding product 210b (0.38 g, 29%). MS (AP$^+$): 362 (M+1)

(210c) Following a procedure similar to 209c, the product from 210b (360 mg, 1.0 mmol) was converted to the corresponding mesylate in quantitative yield. MS (AP$^+$): 440 (M+1).

(210d) Following a procedure similar to 209d, the product from 210c (430 mg, 1.0 mmol) was reduced to the desired product 210d in quantitative yield. MS (ES$^+$): 346 (M+1).

(210e) Following a procedure similar to 209e, the product from 210d (340 mg, 1.0 mmol) was converted to the corresponding acid 210e (320 mg, >95%). MS (AP$^+$): 332 (M+1).

Example 211

4-[(2-ethyl-4-quinolinyl)methoxy]benzoic acid (211a) To a flask were charged aniline (18.6 g, 0.2 mol), methyl propionylacetate (26.0 g, 0.2 mol), p-TsOH (0.3 g) and 100 mL of benzene. The mixture was heated to reflux and water was removed via Dean-Stark apparatus. After cooled down, insoluble material was filtered and the filtrate was concentrated to provide crude material in quantitative yield. The crude material was pure enough for next step. The crude material obtained was dissolved in 150 mL of Ph$_2$O and the solution was heated to 240° C. for 1 hr. After cooled down, the solution was diluted with hexane and the precipitate 211a (5.3 g, 15%) was collected. MS (ES$^+$): 174 (M+1)

(211b) Following a procedure similar to 209a, 4-hydroxy-2-ethylquinoline, 211a (5.0 g, 28.9 mmol) was converted to the corresponding bromide (3.6 g, 53%). MS (ES$^+$): 238 (M+1).

(211c) Following a procedure similar to 209b, the product from 211b (3.0 g, 12.7 mmol) was converted to the desired product 211c (2.82 g, 69%). MS (AP$^+$): 322 (M+1).

(211d) Following a procedure similar to 209c, the product from 211c (3.0 g, 9.3 mmol) was converted to the corresponding mesylate 211d in quantitative yield. MS (AP$^+$): 400 (M+1).

(211e) Following a procedure similar to 209d, the product from 211d (3.7 g, 9.3 mmol) was reduced to the desired product 211e (2.65 g, 94%). MS (AP$^+$): 306 (M+1).

(211f) Following a procedure similar to (109e), the product from 211e (2.6 g, 8.5 mmol) was converted to the corresponding acid 211f (2.4 g, >95%). MS (ES$^+$): 292 (M+1).

Example 212

4-(1,3-dihydrofuro[3,4-b]quinolin-9-ylmethyl)benzoic acid (212a) Following a procedure similar to (211a), methyl 4-oxotetrahydro-3-furancarboxylate (15.0 g, 0.1 mol) was condensed with aniline to provide the desired product (212a) (10.5 g, 56%). MS (ES$^+$): 188 (M+1).

(212b) To a solution of 212a (1.0 g, 5.3 mmol) in 50 mL of anhydrous THF at −78° C. was added LiHMDS (1.0 M, 5.3 mL, 5.3 mmol). The solution was stirred for 1 hr, followed by addition of a solution of 2-[N,N-bis(trifluoromethylsulfonyl)amino]-5-chloropyridine (2.33 g, 5.9 mmol) in 10 mL of THF. The mixture was allowed to warm to room temperature overnight. The reaction was quenched with 100 mL of H$_2$O and THF was removed under reduced pressure. The aqueous layer was extracted with EtOAc (4×75 mL) and the combined organic layer was dried over MgSO$_4$. After concentration, the residue was purified on silica gel column to provide the corresponding triflate 212b (850 mg, 50%). MS (ES$^+$): 320 (M+1).

(212c) To a solution of 212b (0.85 g, 2.66 mmol) in 15 mL of DMF were added LiCl (0.23 g, 5.3 mmol), Pd(PPh$_3$)$_4$ (0.31 g, 10 mol %, 0.27 mmol) and 4-(methoxycarbonyl)-benzyl zinc bromide (0.5 M, 12.5 mL) (Shiota, T. et. al. *J. Org. Chem.* 1999, 64, 453). The solution was stirred at room temperature overnight. DMF solvent was removed under reduced pressure and the residue was taken into 100 mL of H$_2$O. The aqueous phase was extracted by EtOAc (5×50 mL). The combined organic layer was washed with H$_2$O and saturated NaCl and dried over MgSO$_4$. After concentration, the residue was purified on silica gel column to give the desired product 212c (0.45 g, 45%). (290 mg, 34%). MS (ES$^+$): 320 (M+1).

(212d) Following a procedure similar to (209e), the product from 212c (0.29 g, 0.91 mmol) was converted to the corresponding acid 212d (0.25 g, 86%). MS (ES$^-$): 304 (M−1).

Example 213

4-[(2,3,5-trimethyl-4-pyridinyl)methyl]benzoic acid (213a) To a solution of 4-methoxy-3,5-dimethyl-2-pyridinemethanol (2.0 g, 12 mmol) in 40 mL of CH$_2$Cl$_2$ at 0° C. were added DIEA (6.25 mL, 36 mmol) and MsCl (1.25 mL, 12 mmol). The mixture was stirred from 0° C. to room temperature for 1 hr. The reaction was quenched by addition of H$_2$O and diluted with EtOAc. The organic layer was washed with NaHCO$_3$, H$_2$O and brine. The organic layer was dried over MgSO$_4$. After filtration and concentration, the crude product 213a (2.31 g, 78%) was carried over for next reaction. MS (AP$^+$): 264 (M+1).

(213b) To a solution of 213a (2.3 g, 9.4 mmol) in 50 mL of MeOH was added 3 g of 20% Pd(OH)$_2$/C. The reaction mixture was stirred under H$_2$ overnight. The catalyst was filtered off and rinsed with MeOH. After concentration, the desired product 213b (2.3 g, >95%) was obtained. MS (AP$^+$): 152 (M+1).

(213c) To a solution of 213b (1.5 g, 10 mmol) in 10 ml of CH$_2$Cl$_2$ was added BBr$_3$ (1.0 M, 20 mL). The mixture was stirred overnight and the solvent was removed. The residue was neutralized with sat. Na$_2$CO$_3$ and the resulting solution was stripped off to dryness. The residue was dissolved in 20% MeOH in CHCl$_3$ and the insoluble was filtered off. After concentration, the demethylation product 213c was obtained in quantitative yield. MS (AP$^+$): 275 (2M+1).

(213d) To a flask were added compound 213c (1.0 g, 7.3 mmol) and POBr$_3$ (3.1 g, 11 mmol). The flask was heated to 130° C. for 90 mins and cooled to room temperature. It was quenched with iced water and basified with conc. Na$_2$CO$_3$. The aliquot was extracted with EtOAc (40 mL×5) and the combined organic layer was washed with H20 and brine and dried over MgSO$_4$. After filtration and concentration, the desired product 213d (0.86 g) was obtained in 56% yield. MS (AP$^+$): 201 (M+1).

(213e) Following a procedure similar to 209b, the product from 213d (0.2 g, 1 mmol) was converted to the corresponding adduct 213e (0.12 g, 42%). MS (ES$^+$): 286 (M+1).

(213f) Following a procedure similar to (209c), the product from 213e (120 mg, 0.4 mmol) was converted to the corresponding mesylate (156 mg) in quantitative yield. MS (ES$^+$): 364 (M+1)

(213 g) Following a procedure similar to 209d, the product from 213f (155 mg, 0.4 mmol) was reduced to the desired product as a methanesulfonic acid salt 213 g (146 mg) in 94 yield. MS (AP$^+$): 270 (M+1).

(213i) Following a procedure similar to 209e, the product from 213 g (146 mg, 0.4 mmol) was converted to the corresponding acid 213i (80 mg, 78%). MS (AP$^+$): 256 (M+1).

Example 214

{4-[(2-methyl-4-quinolinyl)-methoxy]phenyl}acetic acid

To a solution of methyl (4-hydroxyphenyl)acetate (10.0 g, 60.2 mmol) in 400 mL THF was added 4-chloromethyl-2-methylquinoline (11.5 g, 60.2 mmol), cesium carbonate (29.4 g, 90.3 mmol), and sodium iodide (451 mg, 3 mmol).

The reaction was heated to reflux for 72 hr, after which the reaction was extracted from sat KH$_2$PO$_4$ with EtOAc ×3. The combined organic layers were dried with MgSO$_4$, filtered, and concentrated. This residue was taken up in 200 mL MeOH and treated with 1 M NaOH (100 mL) for 16 hr. The reaction was treated with dilute KH$_2$PO$_4$ and EtOAc. A solid formed between the layers that was filtered through a sintered glass funnel and recrystallized from EtOH/water to give 14 g (76%) of the product acid. MS found: (M+H)=308.

Example 215

4-[(2-methyl-4-quinolinyl)methoxy]benzoic acid

This compound was prepared starting from methyl 4-hydroxy benzoate using the analogous procedure as used for Example 214. MS found: (M+H)=294.

Example 216

4-(1-naphthylmethoxy)benzoic acid

This compound was prepared starting from methyl 4-hydroxy benzoate and 1-chloromethylnaphthalene using the analogous procedure as used for Example 214. MS found: (M+H)=279.

Example 217

4-[(5-isoquinolinyloxy)methyl]benzoic acid

Methyl 4-(bromomethyl)benzoate was alkylated with commercially available 5-hydroxyisoquinoline using the analogous procedure as used for Example 202. MS found: (M+H)=280.

Example 218

4-{{(2-methyl-8-quinolinyl)oxy]methyl}benzoic acid

Methyl 4-(bromomethyl)benzoate was alkylated with commercially available 8-hydroxyisoquinaldine using the analogous procedure as used for Example 202. MS found: (M+H)=294.

Example 219

4-[(5-quinolinyloxy)methyl]benzoic acid

Methyl 4-(bromomethyl)benzoate was alkylated with commercially available 5-hydroxyquinoline using the analogous procedure as used for Example 202. MS found: (M+H)=280.

Example 220

4-(2-methyl-4-quinolinyl)benzoic acid

To 1-methylcarboxyphenylboronic acid (1.0 g, 5.6 mmol) and 4-bromo-2-methylquinoline (1.24 g, 5.6 mmol) in THF/aq K2CO3 was added Pd(PPh3)4 and the reaction was heated to 70° C. for 16 hr. Aqueous workup using NaHCO$_3$ and EtOAc, column chromatography and saponification using the same conditions as for Example 214 gave the final product. MS found: (M+H)=264.

Example 221

4-[(2-methyl-1-oxido-4-quinolinyl)methoxy]benzoic acid

This compound was prepared using the analogous procedure as used for Example 209 followed by Oxone® oxidation of the quinoline to the N-oxide. MS found: (M+H)=280.

Example 222

4-[(2-methyl-4-quinolinyl)methoxy]benzenethiol (222a) To a solution of 4-mercaptophenol (15.0 g, 118 mmol) in 250 mL MeOH was added sodium bicarbonate (27.8 g, 330 mmol) and iodine (15.2 g, 60 mmol). After stirring overnight, MeOH was removed by rotary evaporator and the residue partitioned between EtOAc and 2×NaHSO$_3$. The organic phase was dried over MgSO$_4$, filtered, and concentrated on a rotary evaporator to give 14.9 g (50%) of 222a. MS found: (M+H)=251.

(222b) A solution of 220a (7.0 g, 28 mmol), 4-(chloromethyl)-2-methyl-quinoline (11.0 g, 57.4 mmol), and potassium carbonate (19.0 g, 137 mmol) in 200 mL CH$_3$CN was refluxed overnight. The reaction was cooled and CH$_3$CN was removed by rotary evaporator. The residue was partitioned between EtOAc and brine and the organic phase was dried over MgSO$_4$, filtered, and concentrated on a rotary evaporator to give 15 g (96%) of 222b. MS found: (M+H)=561.

(222c) A solution of 220b (7.1 g, 12.6 mmol) was dissolved in THF, cooled to 0° C., and treated with 2.0M lithium borohydride in THF (15 mL, 30 mmol) the reaction was warmed to rt and stirred overnight. The residue was partitioned between EtOAc and brine and washed with sat KH$_2$PO$_4$. The organic phase was dried over MgSO$_4$, filtered, and concentrated on a rotary evaporator to give 6.4 g (90%) of 222c. MS found: (M+H)=282.

Example 223

4-[(2-methyl-4-quinolinyl)methoxy]benzenesulfonyl chloride HCl salt (223a) To commercially available 4-hydroxybenzenesulfonic acid sodium salt (6.0 g, 26 mmol) and 4-(chloromethyl)-2-methylquinoline (7.5 g, 39 mmol) in a mixture of 15% NaOH (9.7 mL) and EtOH (100mL) was added sodium iodide (292 mg, 5 mol %) and the reaction was refluxed for 16 hr. The reaction was cooled to rt, filtered, and the solid was washed with EtOH, then DCM and dried in vacuo to give 8.4 g (92%) of the alkylated sodium salt.

(223b) Compound 223a (1.92 g, 5.5 mmol) was dissolved in thionyl chloride (4 mL) followed by a catalytic amount of DMF and refluxed for 2 hr. The reaction was cooled to rt, concentrated in vacuo, and the residue was washed with DCM×2, then THF×2, and dried in vacuo. 1.3 g (69%) of the sulfonyl chloride HCl salt was obtained. MS found: (M+H)=348.

Example 224

4-(1,1-dioxido-3,4-dihydro-2H-1-benzothiopyran-4-yl)benzoic acid (224a) To a solution of thiochroman-4-one (2.0 g, 12.2 mmol) in DCM (100 mL) was added 2,6-ditert-butylpyridine (2.63 g, 12.8 mmol) followed by dropwise addition of trifluoromethanesulfonic anhydride (3.8 g, 13.4 mmol) and the reaction was heated to reflux for 2 hr. The reaction was cooled, concentrated, and treated with hexane. The salts were filtered off and the filtrate was concentrated in vacuo to give 1.84 g (51%) of 224a which was taken directly to the next reaction.

(224b) To compound 224a (1.83 g, 6.17 mmol), 1-(methylcarboxy)phenyl-4-boronic acid (1.11 g, 6.17 mmol) dissolved in ethanol/toluene (15 mL/30 mL) was added lithium chloride (524 mg, 12.4 mmol), potassium carbonate (4.7 mL, 2.65 M in water), and Pd(PPh$_3$)$_4$ (357 mg, 0.31 mmol) under a blanket of N$_2$. The reaction was heated to reflux for 2 hr, cooled and extracted from water with EtOAc×2. The combined organic layers were washed with water×1, brine×2, dried over MgSO$_4$, filtered, and concentrated. The residue was purified by column chromatography on SiO$_2$ using 15:85 EtOAc/hexane to give 1.18 g (67%) of the product 224b.

(224c) To compound 224b (777 mg, 2.75 mmol) in MeOH (30 mL) cooled to 0° C. was added a solution of Oxone® (6.78 g, 11 mmol) in 7 mL water. After 30 min, the reaction was warmed to rt for 1 h, diluted with water, basified with 1 M NaOH to pH 8, and extracted with EtOAc×2. The combined organic layers were washed with water×1, brine×2, dried over MgSO$_4$, filtered, and concentrated to give 784 mg (91%) of the sulfone 224c and taken to the next step.

(224d) To compound 224c (107 mg, 0.34 mmol) in THF/water (1:1, 2 mL) was added lithium hydroxide hydrate (43 mg, 1.0 mmol) and the reaction was stirred for 3 hr. The reaction was concentrated in vacuo, acidified with 1 M HCl, extracted with EtOAc×2 and the combined organic extracts were washed with water×1, brine×1, dried over MgSO$_4$, filtered, and concentrated in vacuo to give 100 mg (98%) of 224d. MS found: (M+H)$^+$=301.

Example 225

4-[(3,5-dimethyl-1H-pyrazol-4-yl)methyl]benzoic acid (225a) Methyl 4-formylbenzoate (2.00 g, 12.2 mmol), acetyl acetone (1.16 g, 11.6 mmol), piperidine (48 uL, 0.48 mmol), and acetic acid (0.14 mL, 2.44 mmol) were combined in toluene (60 mL) and heated to reflux with a Dean Stark trap attached for water removal. The reaction was complete in 2.5 hr, the Dean Stark trap was removed and the mixture allowed to cool to room temperature. Dilution with ethyl acetate (120 mL) was followed by washing with water, 10% citric acid, NaHCO$_3$×2, and brine. After drying over MgSO$_4$, the solution was filtered and evaporated, then the residue was purified by flash chromatography to provide 42a as a yellow oil (2.43 g, 85%). MS found: (M+H)$^+$=247.

(225b) Methanol (60 mL) was added slowly to 225a (2.42 g, 9.83 mmol) and palladium on carbon (10%, 0.5 g) under a steady stream of nitrogen. A hydrogen balloon was attached via a three way stopcock and the atmosphere above the reaction was removed and replaced with hydrogen three times. After 1 h no starting material was detectable by TLC and the hydrogen was removed and replaced with nitrogen. The catalyst was filtered and the solvent removed by evaporation in vacuo. The residue was purified by flash chromatography to provide 225b (1.91 g, 78%) as a clear oil. MS found: (M+H)$^+$=249.

(225c) Hydrazine hydrate (0.14 g, 2.76 mmol) and 225b (0.62 g, 2.51 mmol) were combined in methanol (15 mL) and heated to reflux for 1.5 hr. The reaction was cooled to room temperature and the solvent removed in vacuo. The residue was purified by flash chromatography to provide 225c as a waxy solid (585 mg, 95%). MS found: (M+H)$^+$=245.

(225d) Sodium hydroxide (0.33 g, 8.33 mmol) was dissolved in water (5 mL) then added to 225c (585 mg, 2.39 mmol) in methanol/THF (1:1, 10 mL). The solution was stirred overnight and solvent was removed in vacuo. The residue was taken up in water (20 mL) and the aqueous phase was washed with ether×2, then neutralized by the addition of 1N HCl (8.3 mL). The resulting solid was filtered and dried under vacuum to provide 225d as a white solid (288 mg, 88%). MS found: (M+H)$^+$=231.

Example 226

4-[(1,3,5-trimethyl-1H-pyrazol-4-yl)methyl]benzoic acid (226) Example 226 was prepared in an analogous manner to example 225 by substituting N-methyl hydrazine for hydrazine hydrate in step 225c. Compound 226 was isolated as a white solid (79 mg, 80%). MS found: (M+H)$^+$=427.

Tables 1-3 below provide representative Examples, the synthesis of which is described above, of the compounds of the present invention.

TABLE 1

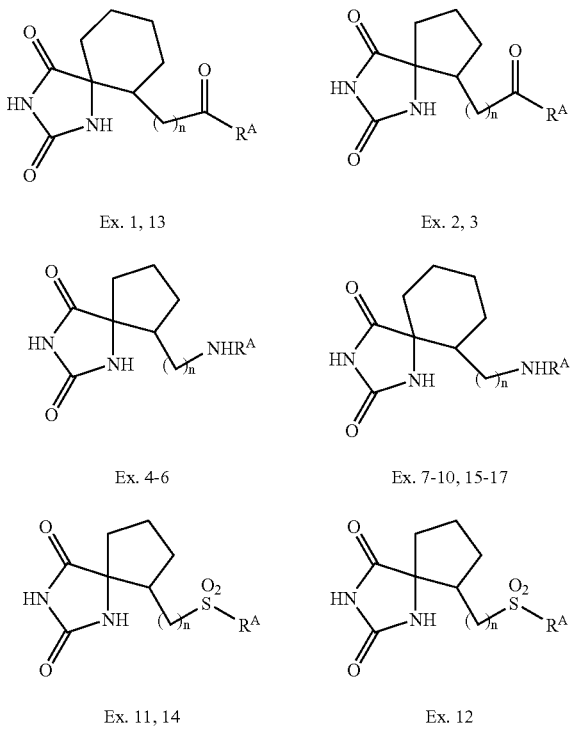

Ex. 1, 13       Ex. 2, 3

Ex. 4-6         Ex. 7-10, 15-17

Ex. 11, 14      Ex. 12

TABLE 1-continued

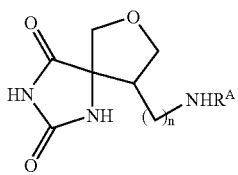

Ex. 18

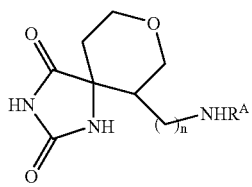

Ex. 19-21

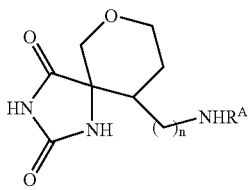

Ex. 22-41

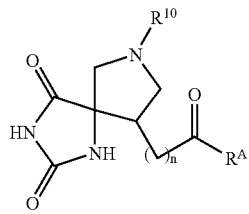

Ex. 43-44

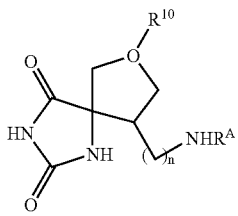

Ex. 45-96

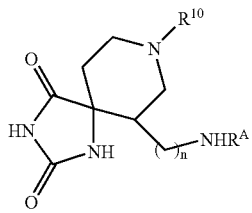

Ex. 97-99

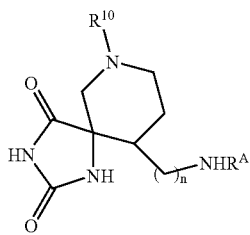

Ex. 100

| Ex | $R^A$ | $R^{10}$ | n | MS (M + H) |
|---|---|---|---|---|
| 1 | 4-[(2-methyl-4-quinolinyl)methoxy]anilino | — | 0 | 459 |
| 2 | 4-[(2-methyl-4-quinolinyl)methoxy]anilino | — | 0 | 445 |
| 3 | 4-[(2-methyl-4-quinolinyl)methoxy]anilino | — | 1 | 459 |
| 4 | 4-[(2-methyl-4-quinolinyl)methoxy]benzoyl | — | 0 | 445 |
| 5 | {4-[(2-methyl-4-quinolinyl)methoxy]phenyl}acetyl | — | 0 | 459 |
| 6 | 4-[(2-metbyl-4-quinolinyl)methoxy]benzenesulfonyl | — | 0 | 481 |
| 7 | 4-[(2-methyl-4-quinolinyl)methoxy]benzoyl | — | 1 | 473 |
| 8 | 4-[(2-methyl-4-quinolinyl)methoxy]benzenesulfonyl | — | 1 | 509 |
| 9 | 4-[(2-methyl-4-quinolinyl)methoxy]benzoyl | — | 1 | 473 |
| 10 | 4-[(2-methyl-4-quinolinyl)methoxy]benzenesulfonyl | — | 1 | 509 |
| 11 | 4-[(2-methyl-4-quinolinyl)methoxy]phenyl | — | 0 | 466 |

TABLE 1-continued

| | | | | |
|---|---|---|---|---|
| 12 | 4-[(2-methyl-4-quinolinyl)methoxy]phenyl | — | 0 | 480 |
| 13 | 4-[(2-methyl-4-quinolinyl)methoxy]anilino | — | 1 | 473 |
| 14 | 4-[(2-methyl-4-quinolinyl)methoxy]phenyl | — | 1 | 480 |
| 15 | 4-[(2-methyl-4-quinolinyl)methoxy]benzoyl | — | 0 | 459 |
| 16 | 4-[(1,1-dioxido-2,3-dihydro-4H-1,4-benzothiazin-4-yl)methyl]benzoyl | — | 0 | 483 |
| 17 | 4-[(2-methyl-4-quinolinyl)methoxy]benzenesulfonyl | — | 0 | 509 |
| 18 | 4-[(2-methyl-4-quinolinyl)methoxy]benzoyl | — | 0 | 447 |
| 19 | 4-[(2-methyl-4-quinolinyl)methoxy]benzoyl | — | 0 | 461 |
| 20 | 4-[(1,1-dioxido-2,3-dihydro-4H-1,4-benzothiazin-4-yl)methyl]benzoyl | — | 0 | (M + TFA) 597 |
| 21 | 4-[(2-methyl-4-quinolinyl)methyl]benzoyl | — | 0 | 445 |
| 22 | 4-[(2-methyl-4-quinolinyl)methoxy]benzoyl | — | 0 | 461 |
| 23 | 4-[(2-methyl-4-quinolinyl)methyl]benzoyl | — | 0 | 445 |
| 24 | 4-[(2-methyl-4-quinolinyl)methyl]benzoyl | — | 0 | 445 |
| 25 | 4-{[(2-trifluoromethyl-1H-benzimidazol-1-yl)]methyl}benzoyl | — | 0 | 488 |
| 26 | 4-[(2-ethylpyrazolo[1,5-a]pyridin-3-yl)-methyl]benzoyl | — | 0 | 448 |
| 29 | 4-(1,3-dihydrofuro[3,4-b]quinolin-9-ylmethyl)benzoyl | — | 0 | 473 |
| 30 | 4[(2-ethyl-4-quinolinyl)methyl]benzamide | — | 0 | 459 |
| 31 | 4-[(3,5-dimethyl-1H-pyrazol-4-yl)methyl]benzoyl | — | 0 | 398 |
| 32 | 4-{[2-(trifluoromethyl)-4-quinolinyl]methyl}benzamide | — | 0 | 499 |
| 33 | 4-[(2-methyl-1H-indol-3-yl)methyl]benzoyl | — | 0 | 433 |
| 34 | 4-[(1,3,5-trimethyl-1H-pyrazol-4-yl)methyl]benzoyl | — | 0 | 412 |
| 35 | 4-[(2-isopropyl-1H-benzimidazol-1-yl)methyl]benzoyl | — | 0 | 462 |
| 36 | 4-[(2-methyl-1-oxido-4-quinolinyl)methoxy]benzoyl | — | 0 | 461 |
| 37 | 4-[(2,3,5-trimethyl-4-pyridinyl)methyl]benzoyl | — | 0 | 423 |
| 38 | 4-{[2-(methylthio)-1H-benzimidazol-1-yl]methyl}benzoyl | — | 0 | 466 |
| 39 | 4-[(2-methyl-1H-indol-1-yl)methyl]benzoyl | — | 0 | 461 |
| 40 | 4-[(1,1-dioxido-2,3-dihydro-4H-1,4-benzothiazin-4-yl)methyl]benzoyl | — | 0 | 485 |
| 41 | 4-[(2-methyl-4-quinolinyl)methoxy]benzenesulfonyl | — | 0 | 497 |
| 43 | 4-[(2-methyl-4-quinolinyl)methoxy]anilino | t-butoxycarbonyl | 1 | 560 |
| 44 | 4-17(2-methyl-4-quinolinyl)methoxy]anilino | H | 1 | 460 |
| 45 | 4-[(2-methyl-4-quinolinyl)methoxy]benzoyl | t-butoxycarbonyl | 0 | 546 |
| 46 | 4-[(2-methyl-4-quinolinyl)methoxy]benzoyl | H | 0 | 446 |
| 47 | 4[(2-methyl-4-quinolinyl)methoxy]benzoyl | acetyl | 0 | 488 |
| 48 | 4-[(2-methyl-4-quinolinyl)methoxy]benzoyl | methanesulfonyl | 0 | 524 |

TABLE 1-continued

| | | | | |
|---|---|---|---|---|
| 49 | 4-[(2-methyl-4-quinolinyl)methoxy]benzoyl | [1-(t-butoxycarbonyl)-4-piperidinyl]carbonyl | 0 | 657 |
| 50 | 4-[(2-methyl-4-quinolinyl)methoxy]benzoyl | 4-piperidinylcarbonyl | 0 | 557 |
| 51 | 4-[(2-methyl-4-quinolinyl)methoxy]benzoyl | isonicotinoyl | 0 | 551 |
| 52 | 4-[(2-methyl-4-quinolinyl)methoxy]benzoyl | phenoxyacetyl | 0 | 580 |
| 53 | 4-[(2-methyl-4-quinolinyl)methoxy]benzoyl | 3-methylbutanoyl | 0 | 530 |
| 54 | 4-[(2-methyl-4-quinolinyl)methoxy]benzoyl | 3-pyridinylcarbonyl | 0 | 551 |
| 55 | 4-[(2-methyl-4-quinolinyl)methoxy]benzoyl | isobutyryl | 0 | 516 |
| 56 | 4-[(2-methyl-4-quinolinyl)methoxy]benzoyl | 4-morpholinylacetyl | 0 | 573 |
| 57 | 4-[(2-methyl-4-quinolinyl)methoxy]benzoyl | 3-pyridinylmethyl | 0 | 538 |
| 58 | 4-[(2-methyl-4-quinolinyl)methoxy]benzoyl | 4-pyridinylmethyl | 0 | 537 |
| 59 | 4-[(2-methyl-4-quinolinyl)methoxy]benzoyl | isopropyl | 0 | 488 |
| 60 | 4-[(2-methyl-4-quinolinyl)methoxy]benzoyl | isobytyl | 0 | 502 |
| 61 | 4-[(2-methyl-4-quinolinyl)methyl]benzoyl | t-butoxycarbonyl | 0 | 530 |
| 62 | 4-[(2-methyl-4-quinolinyl)methyl]benzoyl | H | 0 | 430 |
| 63 | 4-[(2-methyl-4-quinolinyl)methyl]benzoyl | [1-(t-butoxycarbonyl)-4-piperidinyl]carbonyl | 0 | 641 |
| 64 | 4-[(2-methyl-4-quinolinyl)methyl]benzoyl | 4-piperidinylcarbonyl | 0 | 541 |
| 65 | 4-[(2-methyl-4-quinolinyl)methyl]benzoyl | isonicotinoyl | 0 | 535 |
| 66 | 4-[(2-methyl-4-quinolinyl)methyl]benzoyl | phenoxyacetyl | 0 | 564 |
| 67 | 4-[(2-methyl-4-quinolinyl)methyl]benzoyl | 3-methylbutanoyl | 0 | 514 |
| 68 | 4-[(2-methyl-4-quinolinyl)methyl]benzoyl | 3-pyridinylcarbonyl | 0 | 535 |
| 69 | 4-[(2-methyl-4-quinolinyl)methyl)]benzoyl | isobutyryl | 0 | 500 |
| 70 | 4-[(2-methyl-4-quinolinyl)methyl]benzoyl | 4-morpholinylacetyl | 0 | 557 |
| 71 | 4-[(2-methyl-4-quinolinyl)methyl]benzoyl | 3-pyridinylmethyl | 0 | 521 |
| 72 | 4-[(2-methyl-4-quinolinyl)methyl]benzoyl | 4-pyiridinylmethyl | 0 | 521 |
| 73 | 4-[(2-methyl-4-quinolinyl)methyl]benzoyl | isopropyl | 0 | 472 |
| 74 | 4-[(2-methyl-4-quinolinyl)methyl]benzoyl | isobytyl | 0 | 486 |
| 75 | 4-[(1,1-dioxido-2,3-dihydro-4H-1,4-benzothiazin-4-yI)methyl]benzoyl | t-butoxycarbonyl | 0 | 570 |
| 76 | 4-[(1,1-dioxido-2,3-dihydro-4H-1,4-benzothiazin-4-yI)methyl]benzoyl | H | 0 | 470 |
| 77 | 4-[(1,1-dioxido-2,3-dihydro-4H-1,4-benzothiazin-4-yI)methyl]benzoyl | [1-(t-butoxycarbonyl)-4-piperidinyl]caronyl | 0 | 681 |
| 78 | 4-[(1,1-dioxido-2,3-dihydro-4H-1,4-benzothiazin-4-yl)methyl]benzoyl | 4-piperidinylcarbonyl | 0 | 581 |
| 79 | 4-[(1,1-dioxido-2,3-dihydro-4H-1,4-benzothiazin-4-yl)methyl]benzoyl | isonicotinoyl | 0 | 575 |
| 80 | 4-[(1,1-dioxido-2,3-dihydro-4H-1,4-benzothiazin-4-yl)methyl]benzoyl | phenoxyacetyl | 0 | 604 |
| 81 | 4-[(1,1-dioxido-2,3-dihydro-4H-1,4-benzothiazin-4-yl)methyl]benzoyl | 3-methylbutanoyl | 0 | 554 |
| 82 | 4-[(1,1-dioxido-2,3-dihydro-4H-1,4-benzothiazin-4-yl)methyl]benzoyl | 3-pyridinylcarbonyl | 0 | 575 |
| 83 | 4-[(1,1-dioxido-2,3-dihydro-4H-1,4-benzothiazin-4-yl)methyl]benzoyl | isobutyryl | 0 | 540 |

TABLE 1-continued

| | | | | |
|---|---|---|---|---|
| 84 | 4-[(1,1-dioxido-2,3-dihydro-4H-1,4-benzothiazin-4-yl)methyl]benzoyl | 4-morpholinylacetyl | 0 | 597 |
| 85 | 4-[(1,1-dioxido-2,3-dihydro-4H-1,4-benzothiazin-4-yl)methyl]benzoyl | 3-pyridinylmethyl | 0 | 561 |
| 86 | 4-[(1,1-dioxido-2,3-dihydro-4H-1,4-benzothiazin-4-yl)methyl]benzoyl | 4-pyridinylmethyl | 0 | 561 |
| 87 | 4-[(1,1-dioxido-2,3-dihydro-4H-1,4-benzothiazin-4-yl)methyl]benzoyl | isopropyl | 0 | 512 |
| 88 | 4-[(1,1-dioxido-2,3-dihydro-4H-1,4-benzothiazin-4-yl)methyl]benzoyl | isobutyl | 0 | 526 |
| 89 | 4-[(2-isopropyl-1H-benzimidazol-1-yl)methyl]benzoyl | t-butoxycarbonyl | 0 | 547 |
| 90 | 4-[(2-isopropyl-1H-benzimidazol-1-yl)methyl]benzoyl | H | 0 | 447 |
| 91 | 4-[(2-methyl-4-quinolinyl)methoxy]benzenesulfonyl | t-butoxycarbonyl | 0 | 582 |
| 92 | 4-[(2-methyl-4-quinolinyl)methoxy]benzenesulfonyl | H | 0 | 482 |
| 93 | 4-[(2-methyl-4-quinolinyl)methoxy]benzoyl | t-butoxycarbonyl | 1 | 560 |
| 94 | 4[(2-methyl-4-quinolinyl)methoxy]benzoyl | H | 1 | 460 |
| 95 | 4-[(2-methyl-4-quinolinyl)methyl]benzoyl | t-butoxycarbonyl | 1 | 544 |
| 96 | 4-[(2-isopropyl-1H-benzimidazol-1-yl)methyl]benzoyl | t-butoxycarbonyl | 1 | 561 |
| 97 | 4-[(2-methyl-4-quinolinyl)methoxy]benzoyl | t-butoxycarbonyl | 0 | 560 |
| 98 | 4-[(2-methyl-4-quinolinyl)methoxy]benzoyl | H | 0 | 460 |
| 99 | 4[(2-methyl-4-quinolinyl)methoxy]benzoyl | acetyl | 0 | 502 |
| 100 | 4-[(2-methyl-4-quinolinyl)methoxy]benzoyl | t-butoxycarbonyl | 0 | 560 |

TABLE 2

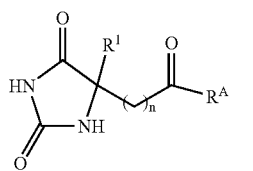

Ex. 101-104, 106

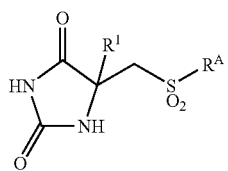

Ex. 107

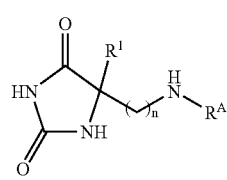

Ex. 108-112

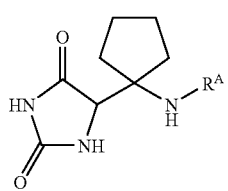

Ex. 113

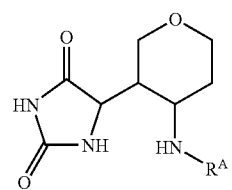

Ex. 148

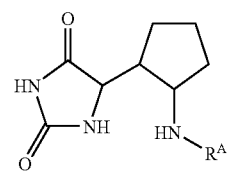

Ex. 149-150

| Ex | R$^A$ | R$^1$ | n | MS |
|---|---|---|---|---|
| 101 | 4-[(2-methyl-4-quinolinyl)methoxy]anilino | H | 1 | 406 |
| 102 | 4-[(2-isopropyl-1H-benzimidazol-1-yl)methyl]anilino | H | 1 | 406 |
| 103 | 4-[(2-methyl-4-quinolinyl)methoxy]anilino | methyl | 1 | 419 |
| 104 | 4-phenoxybenzylamino | methyl | 1 | 354 |
| 106 | 4-[(2-methyl-4-quinolinyl)methoxy]anilino | H | 2 | 419 |
| 107 | 4-[(2-methyl-4-quinolinyl)methoxy]anilino | methyl | — | 440 |
| 108 | 4-phenoxybenzoyl | methyl | — | 340 |
| 109 | 4-[(2-methyl-4-quinolinyl)methoxy]benzoyl | methyl | — | 419 |

TABLE 2-continued

| | | | | |
|---|---|---|---|---|
| 110 | 4-[(2-methyl-4-quinolinyl)methoxy]phenyl acetyl | methyl | — | 433 |
| 111 | 4-{[(2-(methylthio)-1H-benzimidazol-1-yl]methyl}benzoyl | methyl | — | 425 |
| 112 | 4-[(2-methyl-4-quinolinyl)methoxy]benzene sulfonyl | methyl | — | 456 |
| 113 | 4-[(2-methyl-4-quinolinyl)methoxy]benzoyl | — | — | 459 |
| 148 | 4-[(2-methyl-4-quinolinyl)methoxy]benzoyl | — | — | 475 |
| 149 | 4-[(2-methyl-4-quinolinyl)methoxy]benzoyl | — | — | 459 |
| 150 | 4-{[(2-(trifluoromethyl)-1H-benzimidazol-1-yl]methyl}benzoyl | — | — | 486 |

TABLE 3

Ex. 105 / Ex. 114-147

| Ex | $R^A$ | $R^2$ | MS |
|---|---|---|---|
| 105 | 4-[(2-methyl-4-quinolinyl)methoxy]benzoyl | methyl | 419 |
| 114 | 4-[(2-methyl-4-quinolinyl)methoxy]benzoyl | methyl | 419 |
| 115 | 4-[(2-methyl-4-quinolinyl)methoxy]benzoyl | 4-morpholinomethyl | 503 |
| 116 | 4-[(2-methyl-4-quinolinyl)methoxy]benzoyl | isopropyl | 447 |
| 117 | 4-[(2-methyl-4-quinolinyl)methoxy]benzoyl | isobutyl | 461 |
| 118 | 4-[(2-methyl-4-quinolinyl)methoxy]benzoyl | cyclopentyl | 473 |
| 119 | 4-[(2-methyl-4-quinolinyl)methoxy]benzoyl | benzyl | 495 |
| 120 | 4-[(2-methyl-4-quinolinyl)methoxy]benzoyl | tetrahydro-2H-pyran-4-yl | 489 |
| 121 | 4-[(2-methyl-4-quinolinyl)methoxy]benzoyl | 1-(t-butoxycarbonyl)-4-piperidinyl | 588 |
| 122 | 4-[(2-methyl-4-quinolinyl)methoxy]benzoyl | 4-piperidinyl | 489 |
| 123 | 4-[(2-methyl-4-quinolinyl)methoxy]benzoyl | 1-(3-pyridinylmethyl)-4-piperdinyl | 579 |
| 124 | 4-[(2-methyl-4-quinolinyl)methoxy]benzoyl | 1-(4-pyridinylmethyl)-4-piperdinyl | 579 |
| 125 | 4-[(2-methyl-4-quinolinyl)methoxy]benzoyl | 1-acetyl-4-piperidinyl | 530 |
| 126 | 4[(2-methyl-4-quinolinyl)methoxy]benzoyl | 1-(2-propynyl)-4-piperidinyl | 526 |
| 127 | 4-[(2-methyl-4-quinolinyl)methoxy]benzoyl | 1-(2,2-dimethylpropanoyl)-4-piperidinyl | 572 |
| 128 | 4-[(2-methyl-4-quinolinyl)methoxy]benoyl | 1-(methylsulfonyl)-4-piperdinyl | 566 |
| 129 | 4-[(2-methyl-4-quinolinyl)methyl]benzoyl | 1-acetyl-4-piperidinyl | 514 |
| 130 | 4-[(1,1-dioxido-2,3-dihydro-4H-1,4-benzothiazin-4-yl)methyl]benzoyl | 1-acetyl-4-piperidinyl | 554 |
| 131 | 4-(1,1-dioxido-2,4dihydro-2H-1-benzothiopyran-4-yl)benzoyl | 1-acetyl-4-piperidinyl | 539 |
| 132 | 4-(2-methyl-4-quinolinyl)benzoyl | 1-acetyl-4-piperidinyl | 500 |
| 133 | 4-(1-naphthylmethoxy)benzoyl | 1-acetyl-4-piperidinyl | 515 |
| 134 | 4-[(5-quinolinyloxy)methyl]benzoyl | 1-acetyl-4-piperidinyl | 516 |
| 135 | 4-[(5-isoquinolinyloxy)methyl]benzoyl | 1-acetyl-4-piperidinyl | 516 |
| 136 | 4-{[(2-methyl-8-quinolinyl)oxy]methyl}benzoyl | 1-acetyl-4-piperidinyl | 530 |
| 137 | 4-[(2-methyl-4-quinolinyl)methoxy]benzene sulfonyl | 1-acetyl-4-piperidinyl | 566 |
| 138 | 4-[(2-methyl-4-quinolinyl)methoxy]benzoyl | 4-morpholinylcarbonyl | 518 |
| 139 | 4-[(2-methyl-4-quinolinyl)methoxy]benzoyl | (t-butoxycarbonyl)methyl | 519 |
| 140 | 4-[(2-methyl-4-quinolinyl)methoxy]benzoyl | 2-hydroxy-2-oxoethyl | 463 |
| 141 | 4-[(2-methyl-4-quinolinyl)methoxy]benzoyl | 2-(4-morpholinyl)-2-oxoethyl | 532 |
| 142 | 4-[(2-methyl-4-quinolinyl)methoxy]benzoyl | 2-(methylamino)-2-oxoethyl | 476 |
| 143 | 4-[(2-methyl-4-quinolinyl)methoxy]benzoyl | 2-(t-butylamino)-2-oxoethyl | 518 |
| 144 | 4-[(2-methyl-4-quinolinyl)methoxy]benzoyl | 2-(1-piperazinyl)-2-oxoethyl | 531 |
| 145 | 4-[(2-methyl-4-quinolinyl)methoxy]benzoyl | 2-(4-methyl-1-piperazinyl)-2-oxoethyl | 545 |
| 146 | 4-[(2-methy-4-quinolinyl)methyl]benzoyl | 2-(4-morpholinyl)-2-oxoethyl | 516 |
| 147 | 4-[(1,1-dioxido-2,3-dihydro-4H-1,4-benzothiazin-4-yl)methyl]benzoyl | 2-(4-morpholinyl)-2-oxoethyl | 556 |

Table 4 demonstrates additional representative examples of the present invention. Each entry $R^B$ in the table is intended to be paired independently with each formula at the start of the table. For example, example 1 in Table 4 is intended to be paired with each of the following formulae A-BZ. From formulae A-AD, if a formula contains variables $R^{10}$ and/or n, each entry $R^B$ is intended to be paired with individual designation of $R^{10}$ and/or n, independently at each occurrence, listed below.

$R^{10}$ is H, methyl, ethyl, isopropyl, isobutyl, 2-propynyl, acetyl, 2,2-dimethylpropanoyl, t-butoxycarbonyl, 3-methylbutanoyl, isobutyryl, isonicotinoyl, phenoxyacetyl, methanesulfonyl, 3-pyridinylmethyl, 4-pyridinylmethyl, 3-pyridinylcarbonyl, 4-piperidinylcarbonyl, 4-morpholinylacetyl, 4-morpholinomethyl, or [1-(t-butoxycarbonyl)-4-piperidinyl]carbonyl;

n is 0 or 1.

From formulae AE-BZ, if a formula contains variables $R^{10}$ and/or n, each entry $R^B$ is intended to be paired with individual designation of $R^{10}$ and/or $R^1$, independently at each occurrence, listed below.

$R^{10}$ is H, methyl, ethyl, isopropyl, isobutyl, 2-propynyl, acetyl, 2,2-dimethylpropanoyl, t-butoxycarbonyl, 3-methylbutanoyl, isobutyryl, isonicotinoyl, phenoxyacetyl, methanesulfonyl, 3-pyridinylmethyl, 4-pyridinylmethyl, 3-pyridinylcarbonyl, 4-piperidinylcarbonyl, 4-morpholinylacetyl, 4-morpholinomethyl, or [1-(t-butoxycarbonyl)-4-piperidinyl]carbonyl;
$R^1$ is H or methyl.
TABLE 4
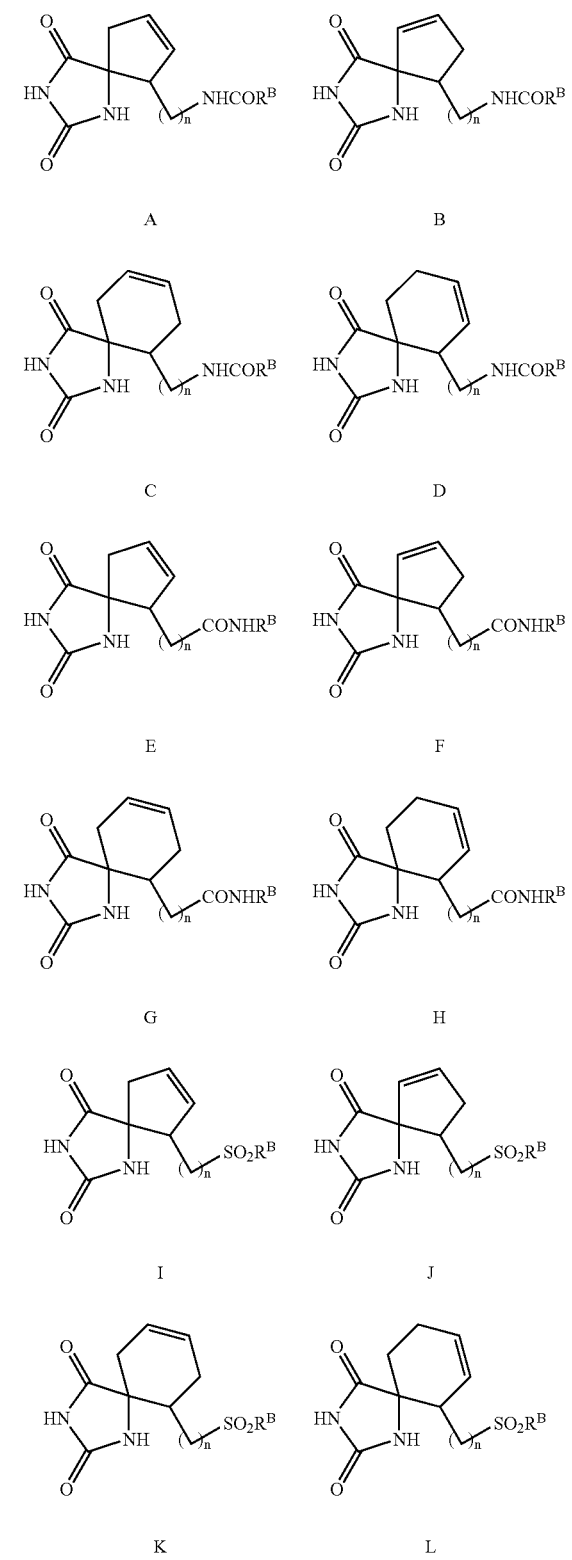
TABLE 4-continued
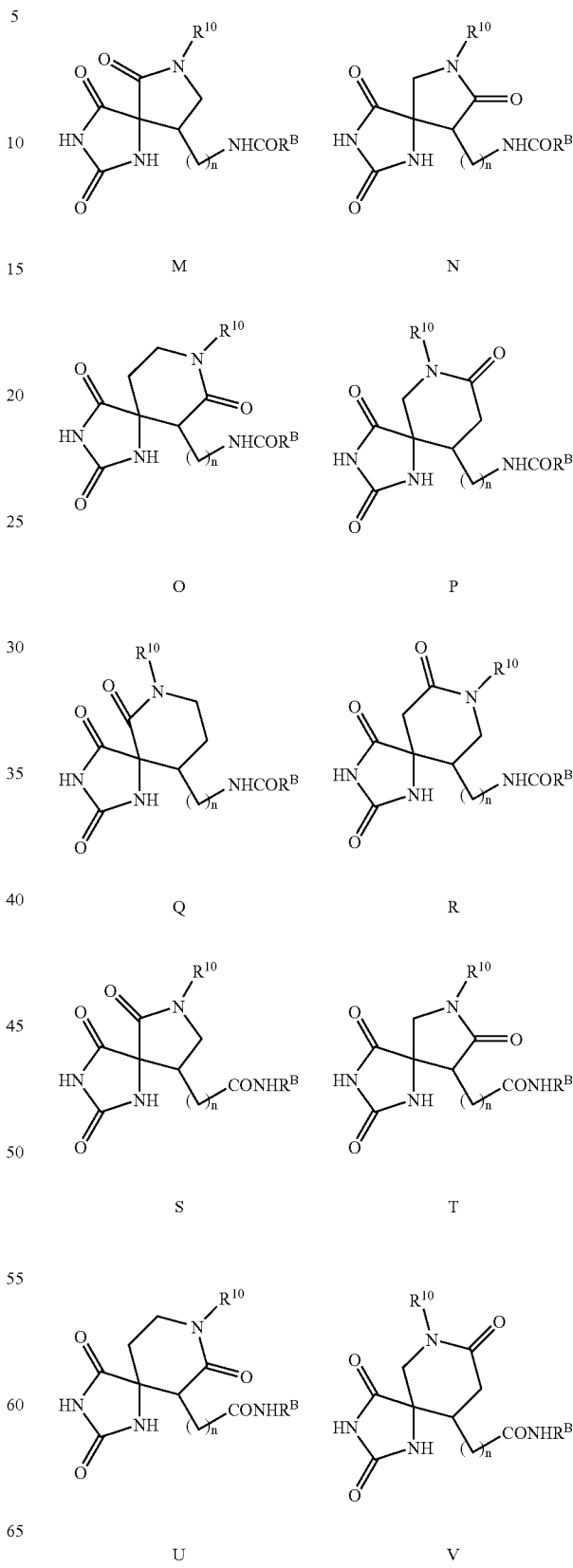

TABLE 4-continued
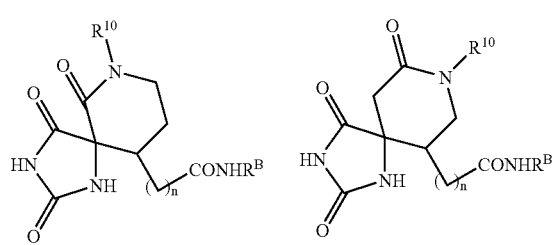
W         X
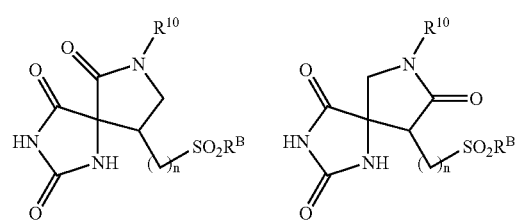
Y         Z
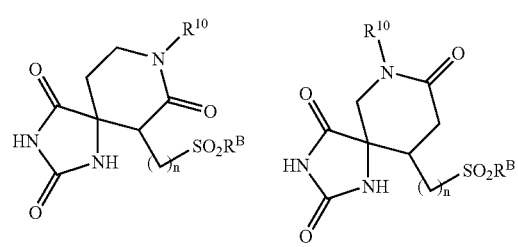
AA        AB
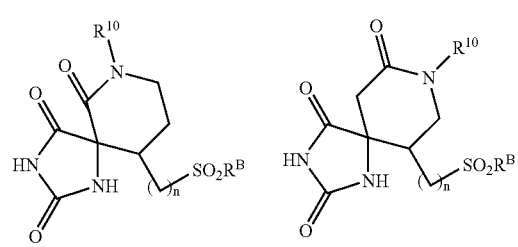
AC        AD
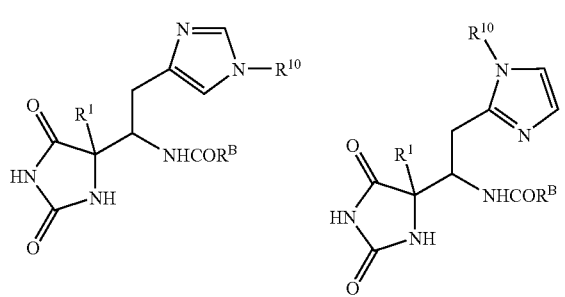
AE        AF
TABLE 4-continued
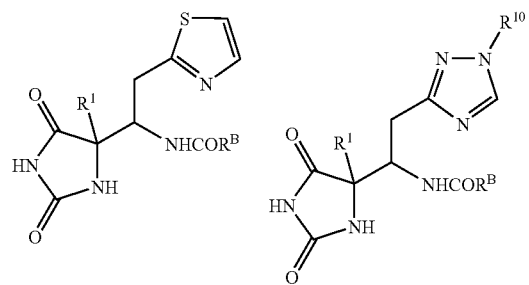
AG        AH
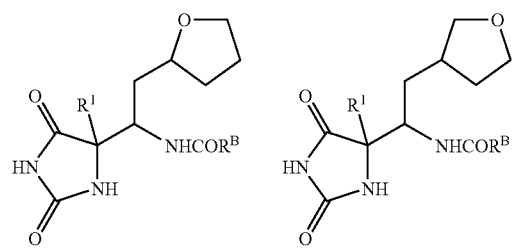
AI         AJ
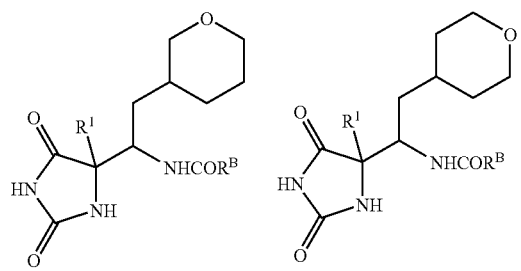
AK        AL
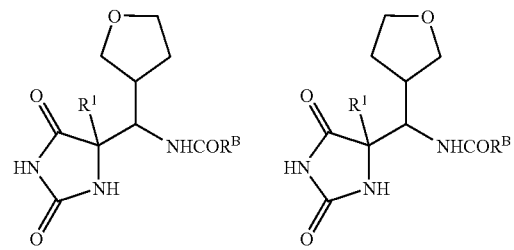
AM        AN
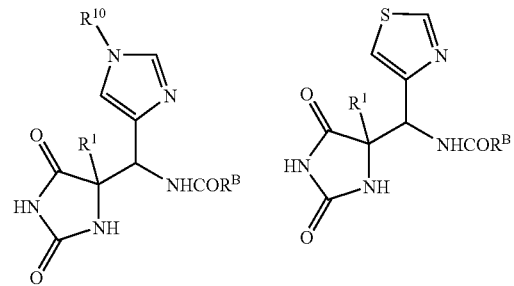
AO        AP TABLE 4-continued
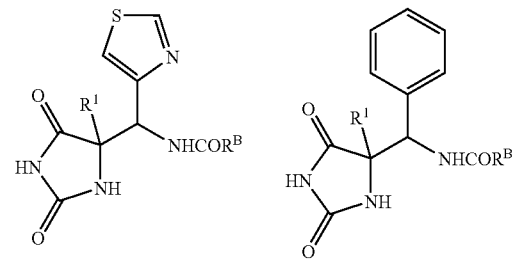
AQ  AR
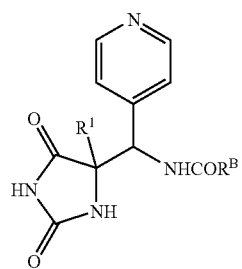
AS  AT
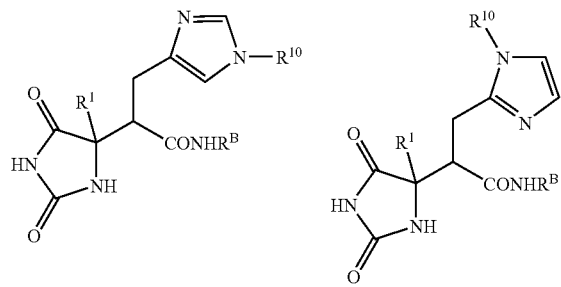
AU  AV
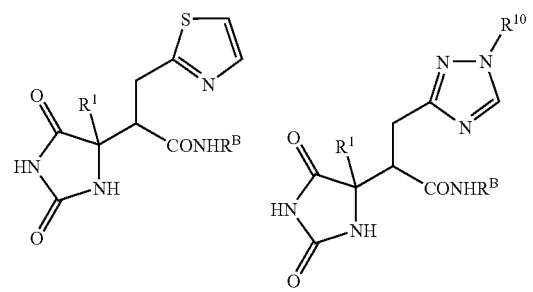
AW  AX
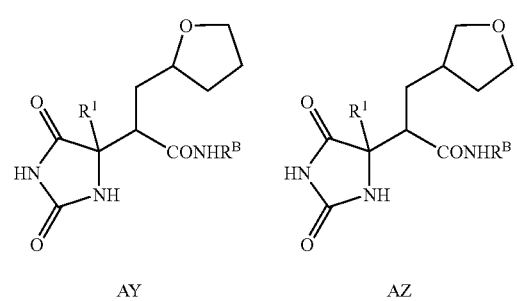
AY  AZ
TABLE 4-continued
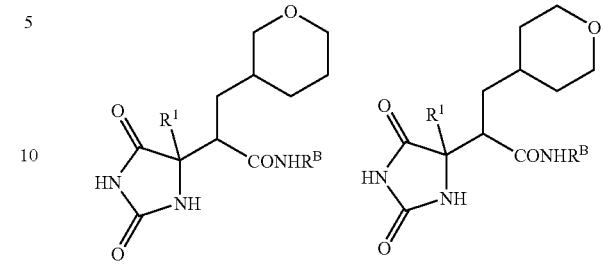
BA  BB
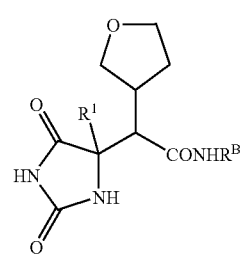
BC  BD
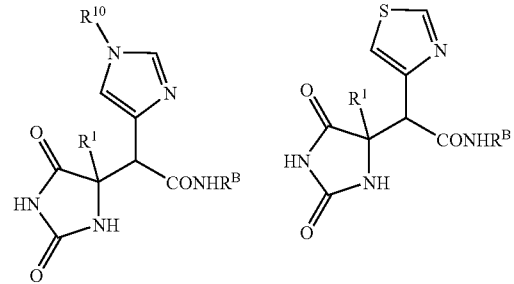
BE  BF
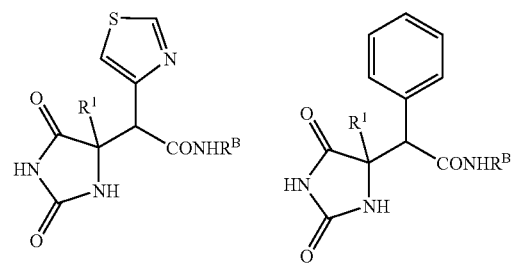
BG  BH
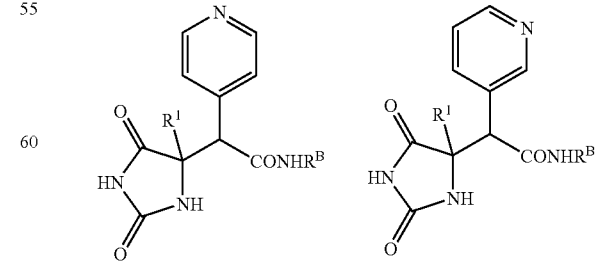
BI  BJ TABLE 4-continued

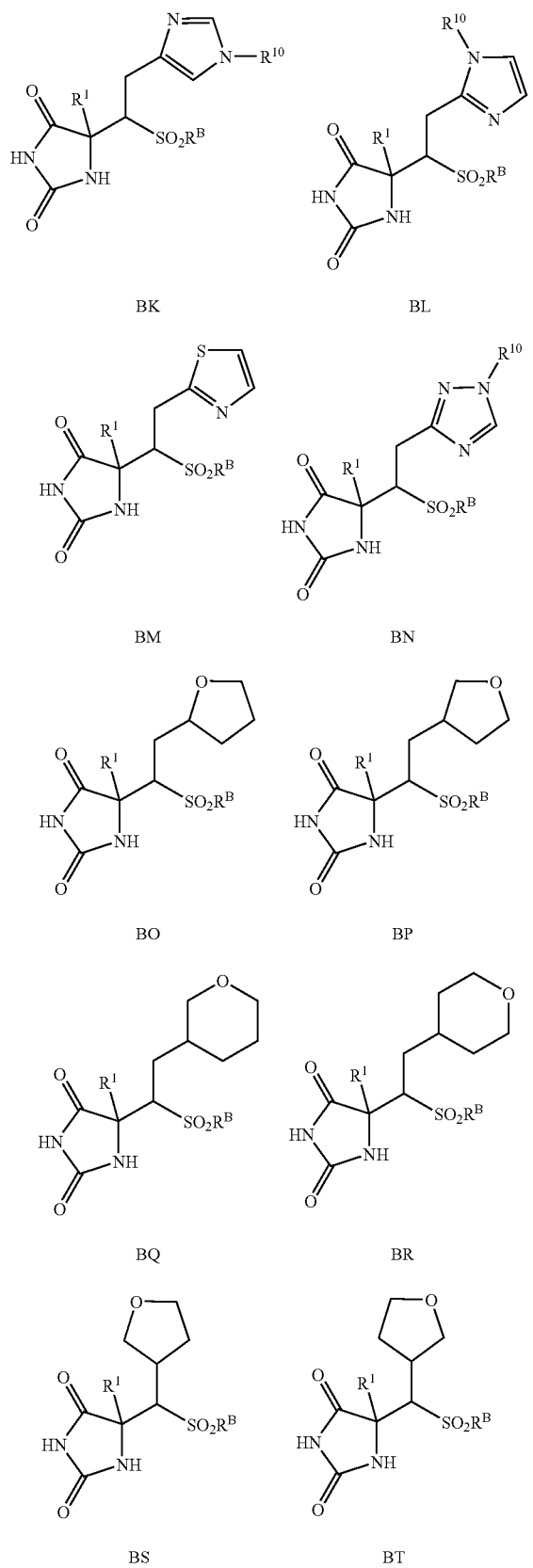
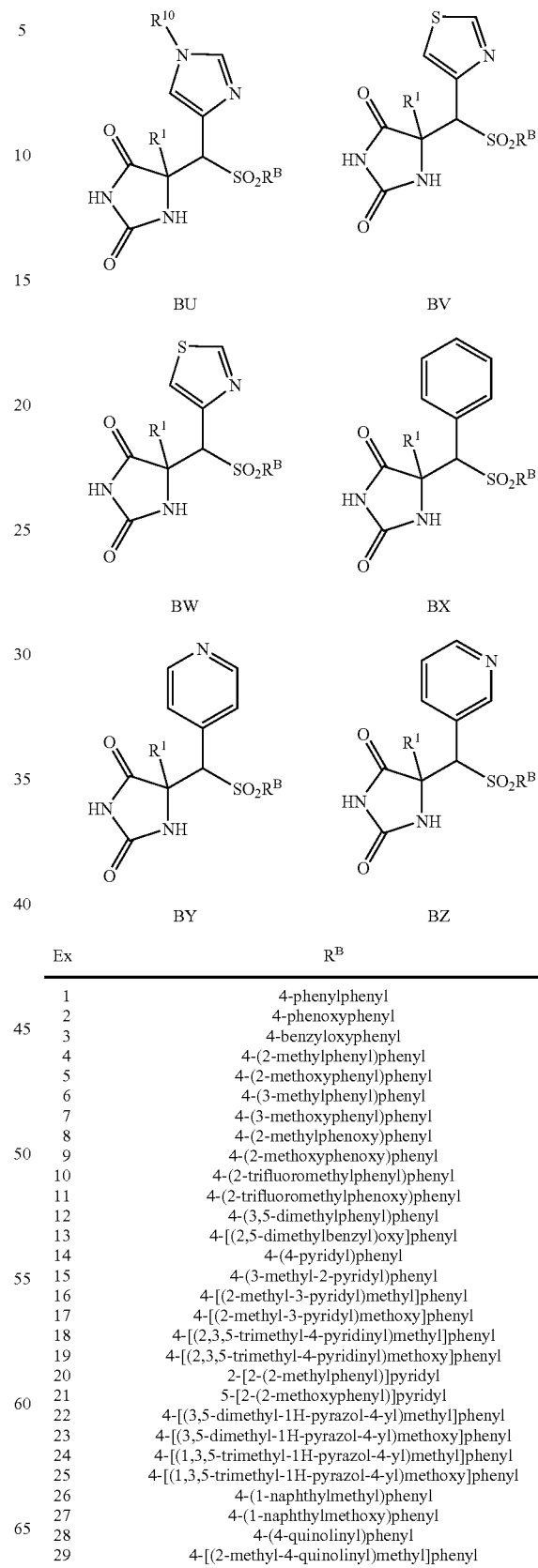

| Ex | R^B |
|---|---|
| 1 | 4-phenylphenyl |
| 2 | 4-phenoxyphenyl |
| 3 | 4-benzyloxyphenyl |
| 4 | 4-(2-methylphenyl)phenyl |
| 5 | 4-(2-methoxyphenyl)phenyl |
| 6 | 4-(3-methylphenyl)phenyl |
| 7 | 4-(3-methoxyphenyl)phenyl |
| 8 | 4-(2-methylphenoxy)phenyl |
| 9 | 4-(2-methoxyphenoxy)phenyl |
| 10 | 4-(2-trifluoromethylphenyl)phenyl |
| 11 | 4-(2-trifluoromethylphenoxy)phenyl |
| 12 | 4-(3,5-dimethylphenyl)phenyl |
| 13 | 4-[(2,5-dimethylbenzyl)oxy]phenyl |
| 14 | 4-(4-pyridyl)phenyl |
| 15 | 4-(3-methyl-2-pyridyl)phenyl |
| 16 | 4-[(2-methyl-3-pyridyl)methyl]phenyl |
| 17 | 4-[(2-methyl-3-pyridyl)methoxy]phenyl |
| 18 | 4-[(2,3,5-trimethyl-4-pyridinyl)methyl]phenyl |
| 19 | 4-[(2,3,5-trimethyl-4-pyridinyl)methoxy]phenyl |
| 20 | 2-[2-(2-methylphenyl)]pyridyl |
| 21 | 5-[2-(2-methoxyphenyl)]pyridyl |
| 22 | 4-[(3,5-dimethyl-1H-pyrazol-4-yl)methyl]phenyl |
| 23 | 4-[(3,5-dimethyl-1H-pyrazol-4-yl)methoxy]phenyl |
| 24 | 4-[(1,3,5-trimethyl-1H-pyrazol-4-yl)methyl]phenyl |
| 25 | 4-[(1,3,5-trimethyl-1H-pyrazol-4-yl)methoxy]phenyl |
| 26 | 4-(1-naphthylmethyl)phenyl |
| 27 | 4-(1-naphthylmethoxy)phenyl |
| 28 | 4-(4-quinolinyl)phenyl |
| 29 | 4-[(2-methyl-4-quinolinyl)methyl]phenyl |

TABLE 4-continued

| | |
|---|---|
| 30 | 4-(2-methyl-4-quinolinylmethoxy)phenyl |
| 31 | 4-(2-methyl-1-oxo-4-quinolinylmethyl)phenyl |
| 32 | 4-(2-methyl-1-oxo-4-quinolinylmethoxy)phenyl |
| 33 | 4-{[(2-methyl-4-quinolinyl)methyl]amino}phenyl |
| 34 | {4-[(2-methyl-4-quinolinyl)methyl]phenyl}methyl |
| 35 | 4-[(2-ethyl-4-quinolinyl)methyl]phenyl |
| 36 | 4-[(2-ethyl-4-quinolinyl)methoxy]phenyl |
| 37 | 4-{[2-(trifluoromethyl)-4-quinolinyl]methyl}phenyl |
| 38 | 4-{[2-(trifluoromethyl)-4-quinolinyl]methoxy}phenyl |
| 39 | 4-[(5-quinolinyloxy)methyl]phenyl |
| 40 | 4-[(5-quinolinyloxy)methoxy]phenyl |
| 41 | 4-{[(2-methyl-8-quinolinyl)oxy]methyl}phenyl |
| 42 | 4-{[(2-methyl-8-quinolinyl)oxy]methoxy}phenyl |
| 43 | 4-[(5-isoquinolinyloxy)methyl]phenyl |
| 44 | 4-[(5-isoquinolinyloxy)methoxy]phenyl |
| 45 | 4-(3-phenyl-4,5-dihydro-5-isoxazolyl)phenyl |
| 46 | 4-[3-(4-pyridyl)-4,5-dihydro-5-isoxazolyl]phenyl |
| 47 | 4-[3-(3-pyridyl)-4,5-dihydro-5-isoxazolyl]phenyl |
| 48 | 4-[3-(2-pyridyl)-4,5-dihydro-5-isoxazolyl]phenyl |
| 49 | 4-[3-(4-quinolinyl)-4,5-dihydro-5-isoxazolyl]phenyl |
| 50 | 4-[3-(2,6-dimethyl-4-pyridyl)-4,5-dihydro-5-isoxazolyl]phenyl |
| 51 | 3-methoxy-4-[3-(4-pyridyl)-4,5-dihydro-5-isoxazolyl]phenyl |
| 52 | 4-[5-(4-pyridyl)-4,5-dihydro-3-isoxazolyl]phenyl |
| 53 | 4-(5-(3-pyridyl)-4,5-dihydro-3-isoxazolyl]phenyl |
| 54 | 4-[5-(2-pyridyl)-4,5-dihydro-3-isoxazolyl]phenyl |
| 55 | 1-[(2-methyl-4-quinolinyl)methyl]-1H-indol-5-yl |
| 56 | 1-[(2-methyl-4-quinolinyl)methoxy]-1H-indol-5-yl |
| 57 | 4-(1H-indol-3-ylmethyl)phenyl |
| 58 | 4-(1H-indol-3-ylmethoxy)phenyl |
| 59 | 4-[(2-methyl-1H-indol-3-yl)methyl]phenyl |
| 60 | 4-[(2-methyl-1H-indol-3-yl)methoxy]phenyl |
| 61 | 4-[(2-methyl-1H-indol-1-yl)-methyl]phenyl |
| 62 | 4-[(2-methyl-1H-indol-1-yl)-methoxy)phenyl |
| 63 | 6-[(2-methyl-4-quinolinyl)methyl]-1-naphthyl |
| 64 | 6-[(2-methyl-4-quinolinyl)methoxy]-1-naphthyl |
| 65 | 6-[(2-methyl-4-quinolinyl)methyl]-1,2,3,4-tetrahydro-1-isoquinolinyl |
| 66 | 6-[(2-methyl-4-quinolinyl)methoxy]-1,2,3,4-tetrahydro-1-isoquinolinyl |
| 67 | 4-[(1H-benzimidazol-1-yl)methyl]phenyl |
| 68 | 4-[(1H-benzimidazol-1-yl)methoxy]phenyl |
| 69 | 4-[(2-methyl-1H-benzimidazol-1-yl)methyl]phenyl |
| 70 | 4-[(2-methyl-1H-benzimidazol-1-yl)methoxy]phenyl |
| 71 | 4-[(2-isopropyl-1H-benzimidazol-1-yl)methyl]phenyl |
| 72 | 4-[(2-isopropyl-1H-benzimidazol-1-yl)methoxy]phenyl |
| 73 | 4-{[(2-trifluoromethyl-1H-benzimidazol-1-yl)]methyl}phenyl |
| 74 | 4-{[(2-trifluoromethyl-1H-benzimidazol-1-yl)]methoxy}phenyl |
| 75 | 4-{[(2-(methylthio)-1H-benzimidazol-1-yl]methyl}phenyl |
| 76 | 4-{[(2-(methylthio)-1H-benzimidazol-1-yl]methoxy}phenyl |
| 77 | 4-[(5-phenyl-1H-imidazol-1-yl)methyl]phenyl |
| 78 | 4-[(5-phenyl-1H-imidazol-1-yl)methoxy]phenyl |
| 79 | 4-[(1,1-dioxido-2,3-dihydro-4H-1,4-benzothiazin-4-yl)methyl]phenyl |
| 80 | 4-[(1,1-dioxido-2,3-dihydro-4H-1,4-benzothiazin-4-yl)methoxy]phenyl |
| 81 | 4-[2,2-dimethyl-1,1-dioxido-2,3-dihydro-4H-1,4-benzothiazin-4-yl)methyl]phenyl |
| 82 | 4-[2,2-dimethyl-1,1-dioxido-2,3-dihydro-4H-1,4-benzothiazin-4-yl)methoxy]phenyl |
| 83 | 4-[(2-ethylpyrazolo[1,5-a]pyridin-3-yl)-methyl]phenyl |
| 84 | 4-[(2-ethylpyrazolo[1,5-a]pyridin-3-yl)-methoxy]phenyl |
| 85 | 4-(1,3-dihydrofuro[3,4-b]quinolin-9-ylmethyl)phenyl |
| 86 | 4-(1,3-dihydrofuro[3,4-b]quinolin-9-ylmethoxy)phenyl |
| 87 | 4-[(2-methyl-1-oxido-4-quinolinyl)methyl]phenyl |
| 88 | 4-[(2-methyl-1-oxido-4-quinolinyl)methoxy]phenyl |

Utility

The compounds of formula I are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289-303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TACE and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstructive pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

The compounds of the present invention can be administered alone or in combination with one or more additional anti-inflammatory agents. These agents include, but are not limited to, selective COX-2 inhibitors, interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denotes agents that selectively inhibit COX-2 function. Such agents include, but are not limited to, celecoxib (Celebrex), rofecoxib (Vioxx), meloxicam (Movicox), etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel), infliximab (Remicade), adalimumab (D2E7), CDP-571 (Humicade), and CDP-870.

Other anti-inflammatory agents that may be used in combination with the compounds of this invention, include, but are not limited to, methotrexate, interleukin-1 antagonists (e.g., anakinra (Kineret)), dihydroorotate synthase inhibitors (e.g., leflunomide (Arava)), and p38 MAP kinase inhibitors.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M", denotes molar and "nm" denotes nanometer. "Sigma stands for the Sigma-Aldrich Corp. of St. Louis, Mo.

A compound is considered to be active if it has an $IC_{50}$ or $K_i$ value of less than about 10 μM for the inhibition of a desired MP. Preferred compounds of the present invention have $K_i$'s or $IC_{50}$'s of ≦1 μM. More preferred compounds of the present invention have $K_i$'s or $IC_{50}$'s of ≦0.1 μM. Even more preferred compounds of the present invention have $K_i$'s or $IC_{50}$'s of ≦0.01 μM. Still more preferred compounds of the present invention have $K_i$'s or $IC_{50}$'s of ≦0.001 μM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et al. *Trans. Ortho. Res. Soc.* 1995, 20, 341). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799-804, 1995). This antibody recognizes aggrecan fragments with the N-terminus, 374ARGS-VIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4-12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10-30 minutes to achieve optimal color development. Blots are quantitated by scanning densitometry and inhibition of aggrecanase determined by comparing the amount of product produced in the presence versus absence of compound.

TNF PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2\times10^6$ cells/ml in 96 well polystyrene plates. Cells were preincubated 10 minutes with compound, then stimulated with 1 ug/ml LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 µM. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

TNF Induction In Mice

Test compounds are administered to mice either I.P. or P.O. at time zero. Immediately following compound administration, mice receive an I.P. injection of 20 mg of D-galactosamine plus 10 ug of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947-1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, N.Y., 1996, pp 187-223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337-10338). Based on the assumption of competitive inhibiton, the IC50 values were converted to $K_i$ values as previously described.

Compounds tested in the above assay are considered to be active if they exhibit a $K_i$ of $\leq 10$ µM. Preferred compounds of the present invention have $K_i$'s of $\leq 1$ µM. More preferred compounds of the present invention have $K_i$'s of $\leq 0.1$ µM. Even more preferred compounds of the present invention have $K_i$'s of $\leq 0.01$ µM. Still more preferred compounds of the present invention have $K_i$'s of $\leq 0.001$ µM.

Using the methodology described above, a number of compounds of the present invention were found to exhibit $K_i$'s of $\leq 10$ µM, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations.

Various equivalents, changes and modifications may be made without departing from the spirit and scope of this invention, and it is understood that such equivalent embodiments are part of this invention.

What is claimed is:
1. A compound is of the following formulae:

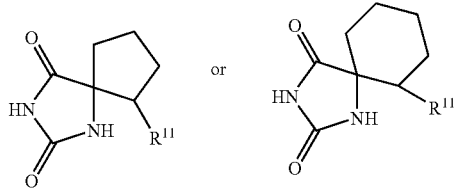

or a stereoisomer or a pharmaceutically acceptable salt form thereof, wherein;

$R^{11}$ is -W-U-X-Y-Z-$U^a$-$X^a$-$Y^a$-$Z^a$-;

W is $(CH_2)_m$;

U is absent or is selected from O, $NR^{a1}$, C(O), C(O)$NR^{a1}$, $NR^{a1}$C(O), S(O)$_p$, S(O)$_p NR^{a1}$, and $NR^{a1}$S(O)$_p$;

X is absent or is methylene;

Y is absent;

Z is phenyl substituted with 0-4 $R^b$;

$U^a$ is absent or is O;

$X^a$ is absent or is selected from $C_{1-4}$ alkylene, $C_{2-4}$ alkenylene, and $C_{2-4}$ alkynylene;

$Y^a$ is absent or is O;

$Z^a$ is selected from: phenyl substituted with 0-3 $R^c$, naphthyl substituted with 0-3 $R^c$; and a heterocycle substituted with 0-3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, pyranyl, pyrazinyl, pyrazolyl, pyridoimidazolyl, pyrrolidinyl, pyrrolyl, quinolinyl, tetrahydroquinolinyl, isoquinolinyl, tetrahydro-isoquinolinyl, imidazolyl, benzimidazolyl, benzothiazinyl, benzofuranyl, benzothiophenyl, benzoxazolyl, benzthiazolyl, benztriazolyl, benzisoxazolyl, benzisothiazolyl, indolyl, indolinyl, indazolyl, isobenzofuranyl, isoindazolyl, isoindolinyl, isoindolyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

$R^a$, at each occurrence, is independently selected from H, and $C_{1-4}$ alkyl;

$R^{a1}$, at each occurrence, is independently selected from H, and $C_{1-4}$ alkyl;

$R^{a3}$, at each occurrence, is independently selected from H, $C_{1-4}$ alkyl, phenyl, and benzyl;

$R^b$, at each occurrence, is independently selected from $C_{1-6}$ alkyl substituted with 0-1 $R^{c1}$, $OR^a$, $SR^a$, Cl, F, Br, I, =O, —CN, $NO_2$, $NR^a R^{a1}$, C(O)$R^a$, C(O)$OR^a$, C(O)$NR^a R^{a1}$, C(S)$NR^a R^{a1}$, $NR^a$C(O)$NR^a R^{a1}$, OC(O)$NR^a R^{a1}$, $NR^a$C(O)$OR^a$, S(O)$_2 NR^a R^{a1}$, $NR^a$S(O)$_2 R^{a3}$, $NR^a$S(O)$_2 NR^a R^{a1}$, OS(O)$_2 NR^a R^{a1}$, S(O)$_p R^{a3}$, $CF_3$, $CF_2 CF_3$, $CHF_2$, $CH_2 F$, and phenyl;

$R^c$, at each occurrence, is independently selected from $C_{1-6}$ alkyl, $C_{2-6}$ alkenyl, $C_{2-6}$ alkynyl, $OR^a$, Cl, F, Br, =O, $CF_3$, $CH_2 F$, $CHF_2$, $NR^a R^{a1}$, $(CR^a R^{a1})_r C(O)R^{a1}$, $(CR^a R^{a1})_r C(O)OR^{a1}$, $(CR^a R^{a1})_r C(O)NR^a R^{a1}$, $(CR^a R^{a1})_r NR^a C(O)R^{a1}$, $(CR^a R^{a1})_r S(O)_p R^{a3}$, $(CR^a R^{a1})_r SO_2 NR^a R^{a1}$, $(CR^a R^{a1})_r NR^a SO_2 R^{a3}$, and phenyl; alternatively, when two $R^c$ groups are attached to adjacent carbon atoms, together with the carbon atoms to which they are attached they form a 5-6 membered carbocyclic or heterocyclic ring D substituted with 0-2 $R^{c1}$ and consisting of carbon atoms, 0-2 heteroatoms selected from the group consisting of N, O, and $S(O)_p$, and 0-3 double bonds;

$R^{c1}$, at each occurrence, is independently selected from H, $C_{1-4}$ alkyl, $OR^a$, Cl, F, Br, I, =O, $CF_3$, —CN, $NO_2$, $C(O)R^a$, $C(O)OR^a$, $C(O)NR^aR^a$, and $S(O)_pR^a$;

$R^e$, at each occurrence, is independently selected from H, $C_{1-6}$ alkyl, $C_{1-6}$ alkoxy, phenoxy, benzoxy, C3-6 carbocycle substituted with 0-2 $R^{c1}$, and a 5-6 membered heterocycle consisting of carbon atoms and 1-4 heteroatoms selected from the group consisting of N, O, and $S(O)_p$, and substituted with 0-2 $R^{c1}$;

$R^{10}$, at each occurrence, is independently selected from H, $(CH_2)_rC(O)(CH_2)_sR^e$, $(CH_2)_rC(O)OR^{a1}$, $(CR^aR^{a1})_rC(O)NR^aR^{a1}$, $(CH_2)_rS(O)_pR^{a3}$, $(CH^2)_rSO_2NR^aR^{a1}$, $C_{1-4}$ alkyl substituted with 0-1 $R^{c1}$, $C_{2-4}$ alkenyl substituted with 0-1 $R^{c1}$, $C_{2-4}$ alkynyl substituted with 0-1 $R^{c1}$, $(CH_2)_r$-$C_{3-6}$ cycloalkyl substituted with 0-2 $R^{c1}$, $(CH_2)_r$-phenyl substituted with 0-2 $R^{c1}$, and $(CH_2)_r$-5-6 membered heterocycle consisting of carbon atoms and 1-4 heteroatoms selected from the group consisting of N, O, and $S(O)_p$, and substituted with 0-2 $R^{c1}$;

m, at each occurrence, is selected from 0, 1, and 2;
p, at each occurrence, is selected from 0, 1, and 2;
r, at each occurrence, is selected from 0, 1, and 2; and
s, at each occurrence, is selected from 0, 1, and 2.

2. A compound according to claim 1, wherein:
Z is phenyl substituted with 0-1 $R^b$;
$Z^a$ is selected from: phenyl substituted with 0-3 $R^c$, naphthyl substituted with 0-3 $R^c$; and a heterocycle substituted with 0-3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

$R^b$, at each occurrence, is independently selected from $C_{1-6}$ alkyl, $OR^a$, Cl, F, Br, $NR^aR^{a1}$, $C(O)R^a$, $C(O)OR^a$, $C(O)NR^aR^{a1}$, $S(O)_2NR^aR^{a1}$, $NR^aS(O)_2R^{a3}$, $S(O)_pR^{a3}$, and $CF_3$;

$R^c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, and $(CR^aR^{a1})_rNR^aSO_2R^{a3}$;

alternatively, when two $R^c$ groups are attached to adjacent carbon atoms, together with the carbon atoms to which they are attached they form a 5-6 membered carbocyclic or heterocyclic ring consisting of: carbon atoms and 0-1 heteroatoms selected from the group consisting of N, O, and $S(O)_p$; and $R^e$, at each occurrence, is independently selected from H, $C_{1-6}$ alkyl, $C_{1-6}$ alkoxy, phenoxy, benzoxy, phenyl substituted with 0-1 $R^{c1}$, and a 5-6 membered heterocycle consisting of carbon atoms and 1-4 heteroatoms selected from the group consisting of N, O, and $S(O)_p$, and substituted with 0-1 $R^{c1}$.

3. A compound according to claim 1, wherein the compound is selected from the group:

(cis,trans)-N-{4-[(2-methyl-4-quinolinyl)methoxy]phenyl}-2,4-dioxo-1,3-diazaspiro[4.5]decane-6-carboxamide;

(cis,trans)-N-{4-[(2-methyl-4-quinolinyl)methoxy]phenyl}-2,4-dioxo-1,3-diazaspiro[4.4]nonane-6-carboxamide;

(cis,trans)-2-(2,4-dioxo-1,3-diazaspiro[4.4]non-6-yl)-N-{4-[(2-methyl-4-quinolinyl)methoxy]phenyl}acetamide;

(cis,trans)-N-(2,4-dioxo-1,3-diazaspiro[4.4]non-6-yl)-4-[(2-methyl-4-quinolinyl)methoxy]benzamide;

(cis,trans)-N-(2,4-dioxo-1,3-diazaspiro[4.4]non-6-yl)-2-{4-[(2-methyl-4-quinolinyl)methoxy]phenyl}acetamide;

(cis,trans)-N-(2,4-dioxo-1,3-diazaspiro[4.4]non-6-yl)-4-[(2-methyl-4-quinolinyl)methoxy]benzenesulfonamide;

(trans)-N-[(2,4-dioxo-1,3-diazaspiro[4.5]dec-6-yl)methyl]-4-[(2-methyl-4-quinolinyl)methoxy]-benzamide;

(trans)-N-[(2,4-dioxo-1,3-diazaspiro[4.5]dec-6-yl)methyl]-4-[(2-methyl-4-quinolinyl)methoxy]benzenesulfonamide;

(cis)-N-[(2,4-dioxo-1,3-diazaspiro[4.5]dec-6-yl)methyl]-4-[(2-methyl-4-quinolinyl)methoxy]benzamide;

(cis)-N-[(2,4-dioxo-1,3-diazaspiro[4.5]dec-6-yl)methyl]-4-[(2-methyl-4-quinolinyl)methoxy]benzenesulfonamide;

6({4-[(2-methyl-4-quinolinyl)methoxy]phenyl}sulfonyl)-1,3-diazaspiro[4.4]nonane-2,4-dione;

6-({4-[(2-methyl-4-quinolinyl)methoxy]phenyl}sulfonyl)-1,3-diazaspiro[4.5]decanane-2,4-dione;

2-(2,4-dioxo-1,3-diazaspiro[4.5]dec-6-yl)-N-{4-[(2-methyl-4-quinolinyl)methoxy]phenyl}acetamide;

6-({4-[(2-methyl-4-quinolinyl)methoxy]phenyl}sulfonyl)methyl]-1,3-diazaspiro[4.4]nonane-2,4-dione;

N-(2,4-dioxo-1,3-diazaspiro[4.5]dec-6-yl)-4-[(2-methyl-4-quinolinyl)methoxy]benzamide;

4-[(1,1-dioxido-2,3-dihydro-4H-1,4-benzothiazin-4-yl)methyl]-N-(2,4-dioxo-1,3-diazaspiro[4.5]dec-6-yl)benzamide; and (cis,trans)-N-(2,4-dioxo-1,3-diazaspiro[4.5]dec-6-yl)-4-[(2-methyl-4-quinolinyl)methoxy]benzenesulfonamide;

or a pharmaceutically acceptable salt form thereof.

4. A pharmaceutical composition, comprising: a pharmaceutically acceptable carrier and a therapeutically effective amount of a compound according to claim 1 or a pharmaceutically acceptable salt form thereof.

5. A pharmaceutical composition, comprising: a pharmaceutically acceptable carrier and a therapeutically effective amount of a compound according to claim 2 or a pharmaceutically acceptable salt form thereof.

6. A pharmaceutical composition, comprising: a pharmaceutically acceptable carrier and a therapeutically effective amount of a compound according to claim 3 or a pharmaceutically acceptable salt form thereof.

* * * * *

UNITED STATES PATENT AND TRADEMARK OFFICE
CERTIFICATE OF CORRECTION

Page 1 of 1

| | |
|---|---|
| PATENT NO. | : 7,482,372 B2 |
| APPLICATION NO. | : 11/093670 |
| DATED | : January 27, 2009 |
| INVENTOR(S) | : Sheppeck et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 893 days.

Signed and Sealed this
First Day of January, 2013

David J. Kappos
*Director of the United States Patent and Trademark Office*